US012799067B2

(12) United States Patent
Slivensky et al.

(10) Patent No.: US 12,799,067 B2
(45) **Date of Patent: *Nov. 17, 2026**

(54) RECYCLE CONTENT GLYCOL ESTERS

(71) Applicant: ExxonMobil Product Solutions Company, Spring, TX (US)

(72) Inventors: David Eugene Slivensky, Tatum, TX (US); Daryl Bitting, Longview, TX (US); Kenny Randolph Parker, Afton, TN (US); Michael Gary Polasek, Longview, TX (US); William Lewis Trapp, Kingsport, TN (US); Xianchun Wu, Longview, TX (US)

(73) Assignee: ExxonMobil Product Solutions Company, Spring, TX (US)

( * ) Notice: Subject to any disclaimer, the term of this patent is extended or adjusted under 35 U.S.C. 154(b) by 791 days.

This patent is subject to a terminal disclaimer.

(21) Appl. No.: 17/755,357

(22) PCT Filed: Nov. 6, 2020

(86) PCT No.: PCT/US2020/059286

§ 371 (c)(1),
(2) Date: Apr. 27, 2022

(87) PCT Pub. No.: WO2021/092291

PCT Pub. Date: May 14, 2021

(65) Prior Publication Data

US 2022/0396546 A1 Dec. 15, 2022

Related U.S. Application Data

(60) Provisional application No. 62/932,030, filed on Nov. 7, 2019.

(51) Int. Cl.
*C07C 67/44* (2006.01)

(52) U.S. Cl.
CPC ............ *C07C 67/44* (2013.01); *Y02P 20/582* (2015.11)

(58) Field of Classification Search
CPC ......... C07C 67/44; C07C 29/38; C07C 45/50; C07C 45/505; C07C 47/02; C07C 69/24;
(Continued)

(56) References Cited

U.S. PATENT DOCUMENTS 1,048,530 A 12/1912 Harlow
1,219,162 A 3/1917 Runge
(Continued)

FOREIGN PATENT DOCUMENTS

CN 1309112 A 8/2001
CN 1434015 A 8/2003
(Continued)

OTHER PUBLICATIONS

Co-pending U.S. Appl. No. 17/595,511, filed Nov. 18, 2021; Bitting et al.
(Continued)

*Primary Examiner* — Fereydoun G Sajjadi
*Assistant Examiner* — Y. Lynnette Kelly-O'Neill
(74) *Attorney, Agent, or Firm* — C. Tumey Law Group PLLC

(57) ABSTRACT

A composition having a recycle content value is obtained by reacting a recycle content feedstock to make a recycle content glycol ester by deducting from a recycle inventory a recycle content value applied to a glycol ester composition. At least a portion of the recycle content value in the feedstock or in an allotment obtained by a glycol ester manufacturer has its origin in recycled waste and/or pyrolysis of recycled waste and/or in thermal steam cracking of recycle content pyoil.

11 Claims, 23 Drawing Sheets

(58) Field of Classification Search
CPC ....... C07C 69/28; C07C 31/20; Y02P 20/582; Y02P 30/20; C10G 3/40; C10G 1/02; C10G 1/10; C10G 1/08; C10G 11/05
USPC .......................................................... 560/189
See application file for complete search history.

(56) References Cited

U.S. PATENT DOCUMENTS

| | | | |
|---|---|---|---|
| 1,683,347 A | 9/1928 | Gray et al. | |
| 1,698,049 A | 1/1929 | Clarke et al. | |
| 1,880,560 A | 10/1932 | Webber et al. | |
| 1,880,808 A | 10/1932 | Clarke et al. | |
| 1,984,147 A | 12/1934 | Malm | |
| 2,026,985 A | 1/1936 | Malm et al. | |
| 2,129,052 A | 9/1938 | Fordyce | |
| 2,163,013 A | 6/1939 | Schulz | |
| 2,294,984 A | 9/1942 | Hasche | |
| 2,337,004 A | 12/1943 | Schwoegler | |
| 2,368,704 A | 2/1945 | Carlson | |
| 2,464,916 A | 3/1949 | Adams et al. | |
| 2,880,241 A | 3/1959 | Hughes | |
| 2,892,858 A | 6/1959 | Ziegler | |
| 3,091,632 A | 5/1963 | Hagemeyer et al. | |
| 3,239,566 A | 3/1966 | Slaugh et al. | |
| 3,291,821 A | 12/1966 | Perry et al. | |
| 3,340,312 A | 9/1967 | Duke, Jr. et al. | |
| 3,351,657 A | 11/1967 | Duncanson et al. | |
| 3,448,157 A | 6/1969 | Slaugh et al. | |
| 3,448,173 A | 6/1969 | Francis et al. | |
| 3,527,809 A | 9/1970 | Pruett et al. | |
| 3,544,291 A | 12/1970 | Schlinger et al. | |
| 3,617,201 A | 11/1971 | Berni et al. | |
| 3,631,225 A | 12/1971 | Tenney et al. | |
| 3,655,825 A | 4/1972 | Souder et al. | |
| 3,660,447 A | 5/1972 | Cragg et al. | |
| 3,676,523 A | 7/1972 | Mason | |
| 3,686,334 A | 8/1972 | Britton | |
| 3,718,689 A | 2/1973 | McCain et al. | |
| 3,853,968 A | 12/1974 | Bortnick et al. | |
| 3,857,895 A | 12/1974 | Booth | |
| 4,097,363 A | 6/1978 | McKinney et al. | |
| 4,111,982 A | 9/1978 | Eubanks et al. | |
| 4,147,603 A | 4/1979 | Pacifici et al. | |
| 4,148,830 A | 4/1979 | Pruett et al. | |
| 4,169,861 A | 10/1979 | Hughes | |
| 4,216,337 A | 8/1980 | Baba et al. | |
| 4,218,339 A | 8/1980 | Zucchini et al. | |
| 4,225,726 A | 9/1980 | Morris et al. | |
| 4,248,802 A | 2/1981 | Kuntz | |
| 4,263,449 A | 4/1981 | Saito et al. | |
| 4,287,369 A | 9/1981 | Harris et al. | |
| 4,287,370 A | 9/1981 | Harris et al. | |
| 4,303,594 A | 12/1981 | Norton et al. | |
| 4,316,990 A | 2/1982 | Morris | |
| 4,332,564 A | 6/1982 | Lord | |
| 4,350,829 A | 9/1982 | Masuko et al. | |
| 4,436,532 A | 3/1984 | Yamaguchi et al. | |
| 4,443,638 A | 4/1984 | Yates | |
| 4,446,585 A | 5/1984 | Harding et al. | |
| 4,452,999 A | 6/1984 | Besecke et al. | |
| 4,479,012 A | 10/1984 | Fischer et al. | |
| 4,482,640 A | 11/1984 | Knudsen et al. | |
| 4,496,781 A | 1/1985 | Jacobson et al. | |
| 4,515,659 A | 5/1985 | Wingfield, Jr. et al. | |
| 4,536,597 A | 8/1985 | Pesa et al. | |
| 4,548,706 A | 10/1985 | Papadopoulos et al. | |
| 4,564,647 A | 1/1986 | Hayashi et al. | |
| 4,593,127 A | 6/1986 | Bunning et al. | |
| 4,625,068 A | 11/1986 | Young | |
| 4,699,998 A | 10/1987 | Green | |
| 4,742,178 A | 5/1988 | Nelson et al. | |
| 4,755,624 A | 7/1988 | Phillips et al. | |
| 4,758,645 A | 7/1988 | Miyazono et al. | |
| 4,774,362 A | 9/1988 | Devon et al. | |
| 4,808,756 A | 2/1989 | Tokitoh et al. | |
| 4,839,230 A | 6/1989 | Cook | |
| 4,861,629 A | 8/1989 | Nahm | |
| 4,871,878 A | 10/1989 | Puckette et al. | |
| 4,873,213 A | 10/1989 | Puckette et al. | |
| 4,912,155 A | 3/1990 | Burton | |
| 4,960,949 A | 10/1990 | Devon et al. | |
| 5,004,845 A | 4/1991 | Bradley et al. | |
| 5,082,914 A | 1/1992 | Cook et al. | |
| 5,087,763 A | 2/1992 | Sorensen | |
| 5,114,089 A | 5/1992 | Posso | |
| 5,137,954 A | 8/1992 | DasGupta et al. | |
| 5,144,088 A | 9/1992 | Salek et al. | |
| 5,169,985 A | 12/1992 | Ruppert et al. | |
| 5,180,847 A | 1/1993 | Thurman et al. | |
| 5,182,379 A | 1/1993 | Cook et al. | |
| 5,202,463 A | 4/1993 | Ruszkay | |
| 5,264,600 A | 11/1993 | Lappe et al. | |
| 5,292,877 A | 3/1994 | Edgar et al. | |
| 5,292,979 A | 3/1994 | Chauvin et al. | |
| 5,312,951 A | 5/1994 | Herrmann et al. | |
| 5,347,045 A | 9/1994 | Herrmann et al. | |
| 5,364,995 A | 11/1994 | Kirkwood et al. | |
| 5,368,723 A | 11/1994 | Takahashi et al. | |
| 5,384,163 A | 1/1995 | Budde et al. | |
| 5,504,259 A | 4/1996 | Diebold et al. | |
| 5,534,594 A | 7/1996 | Troy et al. | |
| 5,557,014 A | 9/1996 | Grate et al. | |
| 5,639,937 A | 6/1997 | Hover et al. | |
| 5,663,444 A | 9/1997 | Melder et al. | |
| 5,684,097 A | 11/1997 | Palmroos et al. | |
| 5,723,151 A | 3/1998 | Cook et al. | |
| 5,731,483 A | 3/1998 | Stabel et al. | |
| 5,741,901 A | 4/1998 | Cook et al. | |
| 5,750,677 A | 5/1998 | Edgar et al. | |
| 5,770,017 A | 6/1998 | Brown et al. | |
| 5,770,664 A | 6/1998 | Okumura et al. | |
| 5,830,981 A | 11/1998 | Koreishi et al. | |
| 5,852,143 A | 12/1998 | Sishta et al. | |
| 5,866,725 A | 2/1999 | Unruh et al. | |
| 5,871,573 A | 2/1999 | Cook et al. | |
| 5,977,407 A | 11/1999 | Zoeller et al. | |
| 5,981,738 A | 11/1999 | Cook et al. | |
| 5,990,370 A | 11/1999 | Sims | |
| 6,075,168 A | 6/2000 | DiGuilio et al. | |
| 6,090,986 A * | 7/2000 | Godwin | C07C 29/141 562/512 |
| 6,121,394 A | 9/2000 | Sugimoto et al. | |
| 6,184,428 B1 | 2/2001 | Zahoor et al. | |
| 6,277,778 B1 | 8/2001 | Leino et al. | |
| 6,278,030 B1 | 8/2001 | Vargas et al. | |
| 6,331,580 B1 | 12/2001 | Molnar | |
| 6,344,530 B2 | 2/2002 | Sugano et al. | |
| 6,362,367 B2 | 3/2002 | Braithwaite et al. | |
| 6,369,214 B1 | 4/2002 | Tye et al. | |
| 6,458,992 B1 | 10/2002 | Lederer et al. | |
| 6,476,171 B1 | 11/2002 | Lue et al. | |
| 6,492,564 B1 | 12/2002 | Wiese et al. | |
| 6,559,342 B1 | 5/2003 | Tsuneki et al. | |
| 6,642,323 B1 | 11/2003 | Myhre et al. | |
| 6,693,213 B1 | 2/2004 | Kolena et al. | |
| 6,693,219 B2 | 2/2004 | Puckette et al. | |
| 6,730,756 B1 | 5/2004 | Andell et al. | |
| 6,818,584 B2 | 11/2004 | Garoff et al. | |
| 6,825,255 B2 | 11/2004 | Yuan et al. | |
| 6,960,635 B2 | 11/2005 | Stevens et al. | |
| 7,049,473 B2 | 5/2006 | Mackewitz et al. | |
| 7,128,827 B2 | 10/2006 | Tallman et al. | |
| 7,329,774 B2 | 2/2008 | Zuber et al. | |
| 7,420,092 B2 | 9/2008 | Fujita et al. | |
| 7,589,145 B2 | 9/2009 | Brant et al. | |
| 7,601,666 B2 | 10/2009 | Rix et al. | |
| 7,638,314 B2 | 12/2009 | Zappi et al. | |
| 7,767,613 B2 | 8/2010 | Mihan | |
| 7,812,111 B2 | 10/2010 | Hale et al. | |
| 7,816,465 B2 | 10/2010 | Andtsjo | |
| 7,897,679 B2 | 3/2011 | Stevens et al. | |
| 7,935,850 B2 | 5/2011 | Caers et al. | |
| 7,972,498 B2 | 7/2011 | Buchanan et al. | |
| 8,344,195 B2 | 1/2013 | Srinakruang | |

(56) References Cited

U.S. PATENT DOCUMENTS 8,354,563 B2 1/2013 Kharas
8,404,911 B2 3/2013 Srinakruang
8,426,652 B2 4/2013 Jevtic et al.
8,641,787 B2 2/2014 Morgan
8,829,258 B2 9/2014 Gong et al.
8,895,790 B2 11/2014 Narayanaswamy et al.
8,981,165 B2 3/2015 Carbone et al.
9,096,801 B2 8/2015 Baker
9,181,156 B2 11/2015 Ko et al.
9,309,183 B2 4/2016 Storzum et al.
9,505,901 B2 11/2016 Mohanty et al.
9,809,508 B2 11/2017 Keusenkothen et al.
9,856,198 B1 1/2018 Keen et al.
10,040,735 B2 8/2018 Levin
10,214,600 B2 2/2019 Somers et al.
10,233,395 B2 3/2019 Ward et al.
10,344,226 B2 7/2019 Schmidt et al.
10,975,313 B2 4/2021 Ramamurthy et al.
11,319,262 B2 5/2022 Wu et al.
11,447,576 B2 9/2022 Sheppard et al.
12,312,540 B2 5/2025 Wu et al.
2001/0039364 A1 11/2001 Drent et al.
2003/0047437 A1 3/2003 Stankevitch
2004/0267036 A1* 12/2004 Puckette ................ C07C 45/50 556/14
2005/0148487 A1 7/2005 Brownscombe et al.
2005/0182277 A1 8/2005 Totsch et al.
2005/0277778 A1 12/2005 Viswanathan et al.
2006/0014841 A1 1/2006 Melnichuk et al.
2006/0089518 A1 4/2006 Bouvart et al.
2006/0287484 A1 12/2006 Crawford et al.
2006/0287561 A1 12/2006 Choi et al.
2007/0137103 A1 6/2007 Wallace
2007/0179326 A1 8/2007 Baker
2007/0299280 A1 12/2007 Zoeller et al.
2008/0039540 A1 2/2008 Reitz
2008/0194808 A1 8/2008 Buchanan et al.
2008/0228558 A1* 9/2008 Gotthelf ........... G06Q 10/06375 707/999.201
2009/0005605 A1 1/2009 Hassan et al.
2010/0121097 A1 5/2010 Sasaki et al.
2010/0241253 A1* 9/2010 Edwards ................ G06Q 10/06 715/764
2011/0046365 A1 2/2011 Mikkonen et al.
2011/0046429 A1 2/2011 Aliyev et al.
2011/0257317 A1 10/2011 Baugh et al.
2011/0296745 A1 12/2011 Hilten et al.
2011/0308142 A1 12/2011 Abhari et al.
2012/0035404 A1 2/2012 Alegria et al.
2012/0125813 A1 5/2012 Bridges et al.
2012/0160659 A1 6/2012 Koukios
2012/0184787 A1 7/2012 Miller
2012/0232173 A1 9/2012 Juranitch et al.
2012/0238741 A1 9/2012 Buchanan et al.
2012/0238742 A1 9/2012 Buchanan et al.
2012/0310023 A1 12/2012 Huang et al.
2013/0105356 A1 5/2013 Dijs et al.
2013/0178672 A1 7/2013 Chen et al.
2013/0184505 A1 7/2013 Maxwell
2013/0296619 A1 11/2013 Iaccino et al.
2014/0031583 A1 1/2014 Mazanec et al.
2014/0107306 A1 4/2014 Mazanec et al.
2014/0155661 A1 6/2014 Frediani et al.
2014/0296407 A1 10/2014 Marsh et al.
2015/0284645 A1 10/2015 Schmidt et al.
2015/0307417 A1 10/2015 Schmidt et al.
2016/0083323 A1 3/2016 Fruchey et al.
2016/0090539 A1 3/2016 Frey et al.
2016/0097002 A1 4/2016 Sundaram
2016/0155132 A1* 6/2016 Rohlfs ................ G06Q 30/018 705/37
2016/0168491 A1 6/2016 Yao et al.
2016/0244677 A1 8/2016 Froehle
2016/0264874 A1 9/2016 Narayanaswamy et al.
2016/0264883 A1 9/2016 Narayanaswamy et al.
2016/0264884 A1 9/2016 Narayanaswamy et al.
2016/0264885 A1 9/2016 Narayanaswamy et al.
2016/0304788 A1* 10/2016 Sorensen ............ B29C 49/0005
2016/0362609 A1 12/2016 Ward et al.
2017/0240822 A1 8/2017 Karimzadeh
2017/0348741 A1 12/2017 Iijima et al.
2017/0362512 A1 12/2017 Hornung et al.
2018/0002609 A1 1/2018 Narayanaswamy et al.
2018/0216009 A1* 8/2018 Narayanaswamy ..... C10G 1/08
2018/0244905 A1 8/2018 Wang et al.
2018/0346838 A1 12/2018 Vasudevan et al.
2019/0023999 A1 1/2019 Sundaram et al.
2019/0055483 A1 2/2019 Bafna et al.
2019/0161683 A1 5/2019 Narayanaswamy et al.
2019/0177626 A1 6/2019 Ramamurthy et al.
2019/0241838 A1 8/2019 Scheibel et al.
2019/0270939 A1 9/2019 Javeed et al.
2019/0299491 A1 10/2019 Stanislaus et al.
2019/0367428 A1 12/2019 Ramamurthy et al.
2019/0390124 A1 12/2019 Oprins et al.
2020/0017772 A1 1/2020 Ramamurthy et al.
2020/0017773 A1 1/2020 Ramamurthy et al.
2020/0308492 A1 10/2020 Streiff et al.
2020/0369965 A1 11/2020 Bitting et al.
2021/0130262 A1 5/2021 Wu et al.
2021/0130699 A1 5/2021 Bitting et al.
2021/0130700 A1 5/2021 Wu et al.
2021/0130708 A1 5/2021 Xu et al.
2021/0130710 A1 5/2021 Xu et al.
2021/0130712 A1 5/2021 Abudawould et al.
2021/0130713 A1 5/2021 Xu et al.
2021/0130714 A1 5/2021 Abudawould et al.
2021/0130715 A1 5/2021 Xu et al.
2021/0130716 A1 5/2021 Xu et al.
2021/0130717 A1 5/2021 Xu et al.
2021/0139620 A1 5/2021 Slivensky et al.
2022/0195315 A1 6/2022 Zhang et al.
2022/0220389 A1 7/2022 Slivensky et al.
2022/0220391 A1 7/2022 Slivensky et al.
2022/0227892 A1 7/2022 Slivensky et al.
2022/0228071 A1 7/2022 Bitting et al.
2022/0234968 A1 7/2022 Wu et al.
2022/0267679 A1 8/2022 Bitting et al.
2022/0281793 A1 9/2022 Slivensky et al.
2022/0281796 A1 9/2022 Slivensky et al.
2022/0289655 A1 9/2022 Slivensky et al.
2022/0289868 A1 9/2022 Colhoun et al.
2022/0363616 A1 11/2022 Slivensky et al.
2022/0363862 A1 11/2022 Slivensky et al.
2022/0363996 A1 11/2022 Wu et al.
2022/0380328 A1 12/2022 Slivensky et al.
2022/0380680 A1 12/2022 Slivensky et al.
2022/0380683 A1 12/2022 Slivensky et al.
2022/0396546 A1 12/2022 Slivensky et al.
2022/0396736 A1 12/2022 Wu et al.
2022/0402845 A1 12/2022 Slivensky et al.
2022/0402860 A1 12/2022 Slivensky et al.
2022/0403053 A1 12/2022 Slivensky et al.
2023/0134082 A1 5/2023 DeBruin et al.
2023/0134198 A1 5/2023 DeBruin et al.
2023/0134669 A1 5/2023 DeBruin et al.
2023/0135304 A1 5/2023 DeBruin et al.

FOREIGN PATENT DOCUMENTS

CN 1609169 A 4/2005
CN 101948386 A 1/2011
CN 102249909 A 11/2011
CN 102718383 A * 10/2012
CN 103664444 A 3/2014
CN 103130611 B 4/2016
CN 105732354 A 7/2016
CN 106008218 A 10/2016
CN 107075094 A 8/2017
CN 106496378 B1 8/2018
CN 109575978 B1 4/2019
DE 4412941 A1 10/1995
EP 0002908 A1 12/1978
EP 0052419 A1 5/1982

(56) References Cited

FOREIGN PATENT DOCUMENTS

| | | | |
|---|---|---|---|
| EP | 0094456 | A1 | 5/1982 |
| EP | 0103810 | A2 | 3/1984 |
| EP | 0114611 | A2 | 8/1984 |
| EP | 0144745 | A1 | 6/1985 |
| EP | 0183545 | A1 | 11/1985 |
| EP | 0189247 | A1 | 7/1986 |
| EP | 0225143 | A2 | 6/1987 |
| EP | 0285415 | A2 | 3/1988 |
| EP | 0307907 | A2 | 9/1988 |
| EP | 0343475 | A2 | 5/1989 |
| EP | 0648829 | A1 | 10/1994 |
| EP | 0804398 | A1 | 11/1997 |
| EP | 1004563 | B1 | 11/1999 |
| EP | 1732871 | B1 | 1/2005 |
| EP | 3063122 | A1 | 9/2016 |
| GB | 2106893 | A | 4/1983 |
| JP | 2018-511671 | A | 4/2018 |
| RU | 2162461 | C1 | 1/2001 |
| WO | WO 93/04026 | A1 | 3/1993 |
| WO | WO 97/41088 | A1 | 11/1997 |
| WO | WO 98/12162 | A1 | 3/1998 |
| WO | WO 01/05908 | A1 | 1/2001 |
| WO | WO 2004/018584 | A1 | 3/2004 |
| WO | WO 2004/018592 | A1 | 3/2004 |
| WO | WO 2008/100566 | A1 | 8/2008 |
| WO | WO 2010/060862 | A1 | 6/2010 |
| WO | WO 2010/099058 | A2 | 9/2010 |
| WO | WO 2012/099671 | A1 | 7/2012 |
| WO | WO 2012/099679 | A1 | 7/2012 |
| WO | WO 2013/025186 | A1 | 2/2013 |
| WO | WO 2013/037036 | A1 | 3/2013 |
| WO | WO 2014/034015 | A1 | 3/2014 |
| WO | WO 2014/051347 | A1 | 4/2014 |
| WO | WO 2014/178031 | A1 | 11/2014 |
| WO | WO 2014/181248 | A1 | 11/2014 |
| WO | WO 2015/000840 | A1 | 1/2015 |
| WO | WO 2015/104430 | A1 | 7/2015 |
| WO | WO 2016/069622 | A1 | 5/2016 |
| WO | WO 2016/134794 | A1 | 9/2016 |
| WO | WO 2016/142809 | A1 | 9/2016 |
| WO | WO 2016/179476 | A1 | 11/2016 |
| WO | WO 2017/027271 | A1 | 2/2017 |
| WO | WO 2017/146876 | A1 | 8/2017 |
| WO | WO 2018/005074 | A1 | 1/2018 |
| WO | WO 2018/011642 | A1 | 1/2018 |
| WO | WO 2018/024796 | A1 | 2/2018 |
| WO | WO 2018/025103 | A1 | 2/2018 |
| WO | WO 2018/025104 | A1 | 2/2018 |
| WO | WO 2018/039406 | A1 | 3/2018 |
| WO | WO 2018/069794 | A1 | 4/2018 |
| WO | WO 2018/104443 | A1 | 6/2018 |
| WO | WO 2018/127813 | A1 | 7/2018 |
| WO | WO 2018/160588 | A1 | 9/2018 |
| WO | WO 2019/019539 | A1 | 1/2019 |
| WO | WO 2020/152317 | A1 | 7/2020 |
| WO | WO 2020/152320 | A1 | 7/2020 |
| WO | WO 2020/252228 | A1 | 12/2020 |
| WO | WO 2021/021847 | A1 | 2/2021 |
| WO | WO 2021/021849 | A1 | 2/2021 |
| WO | WO 2021/087026 | A1 | 5/2021 |
| WO | WO 2021/092293 | A1 | 5/2021 |
| WO | WO 2021/133889 | A1 | 7/2021 |
| WO | WO 2021/133893 | A1 | 7/2021 |
| WO | WO 2021/133895 | A1 | 7/2021 |
| WO | WO 2021//211508 | A1 | 10/2021 |

OTHER PUBLICATIONS

Co-pending U.S. Appl. No. 17/595,512, filed Nov. 18, 2021; Bitting et al.

Co-pending U.S. Appl. No. 17/083,586, filed Oct. 29, 2020; Bitting et al.

USPTO Office Action dated Sep. 16, 2021 received in co-pending U.S. Appl. No. 17/083,586.

Co-pending U.S. Appl. No. 17/595,514, filed Nov. 18, 2021; Slivensky et al.

Co-pending U.S. Appl. No. 17/594,966, filed Nov. 4, 2021; Slivensky et al.

Co-pending U.S. Appl. No. 17/595,565, filed Nov. 19, 2021;Slivensky et al.

Co-pending U.S. Appl. No. 17/595,515, filed Nov. 18, 2021; Slivensky et al.

Co-pending U.S. Appl. No. 17/597,822, filed Jan. 25, 2022; Slivensky et al.

Co-pending U.S. Appl. No. 17/597,817, filed Jan. 25, 2022; Slivensky et al.

Co-pending U.S. Appl. No. 17/597,726, filed Jan. 20, 2022; Slivensky et al.

Co-pending U.S. Appl. No. 17/090,976, filed Nov. 6, 2020; Slivensky et al.

Co-pending U.S. Appl. No. 17/083,590, filed Oct. 29, 2020; Wu et al.

USPTO Office action dated Jul. 1, 2021 received in co-pending U.S. Appl. No. 17/083,590.

USPTO Notice of Allowance dated Mar. 17, 2022 received in co-pending U.S. Appl. No. 17/083,590.

Shelton, Michael C.; "Cellulose Esters, Inorganic Esters", Kirk-Othmer, Encyclopedia of Chemical Technology, 5th edition, vol. 5, Wiley Interscience, New York (2004), pp. 394-412.

Gedon, Steven, et al.; "Cellulose Esters, Organic Esters", Kirk-Othmer, Encyclopedia of Chemical Technology, 5th edition, vol. 5, Wiley Interscience, New York (2004), pp. 412-444.

Wade, Bruce; "Vinyl Acetal Polymers"; Encyclopdia of Polymer Science & Technology, 3rd edition, vol. 8, pp. 381-399 (2003).

Riesel, L., et al.; "A Simple Synthesis of Fluoro(organyl)phosphnes", Z. Anorg. Allg. Chem., 603, (1991), pp. 145-150.

Tullock, C.W., et al.; "Synthesis of Fluorides by Metathesis with Sodium Fluoride"; Journal of Organic Chemistry, vol. 25 (1960), pp. 2016-2019.

Li, Fuwei et al.; Production of light olefins from catalytic cracking bio-oil model compounds over La203-modified ZSM-5 zeolite; Energy Fuels, 2018, 32, pp. 5910-5922.

White, D.W., et al.; "Structural Implications of Nuclear Magentic Resonance Studies n 1-R-1-Phospha-2,6-dioxacyclohexanes"; Journal of the American Chemical Society, 92:24, Dec. 2, 1970, pp. 7125-7135.

Dwidar, Mohammed et al.; "The Future of Butyric Acid in Industry"; The Scientific World Journal, vol. 2012, Article ID 471417, 9 pages.

Sogancioglu, Merve et al.; "A Comparative Study on Waste Plastics Pyrolysis Liquid Products Quantity and Energy Recovery Potential"; Energy Procedia 188 (2017) 221-226.

Zhang, L. et al.: "Alcohol Stabilization of Low Water Content Pyrolysis Oil during High Temperature Treatment"; Energy Fuels, 2017, vol. 31, pp. 13666-13674.

Thunman, Henrik et al.; "Circular use of plastics-transformation of existing petrochemical clusters into thermochemical recycling plants with 100% plastics recovery"; Sustainable Materials and Technologies 22 (2019) e00124.

Liang, Guanfeng et al.; Production of Primary Amines by Reductive Amination of Biomass-Derived Aldehydes/Ketones; Agnew. Chem. 2017, vol. 129, pp. 3096-3100.

Meyer, Thomas G., et al.; "Preparations and Single Crystal X-ray Diffraction Study of Some Fluorophosphites and Phosphite Esters"; Z Naturforsch, 48b, pp. 659-671 (1993).

ASTM D2887 "Standard Test Method for Boiling Range Distribution of Petroleum Fractions by Gas Chromatography"; Published Jan. 2020.

ASTMD5399 "Standard Test Method for Boiling Point Distribution of Hydrocarbon Solvents by Gas Chromatography"; Published Dec. 2017.

ASTM D6474 "Standard Test Method for Determining Molecular Weight Distribution and Molecular Weight Averages of Polyolefins by High Temperature Gel Permeation Chromatography" Published Apr. 2020.

(56) References Cited

OTHER PUBLICATIONS

ASTM D5296 "Standard Test Method for Molecular Weight Averages and Molecular Weight Distribution of Polystyrene by High Performance Size-Exclusion Chromatography" Published Dec. 2019.
ASTM E308 "Standard Practice for Computing the Colors of Objects by Using the CIE System" Published Sep. 2018.
ASTM D6290 "Standard Test Method for Color Determination of Plastic Pellets" Published Jun. 2019.
ASTM D790 "Standard Test Methods for Flexural Properties of Unreinforced and Reinforced Plastics and Electrical Insulating Materials" Published Jul. 2017.
ASTM D256 "Standard Test Methods for Determining the Izod Pendulum Impact Resistance of Plastics" Published Nov. 2018.
ASTMD3418 "Standard Test Method for Transition Temperatures and Enthalpies of Fusion and Crystallization of Polymers by Differential Scanning Calorimetry" Published Jun. 2015.
ASTM D1003 "Standard Test Method for Haze and Luminous Transmittance of Transparent Plastics" Published Nov. 2013.
ASTM D648 "Standard Test Method for Deflection Temperature of Plastics Under Flexural Load in the Edgewise Position" Published Apr. 2018.
ASTM D4440 "Standard Test Method for Plastics: Dynamic Mechanical Properties Melt Rheology" Published Feb. 2015.
Notification of Transmittal of the International Search Report and the Written Opinion of the International Searching Authority with Date of Mailing Feb. 22, 2021 for International Application No. PCT/US2020/057873.
Notification of Transmittal of the International Search Report and the Written Opinion of the International Searching Authority with Date of Mailing Feb. 23, 2021 for International Application No. PCT/US2020/057876.
Notification of Transmittal of the International Search Report and the Written Opinion of the International Searching Authority with Date of Mailing Sep. 9, 2020 for International Application No. PCT/US2020/034151.
Notification of Transmittal of the International Search Report and the Written Opinion of the International Searching Authority with Date of Mailing Sep. 9, 2020 for International Application No. PCT/US2020/034139.
Notification of Transmittal of the International Search Report and the Written Opinion of the International Searching Authority with Date of Mailing Aug. 27, 2020 for International Application No. PCT/US2020/034147.
Notification of Transmittal of the International Search Report and the Written Opinion of the International Searching Authority with Date of Mailing Sep. 4, 2020 for International Application No. PCT/US2020/034166.
Notification of Transmittal of the International Search Report and the Written Opinion of the International Searching Authority with Date of Mailing Sep. 4, 2020 for International Application No. PCT/US2020/034170.
Notification of Transmittal of the International Search Report and the Written Opinion of the International Searching Authority with Date of Mailing Sep. 4, 2020 for International Application No. PCT/US2020/034167.
Notification of Transmittal of the International Search Report and the Written Opinion of the International Searching Authority with Date of Mailing Feb. 26, 2021 for International Application No. PCT/US2020/059310.
Notification of Transmittal of the International Search Report and the Written Opinion of the International Searching Authority with Date of Mailing Apr. 19, 2021 for International Application No. PCT/US2020/059316.
Notification of Transmittal of the International Search Report and the Written Opinion of the International Searching Authority with Date of Mailing Mar. 5, 2021 for International Application No. PCT/US2020/059324.
Notification of Transmittal of the International Search Report and the Written Opinion of the International Searching Authority with Date of Mailing Sep. 4, 2020 for International Application No. PCT/US2020/034172.
Notification of Transmittal of the International Search Report and the Written Opinion of the International Searching Authority with Date of Mailing Nov. 11, 2020 for International Application No. PCT/US2020/043944.
Notification of Transmittal of the International Search Report and the Written Opinion of the International Searching Authority with Date of Mailing Mar. 8, 2021 for International Application No. PCT/US2020/059327.
Notification of Transmittal of the International Search Report and the Written Opinion of the International Searching Authority with Date of Mailing Feb. 26, 2021 for International Application No. PCT/US2020/059282.
Notification of Transmittal of the International Search Report and the Written Opinion of the International Searching Authority with Date of Mailing Feb. 25, 2021 for International Application No. PCT/US2020/059286.
Notification of Transmittal of the International Search Report and the Written Opinion of the International Searching Authority with Date of Mailing Nov. 9, 2020 for International Application No. PCT/US2020/043948.
Notification of Transmittal of the International Search Report and the Written Opinion of the International Searching Authority with Date of Mailing Nov. 6, 2020 for International Application No. PCT/US2020/043956.
Notification of Transmittal of the International Search Report and the Written Opinion of the International Searching Authority with Date of Mailing Apr. 12, 2021 for International Application No. PCT/US2020/059302.
Notification of Transmittal of the International Search Report and the Written Opinion of the International Searching Authority with Date of Mailing Feb. 26, 2021 for International Application No. PCT/US2020/059292.
Notification of Transmittal of the International Search Report and the Written Opinion of the International Searching Authority with Date of Mailing Mar. 31, 2021 for International Application No. PCT/US2020/059306.
Notification of Transmittal of the International Search Report and the Written Opinion of the International Searching Authority with Date of Mailing Jul. 30, 2021 for International Application No. PCT/US2021/027016.
Notification of Transmittal of the International Search Report and the Written Opinion of the International Searching Authority with Date of Mailing Aug. 2, 2021 for International Application No. PCT/US2021/027021.
Notification of Transmittal of the International Search Report and the Written Opinion of the International Searching Authority with Date of Mailing Jul. 30, 2021 for International Application No. PCT/US2021/026998.
The Editors of Encyclopedia Britannica; "Cracking—Chemical Process"; https://web.archive.org/web/20160629203035/https://www.britannica.com/technology/cracking-chemical-process; Publication Date Jun. 29, 2016.
The Editors of Encyclopedia Britannica; "Pyrolysis—Chemical Reaction"; https://web.archibe.org/web/20160611215925/https://www.britannica.com/science/pyrolysis; Published Jun. 11, 2016.
The Editors of Encyclopedia Britannica; "Hydrotreating—Chemical Process"; https://web/archive.org/web/20150915110541 4/https://www.britannica.com/technology/hydrotreating; Published Sep. 15, 2015.
PCT Third Party Observation with Submission Date of Sep. 28, 2021 for International Application No. PCT/US2020/034166.
PCT Third Party Observation with Submission Date of Sep. 24, 2021 for International Application No. PCT/US2020/034172.
PCT Third Party Observation with Submission Date of Sep. 24, 2021 for International Application No. PCT/US2020/034151.
PCT Third Party Observation with Submission Date of Sep. 24, 2021 for International Application No. PCT/US2020/034147.
PCT Third Party Observation with Submission Date of Sep. 24, 2021 for International Application No. PCT/US2020/034139.

(56) References Cited

OTHER PUBLICATIONS

Ellen MacArthur Foundation and CE100; "Driving circular economy with the mass balance approach: BASF joins forces with members of the Ellen MacArthur Foundation's CE100 network for White Paper Publication"; https://www.basf.com/us/en/who-we-are/sustainability/whats-new/sustainability-news/2019/EllenMacArthurfoundation-White_Paper-Mass-balance.html; Published May 10, 2019.
"ISCC 203—Traceability and Chain of Custody"; https://www.iscc-system.org/wp-content/uploads/2017/02/ISCC_203_Traceability_and_Chain-of-Custody_3.0.pdf; Published Aug. 9, 2016.
"BASF for the first time makes products with chemically recycled plastics"; https://www.basf.com/us/en/media/news-releases/2018/12/P-US-18-134.html; Published Dec. 13, 2018.
USPTO Office Action dated Jul. 1, 2024 received in co-pending U.S. Appl. No. 17/755,327.
USPTO Office Action dated Jul. 30, 2024 received in co-pending U.S. Appl. No. 17/595,511.
Notice of Allowance dated Feb. 9, 2024 received in co-pending U.S. Appl. No. 17/595,512.
Co-pending U.S. Appl. No. 17/083,586, filed Mar. 20, 2024; Bitting et al.
Notice of Allwance dated Feb. 14, 2024 received in co-pending U.S. Appl. No. 17/083,586.
Co-pending U.S. Appl. No. 18/610,459, filed Mar. 20, 2024; Bitting et al.
Notice of Allowance dated Apr. 15, 2024 received in co-pending U.S. Appl. No. 17/595,514.
Co-pending U.S. Appl. No. 18/735,232, filed Jun. 6, 2024; Slivensky et al.
USPTO Office Action dated Jan. 13, 2025 received in co-pending U.S. Appl. No. 17/594,966.
USPTO Office Action dated Nov. 20, 2024 received in co-pending U.S. Appl. No. 17/595,565.
USPTO Office Action dated Jun. 3, 2024 received in co-pending U.S. Appl. No. 17/595,515.
USPTO Office Action dated May 20, 2024 received in co-pending U.S. Appl. No. 17/597,822.
USPTO Office Action dated Sep. 13, 2024 received in co-pending U.S. Appl. No. 17/597,726.
USPTO Notice of Allowance dated Aug. 21, 2024 received in co-pending U.S. Appl. No. 17/755,628.
USPTO Notice of Allowance dated Feb. 9, 2024 received in co-pending U.S. Appl. No. 17/755,627.
Co-pending U.S. Appl. No. 18/610,421, filed Mar. 20, 2024; Slivensky et al.
Notification of Transmittal of the International Search Report and the Written Opinion of the International Searching Authority with Date of Mailing Aug. 25, 2022 for International Application No. PCT/US2022/026679.
European Third Party Observation with Submission Date of Oct. 17, 2024 for European Patent Application No. 20812640.9.
European Third Party Observation with Submission Date of Oct. 17, 2024 for European Patent Application No. 20818530.6.
European Search Report for Application No. 21789287.6 dated Jun. 6, 2024.
USPTO Office Action dated Jun. 13, 2024 received in co-pending U.S. Appl. No. 17/755,326.
USPTO Office Action dated Dec. 4, 2024 received in co-pending U.S. Appl. No. 17/755,326.
Co-pending U.S. Appl. No. 19/187,263, filed Apr. 23, 2025; Wu et al.
Co-pending U.S. Appl. No. 18/845,519, filed Sep. 10, 2024; Polasek et al.
Co-pending U.S. Appl. No. 18/845,508, filed Sep. 10, 2024; Hampton, Jr. et al.
Notice of Allowance dated Dec. 20, 2023 received in co-pending U.S. Appl. No. 17/595,512.
USPTO Office Action dated Jul. 20, 2023 received in co-pending U.S. Appl. No. 17/083,586.
USPTO Office Action dated Jan. 16, 2025 received in co-pending U.S. Appl. No. 18/610,459.
USPTO Office Action dated Apr. 30, 2025 received in co-pending U.S. Appl. No. 18/610,459.
USPTO Office Action dated Oct. 23, 2023 received in co-pending U.S. Appl. No. 17/595,514.
USPTO Office Action dated May 6, 2025 received in co-pending U.S. Appl. No. 17/595,565.
USPTO Office Action dated Jan. 23, 2025 received in co-pending U.S. Appl. No. 17/595,515.
USPTO Office Action dated May 28, 2025 received in co-pending U.S. Appl. No. 17/595,515.
USPTO Office Action dated Feb. 12, 2025 received in co-pending U.S. Appl. No. 17/597,822.
Notice of Allowance dated May 15, 2025 received in co-pending U.S. Appl. No. 17/597,822.
Co-pending U.S. Appl. No. 19/211,476, filed May 19, 2025; Slivensky et al.
USPTO Office Action dated Feb. 13, 2025 received in co-pending U.S. Appl. No. 17/555,349.
USPTO Office Action dated Feb. 7, 2025 received in co-pending U.S. Appl. No. 17/555,357.
USPTO Office Action dated May 29, 2025 received in co-pending U.S. Appl. No. 17/597,817.
USPTO Office Action dated Mar. 28, 2024 received in co-pending U.S. Appl. No. 17/755,628.
USPTO Office Action dated Mar. 21, 2025 received in co-pending U.S. Appl. No. 17/755,634.
USPTO Notice of Allowance dated Jan. 9, 2024 received in co-pending U.S. Appl. No. 17/755,627.
Co-pending U.S. Appl. No. 18/837,914, filed Aug. 13, 2024; Bitting et al.
Notification of Transmittal of the International Search Report and the Written Opinion of the International Searching Authority with Date of Mailing Dec. 13, 2022 for International Application No. PCT/US2022/032600.
Notification of Transmittal of the International Search Report and the Written Opinion of the International Searching Authority with Date of Mailing Jun. 8, 2023 for International Application No. PCT/US2023/062545.
Notification of Transmittal of the International Search Report and the Written Opinion of the International Searching Authority with Date of Mailing Jun. 29, 2023 for International Application No. PCT/US2023/064382.
Notification of Transmittal of the International Search Report and the Written Opinion of the International Searching Authority with Date of Mailing Jul. 21, 2023 for International Application No. PCT/US2023/064378.
Scheirs, John et al.; "Feedstock Recycling and Pyrolysis of Waste Plastics"; Wiley Series in Polymer Science; Chapter 13, p. 345-361, (2006).
Paben, Jared; "Pyrolysis firm unveils recycled chemicals to make olefins"; https://resource-recycling.com/plastics/2018/09/06/pyrolysis-firm-unveils-recycled-chemicals-to-make-olefins/; Published Sep. 6, 2018.
Miandad, Rashid et al.; "Catalytic Pyrolysis of Plastic Waste: Moving Toward Pyrolysis Based Biorefineries"; Frontiers in Energy Research, vol. 7m Article 27, pp. 1-17, Published Mar. 19, 2019.
Laermann, Michael; Chemical Recycling of Plastic Waste No More ?; https://sustainablebrands.com/read/chemistry-materials-packaging/chemical-recycling-of-plastic-waste-no-more; Published Apr. 10, 2019.
European Search Report for Application No. 21787871.9 Dated Apr. 12, 2024.
European Search Report for Application No. 21788019.4 dated Jul. 22, 2024.
European Search Report for Application No. 20814027.7 dated Feb. 13, 2023.
European Search Report for Application 20882420.1 dated Feb. 13, 2023.
Malik, Muhammad Irfan, et al.; "Methanol to Formaldehyde: An Overview of Surface Studies and Performance of an Iron Molybdate Catalyst"; Catalysts 2021, 11, 893.

(56) References Cited

OTHER PUBLICATIONS

Lindeberg, et al.; "Encouraging Recycling Using Tradeable Credits"; Journal of Public and International Affairs vol. 4, pp. 182-194 (Year:1993).

* cited by examiner

RECYCLE CONTENT GLYCOL ESTERS

CROSS-REFERENCE TO RELATED APPLICATION(S)

This application is a national stage filing under 35 USC § 371 of International Application Number PCT/US2020/059286, filed on, Nov. 6, 2020 which claims the benefit of the filing date to U.S. Provisional Application No. 62/932,030, filed on Nov. 7, 2019, the entire disclosures of which are incorporated by reference herein.

FIELD OF THE INVENTION

The invention relates to recycle content in glycol esters and, in particular, 2,2,4-trimethyl-1,3-pentanediol monoisobutyrate. In particular, this invention relates to glycol esters where such recycle content was obtained directly or indirectly from effluents generated from pyrolyzing recycled waste material and thermally cracking the resulting recycle content pyoil or generating and using the pygas from the pyrolysis of the recycled waste material.

BACKGROUND OF THE INVENTION

Glycol esters are important products in organic synthesis. Formed by the hydroformylation of olefins with synthesis gas, the resulting aldehydes may be further reacted in the presence of a catalyst to form glycol esters. Glycol esters are commonly used as solvents and/or as intermediates in forming a range of other chemicals, including, for example plasticizers, coatings, paints, and polymer resins.

Moreover, solid waste materials, especially non-biodegradable recycled waste materials, can negatively impact the environment when disposed of in landfills after a single use. Thus, from an environmental standpoint, it is desirable to recycle as much waste material as possible. However, recycling waste materials can be challenging from an economic standpoint.

While some waste materials are relatively easy and inexpensive to recycle, other waste materials require significant and expensive processing in order to be reused. Further, different types of waste materials often require different types of recycling processes.

To maximize recycling efficiency, it would be desirable for large-scale production facilities to be able to process feedstocks having recycle content originating from a variety of recycled waste materials. Commercial facilities involved in the production of non-biodegradable products or products that find their ultimate destination in a landfill could benefit greatly from using recycle content feedstocks.

Some recycling efforts involve complicated and detailed segregation of recycled waste streams, which contributes to the increased cost of obtaining streams of recycled waste content. For example, conventional methanolysis technologies require a high purity stream of PET. Some downstream products are also quite sensitive to the presence of dyes and inks on recycled waste products, and their pretreatment and removal also contributes to increased costs of feedstocks made from such recycled wastes. It would be desirable to establish a recycle content without the necessity for sorting down to a single type of plastic or recycled waste material, or which can tolerate a variety of impurities in recycled waste streams that flow through to a feedstock.

In some cases, it may be difficult to dedicate a product having a recycle content to a particular customer or downstream synthetic process for making a derivate of the product, particularly if the recycle content product is a gas or difficult to isolate. As related to a gas, there is a lack of infrastructure to segregate and distribute a dedicated portion of a gas made exclusively from a recycle content feedstock since the gas infrastructure is continuously fluid and often commingles gas streams from a variety of sources.

Further, it is recognized that some regions desire to move away from sole dependence on natural gas, ethane, or propane as the sole source for making raw materials products such as ethylene and propylene and their downstream derivatives, and alternative or supplemental feedstocks to crackers would be desirable.

It is also desirable to synthesize glycol esters using existing equipment and processes and without the need to invest in additional and expensive equipment in order to establish a recycle content in the manufacture of the chemical compound or polymer.

It is also desirable to continue sourcing a raw material for making glycol esters from olefins obtained from cracker facilities that may find themselves stranded as production from a natural gas field or petroleum becomes economically unattractive.

Further, it is desirable for manufacturers of glycol esters to not be solely dependent on obtaining credits to establish a recycle content in glycol esters and thereby provide the manufacturer with a variety of choices to establish recycle content.

It would also be desirable for manufacturers of glycol esters to be able to determine the amount and timing of establishing recycle content. The manufacturers, at certain times or for different batches, may desire to establish more or less recycle content or no recycle content. The flexibility in this approach without the need to add significant assets is desirable.

SUMMARY OF THE INVENTION

There is now provided a method of obtaining a recycle content recycle content glycol ester composition ("r-GE"), recycle content aldehydes useful to make r-GE, and compositions made from or with or containing recycle content GE, uses thereof, compositions thereof, and systems thereof, each as further described in the claims and detailed description.

DETAILED DESCRIPTION OF THE INVENTION

Figure 1:
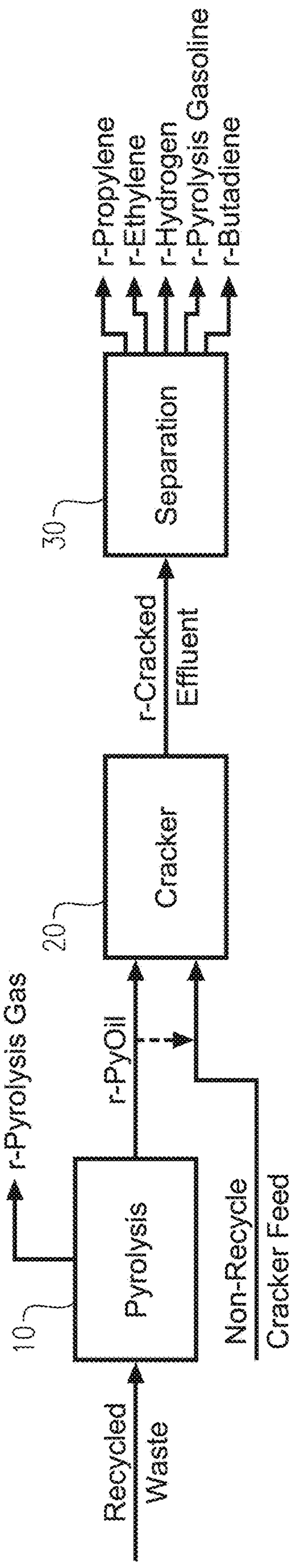
FIG. 1 is an illustration of a process for employing a recycle content pyrolysis oil composition (r-pyoil) to make one or more recycle content compositions into r-compositions.

The word "containing" and "including" is synonymous with comprising. When a numerical sequence is indicated, it is to be understood that each number is modified the same as the first number or last number in the numerical sequence or in the sentence, e.g. each number is "at least," or "up to" or "not more than" as the case may be; and each number is in an "or" relationship. For example, "at least 10, 20, 30, 40, 50, 75 wt. % . . . " means the same as "at least 10 wt. %, or at least 20 wt. %, or at least 30 wt. %, or at least 40 wt. %, or at least 50 wt. %, or at least 75 wt. %," etc.; and "not more than 90 wt. %, 85, 70, 60 . . . " means the same as "not more than 90 wt. %, or not more than 85 wt. %, or not more than 70 wt. % . . . " etc.; and "at least 1%, 2%, 3%, 4%, 5%, 6%, 7%, 8%, 9% or 10% by weight . . . " means the same as "at least 1 wt. %, or at least 2 wt. %, or at least 3 wt. % . . . " etc.; and "at least 5, 10, 15, 20 and/or not more than 99, 95, 90 weight percent" means the same as "at least 5 wt. %, or at least 10 wt. %, or at least 15 wt. % or at least 20 wt. % and/or not more than 99 wt. %, or not more than 95 wt. %, or not more than 90 weight percent . . . " etc.; or "at least 500, 600, 750° C. . . . " means the same as "at least 500° C., or at least 600° C., or at least 750° C. . . . " etc.

All concentrations or amounts are by weight unless otherwise stated. An "olefin-containing effluent" is the furnace effluent obtained by cracking a cracker feed containing r-pyoil. A "non-recycle olefin-containing effluent" is the furnace effluent obtained by cracking a cracker feed that does not contain r-pyoil. Units on hydrocarbon mass flow rate, MF1, and MF2 are in kilo pounds/hr (klb/hr), unless otherwise stated as a molar flow rate.

As used herein, "containing" and "including" are open ended and synonymous with "comprising."

The term "recycle content" is used herein i) as a noun to refer to a physical component (e.g., compound, molecule, or atom) at least a portion of which is derived directly or indirectly from recycled waste or ii) as an adjective modifying a particular composition (e.g., a compound, polymer, feedstock, product, or stream) at least a portion of which is directly or indirectly derived from recycled waste.

As used herein, "recycle content composition," "recycle composition," and "r-composition" mean a composition having recycle content.

The term "pyrolysis recycle content" is used herein i) as a noun to refer to a physical component (e.g., compound, molecule, or atom) at least a portion of which is derived directly or indirectly from the pyrolysis of recycled waste or ii) as an adjective modifying a particular composition (e.g., a feedstock, product, or stream) at least a portion of which is directly or indirectly derived from the pyrolysis of recycled waste. For example, pyrolysis recycle content can be directly or indirectly derived from recycle content pyrolysis oil, recycle content pyrolysis gas, or the cracking of recycle content pyrolysis oil such as through thermal steam crackers or fluidized catalytic crackers.

As used herein, "pyrolysis recycle content composition," "pyrolysis recycle composition," and "pr-composition" mean a composition (e.g., a compound, polymer, feedstock, product, or stream) having pyrolysis recycle content. A pr-composition is a subset of a r-composition, where at least a portion of the recycle content of the r-composition is derived directly or indirectly from the pyrolysis of recycled waste.

As used herein, a composition (e.g., compound, polymer, feedstock, product, or stream) "directly derived" or "derived directly" from recycled waste has at least one physical component that is traceable to recycled waste, while a composition (e.g., a compound, polymer, feedstock, product, or stream) "indirectly derived" or "derived indirectly" from recycled waste has associated with it a recycle content allotment and may or may not contain a physical component that is traceable to recycled waste.

As used herein, a composition (e.g., compound, polymer, feedstock, product, or stream) "directly derived" or "derived directly" from the pyrolysis of recycled waste has at least one physical component that is traceable to the pyrolysis of recycled waste, while a composition (e.g., a compound, polymer, feedstock, product, or stream) "indirectly derived" or "derived indirectly" from the pyrolysis of recycled waste has associated with it a recycle content allotment and may or may not contain a physical component that is traceable to the pyrolysis of recycled waste.

As used herein, “pyrolysis oil” or “pyoil” mean a composition of matter that is liquid when measured at 25° C. and 1 atm and at least a portion of which is obtained from pyrolysis.

As used herein, “recycle content pyrolysis oil,” “recycle pyoil,” “pyrolysis recycle content pyrolysis oil” and “r-pyoil”” mean pyoil, at least a portion of which is obtained from pyrolysis, and having recycle content.

As used herein, “pyrolysis gas” and “pygas” mean a composition of matter that is gas when measured at 25° C. and 1 atm and at least a portion of which is obtained from pyrolysis.

As used herein, “recycle content pyrolysis gas,” “recycle pygas,” “pyrolysis content pyrolysis gas” and “r-pygas” mean pygas, at least a portion of which is obtained from pyrolysis, and having recycle content.

As used herein, “Et” is ethylene composition (e.g., a feedstock, product, or stream) and “Pr” is propylene composition (e.g., a feedstock, product, or stream).

As used herein, “recycle content ethylene,” “r-ethylene” and “r-Et” mean Et having recycle content; and “recycle content propylene,” “r-propylene” and “r-Pr” mean Pr having recycle content.

As used herein, “pyrolysis recycle content ethylene” and “pr-Et” mean r-Et having pyrolysis recycle content; and “pyrolysis recycle content propylene” and “pr-Pr” mean r-Pr having pyrolysis recycle content. As used herein, “recycle content olefin,” “recycle olefin,” “pyrolysis content olefin,” and “r-olefin” mean olefin, at least a portion of which is obtained from pyrolysis, having recycle content.

As used herein, “pyrolysis recycle content olefin” and “pr-olefin” mean r-olefin having pyrolysis recycle content.

As used herein, “recycle content aldehyde,” “recycle aldehyde,” “pyrolysis content aldehyde,” and “r-aldehyde” mean aldehyde, at least a portion of which is obtained from pyrolysis recycle content.

As used herein, “pyrolysis recycle content aldehyde” and “pr-aldehyde” mean r-aldehyde having pyrolysis recycle content.

As used herein, “recycle content glycol ester,” “recycle glycol ester,” “pyrolysis content glycol ester,” and “r-glycol ester” mean glycol ester, at least a portion of which is obtained from pyrolysis, having recycle content.

As used herein, “pyrolysis recycle content glycol ester” and “pr-glycol ester” mean r-glycol ester having pyrolysis recycle content.

As used throughout, the generic description of the compound, composition or stream does not require the presence of its species, but also does not exclude and may include its species. For example, a “glycol ester” or “any glycol ester” can include a glycol ester made by any process and may or may not contain recycle content and may or may not be made from non-recycle content feedstocks or from recycle content feedstocks, and may or may not include r-glycol ester or pr-glycol ester. Likewise, r-glycol ester may or may not include pr-glycol ester, although the mention of r-glycol ester does require it to have recycle content. In another example, an “aldehyde” or “any aldehyde” can include an aldehyde made by any process and may or may not have recycle content, and may or may not include r-aldehyde or pr-aldehyde. Likewise, r-aldehyde may or may not include pr-aldehyde, although the mention of r-aldehyde does require it to have recycle content.

“Pyrolysis recycle content” is a specific subset/type (species) of “recycle content” (genus). Wherever “recycle content” and “r-” are used herein, such usage should be construed as expressly disclosing and providing claim support for “pyrolysis recycle content” and “pr-,” even if not expressly so stated. For example, whenever the term “recycle content glycol ester” or “r-glycol ester” is used herein, it should be construed as also expressly disclosing and providing claim support for “pyrolysis recycle content glycol ester” and “pr-glycol ester.” Similarly, whenever the term “recycle content aldehyde,” or “r-aldehyde,” is used herein, it should be construed as also expressly disclosing and providing claim support for “pyrolysis recycle content aldehyde,” and “pr-aldehyde.”

As used throughout, whenever a cracking of r-pyoil is mentioned, such cracking can be conducted by a thermal cracker, or a thermal steam cracker, in a liquids fed furnace, or in a gas fed furnace, or in any cracking process. In one embodiment or in combination with any of the mentioned embodiments, the cracking is not catalytic or is conducted in the absence of an added catalyst or is not a fluidized catalytic cracking process.

As used throughout, whenever mention is made of pyrolysis of recycle waste, or r-pyoil, all embodiments also include (i) the option of cracking the effluent of pyrolyzing recycle waste or cracking r-pyoil and/or (ii) the option of cracking the effluent or r-pyoil as a feed to a gas fed furnace or to the tubes of gas furnace/cracker.

As used throughout, a “Family of Entities” means at least one person or entity that directly or indirectly controls, is controlled by, or is under common control with another person or entity, where control means ownership of at least 50% of the voting shares, or shared management, common use of facilities, equipment, and employees, or family interest. As used throughout, the mention of a person or entity provides claim support for and includes any person or entity among the Family of Entities.

In an embodiment or in combination with any other mentioned embodiments, the mention of r-aldehyde also includes pr-aldehyde, or pr-aldehyde obtained directly or indirectly from the cracking of r-pyoil or obtained from r-pygas; and r-glycol ester also includes pr-glycol ester, or pr-glycol ester obtained directly or indirectly from the cracking of r-pyoil or obtained from r-pygas.

In one embodiment or in combination with any of the mentioned embodiments, there is provided a method for making an r-aldehyde composition by hydroformylating an olefin feed comprising propylene. The propylene can be an r-propylene. In one embodiment, the method for making an r-aldehyde starts with feeding r-propylene to an hydroformylation reactor for making r-aldehyde. The r-aldehyde, such as r-isobutyraldehyde, may then be further condensed in the presence of a catalyst to provide a glycol ester. In one embodiment, the method for making an r-glycol ester starts with feeding r-olefin or r-aldehyde to a reaction zone (or series of reactors) for making glycol ester.

FIG. 1 is a schematic depiction illustrating an embodiment or in combination with any embodiment mentioned herein of a process for employing a recycle content pyrolysis oil composition (r-pyoil) to make one or more recycle content compositions (e.g. ethylene, propylene, butadiene, hydrogen, and/or pyrolysis gasoline): the r-composition. One or more of the products from the separation zone may then be used to form a variety of end products, including, for example, to make glycol esters.

As shown in FIG. 1, recycled waste can be subjected to pyrolysis in pyrolysis unit 10 to produce a pyrolysis product/ effluent comprising a recycle content pyrolysis oil composition (r-pyoil). The r-pyoil can be fed to a cracker 20, along with a non-recycle cracker feed (e.g., propone, ethane, and/or natural gasoline). A recycle content cracked effluent (r-cracked effluent) can be produced from the cracker and then subjected to separation in a separation train 30. In an embodiment or in combination with any embodiment mentioned herein, the r-composition can be separated and recovered from the r-cracked effluent. The r-propylene stream can contain predominantly propylene, while the r-ethylene stream can contain predominately ethylene.

Figure 5:
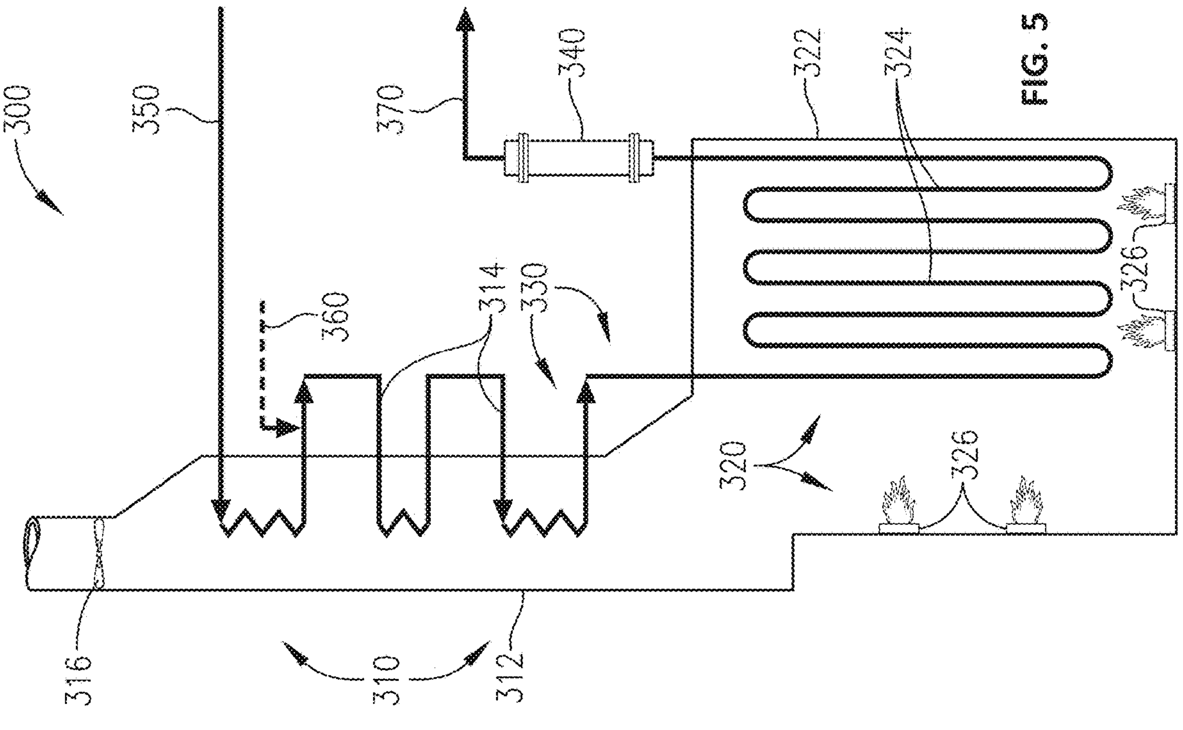
FIG. 5 is a schematic diagram of a cracker furnace suitable for receiving r-pyoil.

As used herein, a furnace includes the convection zone and the radiant zone. A convection zone includes the tubes and/or coils inside the convection box that can also continue outside the convection box downstream of the coil inlet at the entrance to the convection box. For example, as shown in FIG. 5, the convection zone 310 includes the coils and tubes inside the convection box 312 and can optionally extend or be interconnected with piping 314 outside the convection box 312 and returning inside the convection box 312. The radiant zone 320 includes radiant coils/tubes 324 and burners 326. The convection zone 310 and radiant zone 320 can be contained in a single unitary box, or in separate discrete boxes. The convection box 312 does not necessarily have to be a separate discrete box. As shown in FIG. 5, the convection box 312 is integrated with the firebox 322.

Unless otherwise specified, all component amounts provided herein (e.g. for feeds, feedstocks, streams, compositions, and products) are expressed on a dry basis.

The terms "recycled waste," "waste stream," and "recycled waste stream" are used interchangeably to mean any type of waste or waste-containing stream that is reused in a production process, rather than being permanently disposed of (e.g., in a landfill or incinerator). The recycled waste stream is a flow or accumulation of recycled waste from industrial and consumer sources that is at least in part recovered.

As used herein, a "r-pyoil" or "r-pyrolysis oil" are interchangeable and mean a composition of matter that is liquid when measured at 25° C. and 1 atm, at least a portion of which is obtained from pyrolysis, and which has recycle content. In one embodiment or in combination with any of the mentioned embodiments, at least a portion of the composition is obtained from the pyrolysis of recycled waste (e.g., waste plastic or waste stream).

In one embodiment or in combination with any of the mentioned embodiments, the "r-ethylene" can be a composition comprising: (a) ethylene obtained from cracking of a cracker feed containing r-pyoil, or (b) ethylene having a recycle content value attributed to at least a portion of the ethylene; and the "r-propylene" can be a composition comprising (a) propylene obtained from cracking of a cracker feed containing r-pyoil, or (b) propylene having a recycle content value attributed to at least a portion of the propylene.

Reference to a "r-ethylene molecule" means ethylene molecule derived directly or indirectly from recycled waste and reference to a "pr-ethylene molecule" means ethylene molecule derived directly or indirectly from r-pyrolysis effluent (e.g., r-pyoil and/or r-pygas).

As used herein, a "Site" means a largest continuous geographical boundary owned by a glycol ester manufacturer, or by one person or entity, or combination of persons or entities, among its Family of Entities, wherein the geographical boundary contains one or more manufacturing facilities at least one of which is a glycol ester manufacturing facility.

As used herein, the term "predominantly" means more than 50 percent by weight, unless expressed in mole percent, in which case it means more than 50 mole %. For example, a predominantly propane stream, composition, feedstock, or product is a stream, composition, feedstock, or product that contains more than 50 weight percent propane, or if expressed as mole %, means a product that contains more than 50 mole % propane.

As used herein, a composition that is "directly derived" from cracking r-pyoil has at least one physical component that is traceable to an r-composition at least a portion of which is obtained by or with the cracking of r-pyoil, while a composition that is "indirectly derived" from cracking r-pyoil has associated with it a recycle content allotment and may or may not contain a physical component that is traceable to an r-composition at least a portion of which is obtained by or with the cracking of r-pyoil.

As used herein, "recycle content value" and "r-value" mean a unit of measure representative of a quantity of material having its origin in recycled waste. The r-value can have its origin in any type of recycled waste processed in any type of process.

As used herein, the term "pyrolysis recycle content value" and "pr-value" mean a unit of measure representative of a quantity of material having its origin in the pyrolysis of recycled waste. The pr-value is a specific subset/type of r-value that is tied to the pyrolysis of recycled waste. Therefore, the term r-value encompasses, but does not require, a pr-value.

The particular recycle content value (r-value or pr-value) can be by mass or percentage or any other unit of measure and can be determined according to a standard system for tracking, allocating, and/or crediting recycle content among various compositions. A recycle content value can be deducted from a recycle content inventory and applied to a product or composition to attribute recycle content to the product or composition. A recycle content value does not have to originate from making or cracking r-pyoil unless so stated. In one embodiment or in combination with any mentioned embodiments, at least a portion of the r-pyoil from which an allotment is obtained is also cracked in a cracking furnace as described throughout the one or more embodiments herein.

In one embodiment or in combination with any mentioned embodiments, at least a portion of the recycle content allotment or allotment or recycle content value deposited into a recycle content inventory is obtained from r-pyoil. Desirably, at least 60%, or at least 70%, or at least 80%, or at least 90% or at least 95%, or up to 100% of the:

- a. allotments or
- b. deposits into a recycle content inventory, or
- c. recycle content value in a recycle content inventory, or
- d. recycle content value applied to compositions to make a recycle content product, intermediate, or article (Recycle PIA)

are obtained from r-pyoil.

A Recycle PIA or r-PIA is a product, intermediate or article which can include compounds or compositions containing compounds or polymers, and/or an article having an associated recycle content value. A PIA does not have a recycle content value associated with it. A PIA includes, and is not limited to, ethylene oxide, or an alkylene glycol such as ethylene glycol.

As used herein, "recycle content allotment" or "allotment" means a recycle content value that is:

transferred from an originating composition (e.g., compound, polymer, feedstock, product, or stream) at least a portion of which is obtained from recycled waste or which has a recycle content value at least a portion of which originates from recycled waste, optionally originating from r-pyoil, to a receiving composition (the composition receiving the allotment, e.g., compound, polymer, feedstock, product, or stream) that may or may not have a physical component that is traceable to a composition at least a portion of which is obtained from recycled waste; or deposited into a recycle inventory from an originating composition (e.g., compound, polymer, feedstock, product, or stream) at least a portion of which is obtained from or having a recycle content value or pr-value at least a portion of which originates from recycled waste.

As used herein, "pyrolysis recycle content allotment" and "pyrolysis allotment" or "pr-allotment" mean a pyrolysis recycle content value that is:

transferred from an originating composition (e.g., compound, polymer, feedstock, product, or stream) at least a portion of which is obtained from the pyrolysis of recycled waste or which has a recycle content value at least a portion of which originates from the pyrolysis of recycled waste, to a receiving composition (e.g., compound, polymer, feedstock, product, article or stream) that may or may not have a physical component that is traceable to a composition at least a portion of which is obtained from the pyrolysis of recycled waste; or deposited into a recycle inventory from an originating composition (e.g., compound, polymer, feedstock, product, or stream) at least a portion of which is obtained from or having a recycle content value at least a portion of which originates from the pyrolysis of recycled waste.

A pyrolysis recycle content allotment is a specific type of recycle content allotment that is tied to the pyrolysis of recycled waste. Therefore, the term recycle content allotment encompasses pyrolysis recycle content allocation.

In one embodiment or in combination with any of the mentioned embodiments, a pyrolysis recycle content allotment or pyrolysis allotment may have a recycle content value that is:

transferred from an originating composition (e.g., compound, polymer, feedstock, product, or stream) at least a portion of which is obtained from the cracking (e.g. liquid or gas thermal stream cracking) of r-pyoil, or transferred from recycle waste used to make r-pyoil that is cracked, or transferred from r-pyoil that is or will be cracked, or which has a recycle content value at least a portion of which originates from the cracking (e.g. liquid or gas thermal steam cracking) of r-pyoil, to a receiving composition (e.g., compound, polymer, feedstock, product, or stream or PIA) that may or may not have a physical component that is traceable to a composition at least a portion of which is obtained from the cracking of r-pyoil; or deposited into a recycle content inventory and is obtained from a composition (e.g., compound, polymer, feedstock, product, or stream) at least a portion of which is obtained from or having a recycle content value at least a portion of which originates from the cracking (e.g. liquid or gas thermal steam cracking) of r-pyoil (whether or not the r-pyoil is cracked at the time of depositing the allotment into the recycle content inventory provided the r-pyoil from which the allotment is taken is ultimately cracked).

An allotment can be an allocation or a credit.

A recycle content allotment can include a recycle content allocation or a recycle content credit obtained with the transfer or use of a raw material. In one embodiment or in combination with any of the mentioned embodiments, the composition receiving the recycle content allotment can be a non-recycle composition, to thereby convert the non-recycle composition to an r-composition.

As used herein, "non-recycle" means a composition (e.g., compound, polymer, feedstock, product, or stream) none of which was directly or indirectly derived from recycled waste.

As used herein, a "non-recycle feed" in the context of a feed to the cracker or furnace means a feed that is not obtained from a recycled waste stream. Once a non-recycle feed obtains a recycle content allotment (e.g. either through a recycle content credit or recycle content allocation), the non-recycle feed become a recycle content feed, composition, or Recycle PIA.

As used herein, the term "recycle content allocation" is a type of recycle content allotment, where the entity or person supplying a composition sells or transfers the composition to the receiving person or entity, and the person or entity that made the composition has an allotment at least a portion of which can be associated with the composition sold or transferred by the supplying person or entity to the receiving person or entity. The supplying entity or person can be controlled by the same entity or person(s), or Family of Entities, or a different Family of Entities. In one embodiment or in combination with any mentioned embodiments, a recycle content allocation travels with a composition and with the downstream derivates of the composition. In one embodiment or in combination with any mentioned embodiments, an allocation may be deposited into a recycle content inventory and withdrawn from the recycle content inventory as an allocation and applied to a composition to make an r-composition or a Recycle PIA.

As used herein, "recycle content credit" and "credit" mean a type of recycle content allotment, where the allotment is not restricted to an association with compositions made from cracking r-pyoil or their downstream derivatives, but rather have the flexibility of being obtained from r-pyoil and (i) applied to compositions or PIA made from processes other than cracking feedstocks in a furnace, or (ii) applied to downstream derivatives of compositions, through one or more intermediate feedstocks, where such compositions are made from processes other than cracking feedstocks in a furnace, or (iii) available for sale or transfer to persons or entities other than the owner of the allotment, or (iv) available for sale or transfer by other than the supplier of the composition that is transferred to the receiving entity or person. For example, an allotment can be a credit when the allotment is taken from r-pyoil and applied by the owner of the allotment to a BTX composition, or cuts thereof, made by said owner or within its Family of Entities, obtained by refining and fractionation of petroleum rather than obtained by cracker effluent products; or it can be a credit if the owner of the allotment sells the allotment to a third party to allow the third party to either re-sell the product or apply the credit to one or more of a third party's compositions.

A credit can be available for sale or transfer or use, or can be sold or transferred or used, either:

without the sale of a composition, or with the sale or transfer of a composition but the allotment is not associated with the sale or transfer of the composition, or is deposited into or withdrawn from a recycle content inventory that does not track the molecules of a recycle content feedstock to the molecules of the resulting compositions which were made with the recycle content feedstocks, or which does have such tracking capability but which did not track the particular allotment as applied to a composition.

In one embodiment or in combination with any of the mentioned embodiments, an allotment may be deposited into a recycle content inventory, and a credit or allocation may be withdrawn from the inventory and applied to a composition. This would be the case where an allotment is created by making a first composition from the pyrolysis of recycle waste, or from r-pyoil or the cracking of r-pyoil, or by any other method of making a first composition from recycle waste, depositing the allocation associated with such first composition into a recycle content inventory, and deducting a recycle content value from the recycle content inventory and applying it to a second composition that is not a derivate of the first composition or that was not actually made by the first composition as a feedstock. In this system, one need not trace the source of a reactant back to the cracking of pyoil or back to any atoms contained in olefin-containing effluent, but rather can use any reactant made by any process and have associated with such reactant a recycle content allotment.

In one embodiment or in combination with any mentioned embodiments, a composition receiving an allotment is used as a feedstock to make downstream derivatives of the composition, and such composition is a product of cracking a cracker feedstock in a cracker furnace. In one embodiment or in combination with any mentioned embodiments, there is provided a process in which:

a. a r-pyoil is obtained,
b. a recycle content value (or allotment) is obtained from the r-pyoil and
   i. deposited into a recycle content inventory, and an allotment (or credit) is withdrawn from the recycle content inventory and applied to any composition to obtain a r-composition, or
   ii. applied directly to any composition, without depositing into a recycle content inventory, to obtain an r-composition; and
c. at least a portion of the r-pyoil is cracked in a cracker furnace, optionally according to any of the designs or processes described herein; and
d. optionally at least a portion of the composition in step b. originates from a cracking a cracker feedstock in a cracker furnace, optionally the composition having been obtained by any of the feedstocks, including r-pyoil, and methods described herein.

The steps b. and c. do not have to occur simultaneously. In one embodiment or in combination with any mentioned embodiments, they occur within a year of each other, or within six (6) months of each other, or within three (3) months of each other, or within one (1) month of each other, or within two (2) weeks of each other, or within one (1) week of each other, or within three (3) days of each other. The process allows for a time lapse between the time an entity or person receiving the r-pyoil and creating the allotment (which can occur upon receipt or ownership of the r-pyoil or deposit into inventory) and the actual processing of the r-pyoil in a cracker furnace.

As used herein, "recycle content inventory" and "inventory" mean a group or collection of allotments (allocations or credits) from which deposits and deductions of allotments in any units can be tracked. The inventory can be in any form (electronic or paper), using any or multiple software programs, or using a variety of modules or applications that together as a whole tracks the deposits and deductions. Desirably, the total amount of recycle content withdrawn (or applied to compositions) does not exceed the total amount of recycle content allotments on deposit in the recycle content inventory (from any source, not only from cracking of r-pyoil). However, if a deficit of recycle content value is realized, the recycle content inventory is rebalanced to achieve a zero or positive recycle content value available. The timing for rebalancing can be either determined and managed in accordance with the rules of a particular system of accreditation adopted by the olefin-containing effluent manufacturer or by one among its Family of Entities, or alternatively, is rebalanced within one (1) year, or within six (6) months, or within three (3) months, or within one (1) month of realizing the deficit. The timing for depositing an allotment into the recycle content inventory, applying an allotment (or credit) to a composition to make a r-composition, and cracking r-pyoil, need not be simultaneous or in any particular order. In one embodiment or in combination with any mentioned embodiments, the step of cracking a particular volume of r-pyoil occurs after the recycle content value or allotment from that volume of r-pyoil is deposited into a recycle content inventory. Further, the allotments or recycle content values withdrawn from the recycle content inventory need not be traceable to r-pyoil or cracking r-pyoil, but rather can be obtained from any waste recycle stream, and from any method of processing the recycle waste stream. Desirably, at least a portion of the recycle content value in the recycle content inventory is obtained from r-pyoil, and optionally at least a portion of r-pyoil, are processed in the one or more cracking processes as described herein, optionally within a year of each other and optionally at least a portion of the volume of r-pyoil from which a recycle content value is deposited into the recycle content inventory is also processed by any or more of the cracking processes described herein.

The determination of whether an r-composition is derived directly or indirectly from recycled waste is not on the basis of whether intermediate steps or entities do or do not exist in the supply chain, but rather whether at least a portion of the r-composition that is fed to the reactor for making an end product such as an aldehyde or a glycol ester can be traced to an r-composition made from recycled waste.

The determination of whether a pr-composition is derived directly or indirectly from the pyrolysis of recycled waste (e.g., from the cracking of r-pyoil or from r-pygas) is not on the basis of whether intermediate steps or entities do or do not exist in the supply chain, but rather whether at least a portion of the pr-composition that is fed to the reactor for making an end product such as an aldehyde or a glycol ester can be traced to an pr-composition made from the pyrolysis of recycled waste.

As noted above, the end product is considered to be directly derived from cracking r-pyoil or from recycled waste if at least a portion of the reactant feedstock used to make the product can be traced back, optionally through one or more intermediate steps or entities, to at least a portion of the atoms or molecules that make up an r-composition produced from recycled waste or the cracking of r-pyoil fed to a cracking furnace or as an effluent from the cracking furnace).

The r-composition as an effluent may be in crude form that requires refining to isolate the particular r-composition. The r-composition manufacturer can, typically after refining and/or purification and compression to produce the desired grade of the particular r-composition, sell such r-composition to an intermediary entity who then sells the r-composition, or one or more derivatives thereof, to another intermediary for making an intermediate product or directly to the product manufacturer. Any number of intermediaries and intermediate derivates can be made before the final product is made.

The actual r-composition volume, whether condensed as a liquid, supercritical, or stored as a gas, can remain at the facility where it is made, or can be shipped to a different location, or held at an off-site storage facility before utilized by the intermediary or product manufacturer. For purposes of tracing, once r-composition made from recycled waste (e.g., by cracking r-pyoil or from r-pygas) is mixed with another volume of the composition (e.g. r-propylene mixed with non-recycle propylene), for example in a storage tank, salt dome, or cavern, then the entire tank, dome, or cavern at that point becomes an r-composition source, and for purposes of tracing, withdrawal from such storage facility is withdrawing from an r-composition source until such time as when the entire volume or inventory of the storage facility is turned over or withdrawn and/or replaced with non-recycle compositions after the r-composition feed to the tank stops. Likewise, this applies also to any downstream storage facilities for storing the derivatives of the r-compositions.

An r-composition is considered to be indirectly derived from recycled waste or pyrolysis of recycled waste or cracking of r-pyoil if it has associated with it a recycle content allotment and may or may not contain a physical component that is traceable to an r-composition at least a portion of which is obtained from recycled waste/pyrolysis of recycled waste/cracking of r-pyoil. For example, the (i) manufacturer of the product can operate within a legal framework, or an association framework, or an industry recognized framework for making a claim to a recycle content through, for example, a system of credits transferred to the product manufacturer regardless of where or from whom the r-composition, or derivatives thereof, or reactant feedstocks to make the product, is purchased or transferred, or (ii) a supplier of the r-composition or a derivate thereof ("supplier") operates within an allotment framework that allows for associating or applying a recycle content value or pr-value to a portion or all of an olefin-containing effluent or a compound within an olefin-containing effluent or derivate thereof to make an r-composition, and to transfer the recycle content value or allotment to the manufacturer of the product or any intermediary who obtains a supply of r-composition from the supplier. In this system, one need not trace the source of r-olefin, r-aldehyde or r-glycol ester volume back to the manufacture of r-composition from recycled waste/pyrolyzed recycled waste, but rather can use any olefin, or aldehyde composition made by any process and have associated with such olefin or aldehyde composition a recycle content allotment.

Examples of how an olefin composition for making an aldehyde can obtain recycle content include:

(i) a cracker facility in which r-olefin made at the facility, by cracking r-pyoil or obtained from r-pygas, can be in fluid communication, continuously or intermittently and directly or indirectly through intermediate facilities, with an olefin facility (which can be to a storage vessel at the olefin facility or a formation reactor at the olefin facility) through interconnected pipes, optionally through one or more storage vessels and valves or interlocks, and the r-olefin feedstock is drawn through the interconnected piping:
 a. from the cracker facility while r-olefin is being made or thereafter within the time for the r-olefin to transport through the piping to the olefin facility; or
 b. from the one or more storage tanks at any time provided that at least one of the storage tanks was fed with r-olefin, and continue for so long as the entire volume of the one or more storage tanks is replaced with a feed that does not contain r-olefin; or (ii) transporting olefin from a storage vessel, dome, or facility, or in an isotainer via truck or rail or ship or a means other than piping, that contains or has been fed with r-olefin until such time as the entire volume of the vessel, dome or facility has been replaced with an olefin gas feed that does not contain r-olefin; or (iii) the manufacturer of the olefin certifies, represents to its customers or the public, or advertises that its olefin contains recycle content or is obtained from feedstock containing or obtained from recycle content, where such recycle content claim is based in whole or in part on an olefin feedstock associated with an allocation from olefin made from cracking r-pyoil or obtained from r-pygas; or (iv) the manufacturer of the olefin has acquired:
 a. an ethane or propane volume made from r-pyoil or recycled waste material under a certification, representation, or as advertised, or
 b. has transferred credits or allocation with the supply of ethane or propane to the manufacturer of the olefin sufficient to allow the manufacturer of the olefin to satisfy the certification requirements or to make its representations or advertisements, or
 c. the ethane or propane has allocated to it a recycle content where such allocation was obtained, through one or more intermediary entities, from a stream at least part of which is obtained by cracking r-pyoil or obtained from r-pygas.

Similarly, examples of how an aldehyde composition for making a glycol ester can obtain recycle content include:

(i) a cracker facility in which r-olefin, including r-propylene, made at the facility, by cracking r-pyoil or obtained from r-pygas, can be in fluid communication, continuously or intermittently and directly or indirectly through intermediate facilities such an aldehyde facility, with an aldehyde formation facility (which can be to a storage vessel at the aldehyde facility or directly to the aldehyde formation reactor) through interconnected pipes, optionally through one or more storage vessels and valves or interlocks, and the r-olefin feedstock is drawn through the interconnected piping:
 a. from the cracker facility while r-olefin is being made or thereafter within the time for the r-olefin to transport through the piping to the aldehyde formation facility; or
 b. from the one or more storage tanks at any time provided that at least one of the storage tanks was fed with r-olefin, and continue for so long as the entire volume of the one or more storage tanks is replaced with a feed that does not contain r-olefin; or (ii) transporting olefin from a storage vessel, dome, or facility, or in an isotainer via truck or rail or ship or a means other than piping, that contains or has been fed with r-olefin until such time as the entire volume of the vessel, dome or facility has been replaced with an olefin gas feed that does not contain r-olefin; or (iii) the manufacturer of the aldehyde certifies, represents to its customers or the public, or advertises that its aldehyde contains recycle content or is obtained from feedstock containing or obtained from recycle content, where such recycle content claim is based in whole or in part on an olefin feedstock associated with an allocation from olefin made from cracking r-pyoil or obtained from r-pygas; or (iv) the manufacturer of the aldehyde has acquired:
   a. an olefin volume made from r-pyoil under a certification, representation, or as advertised, or
   b. has transferred credits or allocation with the supply of olefin to the manufacturer of the aldehyde sufficient to allow the manufacturer of the aldehyde to satisfy the certification requirements or to make its representations or advertisements, or
   c. the olefin has allocated to it a recycle content where such allocation was obtained, through one or more intermediary entities, from a cracked olefin volume at least part of which is obtained by cracking r-pyoil or obtained from r-pygas.

As discussed above, the recycle content can be a pyrolysis recycle content that is directly or indirectly derived from the pyrolysis of recycled waste (e.g., from cracking r-pyoil or from r-pygas).

A recycle content value that is directly or indirectly "derived from cracking r-pyoil", or a recycle content value that is "obtained from cracking r-pyoil" or originating in cracking r-pyoil does not imply the timing of when the recycle content value or allotment is taken, captured, deposited into a recycle content inventory, or transferred. The timing of depositing the allotment or recycle content value into a recycle content inventory, or realizing, recognizing, capturing, or transferring it, is flexible and can occur as early as receipt of r-pyoil onto the site within a Family of Entities, possessing it, or bringing the r-pyoil into inventory by the entity or person, or within the Family of Entities, owning or operating the cracker facility. Thus, an allotment or recycle content value on a volume of r-pyoil can be obtained, captured, deposited into a recycle content inventory, or transferred to a product without having yet fed that volume to cracker furnace and cracked. The allotment can also be obtained during feeding r-pyoil to a cracker, during cracking, or when an r-composition is made. An allotment taken when r-pyoil is owned, possessed, or received and deposited into a recycle content inventory is an allotment that is associated with, obtained from, or originates from cracking r-pyoil even though, at the time of taking or depositing the allotment, the r-pyoil has not yet been cracked, provided that the r-pyoil is at some future point in time cracked.

A recycled waste stream includes materials, products, and articles (collectively "material(s)," when used alone). Recycled waste materials can be solid or liquid. Examples of a solid recycled waste stream include plastics, rubber (including tires), textiles, wood, biorecycled waste, modified celluloses, wet laid products, and any other material capable of being pyrolyzed. Examples of liquid recycled waste streams include industrial sludge, oils (including those derived from plants and petroleum), recovered lube oil, or vegetable oil or animal oil, and any other chemical streams from industrial plants.

In one embodiment or in combination with any of the mentioned embodiments, the recycled waste stream that is pyrolyzed includes a stream containing at least in part post-industrial, or post-consumer, or both a post-industrial and post-consumer materials. In one embodiment or in combination with any of the mentioned embodiments, a post-consumer material is one that has been used at least once for its intended application for any duration of time regardless of wear, or has been sold to an end use customer, or which is discarded into a recycle bin by any person or entity other than a manufacturer or business engaged in the manufacture or sale of the material.

In one embodiment or in combination with any of the mentioned embodiments, a post-industrial material is one which has been created and has not been used for its intended application, or has not been sold to the end use customer, or discarded by a manufacturer or any other entity engaged in the sale of the material. Examples of post-industrial materials include rework, regrind, scrap, trim, out of specification materials, and finished materials transferred from a manufacturer to any downstream customer (e.g. manufacturer to wholesaler to distributor) but not yet used or sold to the end use customer.

The form of the recycled waste stream, which can be fed to a pyrolysis unit, is not limited, and can include any of the forms of articles, products, materials, or portions thereof. A portion of an article can take the form of sheets, extruded shapes, moldings, films, laminates, foam pieces, chips, flakes, particles, fibers, agglomerates, briquettes, powder, shredded pieces, long strips, or randomly shaped pieces having a wide variety of shapes, or any other form other than the original form of the article and adapted to feed a pyrolysis unit.

In one embodiment or in combination with any of the mentioned embodiments, the recycled waste material is size reduced. Size reduction can occur through any means, including chopping, shredding, harrowing, confrication, pulverizing, cutting a feedstock, molding, compression, or dissolution in a solvent.

Recycled waste plastics can be isolated as one type of polymer stream or may be a stream of mixed recycled waste plastics. The plastics can be any organic synthetic polymer that is solid at 25° C. at 1 atm. The plastics can be thermosetting, thermoplastic, or elastomeric plastics. Examples of plastics include high density polyethylene and copolymers thereof, low density polyethylene and copolymers thereof, polypropylene and copolymers thereof, other polyolefins, polystyrene, polyvinyl chloride (PVC), polyvinylidene chloride (PVDC), polyesters including polyethylene terephthalate, copolyesters and terephthalate copolyesters (e.g. containing residues of TMCD, CHDM, propylene glycol, or NPG monomers), polyethylene terephthalate, polyamides, poly(methyl methacrylate), polytetrafluoroethylene, acrylobutadienestyrene (ABS), polyurethanes, cellulosics and derivates thereof such as cellulose acetate, cellulose diacetate, cellulose triacetate, cellulose propionate, cellulose butyrate; regenerated cellulosics such as viscose and rayons, epoxy, polyamides, phenolic resins, polyacetal, polycarbonates, polyphenylene-based alloys, polypropylene and copolymers thereof, polystyrene, styrenic compounds, vinyl based compounds, styrene acrylonitrile, thermoplastic elastomers, and urea based polymers and melamine containing polymers.

Suitable recycled waste plastics also include any of those having a resin ID code numbered 1-7 within the chasing arrow triangle established by the SPI. In one embodiment or in combination with any of the mentioned embodiments, the r-pyoil is made from a recycled waste stream at least a portion of which contains plastics that are not generally recycled. These would include plastics having numbers 3

(polyvinyl chloride), 5 (polypropylene), 6 (polystyrene), and 7 (other). In one embodiment or in combination with any of the mentioned embodiments, the recycled waste stream that is pyrolyzed contains less than 10 weight percent, or not more than 5 weight percent, or not more than 3 weight percent, or not more than 2 weight percent, or not more than 1 weight percent, or not more than 0.5 weight percent, or not more than 0.2 weight percent, or not more than 0.1 weight percent, or not more and 0.05 weight percent plastics with a number 3 designation (polyvinyl chloride), or optionally plastics with a number 3 and 6 designation, or optionally with a number 3, 6 and 7 designation.

Examples of recycled rubber include natural and synthetic rubber. The form of the rubber is not limited, and includes tires.

Examples of recycled waste wood include soft and hard woods, chipped, pulped, or as finished articles. The source of much recycled waste wood is industrial, construction, or demolition.

Examples of recycled biorecycled waste includes household biorecycled waste (e.g. food), green or garden biorecycled waste, and biorecycled waste from the industrial food processing industry.

Examples of recycled textiles includes natural and/or synthetic fibers, rovings, yarns, nonwoven webs, cloth, fabrics and products made from or containing any of the aforementioned items. Textiles can be woven, knitted, knotted, stitched, tufted, pressing of fibers together such as would be done in a felting operation, embroidered, laced, crocheted, braided, or nonwoven webs and materials. Textiles include fabrics, and fibers separated from a textile or other product containing fibers, scrap or off spec fibers or yarns or fabrics, or any other source of loose fibers and yarns. A textile also includes staple fibers, continuous fibers, threads, tow bands, twisted and/or spun yarns, grey fabrics made from yarns, finished fabrics produced by wet processing gray fabrics, and garments made from the finished fabrics or any other fabrics. Textiles include apparels, interior furnishings, and industrial types of textiles.

Examples of recycled textiles in the apparel category (things humans wear or made for the body) include sports coats, suits, trousers and casual or work pants, shirts, socks, sportswear, dresses, intimate apparel, outerwear such as rain jackets, cold temperature jackets and coats, sweaters, protective clothing, uniforms, and accessories such as scarves, hats, and gloves. Examples of textiles in the interior furnishing category include furniture upholstery and slipcovers, carpets and rugs, curtains, bedding such as sheets, pillow covers, duvets, comforters, mattress covers; linens, tablecloths, towels, washcloths, and blankets. Examples of industrial textiles include transportation (auto, airplanes, trains, buses) seats, floor mats, trunk liners, and headliners; outdoor furniture and cushions, tents, backpacks, luggage, ropes, conveyor belts, calendar roll felts, polishing cloths, rags, soil erosion fabrics and geotextiles, agricultural mats and screens, personal protective equipment, bullet proof vests, medical bandages, sutures, tapes, and the like.

The recycled nonwoven webs can also be dry laid nonwoven webs. Examples of suitable articles that may be formed from dry laid nonwoven webs as described herein can include those for personal, consumer, industrial, food service, medical, and other types of end uses. Specific examples can include, but are not limited to, baby wipes, flushable wipes, disposable diapers, training pants, feminine hygiene products such as sanitary napkins and tampons, adult incontinence pads, underwear, or briefs, and pet training pads. Other examples include a variety of different dry or wet wipes, including those for consumer (such as personal care or household) and industrial (such as food service, health care, or specialty) use. Nonwoven webs can also be used as padding for pillows, mattresses, and upholstery, batting for quilts and comforters. In the medical and industrial fields, nonwoven webs of the present invention may be used for medical and industrial face masks, protective clothing, caps, and shoe covers, disposable sheets, surgical gowns, drapes, bandages, and medical dressings.

Additionally, nonwoven webs may be used for environmental fabrics such as geotextiles and tarps, oil and chemical absorbent pads, as well as building materials such as acoustic or thermal insulation, tents, lumber and soil covers and sheeting. Nonwoven webs may also be used for other consumer end use applications, such as for, carpet backing, packaging for consumer, industrial, and agricultural goods, thermal or acoustic insulation, and in various types of apparel. The dry laid nonwoven webs may also be used for a variety of filtration applications, including transportation (e.g., automotive or aeronautical), commercial, residential, industrial, or other specialty applications. Examples can include filter elements for consumer or industrial air or liquid filters (e.g., gasoline, oil, water), including nanofiber webs used for microfiltration, as well as end uses like tea bags, coffee filters, and dryer sheets. Further, nonwoven webs may be used to form a variety of components for use in automobiles, including, but not limited to, brake pads, trunk liners, carpet tufting, and under padding.

The recycled textiles can include single type or multiple type of natural fibers and/or single type or multiple type of synthetic fibers. Examples of textile fiber combinations include all natural, all synthetic, two or more type of natural fibers, two or more types of synthetic fibers, one type of natural fiber and one type of synthetic fiber, one type of natural fibers and two or more types of synthetic fibers, two or more types of natural fibers and one type of synthetic fibers, and two or more types of natural fibers and two or more types of synthetic fibers.

Examples of recycled wet laid products include cardboard, office paper, newsprint and magazine, printing and writing paper, sanitary, tissue/toweling, packaging/container board, specialty papers, apparel, bleached board, corrugated medium, wet laid molded products, unbleached Kraft, decorative laminates, security paper and currency, grand scale graphics, specialty products, and food and drink products.

Examples of modified cellulose include cellulose acetate, cellulose diacetate, cellulose triacetate, regenerated cellulose such a viscose, rayon, and Lyocel™ products, in any form, such as tow bands, staple fibers, continuous fibers, films, sheets, molded or stamped products, and contained in or on any article such as cigarette filter rods, ophthalmic products, screwdrivers handles, optical films, and coatings.

Examples of recycled vegetable oil or animal oil include the oils recovered from animal processing facilities and recycled waste from restaurants.

The source for obtaining recycled post-consumer or post-industrial recycled waste is not limited, and can include recycled waste present in and/or separated from municipal solid recycled waste streams ("MSW"). For example, an MSW stream can be processed and sorted to several discrete components, including textiles, fibers, papers, wood, glass, metals, etc. Other sources of textiles include those obtained by collection agencies, or by or for or on behalf of textile brand owners or consortiums or organizations, or from brokers, or from postindustrial sources such as scrap from mills or commercial production facilities, unsold fabrics from wholesalers or dealers, from mechanical and/or chemical sorting or separation facilities, from landfills, or stranded on docks or ships.

In one embodiment or in combination with any of the mentioned embodiments, the feed to the pyrolysis unit can comprise at least 30, or at least 35, or at least 40, or at least 45, or at least 50, or at least 55, or at least 60, or at least 65, or at least 70, or at least 75, or at least 80, or at least 85, or at least 90, or at least 95, or at least 99, in each case weight percent of at least one, or at least two, or at least three, or at least four, or at least five, or at least six different kinds of recycled waste. Reference to a "kind" is determined by resin ID code 1-7. In one embodiment or in combination with any of the mentioned embodiments, the feed to the pyrolysis unit contains less than 25, or not more than 20, or not more than 15, or not more than 10, or not more than 5, or not more than 1, in each case weight percent of polyvinyl chloride and/or polyethylene terephthalate. In one embodiment or in combination with any of the mentioned embodiments, the recycled waste stream contains at least one, two, or three kinds of plasticized plastics.

Figure 2:
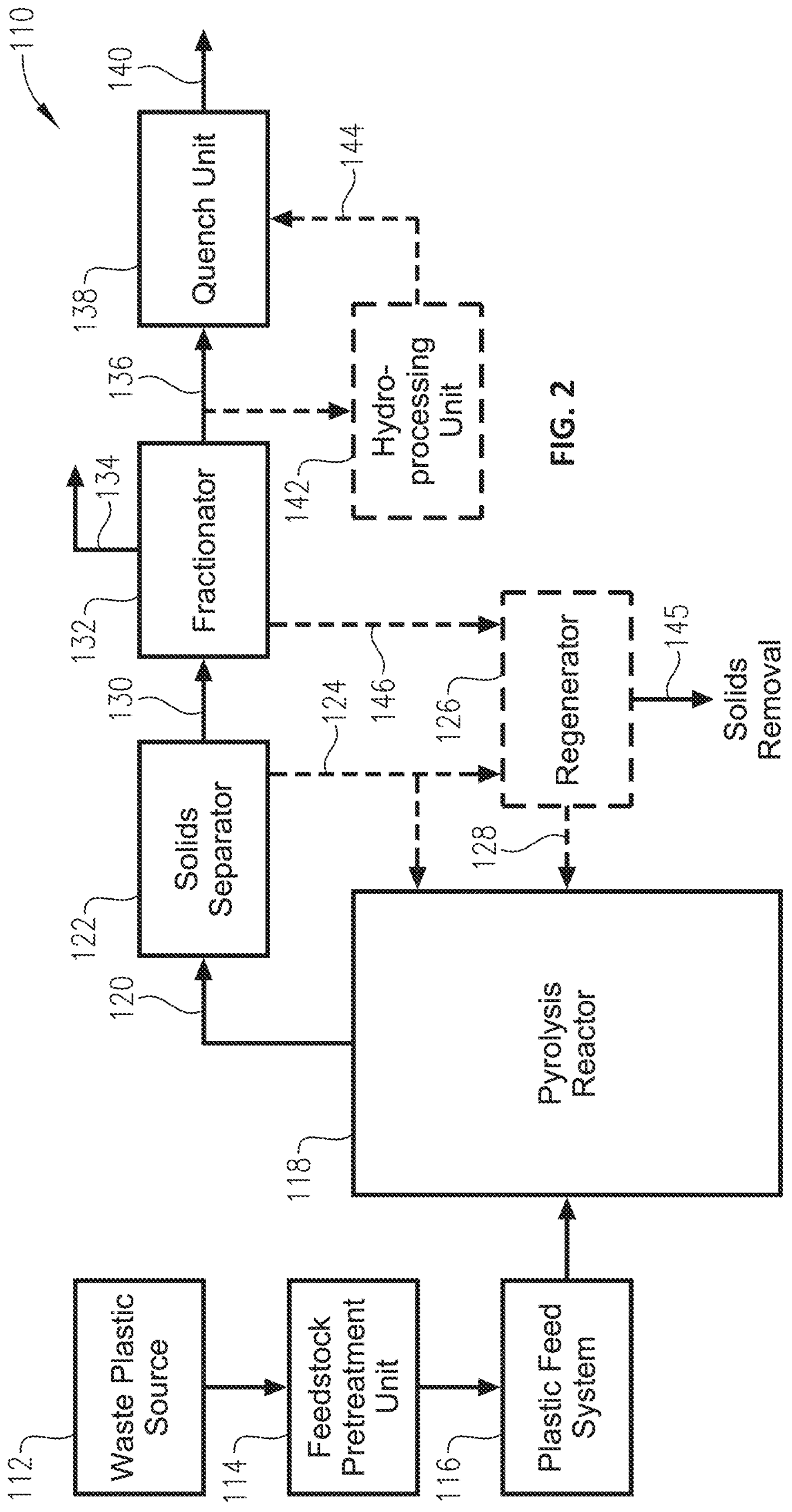
FIG. 2 is an illustration of an exemplary pyrolysis system to at least partially convert one or more recycled waste, particularly recycled plastic waste, into various useful r-products.

FIG. 2 depicts an exemplary pyrolysis system 110 that may be employed to at least partially convert one or more recycled waste, particularly plastic recycled waste, into various useful pyrolysis-derived products. It should be understood that the pyrolysis system shown in FIG. 2 is just one example of a system within which the present disclosure can be embodied. The present disclosure may find application in a wide variety of other systems where it is desirable to efficiently and effectively pyrolyze recycled waste, particularly plastic recycled waste, into various desirable end products. The exemplary pyrolysis system illustrated in FIG. 2 will now be described in greater detail.

As shown in FIG. 2, the pyrolysis system 110 may include a waste plastic source 112 for supplying one or more waste plastics to the system 110. The plastic source 112 can be, for example, a hopper, storage bin, railcar, over-the-road trailer, or any other device that may hold or store waste plastics. In an embodiment or in combination with any of the embodiments mentioned herein, the waste plastics supplied by the plastic source 112 can be in the form of solid particles, such as chips, flakes, or a powder. Although not depicted in FIG. 2, the pyrolysis system 110 may also comprise additional sources of other types of recycled wastes that may be utilized to provide other feed types to the system 110.

In an embodiment or in combination with any of the embodiments mentioned herein, the waste plastics can include one or more post-consumer waste plastic such as, for example, high density polyethylene, low density polyethylene, polypropylene, other polyolefins, polystyrene, polyvinyl chloride (PVC), polyvinylidene chloride (PVDC), polyethylene terephthalate, polyamides, poly(methyl methacrylate), polytetrafluoroethylene, or combinations thereof. In an embodiment or in combination with any of the embodiments mentioned herein, the waste plastics may include high density polyethylene, low density polyethylene, polypropylene, or combinations thereof. As used herein, "post-consumer" refers to non-virgin plastics that have been previously introduced into the consumer market.

In an embodiment or in combination with any of the embodiments mentioned herein, a waste plastic-containing feed may be supplied from the plastic source 112. In an embodiment or in combination with any of the embodiments mentioned herein, the waste plastic-containing feed can comprise, consist essentially of, or consist of high density polyethylene, low density polyethylene, polypropylene, other polyolefins, polystyrene, polyvinyl chloride (PVC), polyvinylidene chloride (PVDC), polyethylene terephthalate, polyamides, poly(methyl methacrylate), polytetrafluoroethylene, or combinations thereof.

In an embodiment or in combination with any of the embodiments mentioned herein, the waste plastic-containing feed can comprise at least 30, or at least 35, or at least 40, or at least 45, or at least 50, or at least 55, or at least 60, or at least 65, or at least 70, or at least 75, or at least 80, or at least 85, or at least 90, or at least 95, or at least 99, in each case weight percent of at least one, two, three, or four different kinds of waste plastic. In an embodiment or in combination with any of the embodiments mentioned herein, the plastic waste may comprise not more than 25, or not more than 20, or not more than 15, or not more than 10, or not more than 5, or not more than 1, in each case weight percent of polyvinyl chloride and/or polyethylene terephthalate. In an embodiment or in combination with any of the embodiments mentioned herein, the waste plastic-containing feed can comprise at least one, two, or three kinds of plasticized plastics. Reference to a "kind" is determined by resin ID code 1-7.

As depicted in FIG. 2, the solid waste plastic feed from the plastic source 112 can be supplied to a feedstock pretreatment unit 114. While in the feedstock pretreatment unit 114, the introduced waste plastics may undergo a number of pretreatments to facilitate the subsequent pyrolysis reaction. Such pretreatments may include, for example, washing, mechanical agitation, flotation, size reduction or any combination thereof. In an embodiment or in combination with any of the embodiments mentioned herein, the introduced plastic waste may be subjected to mechanical agitation or subjected to size reduction operations to reduce the particle size of the plastic waste. Such mechanical agitation can be supplied by any mixing, shearing, or grinding device known in the art which may reduce the average particle size of the introduced plastics by at least 10, or at least 25, or at least 50, or at least 75, in each case percent.

Next, the pretreated plastic feed can be introduced into a plastic feed system 116. The plastic feed system 116 may be configured to introduce the plastic feed into the pyrolysis reactor 118. The plastic feed system 116 can comprise any system known in the art that is capable of feeding the solid plastic feed into the pyrolysis reactor 118. In an embodiment or in combination with any of the embodiments mentioned herein, the plastic feed system 116 can comprise a screw feeder, a hopper, a pneumatic conveyance system, a mechanic metal train or chain, or combinations thereof.

While in the pyrolysis reactor 118, at least a portion of the plastic feed may be subjected to a pyrolysis reaction that produces a pyrolysis effluent comprising a pyrolysis oil (e.g., r-pyoil) and a pyrolysis gas (e.g., r-pyrolysis gas). The pyrolysis reactor 118 can be, for example, an extruder, a tubular reactor, a tank, a stirred tank reactor, a riser reactor, a fixed bed reactor, a fluidized bed reactor, a rotary kiln, a vacuum reactor, a microwave reactor, an ultrasonic or supersonic reactor, or an autoclave, or a combination of these reactors.

Generally, pyrolysis is a process that involves the chemical and thermal decomposition of the introduced feed. Although all pyrolysis processes may be generally characterized by a reaction environment that is substantially free of oxygen, pyrolysis processes may be further defined, for example, by the pyrolysis reaction temperature within the reactor, the residence time in the pyrolysis reactor, the reactor type, the pressure within the pyrolysis reactor, and the presence or absence of pyrolysis catalysts.

In an embodiment or in combination with any of the embodiments mentioned herein, the pyrolysis reaction can involve heating and converting the plastic feed in an atmosphere that is substantially free of oxygen or in an atmosphere that contains less oxygen relative to ambient air. In an embodiment or in combination with any of the embodiments mentioned herein, the atmosphere within the pyrolysis reactor 118 may comprise not more than 5, or not more than 4, or not more than 3, or not more than 2, or not more than 1, or not more than 0.5, in each case weight percent of oxygen gas.

In an embodiment or in combination with any of the embodiments mentioned herein, the pyrolysis process may be carried out in the presence of an inert gas, such as nitrogen, carbon dioxide, and/or steam. Additionally, or alternatively, in an embodiment or in combination with any of the embodiments mentioned herein, the pyrolysis process can be carried out in the presence of a reducing gas, such as hydrogen and/or carbon monoxide.

In an embodiment or in combination with any of the embodiments mentioned herein, the temperature in the pyrolysis reactor 118 can be adjusted to as to facilitate the production of certain end products. In an embodiment or in combination with any of the embodiments mentioned herein, the pyrolysis temperature in the pyrolysis reactor 118 can be at least 325° C., or at least 350° C., or at least 375° C., or at least 400° C., or at least 425° C., or at least 450° C., or at least 475° C., or at least 500° C., or at least 525° C., or at least 550° C., or at least 575° C., or at least 600° C., or at least 625° C., or at least 650° C., or at least 675° C., or at least 700° C., or at least 725° C., or at least 750° C., or at least 775° C., or at least 800° C. Additionally, or alternatively, in an embodiment or in combination with any of the embodiments mentioned herein, the pyrolysis temperature in the pyrolysis reactor 118 can be not more than 1,100° C., or not more than 1,050° C., or not more than 1,000° C., or not more than 950° C., or not more than 900° C., or not more than 850° C., or not more than 800° C., or not more than 750° C., or not more than 700° C., or not more than 650° C., or not more than 600° C., or not more than 550° C., or not more than 525° C., or not more than 500° C., or not more than 475° C., or not more than 450° C., or not more than 425° C., or not more than 400° C. In an embodiment or in combination with any of the embodiments mentioned herein, the pyrolysis temperature in the pyrolysis reactor 118 can range from 325 to 1,100° C., 350 to 900° C., 350 to 700° C., 350 to 550° C., 350 to 475° C., 500 to 1,100° C., 600 to 1,100° C., or 650 to 1,000° C.

In an embodiment or in combination with any of the embodiments mentioned herein, the residence times of the pyrolysis reaction can be at least 1, or at least 2, or at least 3, or at least 4, in each case seconds, or at least 10, or at least 20, or at least 30, or at least 45, or at least 60, or at least 75, or at least 90, in each case minutes. Additionally, or alternatively, in an embodiment or in combination with any of the embodiments mentioned herein, the residence times of the pyrolysis reaction can be not more than 6 hours, or not more than 5, or not more than 4, or not more than 3, or not more than 2, or not more than 1, or not more than 0.5, in each case hours. In an embodiment or in combination with any of the embodiments mentioned herein, the residence times of the pyrolysis reaction can range from 30 minutes to 4 hours, or 30 minutes to 3 hours, or 1 hour to 3 hours, or 1 hour to 2 hours.

In an embodiment or in combination with any of the embodiments mentioned herein, the pressure within the pyrolysis reactor 118 can be maintained at a pressure of at least 0.1, or at least 0.2, or at least 0.3, in each case bar and/or not more than 60, or not more than 50, or not more than 40, or not more than 30, or not more than 20, or not more than 10, or not more than 8, or not more than 5, or not more than 2, or not more than 1.5, or not more than 1.1, in each case bar. In an embodiment or in combination with any of the embodiments mentioned herein, the pressure within the pyrolysis reactor 18 can be maintained at about atmospheric pressure or within the range of 0.1 to 100 bar, or 0.1 to 60 bar, or 0.1 to 30 bar, or 0.1 to 10 bar, or 1.5 bar, 0.2 to 1.5 bar, or 0.3 to 1.1 bar.

In an embodiment or in combination with any of the embodiments mentioned herein, a pyrolysis catalyst may be introduced into the plastic feed prior to introduction into the pyrolysis reactor 118 and/or introduced directly into the pyrolysis reactor 118 to produce an r-catalytic pyoil, or an r-pyoil made by a catalytic pyrolysis process. In an embodiment or in combination with any embodiment mentioned herein or in combination with any of the embodiments mentioned herein, the catalyst can comprise: (i) a solid acid, such as a zeolite (e.g., ZSM-5, Mordenite, Beta, Ferrierite, and/or zeolite-Y); (ii) a super acid, such as sulfonated, phosphated, or fluorinated forms of zirconia, titania, alumina, silica-alumina, and/or clays; (iii) a solid base, such as metal oxides, mixed metal oxides, metal hydroxides, and/or metal carbonates, particularly those of alkali metals, alkaline earth metals, transition metals, and/or rare earth metals; (iv) hydrotalcite and other clays; (v) a metal hydride, particularly those of alkali metals, alkaline earth metals, transition metals, and/or rare earth metals; (vi) an alumina and/or a silica-alumina; (vii) a homogeneous catalyst, such as a Lewis acid, a metal tetrachloroaluminate, or an organic ionic liquid; (viii) activated carbon; or (ix) combinations thereof.

In an embodiment or in combination with any of the embodiments mentioned herein, the pyrolysis reaction in the pyrolysis reactor 118 occurs in the substantial absence of a catalyst, particularly the above-referenced catalysts. In such embodiments, a non-catalytic, heat-retaining inert additive may still be introduced into the pyrolysis reactor 118, such as sand, in order to facilitate the heat transfer within the reactor 118.

In an embodiment or in combination with any of the embodiments mentioned herein, the pyrolysis reaction in the pyrolysis reactor 118 may occur in the substantial absence of a pyrolysis catalyst, at a temperature in the range of 350 to 550° C., at a pressure ranging from 0.1 to 60 bar, and at a residence time of 0.2 seconds to 4 hours, or 0.5 hours to 3 hours.

Referring again to FIG. 2, the pyrolysis effluent 120 exiting the pyrolysis reactor 118 generally comprises pyrolysis gas, pyrolysis vapors, and residual solids. As used herein, the vapors produced during the pyrolysis reaction may interchangeably be referred to as a "pyrolysis oil," which refers to the vapors when condensed into their liquid state. In an embodiment or in combination with any of the embodiments mentioned herein, the solids in the pyrolysis effluent 20 may comprise particles of char, ash, unconverted plastic solids, other unconverted solids from the feedstock, and/or spent catalyst (if a catalyst is utilized).

In an embodiment or in combination with any of the embodiments mentioned herein, the pyrolysis effluent 120 may comprise at least 20, or at least 25, or at least 30, or at least 40, or at least 45, or at least 50, or at least 55, or at least 60, or at least 65, or at least 70, or at least 75, or at least or at least 80, in each case weight percent of the pyrolysis vapors, which may be subsequently condensed into the resulting pyrolysis oil (e.g., r-pyoil). Additionally, or alternatively, in an embodiment or in combination with any of the embodiments mentioned herein, the pyrolysis effluent 120 may comprise not more than 99, or not more than 95, or not more than 90, or not more than 85, or not more than 80, or not more than 75, or not more than 70, or not more than 65, or not more than 60, or not more than 55, or not more than 50, or not more than 45, or not more than 40, or not more than 35, or not more than 30, in each case weight percent of the pyrolysis vapors. In an embodiment or in combination with any of the embodiments mentioned herein, the pyrolysis effluent 120 may comprise in the range of 20 to 99 weight percent, 40 to 90 weight percent, or 55 to 90 weight percent of the pyrolysis vapors.

In an embodiment or in combination with any of the embodiments mentioned herein, the pyrolysis effluent 120 may comprise at least 1, or at least 5, or at least 6, or at least 7, or at least 8, or at least 9, or at least 10, or at least 11, or at least 12, in each case weight percent of the pyrolysis gas (e.g., r-pyrolysis gas). As used herein, a "pyrolysis gas" refers to a composition that is produced via pyrolysis and is a gas at standard temperature and pressure (STP). Additionally, or alternatively, in an embodiment or in combination with any of the embodiments mentioned herein, the pyrolysis effluent 20 may comprise not more than 90, or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15, in each case weight percent of the pyrolysis gas. In an embodiment or in combination with any of the embodiments mentioned herein, the pyrolysis effluent 120 may comprise 1 to 90 weight percent, or 5 to 60 weight percent, or 10 to 60 weight percent, or 10 to 30 weight percent, or 5 to 30 weight percent of the pyrolysis gas.

In an embodiment or in combination with any of the embodiments mentioned herein, the pyrolysis effluent 120 may comprise not more than 15, or not more than 10, or not more than 9, or not more than 8, or not more than 7, or not more than 6, or not more than 5, or not more than 4 or not more than 3, in each case weight percent of the residual solids.

In one embodiment or in combination of any mentioned embodiments, there is provided a cracker feed stock composition containing pyrolysis oil (r-pyoil), and the r-pyoil composition contains recycle content catalytic pyrolysis oil (r-catalytic pyoil) and a recycle content thermal pyrolysis oil (r-thermal pyoil). An r-thermal pyoil is pyoil made without the addition of a pyrolysis catalyst. The cracker feedstock can include at least 5, 10, 15, or 20 weight percent r-catalytic pyoil, optionally that has been hydrotreated. The r-pyoil containing r-thermal pyoil and r-catalytic pyoil can be cracked according to any of the processes described herein to provide an olefin-containing effluent stream. The r-catalytic pyoil can be blended with r-thermal pyoil to form a blended stream cracked in the cracker unit. Optionally, the blended stream can contain not more than 10, 5, 3, 2, 1 weight percent of r-catalytic pyoil that has not been hydrotreated.

In one embodiment or in combination with any mentioned embodiment, the r-pyoil does not contain r-catalytic pyoil.

As depicted in FIG. 2, the conversion effluent 120 from the pyrolysis reactor 118 can be introduced into a solids separator 122. The solids separator 122 can be any conventional device capable of separating solids from gas and vapors such as, for example, a cyclone separator or a gas filter or combination thereof. In an embodiment or in combination with any of the embodiments mentioned herein, the solids separator 122 removes a substantial portion of the solids from the conversion effluent 120. In an embodiment or in combination with any of the embodiments mentioned herein, at least a portion of the solid particles 24 recovered in the solids separator 122 may be introduced into an optional regenerator 126 for regeneration, generally by combustion. After regeneration, at least a portion of the hot regenerated solids 128 can be introduced directly into the pyrolysis reactor 118. In an embodiment or in combination with any of the embodiments mentioned herein, at least a portion of the solid particles 124 recovered in the solids separator 122 may be directly introduced back into the pyrolysis reactor 118, especially if the solid particles 124 contain a notable amount of unconverted plastic waste. Solids can be removed from the regenerator 126 through line 145 and discharged out of the system.

Turning back to FIG. 2, the remaining gas and vapor conversion products 130 from the solids separator 122 may be introduced into a fractionator 132. In the fractionator 132, at least a portion of the pyrolysis oil vapors may be separated from the pyrolysis gas to thereby form a pyrolysis gas product stream 134 and a pyrolysis oil vapor stream 136. Suitable systems to be used as the fractionator 132 may include, for example, a distillation column, a membrane separation unit, a quench tower, a condenser, or any other known separation unit known in the art. In an embodiment or in combination with any of the embodiments mentioned herein, any residual solids 146 accrued in the fractionator 132 may be introduced in the optional regenerator 126 for additional processing.

In an embodiment or in combination with any of the embodiments mentioned herein, at least a portion of the pyrolysis oil vapor stream 136 may be introduced into a quench unit 138 in order to at least partially quench the pyrolysis vapors into their liquid form (i.e., the pyrolysis oil). The quench unit 138 may comprise any suitable quench system known in the art, such as a quench tower. The resulting liquid pyrolysis oil stream 140 may be removed from the system 110 and utilized in the other downstream applications described herein. In an embodiment or in combination with any of the embodiments mentioned herein, the liquid pyrolysis oil stream 140 may not be subjected to any additional treatments, such as hydrotreatment and/or hydrogenation, prior to being utilized in any of the downstream applications described herein.

In an embodiment or in combination with any embodiment mentioned herein or in combination with any of the embodiments mentioned herein, at least a portion of the pyrolysis oil vapor stream 136 may be introduced into a hydroprocessing unit 142 for further refinement. The hydroprocessing unit 142 may comprise a hydrocracker, a catalytic cracker operating with a hydrogen feed stream, a hydrotreatment unit, and/or a hydrogenation unit. While in the hydroprocessing unit 142, the pyrolysis oil vapor stream 136 may be treated with hydrogen and/or other reducing gases to further saturate the hydrocarbons in the pyrolysis oil and remove undesirable byproducts from the pyrolysis oil. The resulting hydroprocessed pyrolysis oil vapor stream 144 may be removed and introduced into the quench unit 138. Alternatively, the pyrolysis oil vapor may be cooled, liquified, and then treated with hydrogen and/or other reducing gases to further saturate the hydrocarbons in the pyrolysis oil. In this case, the hydrogenation or hydrotreating is performed in a liquid phase pyrolysis oil. No quench step is required in this embodiment post-hydrogenation or post-hydrotreating.

The pyrolysis system 110 described herein may produce a pyrolysis oil (e.g., r-pyoil) and pyrolysis gases (e.g., r-pyrolysis gas) that may be directly used in various downstream applications based on their desirable formulations. The various characteristics and properties of the pyrolysis oils and pyrolysis gases are described below. It should be noted that, while all of the following characteristics and properties may be listed separately, it is envisioned that each of the following characteristics and/or properties of the pyrolysis oils or pyrolysis gases are not mutually exclusive and may be combined and present in any combination.

The pyrolysis oil may predominantly comprise hydrocarbons having from 4 to 30 carbon atoms per molecule (e.g., C4 to C30 hydrocarbons). As used herein, the term "Cx" or "Cx hydrocarbon," refers to a hydrocarbon compound including x total carbons per molecule, and encompasses all olefins, paraffins, aromatics, and isomers having that number of carbon atoms. For example, each of normal, iso, and tert butane and butene and butadiene molecules would fall under the general description "C4."

In an embodiment or in combination with any of the embodiments mentioned herein, the pyrolysis oil fed to the cracking furnace may have a $C_4$-$C_{30}$ hydrocarbon content of at least 55, or at least 60, or at least 65, or at least 70, or at least 75, or at least 80, or at least 85, or at least 90, or at least 95, in each case weight percent based on the weight of the pyrolysis oil.

In an embodiment or in combination with any of the embodiments mentioned herein, the pyrolysis oil fed to the furnace can predominantly comprise $C_5$-$C_{25}$, $C_5$-$C_{22}$, or $C_5$-$C_{20}$hydrocarbons, or may comprise at least about 55, or at least 60, or at least 65, or at least 70, or at least 75, or at least 80, or at least 85, or at least 90, or at least 95, in each case weight percent of $C_5$-$C_{25}$, $C_5$-$C_{22}$, or $C_5$-$C_{20}$hydrocarbons, based on the weight of the pyrolysis oil.

The gas furnace can tolerate a wide variety of hydrocarbon numbers in the pyrolysis oil feedstock, thereby avoiding the necessity for subjecting a pyrolysis oil feedstock to separation techniques to deliver a smaller or lighter hydrocarbon cut to the cracker furnace. In one embodiment or in any of the mentioned embodiments, the pyrolysis oil after delivery from a pyrolysis manufacturer is not subjected a separation process for separating a heavy hydrocarbon cut from a lighter hydrocarbon cut, relative to each other, prior to feeding the pyrolysis oil to a cracker furnace. The feed of pyrolysis oil to a gas furnace allows one to employ a pyrolysis oil that contains heavy tail ends or higher carbon numbers at or above 12. In one embodiment or in any of the mentioned embodiments, the pyrolysis oil fed to a cracker furnace is a $C_5$ to $C_{25}$ hydrocarbon stream containing at least 3 wt. %, or at least 5 wt. %, or at least 8 wt. %, or at least 10 wt. %, or at least 12 wt. %, or at least 15 wt. %, or at least 18 wt. %, or at least 20 wt. %, or at least 25 wt. % or at least 30 wt. %, or at least 35 wt. %, or at least 40 wt. %, or at least 45 wt. %, or at least 50 wt. %, or at least 55 wt. %, or at least 60 wt. % hydrocarbons within a range from $C_{12}$ to $C_{25}$, inclusive, or within a range of $C_{14}$ to $C_{25}$, inclusive, or within a range of $C_{16}$ to $C_{25}$, inclusive.

In an embodiment or in combination with any of the embodiments mentioned herein, the pyrolysis oil may have a $C_6$ to $C_{12}$ hydrocarbon content of at least 10, or at least 15, or at least 20, or at least 25, or at least 30, or at least 35, or at least 40, or at least 45, or at least 50, or at least 55, in each case weight percent, based on the weight of the pyrolysis oil. Additionally, or alternatively, in an embodiment or in combination with any of the embodiments mentioned herein, the pyrolysis oil may have a $C_6$-$C_{12}$ hydrocarbon content of not more than 95, or not more than 90, or not more than 85, or not more than 80, or not more than 75, or not more than 70, or not more than 65, or not more than 60, in each case weight percent. In an embodiment or in combination with any of the embodiments mentioned herein, the pyrolysis oil may have a $C_6$-$C_{12}$ hydrocarbon content in the range of 10 to 95 weight percent, 20 to 80 weight percent, or 35 to 80 weight percent.

In an embodiment or in combination with any of the embodiments mentioned herein, the pyrolysis oil may have a $C_{13}$ to $C_{23}$ hydrocarbon content of at least 1, or at least 5, or at least 10, or at least 15, or at least 20, or at least 25, or at least 30, in each case weight percent. Additionally, or alternatively, in an embodiment or in combination with any of the embodiments mentioned herein, the pyrolysis oil may have a $C_{13}$ to $C_{23}$ hydrocarbon content of not more than 80, or not more than 75, or not more than 70, or not more than 65, or not more than 60, or not more than 55, or not more than 50, or not more than 45, or not more than 40, in each case weight percent. In an embodiment or in combination with any of the embodiments mentioned herein, the pyrolysis oil may have a $C_{13}$ to $C_{23}$ hydrocarbon content in the range of 1 to 80 weight percent, 5 to 65 weight percent, or 10 to 60 weight percent.

In an embodiment or in combination with any of the embodiments mentioned herein, the r-pyrolysis oil, or r-pyoil fed to a cracker furnace, or r-pyoil fed to a cracker furnace that, prior to feeding-pyoil, accepts a predominately $C_2$-$C_4$ feedstock (and the mention of r-pyoil or pyrolysis oil throughout includes any of these embodiments), may have a $C_{24+}$ hydrocarbon content of at least 1, or at least 2, or at least 3, or at least 4, or at least 5, in each case weight percent. Additionally, or alternatively, in an embodiment or in combination with any of the embodiments mentioned herein, the pyrolysis oil may have a $C_{24+}$ hydrocarbon content of not more than 15, or not more than 10, or not more than 9, or not more than 8, or not more than 7, or not more than 6, in each case weight percent. In an embodiment or in combination with any of the embodiments mentioned herein, the pyrolysis oil may have a $C_{24+}$ hydrocarbon content in the range of 1 to 15 weight percent, 3 to 15 weight percent, 2 to 5 weight percent, or 5 to 10 weight percent.

The pyrolysis oil may also include various amounts of olefins, aromatics, and other compounds. In an embodiment or in combination with any of the embodiments mentioned herein, the pyrolysis oil includes at least 1, or at least 2, or at least 5, or at least 10, or at least 15, or at least 20, in each case weight percent olefins and/or aromatics. Additionally, or alternatively, in an embodiment or in combination with any of the embodiments mentioned herein, the pyrolysis oil may include not more than 50, or not more than 45, or not more than 40, or not more than 35, or not more than 30, or not more than 25, or not more than 20, or not more than 15, or not more than 10, or not more than 5, or not more than 2, or not more than 1, in each case weight percent olefins and/or aromatics.

In an embodiment or in combination with any of the embodiments mentioned herein, the pyrolysis oil may have an aromatic content of not more than 25, or not more than 20, or not more than 15, or not more than 14, or not more than 13, or not more than 12, or not more than 11, or not more than 10, or not more than 9, or not more than 8, or not more than 7, or not more than 6, or not more than 5, or not more than 4, or not more than 3, or not more than 2, or not more than 1, in each case weight percent. In one embodiment or in combination with any mentioned embodiments, the pyrolysis oil has an aromatic content that is not higher than 15, or not more than 10, or not more than 8, or not more than 6, in each case weight percent.

In an embodiment or in combination with any of the embodiments mentioned herein, the pyrolysis oil may have a naphthene content of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, in each case weight percent. Additionally, or alternatively, in an embodiment or in combination with any of the embodiments mentioned herein, the pyrolysis oil may have a naphthene content of not more than 50, or not more than 45, or not more than 40, or not more than 35, or not more than 30, or not more than 25, or not more than 20, or not more than 10, or not more than 5, or not more than 2, or not more than 1, or not more than 0.5, or no detectable amount, in each case weight percent. In an embodiment or in combination with any of the embodiments mentioned herein, the pyrolysis oil may have a naphthene content of not more than 5, or not more than 2, or not more than 1 wt. %, or no detectable amount, or naphthenes. Alternatively, the pyrolysis oil may contain in the range of 1 to 50 weight percent, 5 to 50 weight percent, or 10 to 45 weight percent naphthenes, especially if the r-pyoil was subjected to a hydrotreating process.

In an embodiment or in combination with any of the embodiments mentioned herein, the pyrolysis oil may have a paraffin content of at least 25, or at least 30, or at least 35, or at least 40, or at least 45, or at least 50, in each case weight percent. Additionally, or alternatively, in an embodiment or in combination with any of the embodiments mentioned herein, the pyrolysis oil may have a paraffin content of not more than 90, or not more than 85, or not more than 80, or not more than 75, or not more than 70, or not more than 65, or not more than 60, or not more than 55, in each case weight percent. In an embodiment or in combination with any of the embodiments mentioned herein, the pyrolysis oil may have a paraffin content in the range of 25 to 90 weight percent, 35 to 90 weight percent, or 40 to 80, or 40-70, or 40-65 weight percent.

In an embodiment or in combination with any of the embodiments mentioned herein, the pyrolysis oil may have an n-paraffin content of at least 5, or at least 10, or at least 15, or at least 25, or at least 30, or at least 35, or at least 40, or at least 45, or at least 50, in each case weight percent. Additionally, or alternatively, in an embodiment or in combination with any of the embodiments mentioned herein, the pyrolysis oil may have an n-paraffin content of not more than 90, or not more than 85, or not more than 80, or not more than 75, or not more than 70, or not more than 65, or not more than 60, or not more than 55, in each case weight percent. In an embodiment or in combination with any of the embodiments mentioned herein, the pyrolysis oil may have an n-paraffin content in the range of 25 to 90 weight percent, 35 to 90 weight percent, or 40-70, or 40-65, or 50 to 80 weight percent.

In an embodiment or in combination with any of the embodiments mentioned herein, the pyrolysis oil may have a paraffin to olefin weight ratio of at least 0.2:1, or at least 0.3:1, or at least 0.4:1, or at least 0.5:1, or at least 0.6:1, or at least 0.7:1, or at least 0.8:1, or at least 0.9:1, or at least 1:1. Additionally, or alternatively, in an embodiment or in combination with any of the embodiments mentioned herein, the pyrolysis oil may have a paraffin to olefin weight ratio not more than 3:1, or not more than 2.5:1, or not more than 2:1, or not more than 1.5:1, or not more than 1.4:1, or not more than 1.3:1. In an embodiment or in combination with any of the embodiments mentioned herein, the pyrolysis oil may have a paraffin to olefin weight ratio in the range of 0.2:1 to 5:1, or 1:1 to 4.5:1, or 1.5:1 to 5:1, or 1.5:1:4.5:1, or 0.2:1 to 4:1, or 0.2:1 to 3:1, 0.5:1 to 3:1, or 1:1 to 3:1.

In an embodiment or in combination with any of the embodiments mentioned herein, the pyrolysis oil may have an n-paraffin to i-paraffin weight ratio of at least 0.001:1, or at least 0.1:1, or at least 0.2:1, or at least 0.5:1, or at least 1:1, or at least 2:1, or at least 3:1, or at least 4:1, or at least 5:1, or at least 6:1, or at least 7:1, or at least 8:1, or at least 9:1, or at least 10:1, or at least 15:1, or at least 20:1. Additionally, or alternatively, in an embodiment or in combination with any of the embodiments mentioned herein, the pyrolysis oil may have an n-paraffin to i-paraffin weight ratio of not more than 100:1, 7 or not more than 5:1, or not more than 50:1, or not more than 40:1, or not more than 30:1. In an embodiment or in combination with any of the embodiments mentioned herein, the pyrolysis oil may have an n-paraffin to i-paraffin weight ratio in the range of 1:1 to 100:1, 4:1 to 100:1, or 15:1 to 100:1.

It should be noted that all of the above-referenced hydrocarbon weight percentages may be determined using gas chromatography-mass spectrometry (GC-MS).

In an embodiment or in combination with any of the embodiments mentioned herein, the pyrolysis oil may exhibit a density at 15° C. of at least 0.6 g/cm$^3$, or at least 0.65 g/cm$^3$, or at least 0.7 g/cm$^3$. Additionally, or alternatively, in an embodiment or in combination with any of the embodiments mentioned herein, the pyrolysis oil may exhibit a density at 15° C. of not more than 1 g/cm$^3$, or not more than 0.95 g/cm$^3$, or not more than 0.9 g/cm$^3$, or not more than 0.85 g/cm$^3$. In an embodiment or in combination with any of the embodiments mentioned herein, the pyrolysis oil exhibits a density at 15° C. at a range of 0.6 to 1 g/cm$^3$, 0.65 to 0.95 g/cm$^3$, or 0.7 to 0.9 g/cm$^3$.

In an embodiment or in combination with any of the embodiments mentioned herein, the pyrolysis oil may exhibit an API gravity at 15° C. of at least 28, or at least 29, or at least 30, or at least 31, or at least 32, or at least 33. Additionally, or alternatively, in an embodiment or in combination with any of the embodiments mentioned herein, the pyrolysis oil may exhibit an API gravity at 15° C. of not more than 50, or not more than 49, or not more than 48, or not more than 47, or not more than 46, or not more than 45, or not more than 44. In an embodiment or in combination with any of the embodiments mentioned herein, the pyrolysis oil exhibits an API gravity at 15° C. at a range of 28 to 50, 29 to 58, or 30 to 44.

In an embodiment or in combination with any of the embodiments mentioned herein, the pyrolysis oil may have a mid-boiling point of at least 75° C., or at least 80° C., or at least 85° C., or at least 90° C., or at least 95° C., or at least 100° C., or at least 105° C., or at least 110° C., or at least 115° C. The values can be measured according to the procedures described in either according to ASTM D-2887, or in the working examples. A mid-boiling point having the stated value are satisfied if the value is obtained under either method. Additionally, or alternatively, in an embodiment or in combination with any of the embodiments mentioned herein, the pyrolysis oil may have a mid-boiling point of not more than 250° C., or not more than 245° C., or not more than 240° C., or not more than 235° C., or not more than 230° C., or not more than 225° C., or not more than 220° C., or not more than 215° C., or not more than 210° C., or not more than 205° C., or not more than 200° C., or not more than 195° C., or not more than 190° C., or not more than 185° C., or not more than 180° C., or not more than 175° C., or not more than 170° C., or not more than 165° C., or not more than 160° C., 1 or not more than 55° C., or not more than 150° C., or not more than 145° C., or not more than 140° C., or not more than 135° C., or not more than 130° C., or not more than 125° C., or not more than 120° C. The values can be measured according to the procedures described in either according to ASTM D-2887, or in the working examples. A mid-boiling point having the stated value are satisfied if the value is obtained under either method. In an embodiment or in combination with any of the embodiments mentioned herein, the pyrolysis oil may have a mid-boiling point in the range of 75 to 250° C., 90 to 225° C., or 115 to 190° C. As used herein, "mid-boiling point" refers to the median boiling point temperature of the pyrolysis oil when 50 weight percent of the pyrolysis oil boils above the mid-boiling point and 50 weight percent boils below the mid-boiling point.

In an embodiment or in combination with any of the embodiments mentioned herein, the boiling point range of the pyrolysis oil may be such that not more than 10 percent of the pyrolysis oil has a final boiling point (FBP) of 250° C., 280° C., 290° C., 300° C., or 310° C., to determine the FBP, the procedures described in either according to ASTM D-2887, or in the working examples, can be employed and a FBP having the stated values are satisfied if the value is obtained under either method.

Turning to the pyrolysis gas, the pyrolysis gas can have a methane content of at least 1, or at least 2, or at least 5, or at least 10, or at least 11, or at least 12, or at least 13, or at least 14, or at least 15, or at least 16, or at least 17, or at least 18, or at least 19, or at least 20 weight percent. Additionally, or alternatively, in an embodiment or in combination with any of the embodiments mentioned herein, the pyrolysis gas can have a methane content of not more than 50, or not more than 45, or not more than 40, or not more than 35, or not more than 30, or not more than 25, in each case weight percent. In an embodiment or in combination with any of the embodiments mentioned herein, the pyrolysis gas can have a methane content in the range of 1 to 50 weight percent, 5 to 50 weight percent, or 15 to 45 weight percent.

In an embodiment or in combination with any of the embodiments mentioned herein, the pyrolysis gas can have a C3 hydrocarbon content of at least 1, or at least 2, or at least 3, or at least 4, or at least 5, or at least 6, or at least 7, or at least 8, or at least 9, or at least 10, or at least 15, or at least 20, or at least 25, in each case weight percent. Additionally, or alternatively, in an embodiment or in combination with any of the embodiments mentioned herein, the pyrolysis gas can have a C3 hydrocarbon content of not more than 50, or not more than 45, or not more than 40, or not more than 35, or not more than 30, in each case weight percent. In an embodiment or in combination with any of the embodiments mentioned herein, the pyrolysis gas can have a C3 hydrocarbon content in the range of 1 to 50 weight percent, 5 to 50 weight percent, or 20 to 50 weight percent.

In an embodiment or in combination with any of the embodiments mentioned herein, the pyrolysis gas can have a C4 hydrocarbon content of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, in each case weight percent. Additionally, or alternatively, in an embodiment or in combination with any of the embodiments mentioned herein, the pyrolysis gas can have a C4 hydrocarbon content of not more than 50, or not more than 45, or not more than 40, or not more than 35, or not more than 30, or not more than 25, in each case weight percent.

In an embodiment or in combination with any of the embodiments mentioned herein, the pyrolysis gas can have a C4 hydrocarbon content in the range of 1 to 50 weight percent, 5 to 50 weight percent, or 20 to 50 weight percent.

In an embodiment or in combination with any of the embodiments mentioned herein, the pyrolysis oils of the present invention may be a recycle content pyrolysis oil composition (r-pyoil).

Various downstream applications that may utilize the above-disclosed pyrolysis oils and/or the pyrolysis gases are described in greater detail below. In an embodiment or in combination with any of the embodiments mentioned herein, the pyrolysis oil may be subjected to one or more treatment steps prior to being introduced into downstream units, such as a cracking furnace. Examples of suitable treatment steps can include, but are not limited to, separation of less desirable components (e.g., nitrogen-containing compounds, oxygenates, and/or olefins and aromatics), distillation to provide specific pyrolysis oil compositions, and preheating.

Figure 3:
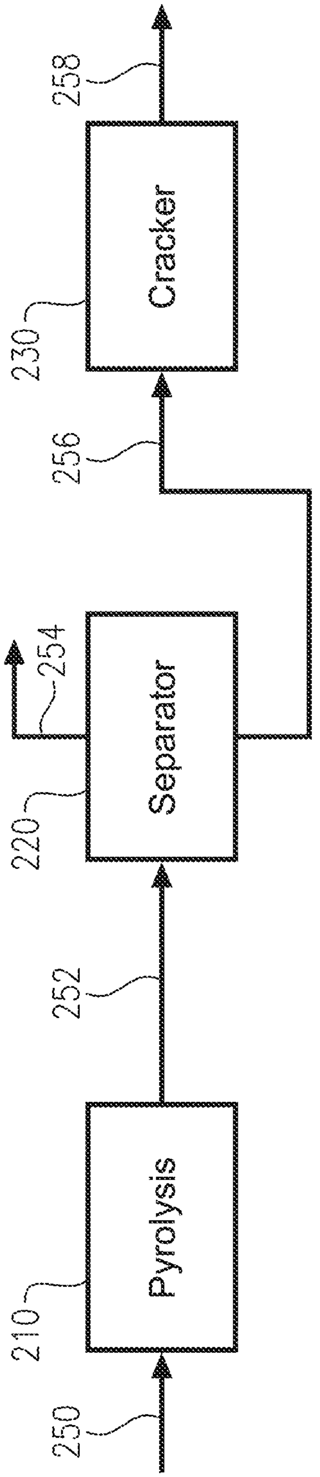
FIG. 3 is a schematic depiction of pyrolysis treatment through production of olefin containing products.

Turning now to FIG. 3, a schematic depiction of a treatment zone for pyrolysis oil according to an embodiment or in combination with any of the embodiments mentioned herein is shown.

As shown in the treatment zone 220 illustrated in FIG. 3, at least a portion of the r-pyoil 252 made from a recycle waste stream 250 in the pyrolysis system 210 may be passed through a treatment zone 220 such as, for example, a separator, which may separate the r-pyoil into a light pyrolysis oil fraction 254 and a heavy pyrolysis oil fraction 256. The separator 220 employed for such a separation can be of any suitable type, including a single-stage vapor liquid separator or "flash" column, or a multi-stage distillation column. The vessel may or may not include internals and may or may not employ a reflux and/or boil-up stream.

In an embodiment or in combination with any of the embodiments mentioned herein, the heavy fraction may have a C4 to C7 content or a C8+ content of at least 10, 15, 20, 25, 30, 35, 40, 45, 50, 55, 60, 65, 70, 75, 80, or 85 weight percent. The light fraction may include at least about 10, 15, 20, 25, 30, 35, 40, 45, 50, 55, 60, 65, 70, 75, 80, or 85 percent of C3 and lighter (C3−) or C7 and lighter (C7−) content. In some embodiments, separator may concentrate desired components into the heavy fraction, such that the heavy fraction may have a C4 to C7 content or a C8+ content that is at least 10, 15, 20, 25, 30, 35, 40, 45, 50, 55, 60, 65, 70, 7, 80, 85, 90, 95, 100, 105, 110, 115, 120, 125, 130, 135, 140, 145, or 150% greater than the $C_4$ to $C_7$ content or the $C_{8+}$ content of the pyrolysis oil withdrawn from the pyrolysis zone. As shown in FIG. 3, at least a portion of the heavy fraction may be sent to the cracking furnace 230 for cracking as or as part of the r-pyoil composition to form an olefin-containing effluent 258, as discussed in further detail below.

In an embodiment or in combination with any of the embodiments mentioned herein, the pyrolysis oil is hydrotreated in a treatment zone, while, in other embodiments, the pyrolysis oil is not hydrotreated prior to entering downstream units, such as a cracking furnace. In an embodiment or in combination with any of the embodiments mentioned herein, the pyrolysis oil is not pretreated at all before any downstream applications and may be sent directly from the pyrolysis oil source. The temperature of the pyrolysis oil exiting the pre-treatment zone can be in the range of 15 to 55° C., 30 to 55° C., 49 to 40° C., 15 to 50° C., 20 to 45° C., or 25 to 40° C.

In an embodiment or in combination with any of the embodiments mentioned herein, the r-pyoil may be combined with the non-recycle cracker stream in order to minimize the amount of less desirable compounds present in the combined cracker feed. For example, when the r-pyoil has a concentration of less desirable compounds (such as, for example, impurities like oxygen-containing compounds, aromatics, or others described herein), the r-pyoil may be combined with a cracker feedstock in an amount such that the total concentration of the less desirable compound in the combined stream is at least 40, 50, 55, 60, 65, 70, 75, 80, 85, 90, or 95 percent less than the original content of the compound in the r-pyoil stream (calculated as the difference between the r-pyoil and combined streams, divided by the r-pyoil content, expressed as a percentage). In some cases, the amount of non-recycle cracker feed to combine with the r-pyoil stream may be determined by comparing the measured amount of the one or more less desirable compounds present in the r-pyoil with a target value for the compound or compounds to determine a difference and, then, based on that difference, determining the amount of non-recycle hydrocarbon to add to the r-pyoil stream. The amounts of r-pyoil and non-recycle hydrocarbon can be within one or more ranges described herein.

At least a portion of the r-ethylene can be derived directly or indirectly from the cracking of r-pyoil. The process for obtaining r-olefins from cracking (r-pyoil) can be as follows and as described in FIG. 4.

Figure 4:
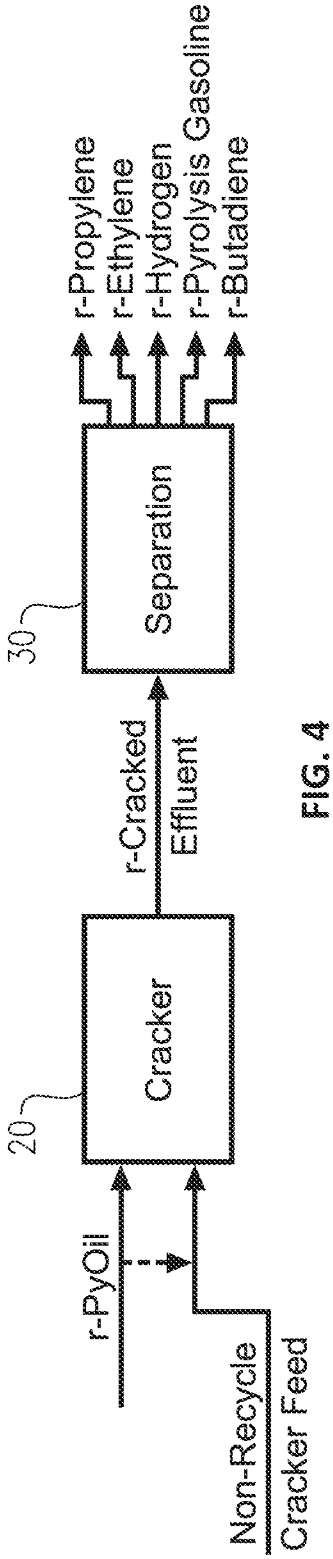
FIG. 4 is a block flow diagram illustrating steps associated with the cracking furnace and separation zones of a system for producing an r-composition obtained from cracking r-pyoil and non-recycle cracker feed.

Turning now to FIG. 4, a block flow diagram illustrating steps associated with the cracking furnace 20 and separation zones 30 of a system for producing an r-composition obtained from cracking r-pyoil. As shown in FIG. 4, a feed stream comprising r-pyoil (the r-pyoil containing feed stream) may be introduced into a cracking furnace 20, alone or in combination with a non-recycle cracker feed stream. A pyrolysis unit producing r-pyoil can be co-located with the production facility. In other embodiments, the r-pyoil can be sourced from a remote pyrolysis unit and transported to the production facility.

In an embodiment or in combination with any of the embodiments mentioned herein, the r-pyoil containing feed stream may contain r-pyoil in an amount of at least 1, or at least 5, or at least 10, or at least 15, or at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, or at least 97, or at least 98, or at least 99, or at least or 100, in each case weight percent and/or not more than 95, or not more than 90, or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, in each case weight percent, based on the total weight of the r-pyoil containing feed stream.

In an embodiment or in combination with any of the embodiments mentioned herein, at least 1, or at least 5, or at least 10, or at least 15, or at least 20, or at least 25, or at least 30, or at least 35, or at least 40, or at least 45, or at least 50, or at least 55, or at least 60, or at least 65, or at least 70, or at least 75, or at least 80, or at least 85, or at least 90 or at least 97, or at least 98, or at least 99, or 100, in each case weight percent and/or not more than 95, or not more than 90, or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15 or not more than 10, in each case weight percent of the r-pyoil is obtained from the pyrolysis of a waste stream. In an embodiment or in combination with any of the embodiments mentioned herein, at least a portion of the r-pyoil is obtained from pyrolysis of a feedstock comprising plastic waste. Desirably, at least 90, or at least 95, or at least 97, or at least 98, or at least 99, or at least or 100, in each case wt. %, of the r-pyoil is obtained from pyrolysis of a feedstock comprising plastic waste, or a feedstock comprising at least 50 wt. % plastic waste, or a feedstock comprising at least 80 wt. % plastic waste, or a feedstock comprising at least 90 wt. % plastic waste, or a feedstock comprising at least 95 wt. % plastic waste.

In an embodiment or in combination with any of the embodiments mentioned herein, the r-pyoil can have any one or combination of the compositional characteristics described above with respect to pyrolysis oil.

In an embodiment or in combination with any of the embodiments mentioned herein, the r-pyoil may comprise at least 55, or at least 60, or at least 65, or at least 70, or at least 75, or at least 80, or at least 85, or at least 90, or at least 95, in each case weight percent of C4-C30 hydrocarbons, and as used herein, hydrocarbons include aliphatic, cycloaliphatic, aromatic, and heterocyclic compounds. In an embodiment or in combination with any of the embodiments mentioned herein, the r-pyoil can predominantly comprise C5-C25, C5-C22, or C5-C20 hydrocarbons, or may comprise at least 55, 60, 65, 70, 75, 80, 85, 90, or 95 weight percent of C5-C25, C5-C22, or C5-C20 hydrocarbons.

In an embodiment or in combination with any embodiment mentioned herein, the r-pyoil composition can comprise C4-C12 aliphatic compounds (branched or unbranched alkanes and alkenes including diolefins, and alicyclics) and C13-C22 aliphatic compounds in a weight ratio of more than 1:1, or at least 1.25:1, or at least 1.5:1, or at least 2:1, or at least 2.5:1, or at least 3:1, or at least 4:1, or at least 5:1, or at least 6:1, or at least 7:1, 10:1, 20:1, or at least 40:1, each by weight and based on the weight of the r-pyoil.

In an embodiment or in combination with any embodiment mentioned herein, the r-pyoil composition can comprise $C_{13}$-$C_{22}$ aliphatic compounds (branched or unbranched alkanes and alkenes including diolefins, and alicyclics) and $C_4$-$C_{12}$ aliphatic compounds in a weight ratio of more than 1:1, or at least 1.25:1, or at least 1.5:1, or at least 2:1, or at least 2.5:1, or at least 3:1, or at least 4:1, or at least 5:1, or at least 6:1, or at least 7:1, 10:1, 20:1, or at least 40:1, each by weight and based on the weight of the r-pyoil.

In an embodiment, the two aliphatic hydrocarbons (branched or unbranched alkanes and alkenes, and alicyclics) having the highest concentration in the r-pyoil are in a range of C5-C18, or C5-C16, or C5-C14, or C5-C10, or C5-C8, inclusive.

The r-pyoil can include one or more of paraffins, naphthenes or cyclic aliphatic hydrocarbons, aromatics, aromatic containing compounds, olefins, oxygenated compounds and polymers, heteroatom compounds or polymers, and other compounds or polymers.

For example, in an embodiment or in combination with any of the embodiments mentioned herein, the r-pyoil may comprise at least 5, or at least 10, or at least 15, or at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, in each case weight percent and/or not more than 99, or not more than 97, or not more than 95, or not more than 93, or not more than 90, or not more than 87, or not more than 85, or not more than 83, or not more than 80, or not more than 78, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15, in each case weight percent of paraffins (or linear or branched alkanes), based on the total weight of the r-pyoil. In an embodiment or in combination with any of the embodiments mentioned herein, the pyrolysis oil may have a paraffin content in the range of 25 to 90, 35 to 90, or 40 to 80, or 40-70, or 40-65 weight percent, or 5-50, or 5 to 40, or 5 to 35, or 10- to 35, or 10 to 30, or 5 to 25, or 5 to 20, in each case as wt. % based on the weight of the r-pyoil composition.

In an embodiment or in combination with any of the embodiments mentioned herein, the r-pyoil can include naphthenes or cyclic aliphatic hydrocarbons in amount of zero, or at least 1, or at least 2, or at least 5, or at least 8, or at least 10, or at least 15, or at least 20, in each case weight percent and/or not more than 50, or not more than 45, or not more than 40, or not more than 35, or not more than 30, or not more than 25, or not more than 20, or not more than 15, or not more than 10, or not more than 5, or not more than 2, or not more than 1, or not more than 0.5, or no detectable amount, in each case weight percent. In an embodiment or in combination with any of the embodiments mentioned herein, the r-pyoil may have a naphthene content of not more than 5, or not more than 2, or not more than 1 wt. %, or no detectable amount, or naphthenes. Examples of ranges for the amount of naphthenes (or cyclic aliphatic hydrocarbons) contained in the r-pyoil is from 0-35, or 0-30, or 0-25, or 2-20, or 2-15, or 2-10, or 1-10, in each case as wt. % based on the weight of the r-pyoil composition.

In an embodiment or in combination with any of the embodiments mentioned herein, the r-pyoil may have a paraffin to olefin weight ratio of at least 0.2:1, or at least 0.3:1, or at least 0.4:1, or at least 0.5:1, or at least 0.6:1, or at least 0.7:1, or at least 0.8:1, or at least 0.9:1, or at least 1:1. Additionally, or alternatively, in an embodiment or in combination with any of the embodiments mentioned herein, the r-pyoil may have a paraffin to olefin weight ratio not more than 3:1, or not more than 2.5:1, or not more than 2:1, or not more than 1.5:1, or not more than 1.4:1, or not more than 1.3:1. In an embodiment or in combination with any of the embodiments mentioned herein, the r-pyoil may have a paraffin to olefin weight ratio in the range of 0.2:1 to 5:1, or 1:1 to 4.5:1, or 1.5:1 to 5:1, or 1.5:1:4.5:1, or 0.2:1 to 4:1, or 0.2:1 to 3:1, 0.5:1 to 3:1, or 1:1 to 3:1.

In an embodiment or in combination with any of the embodiments mentioned herein, the r-pyoil may have an n-paraffin to i-paraffin weight ratio of at least 0.001:1, or at least 0.1:1, or at least 0.2:1, or at least 0.5:1, or at least 1:1, or at least 2:1, or at least 3:1, or at least 4:1, or at least 5:1, or at least 6:1, or at least 7:1, or at least 8:1, or at least 9:1, or at least 10:1, or at least 15:1, or at least 20:1. Additionally, or alternatively, in an embodiment or in combination with any of the embodiments mentioned herein, the r-pyoil may have an n-paraffin to i-paraffin weight ratio of not more than 100:1, or not more than 50:1, or not more than 40:1, or not more than 30:1. In an embodiment or in combination with any of the embodiments mentioned herein, the r-pyoil may have an n-paraffin to i-paraffin weight ratio in the range of 1:1 to 100:1, 4:1 to 100:1, or 15:1 to 100:1.

In an embodiment, the r-pyoil comprises not more than 30, or not more than 25, or not more than 20, or not more than 15, or not more than 10, or not more than 8, or not more than 5, or not more than 2, or not more than 1, in each case weight percent of aromatics, based on the total weight of the r-pyoil. As used herein, the term "aromatics" refers to the total amount (in weight) of benzene, toluene, xylene, and styrene. The r-pyoil may include at least 1, or at least 2, or at least 5, or at least 8, or at least 10, in each case weight percent of aromatics, based on the total weight of the r-pyoil.

In an embodiment or in combination with any of the embodiments mentioned herein, the r-pyoil can include aromatic containing compounds in an amount of not more than 30, or not more than 25, or not more than 20, or not more than 15, or not more than 10, or not more than 8, or not more than 5, or not more than 2, or not more than 1, in each case weight, or not detectable, based on the total weight of the r-pyoil. Aromatic containing compounds includes the above-mentioned aromatics and any compounds containing an aromatic moiety, such as terephthalate residues and fused ring aromatics such as the naphthalenes and tetrahydronaphthalene.

In an embodiment or in combination with any of the embodiments mentioned herein, the r-pyoil can include olefins in amount of at least 1, or at least 2, or at least 5, or at least 8, or at least 10, or at least 15, or at least 20, or at least 30, or at least 40, or at least 45, or at least 50, or at least 55, or at least 60, or at least or at least 65, in each case weight percent olefins and/or not more than 85, or not more than 80, or not more than 75, or not more than 70, or not more than 65, or not more than 60, or not more than 55, or not more than 50, or not more than 45, or not more than 40, or not more than 35, or not more than 30, or not more than 25, or not more than 20, or not more than 15, or not more than 10, in each case weight percent, based on the weight of a r-pyoil. Olefins include mono- and di-olefins. Examples of suitable ranges include olefins present in an amount ranging from 5 to 45, or 10-35, or 15 to 30, or 40-85, or 45-85, or 50-85, or 55-85, or 60-85, or 65-85, or 40-80, or 45-80, or 50-80, or 55-80, or 60-80, or 65-80, 45-80, or 50-80, or 55-80, or 60-80, or 65-80, or 40-75, or 45-75, or 50-75, or 55-75, or 60-75, or 65-75, or 40-70, or 45-70, or 50-70, or 55-70, or 60-70, or 65-70, or 40-65, or 45-65, or 50-65, or 55-65, in each case as wt. % based on the weight of the r-pyoil.

In an embodiment or in combination with any of the embodiments mentioned herein, the r-pyoil can include oxygenated compounds or polymers in amount of zero or at least 0.01, or at least 0.1, or at least 1, or at least 2, or at least 5, in each case weight percent and/or not more than 20, or not more than 15, or not more than 10, or not more than 8, or not more than 6, or not more than 5, or not more than 3, or not more than 2, in each case weight percent oxygenated compounds or polymers, based on the weight of a r-pyoil. Oxygenated compounds and polymers are those containing an oxygen atom. Examples of suitable ranges include oxygenated compounds present in an amount ranging from 0-20, or 0-15, or 0-10, or 0.01-10, or 1-10, or 2-10, or 0.01-8, or 0.1-6, or 1-6, or 0.01-5, in each case as wt. % based on the weight of the r-pyoil.

In an embodiment or in combination with any embodiment mentioned herein, the amount of oxygen atoms in the r-pyoil can be not more than 10, or not more than 8, or not more than 5, or not more than 4, or not more than 3, or not more than 2.75, or not more than 2.5, or not more than 2.25, or not more than 2, or not more than 1.75, or not more than 1.5, or not more than 1.25, or not more than 1, or not more than 0.75, or not more than 0.5, or not more than 0.25, or not more than 0.1, or not more than 0.05, in each case wt. %, based on the weight of the r-pyoil. Examples of the amount of oxygen in the r-pyoil can be from 0-8, or 0-5, or 0-3, or 0-2.5 or 0-2, or 0.001-5, or 0.001-4, or 0.001-3, or 0.001-

2.75, or 0.001-2.5, or 0.001-2, or 0.001-1.5, or 0.001-1, or 0.001-0.5, or 0.001-0.1, in each case as wt. % based on the weight of the r-pyoil.

In an embodiment or in combination with any of the embodiments mentioned herein, the r-pyoil can include heteroatom compounds or polymers in amount of at least 1, or at least 2, or at least 5, or at least 8, or at least 10, or at least 15, or at least 20, in each case weight percent and/or not more than 25, or not more than 20, or not more than 15, or not more than 10, or not more than 8, or not more than 6, or not more than 5, or not more than 3, or not more than 2, in each case weight percent, based on the weight of a r-pyoil. A heterocompound or polymer is defined in this paragraph as any compound or polymer containing nitrogen, sulfur, or phosphorus. Any other atom is not regarded as a heteroatom for purposes of determining the quantity of heteroatoms, heterocompounds, or heteropolymers present in the r-pyoil. The r-pyoil can contain heteroatoms present in an amount of not more than 5, or not more than 4, or not more than 3, or not more than 2.75, or not more than 2.5, or not more than 2.25, or not more than 2, or not more than 1.75, or not more than 1.5, or not more than 1.25, or not more than 1, or not more than 0.75, or not more than 0.5, or not more than 0.25, or not more than 0.1, or not more than 0.075, or not more than 0.05, or not more than 0.03, or not more than 0.02, or not more than 0.01, or not more than 0.008, or not more than 0.006, or not more than 0.005, or not more than 0.003, or not more than 0.002, in each case wt. %, based on the weight of the r-pyoil.

In an embodiment or in combination with any embodiment mentioned herein or in combination with any of the embodiments mentioned herein, the solubility of water in the r-pyoil at 1 atm and 25° C. is less than 2 wt. %, water, or not more than 1.5, or not more than 1, or not more than 0.5, or not more than 0.1, or not more than 0.075, or not more than 0.05, or not more than 0.025, or not more than 0.01, or not more than 0.005, in each case wt. % water based on the weight of the r-pyoil. Desirably, the solubility of water in the r-pyoil is not more than 0.1 wt. % based on the weight of the r-pyoil. In an embodiment or in combination with any embodiment mentioned herein or in combination with any of the embodiments mentioned herein, the r-pyoil contains not more than 2 wt. %, water, or not more than 1.5, or not more than 1, or not more than 0.5, desirably or not more than 0.1, or not more than 0.075, or not more than 0.05, or not more than 0.025, or not more than 0.01, or not more than 0.005, in each case wt. % water based on the weight of the r-pyoil.

In an embodiment or in combination with any embodiment mentioned herein or in combination with any of the embodiments mentioned herein, the solids content in the r-pyoil does not exceed 1, or is not more than 0.75, or not more than 0.5, or not more than 0.25, or not more than 0.2, or not more than 0.15, or not more than 0.1, or not more than 0.05, or not more than 0.025, or not more than 0.01, or not more than 0.005, or does not exceed 0.001, in each case wt. % solids based on the weight of the r-pyoil.

In an embodiment or in combination with any embodiment mentioned herein or in combination with any of the embodiments mentioned herein the sulfur content of the r-pyoil does not exceed 2.5 wt. %, or is not more than 2, or not more than 1.75, or not more than 1.5, or not more than 1.25, or not more than 1, or not more than 0.75, or not more than 0.5, or not more than 0.25, or not more than 0.1, or not more than 0.05, desirably or not more than 0.03, or not more than 0.02, or not more than 0.01, or not more than 0.008, or not more than 0.006, or not more than 0.004, or not more than 0.002, or is not more than 0.001, in each case wt. % based on the weight of the r-pyoil.

In an embodiment or in combination with any embodiment mentioned herein or in combination with any of the embodiments mentioned herein, the r-pyoil can have the following compositional content:

(i) carbon atom content of at least 75 wt. %, or at least or at least 77, or at least 80, or at least 82, or at least 85, in each case wt. %, and/or up to 90, or up to 88, or not more than 86, or not more than 85, or not more than 83, or not more than 82, or not more than 80, or not more than 77, or not more than 75, or not more than 73, or not more than 70, or not more than 68, or not more than 65, or not more than 63, or up to 60, in each case wt. %, desirably at least 82% and up to 93%, and/or (ii) hydrogen atom content of at least 10 wt. %, or at least 13, or at least 14, or at least 15, or at least 16, or at least 17, or at least 18, or not more than 19, or not more than 18, or not more than 17, or not more than 16, or not more than 15, or not more than 14, or not more than 13, or up to 11, in each case wt. %, (iii) an oxygen atom content not to exceed 10, or not more than 8, or not more than 5, or not more than 4, or not more than 3, or not more than 2.75, or not more than 2.5, or not more than 2.25, or not more than 2, or not more than 1.75, or not more than 1.5, or not more than 1.25, or not more than 1, or not more than 0.75, or not more than 0.5, or not more than 0.25, or not more than 0.1, or not more than 0.05, in each case wt. %, in each case based on the weight of the r-pyoil.

In an embodiment or in combination with any embodiment mentioned herein, the amount of hydrogen atoms in the r-pyoil can be in a range of from 10-20, or 10-18, or 11-17, or 12-16 or 13-16, or 13-15, or 12-15, in each case as wt. % based on the weight of the r-pyoil.

In an embodiment or in combination with any embodiment mentioned herein or in combination with any of the embodiments mentioned herein, the metal content of the r-pyoil is desirably low, for example, not more than 2 wt. %, or not more than 1, or not more than 0.75, or not more than 0.5, or not more than 0.25, or not more than 0.2, or not more than 0.15, or not more than 0.1, or not more than 0.05, in each case wt. % based on the weight of the r-pyoil.

In an embodiment or in combination with any embodiment mentioned herein or in combination with any of the embodiments mentioned herein, the alkali metal and alkaline earth metal or mineral content of the r-pyoil is desirably low, for example, not more than 2 wt. %, or not more than 1, or not more than 0.75, or not more than 0.5, or not more than 0.25, or not more than 0.2, or not more than 0.15, or not more than 0.1, or not more than 0.05, in each case wt. % based on the weight of the r-pyoil.

In an embodiment or in combination with any embodiment mentioned herein or in combination with any of the embodiments mentioned herein, the weight ratio of paraffin to naphthene in the r-pyoil can be at least 1:1, or at least 1.5:1, or at least 2:1, or at least 2.2:1, or at least 2.5:1, or at least 2.7:1, or at least 3:1, or at least 3.3:1, or at least 3.5:1, or at least 3.75:1, or at least 4:1, or at least 4.25:1, or at least 4.5:1, or at least 4.75:1, or at least 5:1, or at least 6:1, or at least 7:1, or at least 8:1, or at least 9:1, or at least 10:1, or at least 13:1, or at least 15:1, or at least 17:1, based on the weight of the r-pyoil.

In an embodiment or in combination with any embodiment mentioned herein or in combination with any of the embodiments mentioned herein, the weight ratio of paraffin and naphthene combined to aromatics can be at least 1:1, or at least 1.5:1, or at least 2:1, or at least 2.5:1, or at least 2.7:1, or at least 3:1, or at least 3.3:1, or at least 3.5:1, or at least 3.75:1, or at least 4:1, or at least 4.5:1, or at least 5:1, or at least 7:1, or at least 10:1, or at least 15:1, or at least 20:1, or at least 25:1, or at least 30:1, or at least 35:1, or at least 40:1, based on the weight of the r-pyoil. In an embodiment or in combination with any embodiment mentioned herein, the ratio of paraffin and naphthene combined to aromatics in the r-pyoil can be in a range of from 50:1-1:1, or 40:1-1:1, or 30:1-1:1, or 20:1-1:1, or 30:1-3:1, or 20:1-1:1, or 20:1-5:1, or 50:1-5:1, or 30:1-5:1, or 1:1-7:1, or 1:1-5:1, 1:1-4:1, or 1:1-3:1.

In an embodiment or in combination with any of the embodiments mentioned herein, the r-pyoil may have a boiling point curve defined by one or more of its 10%, its 50%, and its 90% boiling points, as defined below. As used herein, “boiling point” refers to the boiling point of a composition as determined by ASTM D2887 or according to the procedure described in the working examples. A boiling point having the stated values are satisfied if the value is obtained under either method. Additionally, as used herein, an “x % boiling point,” refers to a boiling point at which x percent by weight of the composition boils per either of these methods.

As used throughout, an x % boiling at a stated temperature means at least x % of the composition boils at the stated temperature. In an embodiment or in combination with any of the embodiments mentioned herein, the 90% boiling point of the cracker feed stream or composition can be not more than 350, or not more than 325, or not more than 300, or not more than 295, or not more than 290, or not more than 285, or not more than 280, or not more than 275, or not more than 270, or not more than 265, or not more than 260, or not more than 255, or not more than 250, or not more than 245, or not more than 240, or not more than 235, or not more than 230, or not more than 225, or not more than 220, or not more than 215, not more than 200, not more than 190, not more than 180, not more than 170, not more than 160, not more than 150, or not more than 140, in each case ° C. and/or at least 200, or at least 205, or at least 210, or at least 215, or at least 220, or at least 225, or at least 230, in each case ° C. and/or not more than 25, 20, 15, 10, 5, or 2 weight percent of the r-pyoil may have a boiling point of 300° C. or higher.

Referring again to FIG. 3, the r-pyoil may be introduced into a cracking furnace or coil or tube alone (e.g., in a stream comprising at least 85, or at least 90, or at least 95, or at least 99, or 100, in each case wt. % percent pyrolysis oil based on the weight of the cracker feed stream), or combined with one or more non-recycle cracker feed streams. When introduced into a cracker furnace, coil, or tube with a non-recycle cracker feed stream, the r-pyoil may be present in an amount of at least 1, or at least 2, or at least 5, or at least 8, or at least 10, or at least 12, or at least 15, or at least 20, or at least 25, or at least 30, in each case wt. % and/or not more than 40, or not more than 35, or not more than 30, or not more than 25, or not more than 20, or not more than 15, or not more than 10, or not more than 8, or not more than 5, or not more than 2, in each case weight percent based on the total weight of the combined stream. Thus, the non-recycle cracker feed stream or composition may be present in the combined stream in an amount of at least 20, or at least 25, or at least 30, or at least 35, or at least 40, or at least 45, or at least 50, or at least 55, or at least 60, or at least 65, or at least 70, or at least 75, or at least 80, or at least 85, or at least 90, in each case weight percent and/or not more than 99, or not more than 95, or not more than 90, or not more than 85, or not more than 80, or not more than 75, or not more than 70, or not more than 65, or not more than 60, or not more than 55, or not more than 50, or not more than 45, or not more than 40, in each case weight percent based on the total weight of the combined stream. Unless otherwise noted herein, the properties of the cracker feed stream as described below apply either to the non-recycle cracker feed stream prior to (or absent) combination with the stream comprising r-pyoil, as well as to a combined cracker stream including both a non-recycle cracker feed and a r-pyoil feed.

In an embodiment or in combination with any of the embodiments mentioned herein, the cracker feed stream may comprise a predominantly $C_2$-$C_4$ hydrocarbon containing composition, or a predominantly $C_5$-$C_{22}$hydrocarbon containing composition. As used herein, the term “predominantly $C_2$-$C_4$ hydrocarbon,” refers to a stream or composition containing at least 50 weight percent of $C_2$-$C_4$ hydrocarbon components. Examples of specific types of $C_2$-$C_4$ hydrocarbon streams or compositions include propane, ethane, butane, and LPG. In an embodiment or in combination with any of the embodiments mentioned herein, the cracker feed may comprise at least 50, or at least 55, or at least 60, or at least 65, or at least 70, or at least 75, or at least 80, or at least 85, or at least 90, or at least 95, in each case wt. % based on the total weight of the feed, and/or not more than 100, or not more than 99, or not more than 95, or not more than 92, or not more than 90, or not more than 85, or not more than 80, or not more than 75, or not more than 70, or not more than 65, or not more than 60, in each case weight percent $C_2$-$C_4$ hydrocarbons or linear alkanes, based on the total weight of the feed. The cracker feed can comprise predominantly propane, predominantly ethane, predominantly butane, or a combination of two or more of these components. These components may be non-recycle components. The cracker feed can comprise predominantly propane, or at least 50 mole % propane, or at least 80 mole % propane, or at least 90 mole % propane, or at least 93 mole % propane, or at least 95 mole % propane (inclusive of any recycle streams combined with virgin feed). The cracker feed can comprise HD5 quality propane as a virgin or fresh feed. The cracker can comprise at more than 50 mole % ethane, or at least 80 mole % ethane, or at least 90 mole % ethane, or at least 95 mole % ethane. These components may be non-recycle components.

In an embodiment or in combination with any of the embodiments mentioned herein, the cracker feed stream may comprise a predominantly $C_5$-$C_{22}$ hydrocarbon containing composition. As used herein, “predominantly $C_5$-$C_{22}$ hydrocarbon” refers to a stream or composition comprising at least 50 weight percent of $C_5$-$C_{22}$ hydrocarbon components. Examples include gasoline, naphtha, middle distillates, diesel, kerosene. In an embodiment or in combination with any of the embodiments mentioned herein, the cracker feed stream or composition may comprise at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, in each case wt. % and/or not more than 100, or not more than 99, or not more than 95, or not more than 92, or not more than 90, or not more than 85, or not more than 80, or not more than 75, or not more than 70, or not more than 65, or not more than 60, in each case weight percent $C_5$-$C_{22}$, or $C_5$-$C_{20}$ hydrocarbons, based on the total weight of the stream or composition. In an embodiment or in combination with any of the embodiments mentioned herein, the cracker feed may have a $C_{15}$ and heavier ($C_{15+}$) content of at least 0.5, or at least 1, or at least 2, or at least 5, in each case weight percent and/or not more than 40, or not more than 35, or not more than 30, or not more than 25, or not more than 20, or not more than 18, or not more than 15, or not more than 12, or not more than 10, or not more than 5, or not more than 3, in each case weight percent, based on the total weight of the feed.

The cracker feed may have a boiling point curve defined by one or more of its 10%, its 50%, and its 90% boiling points, the boiling point being obtained by the methods described above Additionally, as used herein, an "x % boiling point," refers to a boiling point at which x percent by weight of the composition boils per the methods described above. In an embodiment or in combination with any of the embodiments mentioned herein, the 90% boiling point of the cracker feed stream or composition can be not more than 360, or not more than 355, or not more than 350, or not more than 345, or not more than 340, or not more than 335, or not more than 330, or not more than 325, or not more than 320, or not more than 315, or not more than 300, or not more than 295, or not more than 290, or not more than 285, or not more than 280, or not more than 275, or not more than 270, or not more than 265, or not more than 260, or not more than 255, or not more than 250, or not more than 245, or not more than 240, or not more than 235, or not more than 230, or not more than 225, or not more than 220, or not more than 215, in each case ° C. and/or at least 200, or at least 205, or at least 210, or at least 215, or at least 220, or at least 225, or at least 230, in each case ° C.

In an embodiment or in combination with any of the embodiments mentioned herein, the 10% boiling point of the cracker feed stream or composition can be at least 40, at least 50, at least 60, at least 70, at least 80, at least 90, at least 100, at least 110, at least 120, at least 130, at least 140, at least 150, or at least 155, in each case ° C. and/or not more than 250, not more than 240, not more than 230, not more than 220, not more than 210, not more than 200, not more than 190, not more than 180, or not more than 170 in each case ° C.

In an embodiment or in combination with any of the embodiments mentioned herein, the 50% boiling point of the cracker feed stream or composition can be at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, or at least 230, in each case ° C., and/or not more than 300, not more than 290, not more than 280, not more than 270, not more than 260, not more than 250, not more than 240, not more than 230, not more than 220, not more than 210, not more than 200, not more than 190, not more than 180, not more than 170, not more than 160, not more than 150, or not more than 145° C. The 50% boiling point of the cracker feed stream or composition can be in the range of 65 to 160, 70 to 150, 80 to 145, 85 to 140, 85 to 230, 90 to 220, 95 to 200, 100 to 190, 110 to 180, 200 to 300, 210 to 290, 220 to 280, 230 to 270, in each case in ° C.

In an embodiment or in combination with any of the embodiments mentioned herein, the 90% boiling point of the cracker feedstock or stream or composition can be at least 350° C., the 10% boiling point can be at least 60° C.; and the 50% boiling point can be in the range of from 95° C. to 200° C. In an embodiment or in combination with any of the embodiments mentioned herein, the 90% boiling point of the cracker feedstock or stream or composition can be at least 150° C., the 10% boiling point can be at least 60° C., and the 50% boiling point can be in the range of from 80 to 145° C. In an embodiment or in combination with any of the embodiments mentioned herein, the cracker feedstock or stream has a 90% boiling point of at least 350° C., a 10% boiling point of at least 150° C., and a 50% boiling point in the range of from 220 to 280° C.

In an embodiment or in combination with any embodiment mentioned herein or in combination with any of the embodiments mentioned herein, the r-pyoil is cracked in a gas furnace. A gas furnace is a furnace having at least one coil which receives (or operated to receive), at the inlet of the coil at the entrance to the convection zone, a predominately vapor-phase feed (more than 50% of the weight of the feed is vapor) ("gas coil"). In an embodiment or in combination with any embodiment mentioned herein, the gas coil can receive a predominately $C_2$-$C_4$ feedstock, or a predominately a $C_2$-$C_3$ feedstock to the inlet of the coil in the convection section, or alternatively, having at least one coil receiving more than 50 wt. % ethane and/or more than 50% propane and/or more than 50% LPG, or in any one of these cases at least 60 wt. %, or at least 70 wt. %, or at least 80 wt. %, based on the weight of the cracker feed to the coil, or alternatively based on the weight of the cracker feed to the convection zone. The gas furnace may have more than one gas coil. In an embodiment or in combination with any embodiment mentioned herein, at least 25% of the coils, or at least 50% of the coils, or at least 60% of the coils, or all the coils in the convection zone or within a convection box of the furnace are gas coils. In an embodiment or in combination with any embodiment mentioned herein, the gas coil receives, at the inlet of the coil at the entrance to the convection zone, a vapor-phase feed in which at least 60 wt. %, or at least 70 wt. %, or at least 80 wt. %, or at least 90 wt. %, or at least 95 wt. %, or at least 97 wt. %, or at least 98 wt. %, or at least 99 wt. %, or at least 99.5 wt. %, or at least 99.9 wt. % of feed is vapor.

In an embodiment or in combination with any embodiment mentioned herein, the r-pyoil is cracked in a split furnace. A split furnace is a type of gas furnace. A split furnace contains at least one gas coil and at least one liquid coil within the same furnace, or within the same convection zone, or within the same convection box. A liquid coil is a coil which receives, at the inlet of coil at the entrance to the convection zone, a predominately liquid phase feed (more than 50% of the weight of the feed is liquid) ("liquid coil"). In an embodiment or in combination with any embodiment mentioned herein, the liquid coil can receive a predominately $C_{5+}$ feedstock to the inlet of the coil at the entrance of the convection section ("liquid coil"). In an embodiment or in combination with any embodiment mentioned herein, the liquid coil can receive a predominately $C_6$-$C_{22}$ feedstock, or a predominately a $C_7$-$C_{16}$ feedstock to the inlet of the coil in the convection section, or alternatively, having at least one coil receiving more than 50 wt. % naphtha, and/or more than 50% natural gasoline, and/or more than 50% diesel, and/or more than JP-4, and/or more than 50% Stoddard Solvent, and/or more than 50% kerosene, and/or more than 50% fresh creosote, and/or more than 50% JP-8 or Jet-A, and/or more than 50% heating oil, and/or more than 50% heavy fuel oil, and/or more than 50% bunker C, and/or more than 50% lubricating oil, or in any one of these cases at least 60 wt. %, or at least 70 wt. %, or at least 80 wt. %, or at least 90 wt. %, or at least 95 wt. %, or at least 98 wt. %, or at least 99 wt. %, based on the weight of the cracker feed to the liquid coil, or alternatively based on the weight of the cracker feed to the convection zone. In an embodiment or in combination with any embodiment mentioned herein, at least one coil and not more than 75% of the coils, or not more than 50% of the coils, or not more than at least 40% of the coils in the convection zone or within a convection box of the furnace are liquid coils. In an embodiment or in combination with any embodiment mentioned herein, the liquid coil receives, at the inlet of the coil at the entrance to the convection zone, a liquid-phase feed in which at least 60 wt. %, or at least 70 wt. %, or at least 80 wt. %, or at least 90 wt. %, or at least 95 wt. %, or at least 97 wt. %, or at least 98 wt. %, or at least 99 wt. %, or at least 99.5 wt. %, or at least 99.9 wt. % of feed is liquid.

In an embodiment or in combination with any embodiment mentioned herein, the r-pyoil is cracked in a thermal gas cracker.

In an embodiment or in combination with any embodiment mentioned herein, the r-pyoil is cracked in a thermal steam gas cracker in the presence of steam. Steam cracking refers to the high-temperature cracking (decomposition) of hydrocarbons in the presence of steam.

In an embodiment or in combination with any embodiment mentioned herein, the r-composition is derived directly or indirectly from cracking r-pyoil in a gas furnace. The coils in the gas furnace can consist entirely of gas coils or the gas furnace can be a split furnace.

When the r-pyoil containing feed stream is combined with the non-recycle cracker feed, such a combination may occur upstream of, or within, the cracking furnace or within a single coil or tube. Alternatively, the r-pyoil containing feed stream and non-recycle cracker feed may be introduced separately into the furnace, and may pass through a portion, or all, of the furnace simultaneously while being isolated from one another by feeding into separate tubes within the same furnace (e.g., a split furnace). Ways of introducing the r-pyoil containing feed stream and the non-recycle cracker feed into the cracking furnace according to an embodiment or in combination with any of the embodiments mentioned herein are described in further detail below.

Turning now to FIG. 5, a schematic diagram of a cracker furnace suitable for use in an embodiment or in combination with any of the embodiments mentioned herein is shown.

In one embodiment or in combination of any of the mentioned embodiments, there is provided a method for making one or more olefins including:

(a) feeding a first cracker feed comprising a recycle content pyrolysis oil composition (r-pyoil) to a cracker furnace;

(b) feeding a second cracker feed into said cracker furnace, wherein said second cracker feed comprises none of said r-pyoil or less of said r-pyoil, by weight, than said first cracker feed stream; and (c) cracking said first and said second cracker feeds in respective first and second tubes to form an olefin-containing effluent stream.

The r-pyoil can be combined with a cracker stream to make a combined cracker stream, or as noted above, a first cracker stream. The first cracker stream can be 100% r-pyoil or a combination of a non-recycle cracker stream and r-pyoil. The feeding of step (a) and/or step (b) can be performed upstream of the convection zone or within the convection zone. The r-pyoil can be combined with a non-recycle cracker stream to form a combined or first cracker stream and fed to the inlet of a convection zone, or alternatively the r-pyoil can be separately fed to the inlet of a coil or distributor along with a non-recycle cracker stream to form a first cracker stream at the inlet of the convection zone, or the r-pyoil can be fed downstream of the inlet of the convection zone into a tube containing non-recycle cracker feed, but before a crossover, to make a first cracker stream or combined cracker stream in a tube or coil. Any of these methods includes feeding the first cracker stream to the furnace.

The amount of r-pyoil added to the non-recycle cracker stream to make the first cracker stream or combined cracker stream can be as described above; e.g. in an amount of at least 1, 5, 10, 15, 20, 25, 30, 35, 40, 45, 50, 55, 60, 65, 70, 75, 80, 85, 90, or 95, in each case weight percent and/or not more than 95, 90, 85, 80, 75, 70, 65, 60, 55, 60, 55, 50, 45, 40, 35, 30, 25, 20, 15, or 1, in each case weight percent, based on the total weight of the first cracker feed or combined cracker feed (either as introduced into the tube or within the tube as noted above). Further examples include 5-50, 5-40, 5-35, 5-30, 5-25, 5-20, or 5-15 wt. %.

The first cracker stream is cracked in a first coil or tube. The second cracker stream is cracked in a second coil or tube. Both the first and second cracker streams and the first and second coils or tubes can be within the same cracker furnace.

The second cracker stream can have none of the r-pyoil or less of said r-pyoil, by weight, than the first cracker feed stream. Also, the second cracker stream can contain only non-recycle cracker feed in the second coil or tube. The second cracker feed stream can be predominantly $C_2$ to $C_4$, or hydrocarbons (e.g. non-recycle content), or ethane, propane, or butane, in each case in amounts of at least 55, 60, 65, 70, 75, 80, 85, or at least 90 weight percent based on the second cracker feed within a second coil or tube. If r-pyoil is included in the second cracker feed, the amount of such r-pyoil can be at least 10% less, 20, 30, 40, 50, 60, 70, 80, 90, 95, 97, or 99% less by weight than the amount of r-pyoil in the first cracker feed.

In an embodiment or in combination with any embodiment mentioned herein, although not shown, a vaporizer can be provided to vaporize a condensed feedstock of $C_2$-$C_5$ hydrocarbons 350 to ensure that the feed to the inlet of the coils in the convection box 312, or the inlet of the convection zone 310, is a predominately vapor phase feed.

The cracking furnace shown in FIG. 5 includes a convection section or zone 310, a radiant section or zone 320, and a cross-over section or zone 330 located between the convection and radiant sections 310 and 320. The convection section 310 is the portion of the furnace 300 that receives heat from hot flue gases and includes a bank of tubes or coils 324 through which a cracker stream 350 passes. In the convection section 310, the cracker stream 350 is heated by convection from the hot flue gasses passing therethrough. The radiant section 320 is the section of the furnace 300 into which heat is transferred into the heater tubes primarily by radiation from the high-temperature gas. The radiant section 320 also includes a plurality of burners 326 for introducing heat into the lower portion of the furnace. The furnace includes a fire box 322 which surrounds and houses the tubes within the radiant section 320 and into which the burners are oriented. The cross-over section 330 includes piping for connecting the convection 310 and radiant sections 320 and may transfer the heated cracker stream internally or externally from one section to the other within the furnace 300.

As hot combustion gases ascend upwardly through the furnace stack, the gases may pass through the convection section 310, wherein at least a portion of the waste heat may be recovered and used to heat the cracker stream passing through the convection section 310. In an embodiment or in combination with any of the embodiments mentioned herein, the cracking furnace 300 may have a single convection (preheat) section 310 and a single radiant 320 section, while, in other embodiments, the furnace may include two or more radiant sections sharing a common convection section. At least one induced draft (I.D.) fan 316 near the stack may control the flow of hot flue gas and heating profile through the furnace, and one or more heat exchangers 340 may be used to cool the furnace effluent 370. In an embodiment or in combination with any of the embodiments mentioned herein (not shown), a liquid quench may be used in addition to, or alternatively with, the exchanger (e.g., transfer line heat exchanger or TLE) shown in FIG. 5, for cooling the cracked olefin-containing effluent.

The furnace 300 also includes at least one furnace coil 324 through which the cracker streams pass through the furnace. The furnace coils 324 may be formed of any material inert to the cracker stream and suitable for withstanding high temperatures and thermal stresses within the furnace. The coils may have any suitable shape and can, for example, have a circular or oval cross-sectional shape.

The coils in the convection section 310, or tubes within the coil, may have a diameter of at least 1, or at least 1.5, or at least 2, or at least 2.5, or at least 3, or at least 3.5, or at least 4, or at least 4.5, or at least 5, or at least 5.5, or at least 6, or at least 6.5, or at least 7, or at least 7.5, or at least 8, or at least 8.5, or at least 9, or at least 9.5, or at least 10, or at least 10.5, in each case cm and/or not more than 12, or not more than 11.5, or not more than 11, 1 or not more than 0.5, or not more than 10, or not more than 9.5, or not more than 9, or not more than 8.5, or not more than 8, or not more than 7.5, or not more than 7, or not more than 6.5, in each case cm. All or a portion of one or more coils can be substantially straight, or one or more of the coils may include a helical, twisted, or spiral segment. One or more of the coils may also have a U-tube or split U-tube design. In an embodiment or in combination with any of the embodiments mentioned herein, the interior of the tubes may be smooth or substantially smooth, or a portion (or all) may be roughened in order to minimize coking. Alternatively, or in addition, the inner portion of the tube may include inserts or fins and/or surface metal additives to prevent coke build up.

In an embodiment or in combination with any of the embodiments mentioned herein, all or a portion of the furnace coil or coils 324 passing through in the convection section 310 may be oriented horizontally, while all, or at least a portion of, the portion of the furnace coil passing through the radiant section 322 may be oriented vertically. In an embodiment or in combination with any of the embodiments mentioned herein, a single furnace coil may run through both the convection and radiant section. Alternatively, at least one coil may split into two or more tubes at one or more points within the furnace, so that cracker stream may pass along multiple paths in parallel. For example, the cracker stream (including r-pyoil) 350 may be introduced into multiple coil inlets in the convection zone 310, or into multiple tube inlets in the radiant 320 or cross-over sections 330. When introduced into multiple coil or tube inlets simultaneously, or nearly simultaneously, the amount of r-pyoil introduced into each coil or tube may not be regulated. In an embodiment or in combination with any of the embodiments mentioned herein, the r-pyoil and/or cracker stream may be introduced into a common header, which then channels the r-pyoil into multiple coil or tube inlets.

Figure 6:
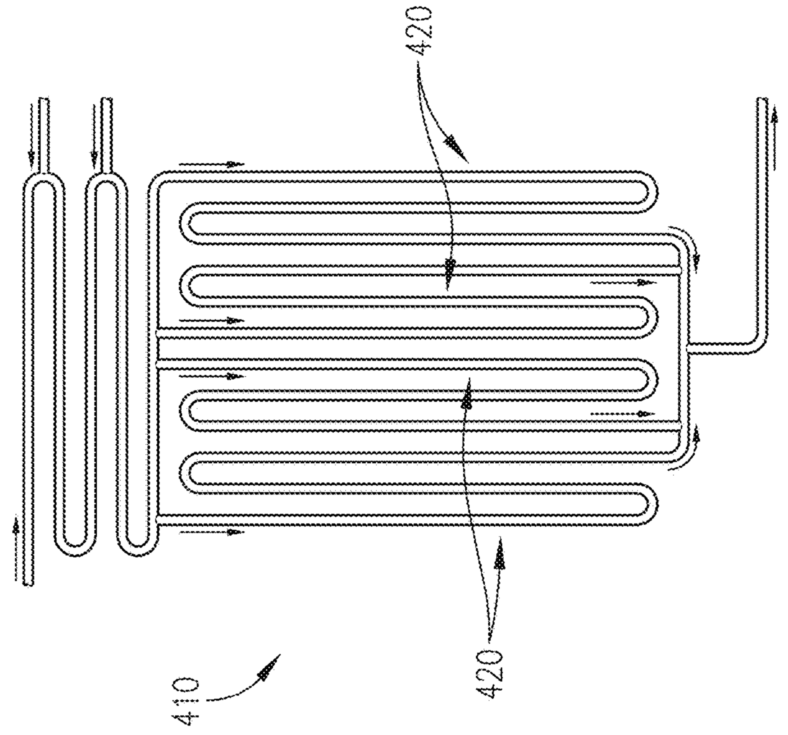
FIG. 6 illustrates a furnace coil configuration having multiple tubes.

A single furnace can have at least 1, or at least 2, or at least 3, or at least 4, or at least 5, or at least 6, or at least 7, or at least 8 or more, in each case coils. Each coil can be from 5 to 100, 10 to 75, or 20 to 50 meters in length and can include at least 1, or at least 2, or at least 3, or at least 4, or at least 5, or at least 6, or at least 7, or at least 8, or at least 10, or at least 12, or at least 14 or more tubes. Tubes of a single coil may be arranged in many configurations and in an embodiment or in combination with any of the embodiments mentioned herein may be connected by one or more 180° ("U") bends. One example of a furnace coil 410 having multiple tubes 420 is shown in FIG. 6.

An olefin plant can have a single cracking furnace, or it can have at least 2, or at least 3, or at least 4, or at least 5, or at least 6, or at least 7, or at least 8 or more cracking furnaces operated in parallel. Any one or each furnace(s) may be gas cracker, or a liquid cracker, or a split furnace. In an embodiment or in combination with any embodiment mentioned herein, the furnace is a gas cracker receiving a cracker feed stream containing at least 50 wt. %, or at least 75 wt. %, or at least 85 wt. % or at least 90 wt. % ethane, propane, LPG, or a combination thereof through the furnace, or through at least one coil in a furnace, or through at least one tube in the furnace, based on the weight of all cracker feed to the furnace. In an embodiment or in combination with any embodiment mentioned herein, the furnace is a liquid or naphtha cracker receiving a cracker feed stream containing at least 50 wt. %, or at least 75 wt. %, or at least 85 wt. % liquid (when measured at 25° C. and 1 atm) hydrocarbons having a carbon number from $C_5$-$C_{22}$. through the furnace, or through at least one coil in a furnace, or through at least one tube in the furnace, based on the weight of all cracker feed to the furnace. In an embodiment or in combination with any embodiment mentioned herein, the cracker is a split furnace receiving a cracker feed stream containing at least 50 wt. %, or at least 75 wt. %, or at least 85 wt. % or at least 90 wt. % ethane, propane, LPG, or a combination thereof through the furnace, or through at least one coil in a furnace, or through at least one tube in the furnace, and receiving a cracker feed stream containing at least 0.5 wt. %, or at least 0.1 wt. %, or at least 1 wt. %, or at least 2 wt. %, or at least 5 wt. %, or at least 7 wt. %, or at least 10 wt. %, or at least 13 wt. %, or at least 15 wt. %, or at least 20 wt. % liquid and/or r-pyoil (when measured at 25° C. and 1 atm), each based on the weight of all cracker feed to the furnace.

Figure 7:
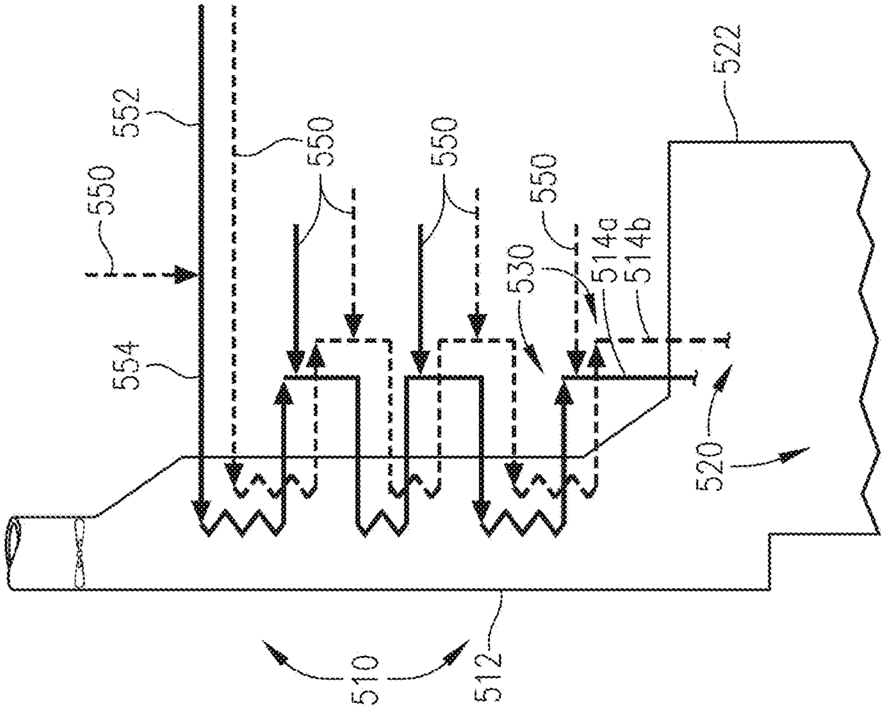
FIG. 7 illustrates a variety of feed locations for r-pyoil into a cracker furnace.

Turning now to FIG. 7, several possible locations for introducing the r-pyoil containing feed stream and the non-recycle cracker feed stream into a cracking furnace are shown.

In an embodiment or in combination with any of the embodiments mentioned herein, an r-pyoil containing feed stream 550 may be combined with the non-recycle cracker feed 552 upstream of the convection section to form a combined cracker feed stream 554, which may then be introduced into the convection section 510 of the furnace. Alternatively, or in addition, the r-pyoil containing feed 550 may be introduced into a first furnace coil, while the non-recycle cracker feed 552 is introduced into a separate or second furnace coil, within the same furnace, or within the same convection zone. Both streams may then travel in parallel with one another through the convection section 510 within a convection box 512, cross-over 530, and radiant section 520 within a radiant box 522, such that each stream is substantially fluidly isolated from the other over most, or all, of the travel path from the inlet to the outlet of the furnace. The pyoil stream introduced into any heating zone within the convection section 510 can flow through the convection section 510 and flow through as a vaporized stream **514*b* into the radiant box 522. In other embodiments, the r-pyoil containing feed stream 550 may be introduced into the non-recycle cracker stream 552 as it passes through a furnace coil in the convection section 510 flowing into the cross-over section 530 of the furnace to form a combined cracker stream 514***a*, as also shown in FIG. 7.

In an embodiment or in combination with any embodiment mentioned herein, the r-pyoil 550 may be introduced into the first furnace coil, or an additional amount introduced into the second furnace coil, at either a first heating zone or a second heating zone as shown in FIG. 7. The r-pyoil 550 may be introduced into the furnace coil at these locations through a nozzle. A convenient method for introducing the feed of r-pyoil is through one or more dilution steam feed nozzles that are used to feed steam into the coil in the convection zone. The service of one or more dilution steam nozzles may be employed to inject r-pyoil, or a new nozzle can be fastened to the coil dedicated to the injection of the r-pyoil. In an embodiment or in combination with any embodiment mentioned herein, both steam and r-pyoil can be co-fed through a nozzle into the furnace coil downstream of the inlet to the coil and upstream of a crossover, optionally at the first or second heating zone within the convection zone as shown in FIG. 7.

The non-recycle cracker feed stream may be mostly liquid and have a vapor fraction of less than 0.25 by volume, or less than 0.25 by weight, or it may be mostly vapor and have a vapor fraction of at least 0.75 by volume, or at least 0.75 by weight, when introduced into the furnace and/or when combined with the r-pyoil containing feed. Similarly, the r-pyoil containing feed may be mostly vapor or mostly liquid when introduced into the furnace and/or when combined with the non-recycle cracker stream.

Figure 8:
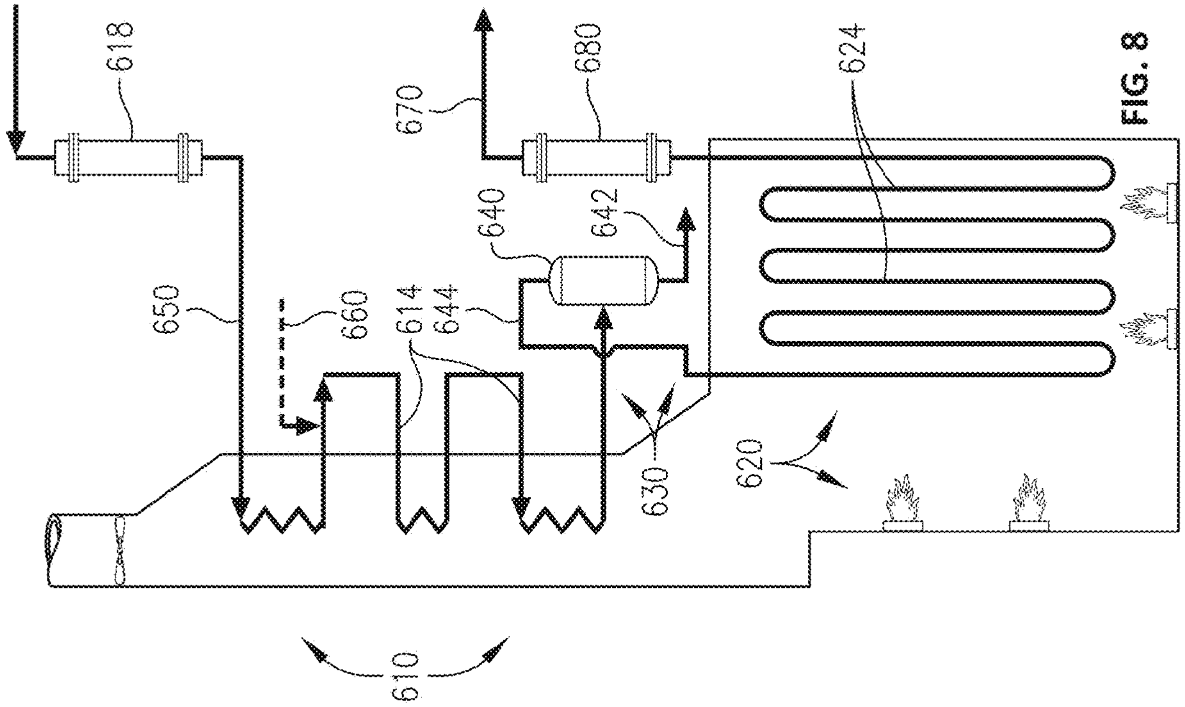
FIG. 8 illustrates a cracker furnace having a vapor-liquid separator.

In an embodiment or in combination with any of the embodiments mentioned herein, at least a portion or all of the r-pyoil stream or cracker feed stream may be preheated prior to being introduced into the furnace. As shown in FIG. 8, the preheating can be performed with an indirect heat exchanger 618 heated by a heat transfer media (such as steam, hot condensate, or a portion of the olefin-containing effluent) or via a direct fired heat exchanger 618. The preheating step can vaporize all or a portion of the stream comprising r-pyoil and may, for example, vaporize at least 50, 55, 60, 65, 70, 75, 80, 85, 90, 95, or 99 weight percent of the stream comprising r-pyoil.

The preheating, when performed, can increase the temperature of the r-pyoil containing stream to a temperature that is within about 50, 45, 40, 35, 30, 25, 20, 15, 10, 5, or 2° C. of the bubble point temperature of the r-pyoil containing stream. Additionally, or in the alternative, the preheating can increase the temperature of the stream comprising r-pyoil to a temperature at least 5, 10, 15, 20, 25, 30, 35, 40, 45, 50, 55, 60, 65, 70, 75, 80, 85, 90, or 100° C. below the coking temperature of the stream. In an embodiment or in combination with any of the embodiments mentioned herein, the preheated r-pyoil stream can have a temperature of at least 200, 225, 240, 250, or 260° C. and/or not more than 375, 350, 340, 330, 325, 320, or 315° C., or at least 275, 300, 325, 350, 375, or 400° C. and/or not more than 600, 575, 550, 525, 500, or 475° C. When the atomized liquid (as explained below) is injected into the vapor phase, heated cracker stream, the liquid may rapidly evaporate such that, for example, the entire combined cracker stream is vapor (e.g., 100 percent vapor) within 5, 4, 3, 2, or 1 second after injection.

In an embodiment or in combination with any of the embodiments mentioned herein, the heated r-pyoil stream (or cracker stream comprising the r-pyoil and the non-recycle cracker stream) can optionally be passed through a vapor-liquid separator to remove any residual heavy or liquid components, when present. The resulting light fraction may then be introduced into the cracking furnace, alone or in combination with one or more other cracker streams as described in various embodiments herein. For example, in an embodiment or in combination with any of the embodiments mentioned herein, the r-pyoil stream can comprise at least 1, 2, 5, 8, 10, or 12 weight percent Cis and heavier components. The separation can remove at least 50, 55, 60, 65, 70, 75, 80, 85, 90, 95, or 99 weight percent of the heavier components from the r-pyoil stream.

Turning back to FIG. 7, the cracker feed stream (either alone or when combined with the r-pyoil feed stream) may be introduced into a furnace coil at or near the inlet of the convection section. The cracker stream may then pass through at least a portion of the furnace coil in the convection section 510, and dilution steam may be added at some point in order to control the temperature and cracking severity in the furnace. In an embodiment or in combination with any of the embodiments mentioned herein, the steam may be added upstream of or at the inlet to the convection section, or it may be added downstream of the inlet to the convection section—either in the convection section, at the cross-over section, or upstream of or at the inlet to the radiant section. Similarly, the stream comprising the r-pyoil and the non-recycle cracker stream (alone or combined with the steam) may also be introduced into or upstream or at the inlet to the convection section, or downstream of the inlet to the convection section—either within the convection section, at the cross-over, or at the inlet to the radiant section. The steam may be combined with the r-pyoil stream and/or cracker stream and the combine stream may be introduced at one or more of these locations, or the steam and r-pyoil and/or non-recycle cracker stream may be added separately.

When combined with steam and fed into or near the cross-over section of the furnace, the r-pyoil and/or cracker stream can have a temperature of 500, 510, 520, 530, 540, 550, 560, 570, 580, 590, 600, 610, 620, 630, 640, 650, 660, 670, or 680° C. and/or not more than 850, 840, 830, 820, 810, 800, 790, 780, 770, 760, 750, 740, 730, 720, 710, 705, 700, 695, 690, 685, 680, 675, 670, 665, 660, 655, or 650° C. The resulting steam and r-pyoil stream can have a vapor fraction of at least 0.75, 0.80, 0.85, 0.90, or at least 0.95 by weight, or at least 0.75, 0.80, 0.85, 0.90, and 0.95 by volume.

When combined with steam and fed into or near the inlet to the convection section 510, the r-pyoil and/or cracker stream can have a temperature of at least 30, 35, 40, 45, 50, 55, 60, or 65 and/or not more than 100, 90, 80, 70, 60, 50, or 45° C.

The amount of steam added may depend on the operating conditions, including feed type and desired product, but can be added to achieve a steam-to-hydrocarbon ratio can be at least 0.10:1, 0.15:1, 0.20:1, 0.25:1, 0.27:1, 0.30:1, 0.32:1, 0.35:1, 0.37:1, 0.40:1, 0.42:1, 0.45:1, 0.47:1, 0.50:1, 0.52:1, 0.55:1, 0.57:1, 0.60:1, 0.62:1, 0.65:1 and/or not more than about 1:1. 0.95:1, 0.90:1, 0.85:1, 0.80:1, 0.75:1, 0.72:1, 0.70:1, 0.67:1, 0.65:1, 0.62:1, 0.60:1, 0.57:1, 0.55:1, 0.52:1, 0.50:1, or it can be in the range of from 0.1:1 to 1.0:1, 0.15:1 to 0.9:1, 0.2:1 to 0.8:1, 0.3:1 to 0.75:1, or 0.4:1 to 0.6:1. When determining the "steam-to-hydrocarbon" ratio, all hydrocarbon components are included and the ratio is by weight. In an embodiment or in combination with any of the embodiments mentioned herein, the steam may be produced using separate boiler feed water/steam tubes heated in the convection section of the same furnace (not shown in FIG. 7). Steam may be added to the cracker feed (or any intermediate cracker stream within the furnace) when the cracker stream has a vapor fraction of 0.60 to 0.95, or 0.65 to 0.90, or 0.70 to 0.90.

When the r-pyoil containing feed stream is introduced into the cracking furnace separately from a non-recycle feed stream, the molar flow rate of the r-pyoil and/or the r-pyoil containing stream may be different than the molar flow rate of the non-recycle feed stream. In one embodiment or in combination with any other mentioned embodiment, there is provided a method for making one or more olefins by:

(a) feeding a first cracker stream having r-pyoil to a first tube inlet in a cracker furnace;

(b) feeding a second cracker stream containing, or predominately containing $C_2$ to $C_4$ hydrocarbons to a second tube inlet in the cracker furnace, wherein said second tube is separate from said first tube and the total molar flow rate of the first cracker stream fed at the first tube inlet is lower than the total molar flow rate of the second cracker stream to the second tube inlet, calculated without the effect of steam. The feeding of step (a) and step (b) can be to respective coil inlets.

For example, the molar flow rate of the r-pyoil or the first cracker stream as it passes through a tube in the cracking furnace may be at least 5, 7, 10, 12, 15, 17, 20, 22, 25, 27, 30, 35, 40, 45, 50, 55, or 60 percent lower than the flow rate of the hydrocarbon components (e.g., $C_2$-$C_4$ or $C_5$-$C_{22}$) components in the non-recycle feed stream, or the second cracker stream, passing through another or second tube. When steam is present in both the r-pyoil containing stream, or first cracker stream, and in the second cracker stream or the non-recycle feed stream, the total molar flow rate of the r-pyoil containing stream, or first cracker stream, (including r-pyoil and dilution steam) may be at least 5, 7, 10, 12, 15, 17, 20, 22, 25, 27, 30, 35, 40, 45, 50, 55, or 60 percent higher than the total molar flow rate (including hydrocarbon and dilution steam) of the non-recycle cracker feedstock, or second cracker stream (wherein the percentage is calculated as the difference between the two molar flow rates divided by the flow rate of the non-recycle stream).

In an embodiment or in combination with any of the embodiments mentioned herein, the molar flow rate of the r-pyoil in the r-pyoil containing feed stream (first cracker stream) within the furnace tube may be at least 0.01, 0.02, 0.025, 0.03, 0.035 and/or not more than 0.06, 0.055, 0.05, 0.045 kmol-lb/hr lower than the molar flow rate of the hydrocarbon (e.g., $C_2$-$C_4$ or $C_5$-$C_{22}$) in the non-recycle cracker stream (second cracker stream). In an embodiment or in combination with any of the embodiments mentioned herein, the molar flow rates of the r-pyoil and the cracker feed stream may be substantially similar, such that the two molar flow rates are within 0.005, 0.001, or 0.0005 kmol-lb/hr of one another. The molar flow rate of the r-pyoil in the furnace tube can be at least 0.0005, 0.001, 0.0025, 0.005, 0.01, 0.02, 0.03, 0.04, 0.05, 0.06, 0.07, 0.08, 0.09, 0.10, 0.11, 0.12, 0.13, 0.14, or 0.15 kilo moles-pound per hour (kmol-lb/hr) and/or not more than 0.25, 0.24, 0.23, 0.22, 0.21, 0.20, 0.19, 0.18, 0.17, 0.16, 0.15, 0.14, 0.13, 0.08, 0.05, 0.025, 0.01, or 0.008 kmol-lb/hr, while the molar flow rate of the hydrocarbon components in the other coil or coils can be at least 0.02, 0.03, 0.04, 0.05, 0.06, 0.07, 0.08, 0.09, 0.10, 0.11, 0.12, 0.13, 0.14, 0.15, 0.16, 0.17, 0.18 and/or not more than 0.30, 0.29, 0.28, 0.27, 0.26, 0.25, 0.24, 0.23, 0.22, 0.21, 0.20, 0.19, 0.18, 0.17, 0.16, 0.15 kmol-lb/hr.

In an embodiment or in combination with any of the embodiments mentioned herein, the total molar flow rate of the r-pyoil containing stream (first cracker stream) can be at least 0.01, 0.02, 0.03, 0.04, 0.05, 0.06, 0.07, 0.08, 0.09 and/or not more than 0.30, 0.25, 0.20, 0.15, 0.13, 0.10, 0.09, 0.08, 0.07, or 0.06 kmol-lb/hr lower than the total molar flow rate of the non-recycle feed stream (second cracker stream), or the same as the total molar flow rate of the non-recycle feed stream (second cracker stream). The total molar flow rate of the r-pyoil containing stream (first cracker stream) can be at least 0.01, 0.02, 0.03, 0.04, 0.05, 0.06, 0.07 and/or not more than 0.10, 0.09, 0.08, 0.07, or 0.06 kmol-lb/hr higher than the total molar flow rate of the second cracker stream, while the total molar flow rate of the non-recycle feed stream (second cracker stream) can be at least 0.20, 0.21, 0.22, 0.23, 0.24, 0.25, 0.26, 0.27, 0.28, 0.29, 0.30, 0.31, 0.32, 0.33 and/or not more than 0.50, 0.49, 0.48, 0.47. 0.46, 0.45, 0.44, 0.43, 0.42, 0.41, 0.40 kmol-lb/hr.

In an embodiment or in combination with any of the embodiments mentioned herein, the r-pyoil containing stream, or first cracker stream, has a steam-to-hydrocarbon ratio that is at least 5, 10, 15, 20, 25, 30, 35, 40, 45, 50, 55, 60, 65, 70, 75, or 80 percent different than the steam-to-hydrocarbon ratio of the non-recycle feed stream, or second cracker stream. The steam-to-hydrocarbon ratio can be higher or lower. For example, the steam-to-hydrocarbon ratio of the r-pyoil containing stream or first cracker stream can be at least 0.01, 0.025, 0.05, 0.075, 0.10, 0.125, 0.15, 0.175, or 0.20 and/or not more than 0.3, 0.27, 0.25, 0.22, or 0.20 different than the steam-to-hydrocarbon ratio of the non-recycle feed stream or second cracker stream. The steam-to-hydrocarbon ratio of the r-pyoil containing stream or first cracker stream can be at least 0.3, 0.32, 0.35, 0.37, 0.4, 0.42, 0.45, 0.47, 0.5 and/or not more than 0.7, 0.67, 0.65, 0.62, 0.6, 0.57, 0.55, 0.52, or 0.5, and the steam-to-hydrocarbon ratio of the non-recycle cracker feed or second cracker stream can be at least 0.02, 0.05, 0.07, 0.10, 0.12, 0.15, 0.17, 0.20, 0.25 and/or not more than 0.45, 0.42, 0.40, 0.37, 0.35, 0.32, or 0.30.

In an embodiment or in combination with any embodiments mentioned herein, the temperature of the r-pyoil containing stream as it passes through a cross-over section in the cracking furnace can be different than the temperature of the non-recycle cracker feed as it passes through the cross-over section, when the streams are introduced into and passed through the furnace separately. For example, the temperature of the r-pyoil stream as it passes through the cross-over section may be at least 0.01, 0.5, 1, 1.5, 2, 5, 10, 15, 20, 25, 30, 35, 40, 45, 50, 55, 60, 65, 70, or 75 percent different than the temperature of the non-recycle hydrocarbon stream (e.g., $C_2$-$C_4$ or $C_5$-$C_{22}$) passing through the cross-over section in another coil. The percentage can be calculated based on the temperature of the non-recycle stream according to the following formula:

[(temperature of r-pyoil stream−temperature of non-recycle cracker stream)]/(temperature of non-recycle cracker steam), expressed as a percentage.

The difference can be higher or lower. The average temperature of the r-pyoil containing stream at the cross-over section can be at least 400, 425, 450, 475, 500, 525, 550, 575, 580, 585, 590, 595, 600, 605, 610, 615, 620, or 625° C. and/or not more than 705, 700, 695, 690, 685, 680, 675, 670, 665, 660, 655, 650, 625, 600, 575, 550, 525, or 500° C., while the average temperature of the non-recycle cracker feed can be at least 401, 426, 451, 476, 501, 526, 551, 560, 565, 570, 575, 580, 585, 590, 595, 600, 605, 610, 615, 620, or 625° C. and/or not more than 705, 700, 695, 690, 685, 680, 675, 670, 665, 660, 655, 650, 625, 600, 575, 550, 525, or 500° C.

The heated cracker stream, which usually has a temperature of at least 500, 510, 520, 530, 540, 550, 560, 570, 580, 590, 600, 610, 620, 630, 640, 650, 660, 670, or 680° C. and/or not more than 850, 840, 830, 820, 810, 800, 790, 780, 770, 760, 750, 740, 730, 720, 710, 705, 700, 695, 690, 685, 680, 675, 670, 665, 660, 655, or 650° C., or in the range of from 500 to 710° C., 620 to 740° C., 560 to 670° C., or 510 to 650° C., may then pass from the convection section of the furnace to the radiant section via the cross-over section.

In an embodiment or in combination with any of the embodiments mentioned herein, the r-pyoil containing feed stream may be added to the cracker stream at the cross-over section. When introduced into the furnace in the cross-over section, the r-pyoil may be at least partially vaporized by, for example, preheating the stream in a direct or indirect heat exchanger. When vaporized or partially vaporized, the r-pyoil containing stream has a vapor fraction of at least 0.5, 0.55, 0.6, 0.65, 0.7, 0.75, 0.8, 0.85, 0.9, 0.95, or 0.99 by weight, or in one embodiment or in combination with any mentioned embodiments, by volume.

When the r-pyoil containing stream is atomized prior to entering the cross-over section, the atomization can be performed using one or more atomizing nozzles. The atomization can take place within or outside the furnace. In an embodiment or in combination with any of the embodiments mentioned herein, an atomizing agent may be added to the r-pyoil containing stream during or prior to its atomization. The atomizing agent can include steam, or it may include predominantly ethane, propane, or combinations thereof. When used the atomizing agent may be present in the stream being atomized (e.g., the r-pyoil containing composition) in an amount of at least 1, 2, 4, 5, 8, 10, 12, 15, 10, 25, or 30 weight percent and/or not more than 50, 45, 40, 35, 30, 25, 20, 15, or 10 weight percent.

The atomized or vaporized stream of r-pyoil may then be injected into or combined with the cracker stream passing through the cross-over section. At least a portion of the injecting can be performed using at least one spray nozzle. At least one of the spray nozzles can be used to inject the r-pyoil containing stream into the cracker feed stream may be oriented to discharge the atomized stream at an angle within about 45, 50, 35, 30, 25, 20, 15, 10, 5, or 0° from the vertical. The spray nozzle or nozzles may also be oriented to discharge the atomized stream into a coil within the furnace at an angle within about 30, 25, 20, 15, 10, 8, 5, 2, or 1° of being parallel, or parallel, with the axial centerline of the coil at the point of introduction. The step of injecting the atomized r-pyoil may be performed using at least two, three, four, five, six or more spray nozzles, in the cross-over and/or convection section of the furnace.

In an embodiment or in combination with any embodiments mentioned herein, atomized r-pyoil can be fed, alone or in combination with an at least partially non-recycle cracker stream, into the inlet of one or more coils in the convection section of the furnace. The temperature of such an atomization can be at least 30, 35, 40, 45, 50, 55, 60, 65, 70, 75, or 80° C. and/or not more than 120, 110, 100, 90, 95, 80, 85, 70, 65, 60, or 55° C.

In an embodiment or in combination with any embodiments mentioned herein, the temperature of the atomized or vaporized stream can be at least 5, 10, 15, 20, 25, 30, 35, 40, 45, 50, 75, 100, 125, 150, 175, 200, 225, 250, 275, 300, 325, 350° C. and/or not more than 550, 525, 500, 475, 450, 425, 400, 375, 350, 325, 300, 275, 250, 225, 200, 175, 150, 125, 100, 90, 80, 75, 70, 60, 55, 50, 45, 40, 30, or 25° C. cooler than the temperature of the cracker stream to which it is added. The resulting combined cracker stream comprises a continuous vapor phase with a discontinuous liquid phase (or droplets or particles) dispersed therethrough. The atomized liquid phase may comprise r-pyoil, while the vapor phase may include predominantly C2-C4 components, ethane, propane, or combinations thereof. The combined cracker stream may have a vapor fraction of at least 0.7, 0.75, 0.8, 0.85, 0.9, 0.95, or 0.99 by weight, or in one embodiment or in combination with any mentioned embodiments, by volume.

The temperature of the cracker stream passing through the cross-over section can be at least 500, 510, 520, 530, 540, 550, 555, 560, 565, 570, 575, 580, 585, 590, 595, 600, 605, 610, 615, 620, 625, 630, 635, 640, 645, 650, 660, 670, or 680° C. and/or not more than 850, 840, 830, 820, 810, 800, 795, 790, 785, 780, 775, 770, 765, 760, 755, 750, 745, 740, 735, 730, 725, 720, 715, 710, 705, 700, 695, 690, 685, 680, 675, 670, 665, 660, 655, 650, 645, 640, 635, or 630° C., or in the range of from 620 to 740° C., 550 to 680° C., 510 to 630° C.

The resulting cracker feed stream then passes into the radiant section. In an embodiment or in combination with any of the embodiments mentioned herein, the cracker stream (with or without the r-pyoil) from the convection section may be passed through a vapor-liquid separator to separate the stream into a heavy fraction and a light fraction before cracking the light fraction further in the radiant section of the furnace. One example of this is illustrated in FIG. 8.

In an embodiment or in combination with any of the embodiments mentioned herein, the vapor-liquid separator 640 may comprise a flash drum, while in other embodiments it may comprise a fractionator. As the stream 614 passes through the vapor-liquid separator 640, a gas stream impinges on a tray and flows through the tray, as the liquid from the tray fall to an underflow 642. The vapor-liquid separator may further comprise a demister or chevron or other device located near the vapor outlet for preventing liquid carry-over into the gas outlet from the vapor-liquid separator 640.

Within the convection section 610, the temperature of the cracker stream may increase by at least 50, 75, 100, 150, 175, 200, 225, 250, 275, or 300° C. and/or not more than about 650, 600, 575, 550, 525, 500, 475, 450, 425, 400, 375, 350, 325, 300, or 275° C., so that the passing of the heated cracker stream exiting the convection section 610 through the vapor-liquid separator 640 may be performed at a temperature of least 400, 425, 450, 475, 500, 525, 550, 575, 600, 625, 650° C. and/or not more than 800, 775, 750, 725, 700, 675, 650, 625° C. When heavier components are present, at least a portion or nearly all of the heavy components may be removed in the heavy fraction as an underflow 642. At least a portion of the light fraction 644 from the separator 640 may be introduced into the cross-over section or the radiant zone tubes 624 after the separation, alone or in combination with one or more other cracker streams, such as, for example, a predominantly $C_5$-$C_{22}$ hydrocarbon stream or a $C_2$-$C_4$ hydrocarbon stream.

Referencing FIGS. 5 and 6, the cracker feed stream (either the non-recycle cracker feed stream or when combined with the r-pyoil feed stream) 350 and 650 may be introduced into a furnace coil at or near the inlet of the convection section. The cracker feed stream may then pass through at least a portion of the furnace coil in the convection section 310 and 610, and dilution steam 360 and 660 may be added at some point in order to control the temperature and cracking severity in the radiant section 320 and 620. The amount of steam added may depend on the furnace operating conditions, including feed type and desired product distribution, but can be added to achieve a steam-to-hydrocarbon ratio in the range of from 0.1 to 1.0, 0.15 to 0.9, 0.2 to 0.8, 0.3 to 0.75, or 0.4 to 0.6, calculated by weight. In an embodiment or in combination with any of the embodiments mentioned herein, the steam may be produced using separate boiler feed water/steam tubes heated in the convection section of the same furnace (not shown in FIG. 5). Steam 360 and 660 may be added to the cracker feed (or any intermediate cracker feed stream within the furnace) when the cracker feed stream has a vapor fraction of 0.60 to 0.95, or 0.65 to 0.90, or 0.70 to 0.90 by weight, or in one embodiment or in combination with any mentioned embodiments, by volume.

The heated cracker stream, which usually has a temperature of at least 500, or at least 510, or at least 520, or at least 530, or at least 540, or at least 550, or at least 560, or at least 570, or at least 580, or at least 590, or at least 600, or at least 610, or at least 620, or at least 630, or at least 640, or at least 650, or at least 660, or at least 670, or at least 680, in each case ° C. and/or not more than 850, or not more than 840, or not more than 830, or not more than 820, or not more than 810, or not more than 800, or not more than 790, or not more than 780, or not more than 770, or not more than 760, or not more than 750, or not more than 740, or not more than 730, or not more than 720, or not more than 710, or not more than 705, or not more than 700, or not more than 695, or not more than 690, or not more than 685, or not more than 680, or not more than 675, or not more than 670, or not more than 665, or not more than 660, or not more than 655, or not more than 650, in each case ° C., or in the range of from 500 to 710° C., 620 to 740° C., 560 to 670° C., or 510 to 650° C., may then pass from the convection section 610 of the furnace to the radiant section 620 via the cross-over section 630. In an embodiment or in combination with any of the embodiments mentioned herein, the r-pyoil containing feed stream 550 may be added to the cracker stream at the cross-over section 530 as shown in FIG. 6. When introduced into the furnace in the cross-over section, the r-pyoil may be at least partially vaporized or atomized prior to being combined with the cracker stream at the cross-over. The temperature of the cracker stream passing through the cross-over 530 or 630 can be at least 400, 425, 450, 475, or at least 500, or at least 510, or at least 520, or at least 530, or at least 540, or at least 550, or at least 560, or at least 570, or at least 580, or at least 590, or at least 600, or at least 610, or at least 620, or at least 630, or at least 640, or at least 650, or at least 660, or at least 670, or at least 680, in each case ° C. and/or not more than 850, or not more than 840, or not more than 830, or not more than 820, or not more than 810, or not more than 800, or not more than 790, or not more than 780, or not more than 770, or not more than 760, or not more than 750, or not more than 740, or not more than 730, or not more than 720, or not more than 710, or not more than 705, or not more than 700, or not more than 695, or not more than 690, or not more than 685, or not more than 680, or not more than 675, or not more than 670, or not more than 665, or not more than 660, or not more than 655, or not more than 650, in each case ° C., or in the range of from 620 to 740° C., 550 to 680° C., 510 to 630° C.

The resulting cracker feed stream then passes through the radiant section, wherein the r-pyoil containing feed stream is thermally cracked to form lighter hydrocarbons, including olefins such as ethylene, propylene, and/or butadiene. The residence time of the cracker feed stream in the radiant section can be at least 0.1, or at least 0.15, or at least 0.2, or at least 0.25, or at least 0.3, or at least 0.35, or at least 0.4, or at least 0.45, in each case seconds and/or not more than 2, or not more than 1.75, or not more than 1.5, or not more than 1.25, or not more than 1, or not more than 0.9, or not more than 0.8, or not more than 0.75, or not more than 0.7, or not more than 0.65, or not more than 0.6, or not more than 0.5, in each case seconds. The temperature at the inlet of the furnace coil is at least 500, or at least 510, or at least 520, or at least 530, or at least 540, or at least 550, or at least 560, or at least 570, or at least 580, or at least 590, or at least 600, or at least 610, or at least 620, or at least 630, or at least 640, or at least 650, or at least 660, or at least 670, or at least 680, in each case ° C. and/or not more than 850, or not more than 840, or not more than 830, or not more than 820, or not more than 810, or not more than 800, or not more than 790, or not more than 780, or not more than 770, or not more than 760, or not more than 750, or not more than 740, or not more than 730, or not more than 720, or not more than 710, or not more than 705, or not more than 700, or not more than 695, or not more than 690, or not more than 685, or not more than 680, or not more than 675, or not more than 670, or not more than 665, or not more than 660, or not more than 655, or not more than 650, in each case ° C., or in the range of from 550 to 710° C., 560 to 680° C., or 590 to 650° C., or 580 to 750° C., 620 to 720° C., or 650 to 710° C.

The coil outlet temperature can be at least 640, or at least 650, or at least 660, or at least 670, or at least 680, or at least 690, or at least 700, or at least 720, or at least 730, or at least 740, or at least 750, or at least 760, or at least 770, or at least 780, or at least 790, or at least 800, or at least 810, or at least 820, in each case ° C. and/or not more than 1000, or not more than 990, or not more than 980, or not more than 970, or not more than 960, or not more than 950, or not more than 940, or not more than 930, or not more than 920, or not more than 910, or not more than 900, or not more than 890, or not more than 880, or not more than 875, or not more than 870, or not more than 860, or not more than 850, or not more than 840, or not more than 830, in each case ° C., in the range of from 730 to 900° C., 750 to 875° C., or 750 to 850° C.

The cracking performed in the coils of the furnace may include cracking the cracker feed stream under a set of processing conditions that include a target value for at least one operating parameter. Examples of suitable operating parameters include, but are not limited to maximum cracking temperature, average cracking temperature, average tube outlet temperature, maximum tube outlet temperature, and average residence time. When the cracker stream further includes steam, the operating parameters may include hydrocarbon molar flow rate and total molar flow rate. When two or more cracker streams pass through separate coils in the furnace, one of the coils may be operated under a first set of processing conditions and at least one of the other coils may be operated under a second set or processing conditions. At least one target value for an operating parameter from the first set of processing conditions may differ from a target value for the same parameter in the second set of conditions by at least 0.01, 0.03, 0.05, 0.1, 0.25, 0.5, 1, 2, 5, 7, 10, 15, 20, 25, 30, 35, 40, 45, 50, 55, 60, 65, 70, 75, 80, 85, 90, or 95 percent and/or not more than about 95, 90, 85, 80, 75, 70, 65, 60, 55, 50, 45, 40, 35, 30, 25, 20, or 15 percent. Examples include 0.01 to 30, 0.01 to 20, 0.01 to 15, 0.03 to 15 percent. The percentage is calculated according to the following formula:

[(measured value for operating parameter)−(target value for operating parameter]/[(target value for operating parameter)], expressed as a percentage.

As used herein, the term “different,” means higher or lower.

The coil outlet temperature can be at least 640, 650, 660, 670, 680, 690, 700, 720, 730, 740, 750, 760, 770, 780, 790, 800, 810, 820° C. and/or not more than 1000, 990, 980, 970, 960, 950, 940, 930, 920, 910, 900, 890, 880, 875, 870, 860, 850, 840, 830° C., in the range of from 730 to 900° C., 760 to 875° C., or 780 to 850° C.

In an embodiment or in combination with any of the embodiments mentioned herein, the addition of r-pyoil to a cracker feed stream may result in changes to one or more of the above operating parameters, as compared to the value of the operating parameter when an identical cracker feed stream is processed in the absence of r-pyoil. For example, the values of one or more of the above parameters may be at least 0.01, 0.03, 0.05, 0.1, 0.25, 0.5, 1, 2, 5, 7, 10, 15, 20, 25, 30, 35, 40, 45, 50, 55, 60, 65, 70, 75, 80, 85, 90, or 95 percent different (e.g., higher or lower) than the value for the same parameter when processing an identical feed stream without r-pyoil, ceteris paribus. The percentage is calculated according to the following formula:

[(measured value for operating parameter)−(target value for operating parameter]/[(target value for operating parameter)], expressed as a percentage.

One example of an operating parameter that may be adjusted with the addition of r-pyoil to a cracker stream is coil outlet temperature. For example, in an embodiment or in combination with any embodiment mentioned herein, the cracking furnace may be operated to achieve a first coil outlet temperature (COT1) when a cracker stream having no r-pyoil is present. Next, r-pyoil may be added to the cracker stream, via any of the methods mentioned herein, and the combined stream may be cracked to achieve a second coil outlet temperature (COT2) that is different than COT1.

In some cases, when the r-pyoil is heavier than the cracker stream, COT2 may be less than COT1, while, in other case, when the r-pyoil is lighter than the cracker stream, COT2 may be greater than or equal to COT1. When the r-pyoil is lighter than the cracker stream, it may have a 50% boiling point that is at least 5, 10, 15, 20, 25, 30, 35, 40, 45, or 50 and/or not more than 80, 75, 70, 65, 60, 55, or 50 percent higher than the 50% boiling point of the cracker stream. The percentage is calculated according to the following formula:

[(50% boiling point of r-pyoil in ° R)−(50% boiling point of cracker stream)]/[(50% boiling point of cracker stream)], expressed as a percentage.

Alternatively, or in addition, the 50% boiling point of the r-pyoil may be at least 5, 10, 15, 20, 25, 30, 35, 40, 45, 50, 55, 60, 65, 70, 75, 80, 85, 90, 95, or 100° C. and/or not more than 300, 275, 250, 225, or 200° C. lower than the 50% boiling point of the cracker stream. Heavier cracker streams can include, for example, vacuum gas oil (VGO), atmospheric gas oil (AGO), or even coker gas oil (CGO), or combinations thereof.

When the r-pyoil is lighter than the cracker stream, it may have a 50% boiling point that is at least 5, 10, 15, 20, 25, 30, 35, 40, 45, or 50 and/or not more than 80, 75, 70, 65, 60, 55, or 50 percent lower than the 50% boiling point of the cracker stream. The percentage is calculated according to the following formula:

[(50% boiling point of r-pyoil)−(50% boiling point of cracker stream)]/[(50% boiling point of cracker stream)], expressed as a percentage.

Additionally, or in the alternative, the 50% boiling point of the r-pyoil may be at least 5, 10, 15, 20, 25, 30, 35, 40, 45, 50, 55, 60, 65, 70, 75, 80, 85, 90, 95, or 100° C. and/or not more than 300, 275, 250, 225, or 200° C. higher than the 50% boiling point of the cracker stream. Lighter cracker streams can include, for example, LPG, naphtha, kerosene, natural gasoline, straight run gasoline, and combinations thereof.

In some cases, COT1 can be at least 5, 10, 15, 20, 25, 30, 35, 40, 45, 50° C. and/or not more than about not more than 150, 140, 130, 125, 120, 110, 105, 100, 90, 80, 75, 70, or 65° C. different (higher or lower) than COT2, or COT1 can be at least 0.3, 0.6, 1, 2, 5, 10, 15, 20, or 25 and/or not more than 80, 75, 70, 65, 60, 50, 45, or 40 percent different than COT2 (with the percentage here defined as the difference between COT1 and COT2 divided by COT1, expressed as a percentage). At least one or both of COT1 and COT2 can be at least 730, 750, 77, 800, 825, 840, 850, 860, 870, 880, 890, 900, 910, 920, 930, 940, 950, 960, 970, 980, 990 and/or not more than 1200, 1175, 1150, 1140, 1130, 1120, 1110, 1100, 1090, 1080, 1070, 1060, 1050, 1040, 1030, 1020, 1010, 1000, 990, 980, 970, 960 950, 940, 930, 920, 910, or 900° C.

In an embodiment or in combination with any of the embodiments mentioned herein, the mass velocity of the cracker feed stream through at least one, or at least two radiant coils (for clarity as determine across the entire coil as opposed to a tube within a coil) is in the range of 60 to 165 kilograms per second (kg/s) per square meter ($m^2$) of cross-sectional area (kg/s/$m^2$), 60 to 130 (kg/s/m2), 60 to 110 (kg/s/m2), 70 to 110 (kg/s/$m^2$), or 80 to 100 (kg/s/$m^2$). When steam is present, the mass velocity is based on the total flow of hydrocarbon and steam.

In one embodiment or in combination with any mentioned embodiments, there is provided a method for making one or more olefins by:

(a) cracking a cracker stream in a cracking unit at a first coil outlet temperature (COT1);

(b) subsequent to step (a), adding a stream comprising a recycle content pyrolysis oil composition (r-pyoil) to said cracker stream to form a combined cracker stream; and (c) cracking said combined cracker stream in said cracking unit at a second coil outlet temperature (COT2), wherein said second coil outlet temperature is lower, or at least 3° C. lower, or at least 5° C. lower than said first coil outlet temperature.

The reason or cause for the temperature drop in the second coil outlet temperature (COT2) is not limited, provided that COT2 is lower than the first coil outlet temperature (COT1). In one embodiment or in combination with any mentioned embodiments, In one embodiment or in combination with any other mentioned embodiments, the COT2 temperature on the r-pyoil fed coils can be set to a temperature that lower than, or at least 1, 2, 3, 4, or at least 5° C. lower than COT1 ("Set" Mode), or it can be allowed to change or float without setting the temperature on the r-pyoil fed coils ("Free Float" Mode").

The COT2 can be set at least 5° C. lower than COT1 in a Set Mode. All coils in a furnace can be r-pyoil containing feed streams, or at least 1, or at least two of the coils can be r-pyoil containing feed streams. In either case, at least one of the r-pyoil containing coils can be in a Set Mode. By reducing the cracking severity of the combined cracking stream, one can take advantage of the lower heat energy required to crack r-pyoil when it has an average number average molecular weight that is higher than the cracker feed stream, such as a gaseous $C_2$-$C_4$ feed. While the cracking severity on the cracker feed (e.g. $C_2$-$C_4$) can be reduced and thereby increase the amount of unconverted $C_2$-$C_4$ feed in a single pass, the higher amount of unconverted feed (e.g. $C_2$-$C_4$ feed) is desirable to increase the ultimate yield of olefins such as ethylene and/or propylene through multiple passes by recycling the unconverted $C_2$-$C_4$ feed through the furnace. Optionally, other cracker products, such as the aromatic and diene content, can be reduced.

In one embodiment or in combination with any mentioned embodiments, the COT2 in a coil can be fixed in a Set Mode to be lower than, or at least 1, 2, 3, 4, or at least 5° C. lower than the COT1 when the hydrocarbon mass flow rate of the combined cracker stream in at least one coil is the same as or less than the hydrocarbon mass flow rate of the cracker stream in step (a) in said coil. The hydrocarbon mass flow rate includes all hydrocarbons (cracker feed and if present the r-pyoil and/or natural gasoline or any other types of hydrocarbons) and other than steam. Fixing the COT2 is advantageous when the hydrocarbon mass flow rate of the combined cracker stream in step (b) is the same as or less than the hydrocarbon mass flow rate of the cracker stream in step (a) and the pyoil has a higher average molecular weight than the average molecular weight of the cracker stream. At the same hydrocarbon mass flow rates, when pyoil has a heavier average molecular weight than the cracker stream, the COT2 will tend to rise with the addition of pyoil because the higher molecular weight molecules require less thermal energy to crack. If one desires to avoid overcracking the pyoil, the lowered COT2 temperature can assist to reduce by-product formation, and while the olefin yield in the singe pass is also reduced, the ultimate yield of olefins can be satisfactory or increased by recycling unconverted cracker feed through the furnace.

In a Set Mode, the temperature can be fixed or set by adjusting the furnace fuel rate to burners.

In one embodiment or in combination with any other mentioned embodiments, the COT2 is in a Free Float Mode and is as a result of feeding pyoil and allowing the COT2 to rise or fall without fixing a temperature to the pyoil fed coils. In this embodiment, not all of the coils contain r-pyoil. The heat energy supplied to the r-pyoil containing coils can be supplied by keeping constant temperature on, or fuel feed rate to the burners on the non-recycle cracker feed containing coils. Without fixing or setting the COT2, the COT2 can be lower than COT1 when pyoil is fed to the cracker stream to form a combined cracker stream that has a higher hydrocarbon mass flow rate than the hydrocarbon mass flow rate of the cracker stream in step (a). Pyoil added to a cracker feed to increase the hydrocarbon mass flow rate of the combined cracker feed lowers the COT2 and can outweigh the temperature rise effect of using a higher average molecular weight pyoil. These effects can be seen while other cracker conditions are held constant, such as the dilution steam ratio, feed locations, composition of the cracker feed and pyoil, and fuel feed rates to the firebox burners in the furnace on the tubes containing only cracker feed and no feed of r-pyoil.

The COT2 can be lower than, or at least 1, 2, 3, 4, 5, 8, 10, 12, 15, 18, 20, 25, 30, 35, 40, 45, 50° C. and/or not more than about not more than 150, 140, 130, 125, 120, 110, 105, 100, 90, 80, 75, 70, or 65° C. lower than COT1.

Independent of the reason or cause of the temperature drop in COT2, the time period for engaging step (a) is flexible, but ideally, step (a) reaches a steady state before engaging step (b). In one embodiment or in combination with any mentioned embodiments, step (a) is in operation for at least 1 week, or at least 2 weeks, or at least 1 month, or at least 3 months, or at least 6 months, or at least 1 year, or at least 1.5 years, or at least 2 years. The step (a) can be represented by a cracker furnace in operation that has never accepted a feed of pyoil or a combined feed of cracker feed and pyoil. Step (b) can be the first time a furnace has accepted a feed of pyoil or a combined cracker feed containing pyoil. In one embodiment or in combination with any other mentioned embodiments, steps (a) and (b) can be cycled multiple times per year, such as at least 2×/yr, or at least 3×/yr, or at least 4×/yr, or at least 5×/yr, or at least 6×/yr, or at least 8×/yr, or at least 12×/yr, as measured on a calendar year. Campaigning a feed of pyoil is representative of multiple cycling of steps (a) and (b). When the feed supply of pyoil is exhausted or shut off, the COT1 is allowed to reach a steady state temperature before engaging step (b).

Alternatively, the feed of pyoil to a cracker feed can be continuous over the entire course of at least 1 calendar year, or at least 2 calendar years.

In one embodiment or in combination with any other mentioned embodiments, the cracker feed composition used in steps (a) and (b) remains unchanged, allowing for regular compositional variations observed during the course of a calendar year. In one embodiment or in combination with any other mentioned embodiments, the flow of cracker feed in step (a) is continuous and remains continuous as pyoil is to the cracker feed to make a combined cracker feed. The cracker feed in steps (a) and (b) can be drawn from the same source, such as the same inventory or pipeline.

In one embodiment or in combination with any mentioned embodiments, the COT2 is lower than, or at least 1, 2, 3, 4, or at least 5° C. lower for at least 30% of the time that the pyoil is fed to the cracker stream to form the combined cracker stream, or at least 40% of the time, or at least 50% of the time, or at least 60% of the time, or at least 70% of the time, or at least 80% of the time, or at least 85% of the time, or at least 90% of the time, or at least 95% of the time, the time measured as when all conditions, other than COT's, are held constant, such as cracker and pyoil feed rates, steam ratio, feed locations, composition of the cracker feed and pyoil, etc.

In one embodiment or in combination with any mentioned embodiments, the hydrocarbon mass flow rate of combined cracker feed can be increased. There is now provided a method for making one or more olefins by:

(a) cracking a cracker stream in a cracking unit at a first hydrocarbon mass flow rate (MF1);
(b) subsequent to step (a), adding a stream comprising a recycle content pyrolysis oil composition (r-pyoil) to said cracker stream to form a combined cracker stream having a second hydrocarbon mass flow rate (MF2) that is higher than MF1; and
(c) cracking said combined cracker stream at MF2 in said cracking unit to obtain an olefin-containing effluent that has a combined output of ethylene and propylene that same as or higher than the output of ethylene and propylene obtained by cracking only said cracker stream at MF1.

The output refers to the production of the target compounds in weight per unit time, for example, kg/hr. Increasing the mass flow rate of the cracker stream by addition of r-pyoil can increase the output of combined ethylene and propylene, thereby increasing the throughput of the furnace. Without being bound to a theory, it is believed that this is made possible because the total energy of reaction is not as endothermic with the addition of pyoil relative to total energy of reaction with a lighter cracker feed such as propane or ethane. Since the heat flux on the furnace is limited and the total heat of reaction of pyoil is less endothermic, more of the limited heat energy becomes available to continue cracking the heavy feed per unit time. The MF2 can be increased by at least 1, 2, 3, 4, 5, 7, 10, 10, 13, 15, 18, or 20% through a r-pyoil fed coil, or can be increased by at least 1, 2, 3, 5, 7, 10, 10, 13, 15, 18, or 20% as measured by the furnace output provided that at least one coil processes r-pyoil. Optionally, the increase in combined output of ethylene and propylene can be accomplished without varying the heat flux in the furnace, or without varying the r-pyoil fed coil outlet temperature, or without varying the fuel feed rate to the burners assigned to heat the coils containing only non-recycle content cracker feed, or without varying the fuel feed rate to any of the burners in the furnace. The MF2 higher hydrocarbon mass flow rate in the r-pyoil containing coils can be through one or at least one coil in a furnace, or two or at least two, or 50% or at least 50%, or 75% or at least 75%, or through all of the coils in a furnace.

The olefin-containing effluent stream can have a total output of propylene and ethylene from the combined cracker stream at MF2 that is the same as or higher than the output of propylene and ethylene of an effluent stream obtained by cracking the same cracker feed but without r-pyoil by at least 0.5%, or at least 1%, or at least 2%, or at least 2.5%, determined as:

$$\%\text{increase} = \frac{Omf2 - Omf1}{Omf1} \times 100$$

where $O_{mf1}$ is the combined output of propylene and ethylene content in the cracker effluent at MF1 made without r-pyoil; and $O_{mf2}$ is the combined output of propylene and ethylene content in the cracker effluent at MF2 made with r-pyoil.

The olefin-containing effluent stream can have a total output of propylene and ethylene from the combined cracker stream at MF2 that is least 1, 5, 10, 15, 20%, and/or up to 80, 70, 65% of the mass flow rate increase between MF2 and MF1 on a percentage basis. Examples of suitable ranges include 1 to 80, or 1 to 70, or 1 to 65, or 5 to 80, or 5 to 70, or 5 to 65, or 10 to 80, or 10 to 70, or 10 to 65, or 15 to 80, or 15 to 70, or 15 to 65, or 20 to 80, or 20 to 70, or 20 to 65, or 25 to 80, or 25 to 70, or 26 to 65, or 35 to 80, or 35 to 70, or 35 to 65, or 40 to 80, or 40 to 70, or 40 to 65, each expressed as a percent %. For example, if the percentage difference between MF2 and MF1 is 5%, and the total output of propylene and ethylene is increased by 2.5%, the olefin increase as a function of mass flow increase is 50% (2.5%/5%×100). This can be determined as:

$$\%\text{relative increase} = \frac{\Delta O\%}{\Delta MF\%} \times 100$$

where ΔO % is percentage increase between the combined output of propylene and ethylene content in the cracker effluent at MF1 made without r-pyoil and MF2 made with r-pyoil (using the aforementioned equation); and ΔMF % is the percentage increase of MF2 over MF1.

Optionally, the olefin-containing effluent stream can have a total wt. % of propylene and ethylene from the combined cracker stream at MF2 that is the same as or higher than the wt. % of propylene and ethylene of an effluent stream obtained by cracking the same cracker feed but without r-pyoil by at least 0.5%, or at least 1%, or at least 2%, or at least 2.5%, determined as:

$$\%\text{increase} = \frac{Emf2 - Emf1}{Emf1} \times 100$$

where $E_{mf1}$ is the combined wt. % of propylene and ethylene content in the cracker effluent at MF1 made without r-pyoil; and $E_{mf2}$ is the combined wt. % of propylene and ethylene content in the cracker effluent at MF2 made with r-pyoil.

There is also provided a method for making one or more olefins, said method comprising:

(a) cracking a cracker stream in a cracking furnace to provide a first olefin-containing effluent exiting the cracking furnace at a first coil outlet temperature (COT1);

(b) subsequent to step (a), adding a stream comprising a recycle content pyrolysis oil composition (r-pyoil) to said cracker stream to form a combined cracker stream; and (c) cracking said combined cracker stream in said cracking unit to provide a second olefin-containing effluent exiting the cracking furnace at a second coil outlet temperature (COT2), wherein, when said r-pyoil is heavier than said cracker stream, COT2 is equal to or less than COT1, wherein, when said r-pyoil is lighter than said cracker stream, COT2 is greater than or equal to COT1.

In this method, the embodiments described above for a COT2 lower than COT1 are also applicable here. The COT2 can be in a Set Mode or Free Float Mode. In one embodiment or in combination with any other mentioned embodiments, the COT2 is in a Free Float Mode and the hydrocarbon mass flow rate of the combined cracker stream in step (b) is higher than the hydrocarbon mass flow rate of the cracker stream in step (a). In one embodiment or in combination with any mentioned embodiments, the COT2 is in a Set Mode.

In one embodiment or in combination with any mentioned embodiments, there is provided a method for making one or more olefins by:

(a) cracking a cracker stream in a cracking unit at a first coil outlet temperature (COT1);

(b) subsequent to step (a), adding a stream comprising a recycle content pyrolysis oil composition (r-pyoil) to said cracker stream to form a combined cracker stream; and (c) cracking said combined cracker stream in said cracking unit at a second coil outlet temperature (COT2), wherein said second coil outlet temperature is higher than the first coil outlet temperature.

The COT2 can be at least 5, 8, 10, 12, 15, 18, 20, 25, 30, 35, 40, 45, 50° C. and/or not more than about not more than 150, 140, 130, 125, 120, 110, 105, 100, 90, 80, 75, 70, or 65° C. higher than COT1.

In one embodiment or in combination with any other mentioned embodiments, r-pyoil is added to the inlet of at least one coil, or at least two coils, or at least 50%, or at least 75%, or all of the coils, to form at least one combined cracker stream, or at least two combined cracker streams, or at least the same number of combined crackers streams as coils accepting a feed of r-pyoil. At least one, or at least two of the combined cracker streams, or at least all of the r-pyoil fed coils can have a COT2 that is higher than their respective COT1. In one embodiment or in combination with any mentioned embodiments, at least one, or at least two coils, or at least 50%, or at least 75% of the coils within said cracking furnace contain only non-recycle content cracker feed, with at least one of the coils in the cracking furnace being fed with r-pyoil, and the coil or at least some of multiple coils fed with r-pyoil having a COT2 higher than their respective COT1.

In one embodiment or in combination with any mentioned embodiments, the hydrocarbon mass flow rate of the combined stream in step (b) is substantially the same as or lower than the hydrocarbon mass flow rate of the cracker stream in step (a). By substantially the same is meant not more than a 2% difference, or not more than a 1% difference, or not more than a 0.25% difference. When the hydrocarbon mass flow rate of the combined cracker stream in step (b) is substantially the same as or lower than the hydrocarbon mass flow rate of the cracker stream (a), and the COT2 is allowed to operate in a Free Float Mode (where at least 1 of the tubes contains non-recycle content cracker stream), the COT2 on the r-pyoil containing coil can rise relative to COT1. This is the case even though the pyoil, having a larger number average molecular weight compared to the cracker stream, requires less energy to crack. Without being bound to a theory, it is believed that one or a combination of factors contribute to the temperature rise, including the following:

(i) lower heat energy is required to crack pyoil in the combined stream and/or (ii) the occurrence of exothermic reactions among cracked products of pyoil, such as diels-alder reactions.

This effect can be seen when the other process variables are constant, such as the firebox fuel rate, dilution steam ratio, location of feeds, and composition of the cracker feed.

In one embodiment or in combination with any mentioned embodiments, the COT2 can be set or fixed to a higher temperature than COT1 (the Set Mode). This is more applicable when the hydrocarbon mass flow rate of the combined cracker stream is higher than the hydrocarbon mass flow rate of the cracker stream which would otherwise lower the COT2. The higher second coil outlet temperature (COT2) can contribute to an increased severity and a decreased output of unconverted lighter cracker feed (e.g. $C_2$-$C_4$ feed), which can assist with downstream capacity restricted fractionation columns.

In one embodiment or in combination with any mentioned embodiments, whether the COT2 is higher or lower than COT1, the cracker feed compositions are the same when a comparison is made between COT2 with a COT1. Desirably, the cracker feed composition in step (a) is the same cracker composition as used to make the combined cracker stream in step (b). Optionally, the cracker composition feed in step (a) is continuously fed to the cracker unit, and the addition of pyoil in step (b) is to the continuous cracker feed in step (a). Optionally, the feed of pyoil to the cracker feed is continuous for at least 1 day, or at least 2 days, or at least 3 days, or at least 1 week, or at least 2 weeks, or at least 1 month, or at least 3 months, or at least 6 months or at least 1 year.

The amount of raising or lowering the cracker feed in step (b) in any of the mentioned embodiments can be at least 2%, or at least 5%, or at least 8%, or at least 10%. In one embodiment or in combination with any mentioned embodiments, the amount of lowering the cracker feed in step (b) can be an amount that corresponds to the addition of pyoil by weight. In one embodiment or in combination with any mentioned embodiments, the mass flow of the combined cracker feed is at least 1%, or at least 5%, or at least 8%, or at least 10% higher than the hydrocarbon mass flow rate of the cracker feed in step (a).

In any or all of the mentioned embodiments, the cracker feed or combined cracker feed mass flows and COT relationships and measurements are satisfied if any one coil in the furnace satisfies the stated relationships but can also be present in multiple tubes depending on how the pyoil is fed and distributed.

In an embodiment or in combination with any of the embodiments mentioned herein, the burners in the radiant zone provide an average heat flux into the coil in the range of from 60 to 160 kW/m$^2$ or 70 to 145 kW/m$^2$ or 75 to 130 kW/m$^2$. The maximum (hottest) coil surface temperature is in the range of 1035 to 1150° C. or 1060 to 1180° C. The pressure at the inlet of the furnace coil in the radiant section is in the range of 1.5 to 8 bar absolute (bara), or 2.5 to 7 bara, while the outlet pressure of the furnace coil in the radiant section is in the range of from 1.03 to 2.75 bara, or 1.03 to 2.06 bara. The pressure drop across the furnace coil in the radiant section can be from 1.5 to 5 bara, or 1.75 to 3.5 bara, or 1.5 to 3 bara, or 1.5 to 3.5 bara.

In an embodiment or in combination with any of the embodiments mentioned herein, the yield of olefin—ethylene, propylene, butadiene, or combinations thereof—can be at least 15, or at least 20, or at least 25, or at least 30, or at least 35, or at least 40, or at least 45, or at least 50, or at least 55, or at least 60, or at least 65, or at least 70, or at least 75, or at least 80, in each case percent. As used herein, the term "yield" refers to the mass of product/mass of feedstock×100%. The olefin-containing effluent stream comprises at least about 30, or at least 40, or at least 50, or at least 60, or at least 70, or at least 75, or at least 80, or at least 85, or at least 90, or at least 95, or at least 97, or at least 99, in each case weight percent of ethylene, propylene, or ethylene and propylene, based on the total weight of the effluent stream.

In an embodiment or in combination with one or more embodiments mentioned herein, the olefin-containing effluent stream 670 can comprise C2 to C4 olefins, or propylene, or ethylene, or C4 olefins, in an amount of at least 5, 10, 15, 20, 25, 30, 35, 40, 45, 50, 55, 60, 65, 70, 75, 80, 85, or 90 weight percent, based on the weight of the olefin-containing effluent. The stream may comprise predominantly ethylene, predominantly propylene, or predominantly ethylene and propylene, based on the olefins in the olefin-containing effluent, or based on the weight of the C1-$C_5$ hydrocarbons in the olefin-containing effluent, or based on the weight of the olefin-containing effluent stream. The weight ratio of ethylene-to-propylene in the olefin-containing effluent stream can be at least about 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, or 2:1 and/or not more than 3:1, 2.9:1, 2.8:1, 2.7:1, 2.5:1, 2.3:1, 2.2:1, 2.1:1, 2:1, 1.7:1, 1.5:1, or 1.25:1. In an embodiment or in combination with one or more embodiments mentioned herein, the olefin-containing effluent stream can have a ratio of propylene:ethylene that is higher than the propylene:ethylene ratio of an effluent stream obtained by cracking the same cracker feed but without r-pyoil at equivalent dilution steam ratios, feed locations, cracker feed compositions (other than the r-pyoil), and allowing the coils fed with r-pyoil to be in the Float Mode, or if all coils in a furnace are fed with r-pyoil, then at the same temperature prior to feeding r-pyoil. As discussed above, this is possible when the mass flow of the cracker feed remains substantially the same resulting in a higher hydrocarbon mass flow rate of the combined cracker stream when r-pyoil is added relative to the original feed of the cracker stream.

The olefin-containing effluent stream can have a ratio of propylene:ethylene that is at least 1% higher, or at least 2% higher, or at least 3% higher, or at least 4% higher, or at least 5% higher or at least 7% higher or at least 10% higher or at least 12% higher or at least 15% higher or at least 17% higher or at least 20% higher than the propylene:ethylene ratio of an effluent stream obtained by cracking the same cracker feed but without r-pyoil. Alternatively or in addition, the olefin-containing effluent stream can have a ratio of propylene:ethylene that is up to 50% higher, or up to 45% higher, or up to 40% higher, or up to 35% higher, or up to 25% higher, or up to 20% higher than the propylene:ethylene ratio of an effluent stream obtained by cracking the same cracker feed but without r-pyoil, in each case determined as:

$$\%\text{increase} = \frac{Er - E}{E} \times 100$$

where E is the propylene:ethylene ratio by wt. % in the cracker effluent made without r-pyoil; and $E_r$ is the propylene:ethylene ratio by wt. % in the cracker effluent made with r-pyoil.

In an embodiment or in combination with any of the embodiments mentioned herein, the amount of ethylene and propylene can remain substantially unchanged or increased in the cracked olefin-containing effluent stream relative to an effluent stream without r-pyoil. It is surprising that a liquid r-pyoil can be fed to a gas fed furnace that accepts and cracks a predominant $C_2$-$C_4$ composition and obtain an olefin-containing effluent stream that can remain substantially unchanged or improved in certain cases relative to a $C_2$-$C_4$ cracker feed without r-pyoil. The heavy molecular weight of r-pyoil could have predominately contributed to the formation of aromatics and participate in the formation of olefins (ethylene and propylene in particular) in only a minor amount. However, we have found that the combined weight percent of ethylene and propylene, and even the output, does not significantly drop, and in many cases stays the same or can increase when r-pyoil is added to a cracker feed to form a combined cracker feed at the same hydrocarbon mass flow rates relative to a cracker feed without r-pyoil. The olefin-containing effluent stream can have a total wt. % of propylene and ethylene that is the same as or higher than the propylene and ethylene content of an effluent stream obtained by cracking the same cracker feed but without r-pyoil by at least 0.5%, or at least 1%, or at least 2%, or at least 2.5%, determined as:

$$\%\text{increase} = \frac{Er - E}{E} \times 100$$

where E is the combined wt. % of propylene and ethylene content in the cracker effluent made without r-pyoil; and $E_r$ is the combined wt. % of propylene and ethylene content in the cracker effluent made with r-pyoil.

In an embodiment or in combination with one or more embodiments mentioned herein, the wt. % of propylene can improve in an olefin-containing effluent stream when the dilution steam ratio (ratio of steam:hydrocarbons by weight) is above 0.3, or above 0.35, or at least 0.4. The increase in the wt. % of propylene when the dilution steam ratio is at least 0.3, or at least 0.35, or at least 0.4 can be up to 0.25 wt. %, or up to 0.4 wt. %, or up to 0.5 wt. %, or up to 0.7 wt. %, or up to 1 wt. %, or up to 1.5 wt. %, or up to 2 wt. %, where the increase is measured as the simple difference between the wt. % of propylene between an olefin-containing effluent stream made with r-pyoil at a dilution steam ratio of 0.2 and an olefin-containing effluent stream made with r-pyoil at a dilution steam ratio of at least 0.3, all other conditions being the same.

When the dilution steam ratio is increased as noted above, the ratio of propylene:ethylene can also increase, or can be at least 1% higher, or at least 2% higher, or at least 3% higher, or at least 4% higher, or at least 5% higher or at least 7% higher or at least 10% higher or at least 12% higher or at least 15% higher or at least 17% higher or at least 20% higher than the propylene:ethylene ratio of an olefin-containing effluent stream made with r-pyoil at a dilution steam ratio of 0.2.

In an embodiment or in combination with one or more embodiments mentioned herein, when the dilution steam ratio is increased, the olefin-containing effluent stream can have a reduced wt. % of methane, when measured relative to an olefin-containing effluent stream at a dilution steam ratio of 0.2. The wt. % of methane in the olefin-containing effluent stream can be reduced by at least 0.25 wt. %, or by at least 0.5 wt. %, or by at least 0.75 wt. %, or by at least 1 wt. %, or by at least 1.25 wt. %, or by at least 1.5 wt. %, measured as the absolute value difference in wt. % between the olefin-containing effluent stream at a dilution steam ratio of 0.2 and at the higher dilution steam ratio value.

In an embodiment or in combination with one or more embodiments mentioned herein, the amount of unconverted products in the olefin-containing effluent is decreased, when measured relative to a cracker feed that does not contain r-pyoil and all other conditions being the same, including hydrocarbon mass flow rate. For example, the amount of propane and/or ethane can be decreased by addition of r-pyoil. This can be advantageous to decrease the mass flow of the recycle loop to thereby (a) decrease cryogenic energy costs and/or (b) potentially increase capacity on the plant if the plant is already capacity constrained. Further it can debottleneck the propylene fractionator if it is already to its capacity limit. The amount of unconverted products in the olefin containing effluent can decrease by at least 2%, or at least 5%, or at least 8%, or at least 10%, or at least 13%, or at least 15%, or at least 18%, or at least 20%.

In an embodiment or in combination with one or more embodiments mentioned herein, the amount of unconverted products (e.g. combined propane and ethane amount) in the olefin-containing effluent is decreased while the combined output of ethylene and propylene does not drop and is even improved, when measured relative to a cracker feed that does not contain r-pyoil. Optionally, all other conditions are the same including the hydrocarbon mass flow rate and with respect to temperature, where the fuel feed rate to heat the burners to the non-recycle content cracker fed coils remains unchanged, or optionally when the fuel feed rate to all coils in the furnace remains unchanged. Alternatively, the same relationship can hold true on a wt. % basis rather than an output basis.

For example, the combined amount (either or both of output or wt. %) of propane and ethane in the olefin containing effluent can decrease by at least 2%, or at least 5%, or at least 8%, or at least 10%, or at least 13,%, or at least 15%, or at least 18%, or at least 20%, and in each case up to 40% or up to 35% or up to 30%, in each case without a decrease in the combined amount of ethylene and propylene, and even can accompany an increase in the combined amount of ethylene and propylene. In another example, the amount of propane in the olefin containing effluent can decrease by at least 2%, or at least 5%, or at least 8%, or at least 10%, or at least 13,%, or at least 15%, or at least 18%, or at least 20%, and in each case up to 40% or up to 35% or up to 30%, in each case without a decrease in the combined amount of ethylene and propylene, and even can accompany an increase in the combined amount of ethylene and propylene. In any one of these embodiments, the cracker feed (other than r-pyoil and as fed to the inlet of the convection zone) can be predominately propane by moles, or at least 90 mole % propane, or at least 95 mole % propane, or at least 96 mole % propane, or at least 98 mole % propane; or the fresh supply of cracker feed can be at least HD5 quality propane.

In an embodiment or in combination with one or more embodiments mentioned herein, the ratio of propane:(ethylene and propylene) in the olefin-containing effluent can decrease with the addition of r-pyoil to the cracker feed when measured relative to the same cracker feed without pyoil and all other conditions being the same, measured either as wt. % or output. The ratio of propane:(ethylene and propylene combined) in the olefin-containing effluent can be not more than 0.50:1, or less than 0.50:1, or not more than 0.48:1, or not more than 0.46:1, or no more than 0.43:1, or no more than 0.40:1, or no more than 0.38:1, or no more than 0.35:1, or no more than 0.33:1, or no more than 0.30:1. The low ratios indicate that a high amount of ethylene+propylene can be achieved or maintained with a corresponding drop in unconverted products such as propane.

In an embodiment or in combination with one or more embodiments mentioned herein, the amount of $C_{6+}$ products in the olefin-containing effluent can be increased, if such products are desired such as for a BTX stream to make derivates thereof, when r-pyoil and steam are fed downstream of the inlet to the convection box, or when one or both of r-pyoil and steam are fed at the cross-over location. The amount of $C_{6+}$ products in the olefin-containing effluent can be increased by 5%, or by 10%, or by 15%, or by 20%, or by 30% when r-pyoil and steam are fed downstream of the inlet to the convection box, when measured against feeding r-pyoil at the inlet to the convection box, all other conditions being the same. The % increase can be calculated as:

$$\%\text{increase} = \frac{Ei - Ed}{Ei} \times 100$$

where $E_i$ is the $C_{6+}$ content in the olefin-containing cracker effluent made by introducing r-pyoil at the inlet of the convection box; and $E_d$ is the $C_{6+}$ content in the olefin-containing cracker effluent made by introducing r-pyoil and steam downstream of the inlet of the convection box.

In an embodiment or in combination with any of the embodiments mentioned herein, the cracked olefin-containing effluent stream may include relatively minor amounts of aromatics and other heavy components. For example, the olefin-containing effluent stream may include at least 0.5, 1, 2, or 2.5 weight percent and/or not more than about 20, 19, 18, 17, 16, 15, 14, 13, 12, 11, 10, 9, 8, 7, 6, 5, 4, 3, 2, or 1 weight percent of aromatics, based on the total weight of the stream. We have found that the level of $C_{6+}$ species in the olefin-containing effluent can be not more than 5 wt. %, or not more than 4 wt. %, or not more than 3.5 wt. %, or not more than 3 wt. %, or not more than 2.8 wt. %, or not more than 2.5 wt. %. The $C_{6+}$ species includes all aromatics, as well as all paraffins and cyclic compounds having a carbon number of 6 or more. As used throughout, the mention of amounts of aromatics can be represented by amounts of $C_{6+}$ species since the amount of aromatics would not exceed the amount of $C_{6+}$ species.

The olefin-containing effluent may have an olefin-to-aromatic ratio, by weight %, of at least 2:1, 3.1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, or 30:1 and/or not more than 100:1, 90:1, 85:1, 80:1, 75:1, 70:1, 65:1, 60:1, 55:1, 50:1, 45:1, 40:1, 35:1, 30:1, 25:1, 20:1, 15:1, 10:1, or 5:1. As used herein, "olefin-to-aromatic ratio" is the ratio of total weight of C2 and C3 olefins to the total weight of aromatics, as defined previously. In an embodiment or in combination with any of the embodiments mentioned herein, the effluent stream can have an olefin-to-aromatic ratio of at least 2.5:1, 2.75:1, 3.5:1, 4.5:1, 5.5:1, 6.5:1, 7.5:1, 8.5:1, 9.5:1, 10.5:1, 11.5:1, 12.5:1, or 13:5:1.

The olefin-containing effluent may have an olefin:$C_{6+}$ ratio, by weight %, of at least 8.5:1, or at least 9.5:1, or at least 10:1, or at least 10.5:1, or at least 12:1, or at least 13:1, or at least 15:1, or at least 17:1, or at least 19:1, or at least 20:1, or at least 25:1, or least 28:1, or at least 30:1. In addition or in the alternative, the olefin-containing effluent may have an olefin:$C_{6+}$ ratio of up to 40:1, or up to 35:1, or up to 30:1, or up to 25:1, or up to 23:1. As used herein, "olefin-to-aromatic ratio" is the ratio of total weight of C2 and C3 olefins to the total weight of aromatics, as defined previously.

Additionally, or in the alternative, the olefin-containing effluent stream can have an olefin-to-C6+ ratio of at least about 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, 5:1, 5.25:1, 5.5:1, 5.75:1, 6:1, 6.25:1, 6.5:1, 6.75:1, 7:1, 7.25:1, 7.5:1, 7.75:1, 8:1, 8.25:1, 8.5:1, 8.75:1, 9:1, 9.5:1, 10:1, 10.5:1, 12:1, 13:1, 15:1, 17:1, 19:1, 20:1, 25:1, 28:1, or 30:1.

In an embodiment or in combination with any of the embodiments mentioned herein, the olefin:aromatic ratio decreases with an increase in the amount of r-pyoil added to the cracker feed. Since r-pyoil cracks at a lower temperature, it will crack earlier than propane or ethane, and therefore has more time to react to make other products such as aromatics. Although the aromatic content in the olefin-containing effluent increases with an increasing amount of pyoil, the amount of aromatics produced is remarkably low as noted above.

The olefin-containing composition may also include trace amounts of aromatics. For example, the composition may have a benzene content of at least 0.25, 0.3, 0.4, 0.5 weight percent and/or not more than about 2, 1.7, 1.6, 1.5 weight percent. Additionally, or in the alternative, the composition may have a toluene content of at least 0.005, 0.010, 0.015, or 0.020 and/or not more than 0.5, 0.4, 0.3, or 0.2 weight percent. Both percentages are based on the total weight of the composition. Alternatively, or in addition, the effluent can have a benzene content of at least 0.2, 0.3, 0.4, 0.5, or 0.55 and/or not more than about 2, 1.9, 1.8, 1.7, or 1.6 weight percent and/or a toluene content of at least 0.01, 0.05, or 0.10 and/or not more than 0.5, 0.4, 0.3, or 0.2 weight percent.

In an embodiment or in combination with any of the embodiments mentioned herein, the olefin-containing effluent withdrawn from a cracking furnace which has cracked a composition comprising r-pyoil may include an elevated amount of one or more compounds or by-products not found in olefin-containing effluent streams formed by processing conventional cracker feed. For example, the cracker effluent formed by cracking r-pyoil (r-olefin) may include elevated amounts of 1,3-butadiene, 1,3-cyclopentadiene, dicyclopentadiene, or a combination of these components. In an embodiment or in combination with any of the embodiments mentioned herein, the total amount (by weight) of these components may be at least 5, 10, 15, 20, 25, 30, 35, 40, 45, 50, 55, 60, 65, 70, 75, 80, or 85 percent higher than an identical cracker feed stream processed under the same conditions and at the same mass feed rate, but without r-pyoil. The total amount (by weight) of 1,3-butadiene may be at least 5, 10, 15, 20, 25, 30, 35, 40, 45, 50, 55, 60, 65, 70, 75, 80, or 85 percent higher than an identical cracker feed stream processed under the same conditions and at the same mass feed rate, but without r-pyoil. The total amount (by weight) of 1,3-cyclopentadiene may be at least 5, 10, 15, 20, 25, 30, 35, 40, 45, 50, 55, 60, 65, 70, 75, 80, or 85 percent higher than an identical cracker feed stream processed under the same conditions and at the same mass feed rate, but without r-pyoil. The total amount (by weight) of dicyclopentadiene may be at least 5, 10, 15, 20, 25, 30, 35, 40, 45, 50, 55, 60, 65, 70, 75, 80, or 85 percent higher than an identical cracker feed stream processed under the same conditions and at the same mass feed rate, but without r-pyoil. The percent difference is calculated by dividing the difference in weight percent of one or more of the above components in the r-pyoil and conventional streams by the amount (in weight percent) of the component in the conventional stream, or:

$$\%\text{increase} = \frac{Er - E}{E} \times 100$$

where E is the wt. % of the component in the cracker effluent made without r-pyoil; and $E_r$ is the wt. % of the component in the cracker effluent made with r-pyoil.

In an embodiment or in combination with any of the embodiments mentioned herein, the olefin-containing effluent stream may comprise acetylene. The amount of acetylene can be at least 2000 ppm, at least 5000 ppm, at least 8000 ppm, or at least 10,000 ppm based on the total weight of the effluent stream from the furnace. It may also be not more than 50,000 ppm, not more than 40,000 ppm, not more than 30,000 ppm, or not more than 25,000 ppm, or not more than 10,000 ppm, or not more than 6,000 ppm, or not more than 5000 ppm.

In an embodiment or in combination with any of the embodiments mentioned herein, the olefin-containing effluent stream may comprise methyl acetylene and propadiene (MAPD). The amount of MAPD may be at least 2 ppm, at least 5 ppm, at least 10 ppm, at least 20 pm, at least 50 ppm, at least 100 ppm, at least 500 ppm, at least 1000 ppm, at least 5000 ppm, or at least 10,000 ppm, based on the total weight of the effluent stream. It may also be not more than 50,000 ppm, not more than 40,000 ppm, or not more than 30,000 ppm, or not more than 10,000 ppm, or not more than 6,000 ppm, or not more than 5,000 ppm.

In an embodiment or in combination with any of the embodiments mentioned herein, the olefin-containing effluent stream may comprise low or no amounts of carbon dioxide. The olefin-containing effluent stream can have an amount, in wt. %, of carbon dioxide that is not more than the amount of carbon dioxide in an effluent stream obtained by cracking the same cracker feed but without r-pyoil at equivalent conditions, or an amount this is not higher than 5%, or not higher than 2% of the amount of carbon dioxide, in wt. %, or the same amount as a comparative effluent stream without r-pyoil. Alternatively or in addition, the olefin-containing effluent stream can have an amount of carbon dioxide that is not more than 1000 ppm, or not more than 500 ppm, or not more than 100 ppm, or not more than 80 ppm, or not more than 50 ppm, or not more than 25 ppm, or not more than 10 ppm, or not more than 5 ppm.

Figure 9:
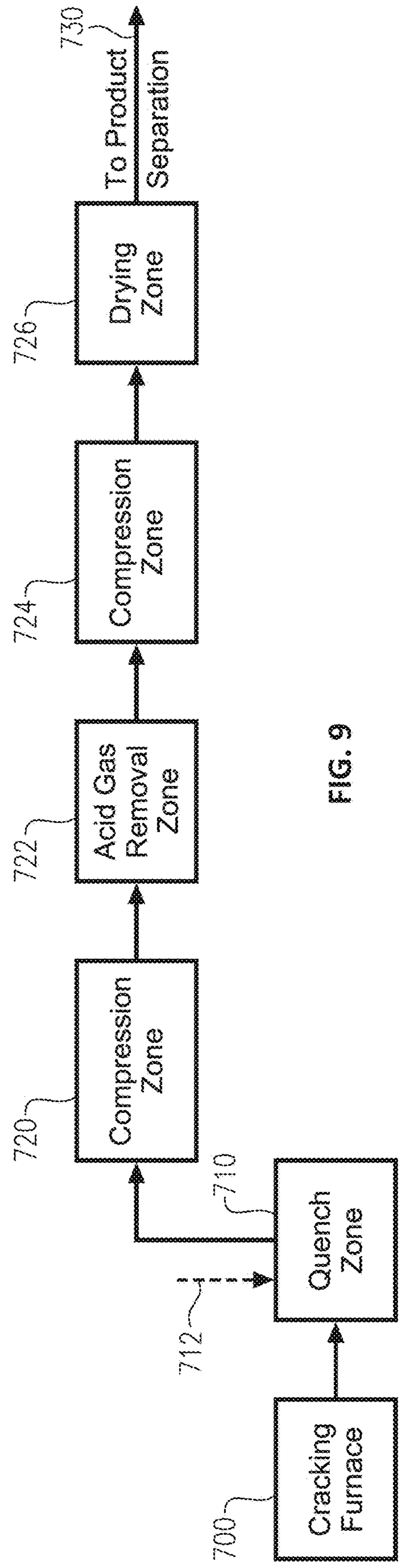
FIG. 9 is a block diagram illustrating the treatment of a recycle content furnace effluent.

Turning now to FIG. 9, a block diagram illustrating the main elements of the furnace effluent treatment section are shown.

As shown in FIG. 9, the olefin-containing effluent stream from the cracking furnace 700, which includes recycle content) is cooled rapidly (e.g., quenched) in a transfer line exchange ("TLE") 680 as shown in FIG. 8 in order to prevent production of large amounts of undesirable by-products and to minimize fouling in downstream equipment, and also to generate steam. In an embodiment or in combination with any of the embodiments mentioned herein, the temperature of the r-composition-containing effluent from the furnace can be reduced by 35 to 485° C., 35 to 375° C., or 90 to 550° C. to a temperature of 500 to 760° C. The cooling step is performed immediately after the effluent stream leaves the furnace such as, for example, within 1 to 30, 5 to 20, or 5 to 15 milliseconds. In an embodiment or in combination with any of the embodiments mentioned herein, the quenching step is performed in a quench zone 710 via indirect heat exchange with high-pressure water or steam in a heat exchanger (sometimes called a transfer line exchanger as shown in FIG. 5 as TLE 340 and FIG. 8 as TLE 680), while, in other embodiments, the quench step is carried out by directly contacting the effluent with a quench liquid 712 (as generally shown in FIG. 9). The temperature of the quench liquid can be at least 65, or at least 80, or at least 90, or at least 100, in each case ° C. and/or not more than 210, or not more than 180, or not more than 165, or not more than 150, or not more than 135, in each case ° C. When a quench liquid is used, the contacting may occur in a quench tower and a liquid stream may be removed from the quench tower comprising gasoline and other similar boiling-range hydrocarbon components. In some cases, quench liquid may be used when the cracker feed is predominantly liquid, and a heat exchanger may be used when the cracker feed is predominantly vapor.

The resulting cooled effluent stream is then vapor liquid separated and the vapor is compressed in a compression zone 720, such as in a gas compressor having, for example, between 1 and 5 compression stages with optional inter-stage cooling and liquid removal. The pressure of the gas stream at the outlet of the first set of compression stages is in the range of from 7 to 20 bar gauge (barg), 8.5 to 18 psig (0.6~1.3 barg), or 9.5 to 14 barg.

The resulting compressed stream is then treated in an acid gas removal zone 722 for removal of acid gases, including CO, $CO_2$, and $H_2S$ by contact with an acid gas removal agent. Examples of acid gas removal agents can include, but are not limited to, caustic and various types of amines. In an embodiment or in combination with any of the embodiments mentioned herein, a single contactor may be used, while, in other embodiments, a dual column absorber-stripper configuration may be employed.

The treated compressed olefin-containing stream may then be further compressed in another compression zone 724 via a compressor, optionally with inter-stage cooling and liquid separation. The resulting compressed stream, which has a pressure in the range of 20 to 50 barg, 25 to 45 barg, or 30 to 40 barg. Any suitable moisture removal method can be used including, for example, molecular sieves or other similar process to dry the gas in a drying zone 726. The resulting stream 730 may then be passed to the fractionation section, wherein the olefins and other components may be separated in to various high-purity product or intermediate streams.

Figure 10:
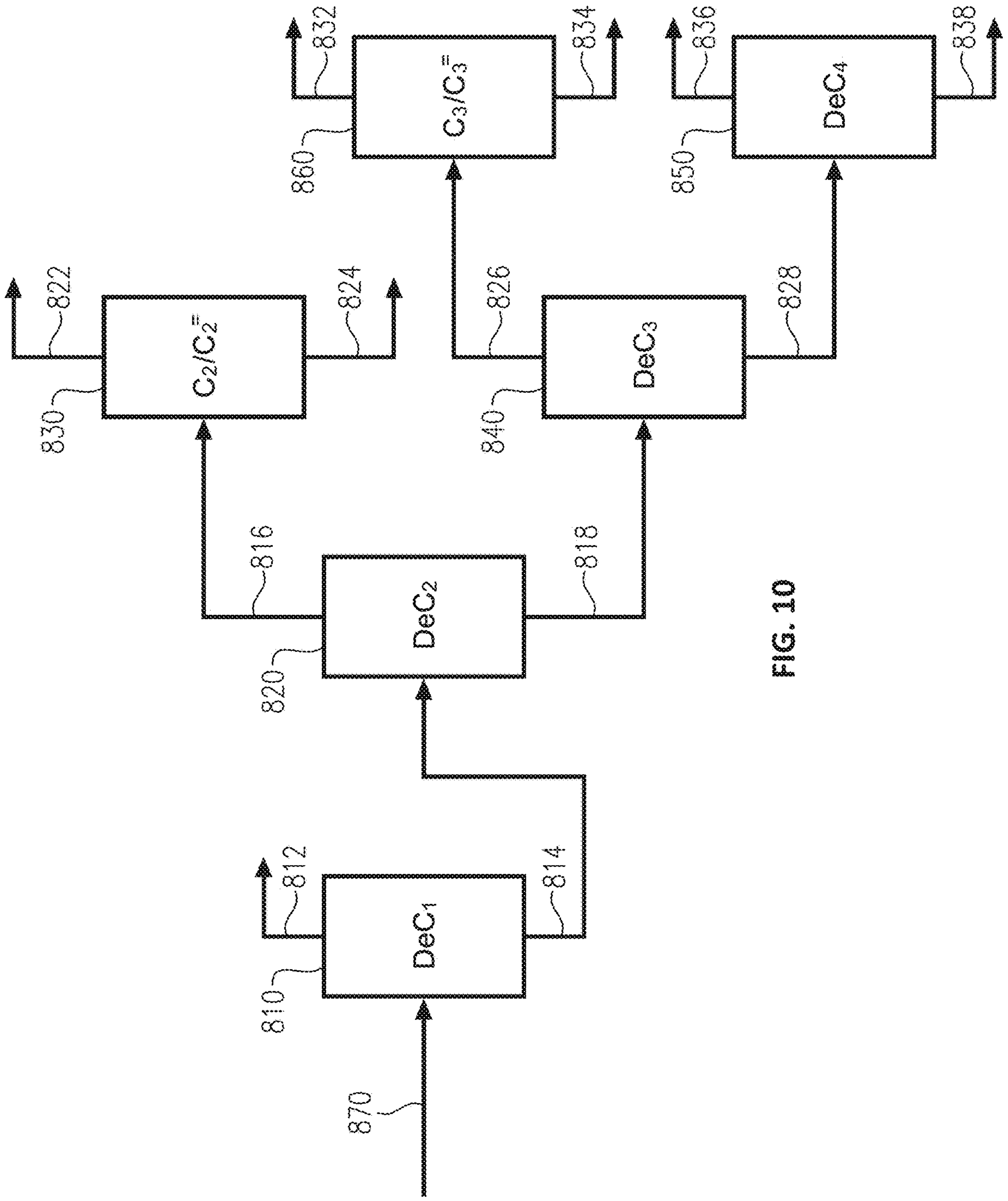
FIG. 10 illustrates a fractionation scheme in a Separation section, including a demethanizer, dethanizer, depropanizer, and the fractionation columns to separate and isolate the main r-compositions, including r-propylene, r-ethylene, r-butylene, and others.

Turning now to FIG. 10, a schematic depiction of the main steps of the fractionation section is provided. In an embodiment or in combination with any of the embodiments mentioned herein, the initial column of the fractionation train may not be a demethanizer 810, but may be a deethanizer 820, a depropanizer 840, or any other type of column. As used herein, the term "demethanizer," refers to a column whose light key is methane. Similarly, "deethanizer," and "depropanizer," refer to columns with ethane and propane as the light key component, respectively.

As shown in FIG. 10, a feed stream 870 from the quench section may introduced into a demethanizer (or other) column 810, wherein the methane and lighter (CO, CO2, H2) components 812 are separated from the ethane and heavier components 814. The demethanizer is operated at a temperature of at least −145, or at least −142, or at least −140, or at least −135, in each case ° C. and/or not more than −120, −125, −130, −135° C. The bottoms stream 814 from the demethanizer column, which includes at least 50, or at least 55, or at least 60, or at least 65, or at least 70, or at least 75, or at least 80, or at least 85, or at least 90, or at least 95 or at least 99, in each case percent of the total amount of ethane and heavier components introduced into the column, is then introduced into a deethanizer column 820, wherein the C2 and lighter components 816 are separated from the C3 and heavier components 818 by fractional distillation. The deethanizer 820 can be operated with an overhead temperature of at least −35, or at least −30, or at least −25, or at least −20, in each case ° C. and/or not more than −5, −10, −10, −20° C., and an overhead pressure of at least 3, or at least 5, or at least 7, or at least 8, or at least 10, in each case barg and/or not more than 20, or not more than 18, or not more than 17, or not more than 15, or not more than 14, or not more than 13, in each case barg. The deethanizer column 820 recovers at least 60, or at least 65, or at least 70, or at least 75, or at least 80, or at least 85, or at least 90, or at least 95, or at least 97, or at least 99, in each case percent of the total amount of C2 and lighter components introduced into the column in the overhead stream. In an embodiment or in combination with any of the embodiments mentioned herein, the overhead stream 816 removed from the deethanizer column comprises at least 50, or at least 55, or at least 60, or at least 65, or at least 70, or at least 75, or at least 80, or at least 85, or at least 90, or at least 95, in each case weight percent of ethane and ethylene, based on the total weight of the overhead stream.

As shown in FIG. 10, the $C_2$ and lighter overhead stream 816 from the deethanizer 820 is further separated in an ethane-ethylene fractionator column (ethylene fractionator) 830. In the ethane-ethylene fractionator column 830, an ethylene and lighter component stream 822 can be withdrawn from the overhead of the column 830 or as a side stream from the top ½ of the column, while the ethane and any residual heavier components are removed in the bottoms stream 824. The ethylene fractionator 830 may be operated at an overhead temperature of at least −45, or at least −40, or at least −35, or at least −30, or at least −25, or at least −20, in each case ° C. and/or not more than −15, or not more than −20, or not more than −25, in each case ° C., and an overhead pressure of at least 10, or at least 12, or at least 15, in each case barg and/or not more than 25, 22, 20 barg. The overhead stream 822, which is enriched in ethylene, can include at least 70, or at least 75, or at least 80, or at least 85, or at least 90, or at least 95, or at least 97, or at least 98, or at least 99, in each case weight percent ethylene, based on the total weight of the stream and may be sent to downstream processing unit for further processing, storage, or sale. The overhead ethylene stream 822 produced during the cracking of a cracker feedstock containing r-pyoil is a r-ethylene composition or stream. In an embodiment or in combination with any of the embodiments mentioned herein, the r-ethylene stream may be used to make one or more petrochemicals.

The bottoms stream from the ethane-ethylene fractionator 824 may include at least 40, or at least 45, or at least 50, or at least 55, or at least 60, or at least 65, or at least 70, or at least 75, or at least 80, or at least 85, or at least 90, or at least 95, or at least 98, in each case weight percent ethane, based on the total weight of the bottoms stream. All or a portion of the recovered ethane may be recycled to the cracker furnace as additional feedstock, alone or in combination with the r-pyoil containing feed stream, as discussed previously.

The liquid bottoms stream 818 withdrawn from the deethanizer column, which may be enriched in C3 and heavier components, may be separated in a depropanizer 840, as shown in FIG. 10. In the depropanizer 840, C3 and lighter components are removed as an overhead vapor stream 826, while C4 and heavier components may exit the column in the liquid bottoms 828. The depropanizer 840 can be operated with an overhead temperature of at least 20, or at least 35, or at least 40, in each case ° C. and/or not more than 70, 65, 60, 55° C., and an overhead pressure of at least 10, or at least 12, or at least 15, in each case barg and/or not more than 20, or not more than 17, or not more than 15, in each case barg. The depropanizer column 840 recovers at least 60, or at least 65, or at least 70, or at least 75, or at least 80, or at least 85, or at least 90, or at least 95, or at least 97, or at least 99, in each case percent of the total amount of C3 and lighter components introduced into the column in the overhead stream 826. In an embodiment or in combination with any of the embodiments mentioned herein, the overhead stream 826 removed from the depropanizer column 840 comprises at least or at least 50, or at least 55, or at least 60, or at least 65, or at least 70, or at least 75, or at least 80, or at least 85, or at least 90, or at least 95, or at least 98, in each case weight percent of propane and propylene, based on the total weight of the overhead stream 826.

The overhead stream 826 from the depropanizer 840 are introduced into a propane-propylene fractionator (propylene fractionator) 860, wherein the propylene and any lighter components are removed in the overhead stream 832, while the propane and any heavier components exit the column in the bottoms stream 834. The propylene fractionator 860 may be operated at an overhead temperature of at least 20, or at least 25, or at least 30, or at least 35, in each case ° C. and/or not more than 55, 50, 45, 40° C., and an overhead pressure of at least 12, or at least 15, or at least 17, or at least 20, in each case barg and/or not more than 20, or not more than 17, or not more than 15, or not more than 12, in each case barg. The overhead stream 860, which is enriched in propylene, can include at least 70, or at least 75, or at least 80, or at least 85, or at least 90, or at least 95, or at least 97, or at least 98, or at least 99, in each case weight percent propylene, based on the total weight of the stream and may be sent to downstream processing unit for further processing, storage, or sale. The overhead propylene stream produced during the cracking of a cracker feedstock containing r-pyoil is a r-propylene composition or stream. In an embodiment or in combination with any of the embodiments mentioned herein, the stream may be used to make one or more petrochemicals.

The bottoms stream 834 from the propane-propylene fractionator 860 may include at least 40, or at least 45, or at least 50, or at least 55, or at least 60, or at least 65, or at least 70, or at least 75, or at least 80, or at least 85, or at least 90, or at least 95, or at least 98, in each case weight percent propane, based on the total weight of the bottoms stream 834. All or a portion of the recovered propane may be recycled to the cracker furnace as additional feedstock, alone or in combination with r-pyoil, as discussed previously.

Referring again to FIG. 10, the bottoms stream 828 from the depropanizer column 840 may be sent to a debutanizer column 850 for separating C4 components, including butenes, butanes and butadienes, from $C_{5+}$ components. The debutanizer can be operated with an overhead temperature of at least 20, or at least 25, or at least 30, or at least 35, or at least 40, in each case ° C. and/or not more than 60, or not more than 65, or not more than 60, or not more than 55, or not more than 50, in each case ° C. and an overhead pressure of at least 2, or at least 3, or at least 4, or at least 5, in each case barg and/or not more than 8, or not more than 6, or not more than 4, or not more than 2, in each case barg. The debutanizer column recovers at least 60, or at least 65, or at least 70, or at least 75, or at least 80, or at least 85, or at least 90, or at least 95, or at least 97, or at least 99, in each case percent of the total amount of C4 and lighter components introduced into the column in the overhead stream 836. In an embodiment or in combination with any of the embodiments mentioned herein, the overhead stream 836 removed from the debutanizer column comprises at least 30, or at least 35, or at least 40, or at least 45, or at least 50, or at least 55, or at least 60, or at least 65, or at least 70, or at least 75, or at least 80, or at least 85, or at least 90, or at least 95, in each case weight percent of butadiene, based on the total weight of the overhead stream. The overhead stream 836 produced during the cracking of a cracker feedstock containing r-pyoil is a r-butadiene composition or stream. The bottoms stream 838 from the debutanizer includes mainly $C_5$ and heavier components, in an amount of at least 50, or at least 60, or at least 70, or at least 80, or at least 90, or at least 95 weight percent, based on the total weight of the stream. The debutanizer bottoms stream 838 may be sent for further separation, processing, storage, sale or use.

The overhead stream 836 from the debutanizer, or the C4s, can be subjected to any conventional separation methods such as extraction or distillation processes to recover a more concentrated stream of butadiene.

Production and Use of Glycol Esters

In one embodiment or in combination with any of the mentioned embodiments, there is now provided a method for processing recycle content olefin including, for example, recycle content propylene, by feeding the r-olefin to a reactor in which is made r-aldehydes, which are subsequently condensed in the presence of a catalyst to form glycol esters. In some embodiments, the r-aldehydes may include r-butyraldehyde, and in particular, isobutyraldehyde, which may react to form glycol esters, including monoesters and diesters.

In one embodiment or in combination with any of the mentioned embodiments, the concentration of r-olefin, introduced into a reactor vessel is at least 90 wt. %, or at least 95 wt. %, or at least 97 wt. %, or at least 99 wt. %, based on the weight of the olefin composition fed to the aldehyde reactor.

Similarly, in one embodiment or in combination with any of the mentioned embodiments, the concentration of r-aldehyde, introduced into a reactor vessel for reacting aldehyde to form a glycol ester is at least 90 wt. %, or at least 95 wt. %, or at least 97 wt. %, or at least 99 wt. %, based on the weight of the aldehyde composition fed to the glycol ester reactor.

In one embodiment or in combination with any of the mentioned embodiments, the olefin or aldehyde fed to the reaction vessel does not contain recycle content. In another embodiment, at least a portion of the olefin or aldehyde composition fed to the reaction vessel is derived directly or indirectly from the cracking of r-pyoil or obtained from r-pygas. For example, at least 0.005 wt. %, or at least 0.01 wt. %, or at least 0.05 wt. %, or at least 0.1 wt. %, or at least 0.15 wt. %, or at least 0.2 wt. %, or at least 0.25 wt. %, or at least 0.3 wt. %, or at least 0.35 wt. %, or at least 0.4 wt. %, or at least 0.45 wt. %, or at least 0.5 wt. %, or at least 0.6 wt. %, or at least 0.7 wt. %, or at least 0.8 wt. %, or at least 0.9 wt. %, or at least 1 wt. %, or at least 2 wt. %, or at least 3 wt. %, or at least 4 wt. %, or at least 5 wt. %, or at least 6 wt. %, or at least 7 wt. %, or at least 8 wt. %, or at least 9 wt. %, or at least 10 wt. %, or at least 11 wt. %, or at least 13 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 70 wt. %, or at least 80 wt. %, or at least 90 wt. %, or at least 95 wt. %, or at least 98 wt. %, or at least 99 wt. %, or 100 wt. % of the olefin composition is r-olefin or pr-olefin or r-aldehyde or pr-aldehyde.

In addition, or in the alternative, up to 100 wt. %, or up to 98 wt. %, or up to 95 wt. %, or up to 90 wt. %, or up to 80 wt. %, or up to 75 wt. %, or up to 70 wt. %, or up to 60 wt. %, or up to 50 wt. %, or up to 40 wt. %, or up to 30 wt. %, or up to 20 wt. %, or up to 10 wt. %, or up to 8 wt. %, or up to 5 wt. %, or up to 4 wt. %, or up to 3 wt. %, or up to 2 wt. %, or up to 1 wt. %, or up to 0.8 wt. %, or up to 0.7 wt. %, or up to 0.6 wt. %, or up to 0.5 wt. %, or up to 0.4 wt. %, or up to 0.3 wt. %, or up to 0.2 wt. %, or up to 0.1 wt. %, or up to 0.09 wt. %, or up to 0.07 wt. %, or up to 0.05 wt. %, or up to 0.03 wt. %, or up to 0.02 wt. %, or up to 0.01 wt. % of the olefin composition is pr-olefin, based on the weight the olefin composition fed to the reaction vessel.

Alternatively, or in addition, at least 0.005 wt. %, or at least 0.01 wt. %, or at least 0.05 wt. %, or at least 0.1 wt. %, or at least 0.15 wt. %, or at least 0.2 wt. %, or at least 0.25 wt. %, or at least 0.3 wt. %, or at least 0.35 wt. %, or at least 0.4 wt. %, or at least 0.45 wt. %, or at least 0.5 wt. %, or at least 0.6 wt. %, or at least 0.7 wt. %, or at least 0.8 wt. %, or at least 0.9 wt. %, or at least 1 wt. %, or at least 2 wt. %, or at least 3 wt. %, or at least 4 wt. %, or at least 5 wt. %, or at least 6 wt. %, or at least 7 wt. %, or at least 8 wt. %, or at least 9 wt. %, or at least 10 wt. %, or at least 11 wt. %, or at least 13 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 70 wt. %, or at least 80 wt. %, or at least 90 wt. %, or at least 95 wt. %, or at least 98 wt. %, or at least 99 wt. %, or 100 wt. % of the aldehyde composition is r-aldehyde or pr-aldehyde.

In addition, or in the alternative, up to 100 wt. %, or up to 98 wt. %, or up to 95 wt. %, or up to 90 wt. %, or up to 80 wt. %, or up to 75 wt. %, or up to 70 wt. %, or up to 60 wt. %, or up to 50 wt. %, or up to 40 wt. %, or up to 30 wt. %, or up to 20 wt. %, or up to 10 wt. %, or up to 8 wt. %, or up to 5 wt. %, or up to 4 wt. %, or up to 3 wt. %, or up to 2 wt. %, or up to 1 wt. %, or up to 0.8 wt. %, or up to 0.7 wt. %, or up to 0.6 wt. %, or up to 0.5 wt. %, or up to 0.4 wt. %, or up to 0.3 wt. %, or up to 0.2 wt. %, or up to 0.1 wt. %, or up to 0.09 wt. %, or up to 0.07 wt. %, or up to 0.05 wt. %, or up to 0.03 wt. %, or up to 0.02 wt. %, or up to 0.01 wt. % of the aldehyde composition is r-aldehyde or pr-aldehyde, based on the weight the composition fed to the reaction vessel.

In each case, the stated amounts are also applicable to not only olefin or aldehyde as fed into the reactor, but alternatively or in addition, to the pr-olefin or pr-aldehyde stock supplied to a manufacturer of the glycol ester, or can be used as a basis for associating or calculating the amount of recycle content in pr-olefin or pr-aldehyde, such as when blending a source of pr-olefin or pr-aldehyde with non-recycle content olefin or aldehyde to make an olefin or aldehyde composition having pr-olefin or pr-aldehyde in quantities mentioned above.

The recycle content associated with the glycol ester can be established by applying a recycle content value to the glycol ester, such as through deducting the recycle content value from a recycle inventory populated with allotments (credit or allocation) or by reacting an r-olefin or r-aldehyde feedstock to make r-glycol ester. The allotment can be contained in a recycle inventory created, maintained or operated by or for the glycol ester manufacturer. The allotments are obtained from any source along any manufacturing chain of products. In one embodiment, the origin of the allotment is derived indirectly from pyrolyzing recycled waste, or from cracking r-pyoil or from r-pygas.

The amount of recycle content in an r-olefin or r-aldehyde raw material fed to a glycol ester reactor, or the amount of recycle content applied to the r-glycol ester, or the amount of r-olefin or r-aldehyde needed to feed the reactor to claim a desired amount of recycle content in the glycol ester in the event that all the recycle content from the r-olefin or r-aldehyde is applied to the glycol ester, can be determined or calculated by any of the following methods:

(i) the amount of an allotment associated with the r-olefin or r-aldehyde used to feed the reactor applied determined by the amount certified or declared by the supplier of the olefin or aldehyde composition transferred to the manufacturer of the glycol ester, or (ii) the amount of allocation declared by the glycol ester manufacturer as fed to the glycol ester reactor, or (iii) using a mass balance approach to back-calculate the minimum amount of recycle content in the feedstock from an amount of recycle content declared, advertised, or accounted for by the manufacturer, whether or not accurate, as applied to the glycol ester product, or (iv) blending of non-recycle content with recycle content feedstock olefin or aldehyde or associating recycle content to a portion of the feedstock, using pro-rata mass approach.

Satisfying any one of the methods (i)-(iv) is sufficient to establish the portion of r-olefin or r-aldehyde that is derived directly or indirectly from recycled waste, the pyrolysis of recycled waste, pyrolysis gas produced from the pyrolysis of recycled waste, and/or the cracking of r-pyoil produced from the pyrolysis of recycled waste. In the event that an r-olefin or r-aldehyde feed is blended with a recycle feed from other recycle sources, a pro-rata approach to the mass of r-olefin or r-aldehyde directly or indirectly obtained from recycled waste, the pyrolysis of recycled waste, pyrolysis gas produced from the pyrolysis of recycled waste, and/or the cracking of r-pyoil produced from the pyrolysis of recycled waste to the mass of recycle olefin or aldehyde from other sources is adopted to determine the percentage in the declaration attributable to r-olefin or r-aldehyde obtained directly or indirectly from recycled waste, the pyrolysis of recycled waste, pyrolysis gas produced from the pyrolysis of recycled waste, and/or the cracking of r-pyoil produced from the pyrolysis of recycled waste.

Methods (i) and (ii) need no calculation since they are determined based on what the olefin or aldehyde manufacturer or glycol ester manufacturer or suppliers declare, claim, or otherwise communicate to each other or the public. Methods (iii) and (iv) are calculated.

In one embodiment or in combination with any of the mentioned embodiments, the minimum amount of recycle content olefin or aldehyde fed to the reactor can be determined by knowing the amount of recycle content associated with the end product glycol ester and assuming that the entire recycle content in the glycol ester is attributable to the r-olefin or r-aldehyde fed to the reactor and none to any other components in the reaction zone.

The minimum portion of r-olefin or r-aldehyde content derived directly or indirectly from recycled waste, the pyrolysis of recycled waste, pyrolysis gas produced from the pyrolysis of recycled waste, and/or the cracking of r-pyoil produced from the pyrolysis of recycled waste, to make a glycol ester product associated with a particular amount of recycle content, can be calculated as:

$$P = \left(\frac{\%D}{100}\right) \times \left(\frac{Pm}{Rm}\right) \times \left(\frac{100}{Y}\right) \times 100$$

where P means the minimum portion of r-olefin or r-aldehyde derived directly or indirectly recycled waste, the pyrolysis of recycled waste, pyrolysis gas produced from the pyrolysis of recycled waste, and/or the cracking of r-pyoil produced from the pyrolysis of recycled waste, and % D means the percentage of recycle content declared in product r-glycol ester, and Pm means the molecular weight of product glycol ester, and Rm means the molecular weight of reactant olefin or aldehyde as a moiety in glycol ester product, not to exceed the molecular weight of the reactant olefin or aldehyde, and Y means the percent yield of the product, e.g. glycol ester, determined as an average annual yield regardless of whether or not the feedstock is r-olefin or r-aldehyde. If an average annual yield is not known, the yield can be assumed to be industry average using the same process technology.

The amount of recycle content in the r-olefin or r-aldehyde feed can be greater than the minimum, resulting in excess recycle content left over if for a given designation of recycle content in the glycol ester. In such a case, the remainder of recycle content available may be reserved in a recycle inventory. The excess recycle content may be stored in a recycle inventory and applied to other glycol ester products that either are not made with r-olefin or r-aldehyde or with a deficient amount of r-olefin or r-aldehyde recycle content relative to the amount of recycle content one desires to apply to the glycol ester. However, whether or not the r-olefin or r-aldehyde feedstock actually was designated by the manufacturer of the glycol ester as containing the minimum amount of recycle content, an r-glycol ester designated as containing a certain recycle content is nevertheless deemed to have been made from an r-olefin or r-aldehyde feedstock containing the minimum recycle content by the calculation method described above.

In the case of a pro-rata mass approach in method (iv), the portion of r-olefin or r-aldehyde derived directly or indirectly from recycled waste, the pyrolysis of recycled waste, pyrolysis gas produced from the pyrolysis of recycled waste, and/or the cracking of r-pyoil produced from the pyrolysis of recycled waste would be calculated on the basis of the mass of recycle content available to the glycol ester manufacturer by way of purchase or transfer or created in case the olefin or aldehyde is integrated into r-olefin or r-aldehyde production, that is attributed to the feedstock on a daily run divided by the mass of the r-olefin or r-aldehyde feedstock, or:

$$P = \frac{Mr}{Ma} \times 100$$

where P means the percentage of recycle content in the glycol ester feedstock stream, and where Mr is the mass of recycle content attributed to the r-olefin or r-aldehyde stream on a daily basis, and Ma is the mass of the entire olefin or aldehyde feedstock used to make glycol ester on the corresponding day.

For example, if a glycol ester manufacturer has available 1000 kg of a recycle allocation or credit that has its origin in pyrolyzing recycled waste, and the glycol ester manufacturer elects to attribute 10 kg of the recycle allocation to an olefin or aldehyde feedstock used to make the glycol ester, and the olefin or aldehyde feedstock employs 100 kg per day to make glycol ester, the portion P of the r-olefin or r-aldehyde feedstock derived directly or indirectly from cracking pyoil would be 10 kg/100 kg, or 10 wt %. The olefin or aldehyde feedstock composition would be considered to be an r-olefin or r-aldehyde composition because a portion of the recycle allocation is applied to the olefin or aldehyde feedstock used to make the glycol ester.

In another embodiment, there is provided a variety of methods for apportioning the recycle content among the various products made by a glycol ester manufacturer or the products made by any one entity or a combinations of entities among the Family of Entities of which the glycol ester manufacturer is a part. For example, the glycol ester manufacturer, of any combination or the entirety of its Family of Entities, or a Site, can:

a. adopt a symmetric distribution of recycle content values among its product(s) based on the same fractional percentage of recycle content in one or more feedstocks, or based on the amount of allotment received. For example, if 5 wt. % of the olefin or aldehyde feedstock is r-olefin or r-aldehyde, or if the allotment value is 5 wt. % of the entire olefin or aldehyde feedstock, then all glycol ester made with the olefin or aldehyde feedstock may contain 5 wt. % recycle content value. In this case, the amount of recycle content in the products is proportional to the amount of recycle content in the feedstock to make the products; or b. adopt an asymmetric distribution of recycle content values among its product(s) based on the same fractional percentage of recycle content in the one or more feedstocks, or based on the amount of allotment received. For example, if 5 wt. % of the olefin or aldehyde feedstock is r-olefin or r-aldehyde, or if the allotment value is 5 wt. % of the entire olefin or aldehyde feedstock, then one volume or batch of glycol ester can receive a greater amount of recycle content value that other batches or volume of glycol ester made, provided that the total amount of recycle content does not exceed the total amount of r-olefin or r-aldehyde or allotment received, or the total amount of recycle content in the recycle inventory. One batch of glycol ester can contain 5% recycle content by mass, and another batch can contain zero 0% recycle content, even though both volumes are made from the same volume of olefin or aldehyde feedstock. In the asymmetric distribution of recycle content, a manufacturer can tailor the recycle content to volumes of glycol ester sold as needed among customers, thereby providing flexibility among customers some of whom may need more recycle content than others in a glycol ester volume.

Both the symmetric distribution and the asymmetric distribution of recycle content can be proportional on a site wide basis, or on a multi-site basis. In one embodiment or in combination with any of the mentioned embodiments, the recycle content input (recycle content feedstock or allotments) can be to a Site, and recycle content values from said inputs are applied to one or more products made at the same Site, and at least one of the products made at the Site is glycol ester, and optionally at least a portion of the recycle content value is applied to the glycol ester products. The recycle content values can be applied symmetrically or asymmetrically to the products at the Site. The recycle content values can be applied across different glycol ester volumes symmetrically or asymmetrically, or applied across a combination of glycol ester and other products made at the Site. For example, a recycle content value is transferred to a recycle inventory at a Site, created at a Site, or a feedstock containing recycle content value is reacted at a Site (collectively the "a recycle input"), and recycle content values obtained from said inputs are:

a. distributed symmetrically across at least a portion or across all glycol ester volume made at the Site over a period of time (e.g. within 1 week, or within 1 month, or within 6 months, or within the same calendar year, or continuously); or b. distributed symmetrically across at least a portion or across all glycol ester volume made at the Site and across at least a portion or across a second different product made at the same Site, each over the same period of time (e.g. within 1 week, or within 1 month, or within 6 months, or within the same calendar year, or continuously); or c. recycle content is distributed symmetrically across all products to which recycle content is actually applied that are made at the Site, over the same period of time (e.g. within the same day, or within 1 week, or within 1 month, or within 6 months, or within the same calendar year, or continuously). While a variety of products can be made at a Site, in this option, not all product have to receive a recycle content value, but for all products that do receive or to which are applied a recycle content value, the distribution is symmetrical; or d. distributed asymmetrically across at least two glycol ester volumes made at the same Site, optionally either over the same period of time (e.g. within 1 day, or within 1 week, or within 1 month, or within 6 months, or within a calendar year, or continuously), or as sold to at least two different customers. For example, one volume of glycol ester made can have a greater recycle content value than a second volume of glycol ester made at the Site, or one volume of glycol ester made at the Site and sold to one customer can have a greater recycle content value than a second volume of glycol ester made at the Site and sold to a second different customer, or e. distributed asymmetrically across at least one volume of glycol ester and at least one volume of a different product, each made at the same Site, optionally either over the same period of time (e.g. within 1 day, or within 1 week, or within 1 month, or within 6 months, or within a calendar year, or continuously), or as sold to at least two different customers.

In one embodiment or in combination with any of the mentioned embodiments, the recycle content input or creation (recycle content feedstock or allotments) can be to or at a first Site, and recycle content values from said inputs are transferred to a second Site and applied to one or more products made at a second Site, and at least one of the products made at the second Site is glycol ester, and optionally at least a portion of the recycle content value is applied to glycol ester products made at the second Site. The recycle content values can be applied symmetrically or asymmetrically to the products at the second Site. The recycle content values can be applied across different glycol ester volumes symmetrically or asymmetrically, or applied across a combination of glycol ester and other products made at the second Site. For example, a recycle content value is transferred to a recycle inventory at a first Site, created at a first Site, or a feedstock containing recycle content value is reacted at a first Site (collectively the "a recycle input"), and recycle content values obtained from said inputs are:

a. distributed symmetrically across at least a portion or across all glycol ester volume made at a second Site over a period of time (e.g. within 1 week, or within 1 month, or within 6 months, or within the same calendar year, or continuously); or b. distributed symmetrically across at least a portion or across all glycol ester volume made at the second Site and across at least a portion or across a second different product made at the same second Site, each over the same period of time (e.g. within 1 week, or within 1 month, or within 6 months, or within the same calendar year, or continuously); or c. recycle content is distributed symmetrically across all products to which recycle content is actually applied that are made at the second Site, over the same period of time (e.g. within the same day, or within 1 week, or within 1 month, or within 6 months, or within the same calendar year, or continuously). While a variety of products can be made at a second Site, in this option, not all products have to receive a recycle content value, but for all products that do receive or to which are applied a recycle content value, the distribution is symmetrical; or d. distributed asymmetrically across at least two glycol ester volumes made at the same second Site, optionally either over the same period of time (e.g. within 1 day, or within 1 week, or within 1 month, or within 6 months, or within a calendar year, or continuously), or as sold to at least two different customers. For example, one volume of glycol ester made can have a greater recycle content value than a second volume of glycol ester each made at the second Site, or one volume of glycol ester made at the second Site and sold to one customer can have a greater recycle content value than a second volume of glycol ester made at the second Site and sold to a second different customer, or e. distributed asymmetrically across at least one volume of glycol ester and at least one volume of a different product, each made at the same second Site, optionally either over the same period of time (e.g. within 1 day, or within 1 week, or within 1 month, or within 6 months, or within a calendar year, or continuously), or as sold to at least two different customers.

In one embodiment or in combination with any of the mentioned embodiments, the glycol ester manufacturer, or one among its Family of Entities, can make glycol ester, or process an olefin or aldehyde, or process olefin or aldehyde and make an r-glycol ester, or make r-glycol ester, by obtaining any source of an olefin or aldehyde composition from a supplier, whether or not such olefin or aldehyde composition has any direct or indirect recycle content, and either:

i. from the same supplier of the olefin or aldehyde composition, also obtain a recycle content allotment, or ii. from any person or entity, obtaining a recycle content allotment without a supply of an olefin or aldehyde composition from the person or entity transferring the recycle content allotment.

The allotment in (i) is obtained from an olefin or aldehyde supplier, and the olefin or aldehyde supplier also supplies olefin or aldehyde to the glycol ester manufacturer or within its Family of Entities. The circumstance described in (i) allows a glycol ester manufacturer to obtain a supply of an olefin or aldehyde composition that is a non-recycle content olefin or aldehyde, yet obtain a recycle content allotment from the olefin or aldehyde supplier. In one embodiment or in combination with any of the mentioned embodiments, the olefin or aldehyde supplier transfers a recycle content allotment to the glycol ester manufacturer and a supply of olefin or aldehyde to the glycol ester manufacturer, where the recycle content allotment is not associated with the olefin or aldehyde supplied, or even not associated with any olefin or aldehyde made by the olefin or aldehyde supplier. The recycle content allotment does not have to be tied to an amount of recycle content in an olefin or aldehyde composition or to any compound used to make glycol ester, but rather the recycle content allotment transferred by the olefin or aldehyde supplier can be associated with other products derived directly or indirectly from recycled waste, the pyrolysis of recycled waste, pyrolysis gas produced from the pyrolysis of recycled waste, and/or the cracking of r-pyoil produced from the pyrolysis of recycled waste or the recycle content of any downstream compounds obtained from the pyrolysis of recycled waste, such as r-ethylene, r-propylene, r-butadiene, r-aldehydes, r-alcohols, r-benzene, etc. For example, the olefin or aldehyde supplier can transfer to the glycol ester manufacturer a recycle content associated with r-olefin or r-aldehyde and also supply a quantity of olefin or aldehyde even though r-olefin or r-aldehyde was not used in the synthesis of the olefin or aldehyde. This allows flexibility among the olefin or aldehyde supplier and glycol ester manufacturer to apportion a recycle content among the variety of products they each make. In each of these cases, however, the recycle content allotment is associated with cracking r-pyoil.

In one embodiment or in combination with any of the mentioned embodiments, the olefin or aldehyde supplier transfers a recycle content allotment to the glycol ester manufacturer and a supply of olefin or aldehyde to the glycol ester manufacturer, where the recycle content allotment is associated with the olefin or aldehyde. In this case, the olefin or aldehyde transferred does not have to be an r-olefin or r-aldehyde (one that is derived directly or indirectly from the pyrolysis of recycled waste); rather the olefin or aldehyde supplied by the supplier can be any olefin or aldehyde such as a non-recycle content olefin or aldehyde, so long as the allocation supplied is associated with a manufacture of olefin or aldehyde. Optionally, the olefin or aldehyde being supplied can r-olefin or r-aldehyde and at least a portion of the recycle content allotment being transferred can be the recycle content in the r-olefin or r-aldehyde. The recycle content allotment transferred to the glycol ester manufacturer can be up front with the olefin or aldehyde supplied in installments, or with each olefin or aldehyde installment, or apportioned as desired among the parties.

The allotment in (ii) is obtained by the glycol ester manufacturer (or its Family of Entities) from any person or entity without obtaining a supply of olefin or aldehyde from the person or entity. The person or entity can be an olefin or aldehyde manufacturer that does not supply olefin or aldehyde to the glycol ester manufacturer or its Family of Entities, or the person or entity can be a manufacturer that does not make olefin or aldehyde.

In either case, the circumstances of (ii) allows a glycol ester manufacturer to obtain a recycle content allotment without having to purchase any olefin or aldehyde from the entity supplying the recycle content allotment. For example, the person or entity may transfer a recycle content allotment through a buy/sell model or contract to the glycol ester manufacturer or its Family of Entities without requiring purchase or sale of a allotment (e.g. as a product swap of products that are not olefin or aldehyde), or the person or entity may outright sell the allotment to the glycol ester manufacturer or one among its Family of Entities. Alternatively, the person or entity may transfer a product, other than olefin or aldehyde, along with its associated recycle content allotment to the glycol ester manufacturer. This can be attractive to a glycol ester manufacturer that has a diversified business making a variety of products other than glycol ester requiring raw materials other than olefin or aldehyde that the person or entity can supply to the glycol ester manufacturer.

The glycol ester manufacturer can deposit the allotment into a recycle inventory. The glycol ester manufacturer also makes glycol ester, whether or not a recycle content is applied to the glycol ester so made and whether or not a recycle content value, if applied to the glycol ester, is drawn from the recycle inventory. For example, the glycol ester manufacturer, or any entity among its Family of Entities may:

a. deposit the allotment into a recycle inventory and merely store it; or
b. deposit the allotment into a recycle inventory and apply a recycle content value from the recycle inventory to products other than glycol ester made by the glycol ester manufacturer, or
c. sell or transfer an allotment from the recycle inventory into which the allotment obtained as noted above was deposited.

If desired, however, from that recycle inventory, any allotment can be deducted and applied to the glycol ester product in any amount and at any time up to the point of sale or transfer of the glycol ester to a third party. Thus, the recycle content allotment applied to the glycol ester can be derived directly or indirectly from pyrolyzing recycled waste, or the recycle content allotment applied to the glycol ester is not derived directly or indirectly from the pyrolysis of recycled waste.

For example, a recycle inventory of allotments can be generated having a variety of sources for creating the allotments. Some recycle content allotments (credits) can have their origin in methanolysis of recycled waste, or from gasification of recycled waste, or from mechanical recycling of waste plastic or metal recycling, and/or from pyrolyzing recycled waste, or from any other chemical or mechanical recycling technology. The recycle inventory may or may not track the origin or basis of obtaining a recycle content, or the recycle inventory may not allow one to associate the origin or basis of an allocation to the allocation applied to glycol ester. Thus, in this embodiment, it is sufficient that a recycle content value is deducted from recycle inventory and applied to glycol ester regardless of the source or origin of the recycle content value, provided that an allotment derived from pyrolyzing recycled waste is also obtained by the glycol ester manufacturer as specified in step (i) or step (ii), whether or not that allotment is actually deposited into the recycle inventory. In one embodiment or in combination with any of the mentioned embodiments, the allotment obtained in step (i) or (ii) is deposited into a recycle inventory of allotments. In one embodiment or in combination with any of the mentioned embodiments, the recycle content value deducted from the recycle inventory and applied to the glycol ester originates from pyrolyzing recycled waste.

As used throughout, the recycle inventory of allotments can be owned by the glycol ester manufacturer, operated by the glycol ester manufacturer, owned or operated by other than the glycol ester manufacturer but at least in part for the glycol ester manufacturer, or licensed by the glycol ester manufacturer. Also, as used throughout, the glycol ester manufacturer may also include its Family of Entities. For example, while the glycol ester manufacturer may not own or operate the recycle inventory, one among its Family of Entities may own such a platform, or license it from an independent vendor, or operate it for the glycol ester manufacturer. Alternatively, an independent entity may own and/or operate the recycle inventory and for a service fee operate and/or manage at least a portion of the recycle inventory for the glycol ester manufacturer.

In one embodiment or in combination with any of the mentioned embodiments, the glycol ester manufacturer obtains a supply of olefin or aldehyde from a supplier, and also obtains an allotment from either (i) the supplier or (ii) from any other person or entity, where such allotment is derived from recycled waste, the pyrolysis of recycled waste, pyrolysis gas produced from the pyrolysis of recycled waste, and/or the cracking of r-pyoil produced from the pyrolysis of recycled waste, and optionally the allotment is obtained from the olefin or aldehyde supplier and can even be an allotment by virtue of obtaining an r-olefin or r-aldehyde from the supplier. The glycol ester manufacturer is deemed to obtain the supply of olefin or aldehyde from a supplier if the supply is obtained by a person or entity within the Family of Entities of the glycol ester manufacturer. The glycol ester manufacturer then carries out one or more of the following steps:

a. applying the allotment to glycol ester made by the supply of olefin or aldehyde;
b. applying the allotment to glycol ester not made by the supply of olefin or aldehyde, such as would be the case where glycol ester is already made and stored in recycle inventory, or to future made glycol ester; or
c. depositing the allotment into a recycle inventory from which is deducted a recycle content value and applying at least a portion of the recycle content value to:
    i. glycol ester to thereby obtain r-glycol ester, or
    ii. to a compound or composition other than glycol ester, or
    iii. both;

whether or not r-olefin or r-aldehyde is used to make the glycol ester composition, and whether or not the recycle content value applied to glycol ester was obtained from a recycle content value in the allotment obtained in step (i) or step (ii) or deposited into the recycle inventory; or d. as described above, can merely be deposited into a recycle inventory and stored.

It is not necessary in all embodiments that r-olefin or r-aldehyde is used to make the r-glycol ester composition or that the r-glycol ester was obtained from a recycle content allotment associated with an olefin or aldehyde composition. Further, it is not necessary that an allotment be applied to the feedstock for making the glycol ester to which recycle content is applied. Rather, as noted above, the allotment, even if associated with an olefin or aldehyde composition when the olefin or aldehyde composition is obtained from a supplier, can be deposited into an electronic recycle inventory. In one embodiment or in combination with any of the mentioned embodiments, however, r-olefin or r-aldehyde is used to make the r-glycol ester composition. In one embodiment or in combination with any of the mentioned embodiments, the r-glycol ester is obtained from a recycle content allotment associated with an alkylene composition. In one embodiment or in combination with any of the mentioned embodiments, at least a portion of r-olefin or r-aldehyde allotments are applied to glycol ester to make an r-glycol ester.

The glycol ester composition can be made from any source of an olefin or aldehyde composition, whether or not the olefin or aldehyde composition is an r-olefin or r-aldehyde, and whether or not the olefin or aldehyde is obtained from a supplier or made by the glycol ester manufacturer or within its Family of Entities. Once a glycol ester composition is made, it can be designated as having recycle content based on and derived from at least a portion of the allotment, again whether or not the r-olefin or r-aldehyde is used to make the r-glycol ester composition and regardless of the source of olefin or aldehyde used to make the glycol ester. The allocation can be withdrawn or deducted from recycle inventory. The amount of the deduction and/or applied to the glycol ester can correspond to any of the methods described above, e.g. a mass balance approach.

In one embodiment or in combination with any of the mentioned embodiments, a recycle content glycol ester composition can be made by reacting an olefin or aldehyde composition obtained from any source in a synthetic process to make a glycol ester, and a recycle content value can be applied to at least a portion of the glycol ester to thereby obtain r-glycol ester. Optionally, a recycle content value can be obtained by deducting from a recycle inventory. The entire amount of recycle content value in the glycol ester can correspond to the recycle content value deducted from the recycle inventory. Recycle content value deducted from the recycle inventory can be applied to both glycol ester and products or compositions other than glycol ester made by the glycol ester manufacturer or a person or entity among its Family of Entities.

The olefin or aldehyde composition can be obtained from a third party, or made by the glycol ester manufacturer, or made by a person or entity amount the Family of Entities of the glycol ester manufacturer and transferred to the glycol ester manufacturer. In another example, the glycol ester manufacturer or its Family of Entities can have a first facility for making olefin or aldehyde within a first Site, and a second facility within the first Site or a second facility within a second Site where the second facility makes glycol ester, and transfer the olefin or aldehyde from the first facility or first Site to the second facility or second Site. The facilities or Sites can be in direct or indirect, continuous or discontinuous, fluid communication or pipe communication with each other. A recycle content value is then applied to (e.g. assigned to, designate to correspond to, attributed to, or associated with) the glycol ester to make an r-glycol ester. At least a portion of the recycle content value applied to the glycol ester is obtained from a recycle inventory.

Optionally, one may communicate to a third party that the r-glycol ester has recycle content or is obtained or derived from recycled waste. In one embodiment or in combination with any of the mentioned embodiments, one may communicate recycle content information about the glycol ester to a third party where such recycle content information is based on or derived from at least a portion of the allocation or credit. The third party may be a customer of the glycol ester manufacturer or supplier, or may be any other person or entity or governmental organization other than the entity owning the glycol ester. The communication may electronic, by document, by advertisement, or any other means of communication.

In one embodiment or in combination with any of the mentioned embodiments, a recycle content glycol ester composition is obtained by either making a first r-glycol ester or by merely possessing (e.g. by way of purchase, transfer, or otherwise) a first r-glycol ester already having a recycle content, and transferring a recycle content value between a recycle inventory and the first r-glycol ester to obtain a second r-glycol ester having different recycle content value than the first r-glycol ester.

In one embodiment or in combination with any of the mentioned embodiments, the transferred recycle content value described above is deducted from the recycle inventory and applied to the first r-glycol ester to obtain a second r-glycol ester having a second recycle content value higher than the first r-glycol ester contains, to thereby increase the recycle content in first r-glycol ester.

The recycle content in the first r-glycol ester need not be obtained from a recycle inventory, but rather can be attributed to glycol ester by any of the methods described herein (e.g. by virtue of using an r-olefin or r-aldehyde as a reactant feed), and the glycol ester manufacturer may seek to further increase the recycle content in the first r-glycol ester so made. In another example, a glycol ester distributor may have r-glycol ester in its inventory and seek to increase the recycle content value of the first r-glycol ester in its possession. The recycle content in the first r-glycol ester can be increased by applying a recycle content value withdrawn from a recycle inventory.

The recycle content value quantity that is deducted from recycle inventory is flexible and will depend on the amount of recycle content applied to the glycol ester. In one embodiment or in combination with any of the mentioned embodiments, it is at least sufficient to correspond with at least a portion of the recycle content in the r-glycol ester. This is useful if, as noted above, a portion of the glycol ester was made with r-olefin or r-aldehyde where the recycle content value in the r-olefin or r-aldehyde was not deposited into a recycle inventory, resulting in an r-glycol ester and one desires to increase the recycle content in the r-glycol ester by applying a recycle content value withdrawn from a recycle inventory; or where one possesses r-glycol ester (by way of purchase, transfer, or otherwise) and desires to increase its recycle content value. Alternatively, the entire recycle content in the r-glycol ester can be obtained by applying a recycle content value to the glycol ester obtained from a recycle inventory.

The method for calculating the recycle content value is not limited, and can include the mass balance approach or the methods of calculation described above. The recycle inventory can be established on any basis and be a mix of bases. Examples of the origin for obtaining allotments deposited into a recycle inventory can be from pyrolyzing recycled waste, gasification of recycled waste, depolymerization of recycled waste such as through hydrolysis or methanolysis, and so on. In one embodiment or in combination with any of the mentioned embodiments, at least a portion of the allocations deposited into the recycle inventory is attributable to pyrolyzing recycled waste (e.g. obtained from cracking r-pyoil or obtained from r-pygas). The recycle inventory may or may not track the origin of recycle content value deposited into the recycle inventory. In one embodiment or in combination with any of the mentioned embodiments, the recycle inventory distinguishes between a recycle content value obtained from pyrolyzing recycled waste (i.e., pyrolysis recycle content value) and recycle content values having their origin in other technologies (i.e., recycle content value). This may be accomplished simply by assigning distinguishing units of measure to the recycle content values having is origin in pyrolyzing recycled waste, or tracking the origin of the allocation by assigning or placing the allocation into a unique module, unique spreadsheet, unique column or row, unique database, unique taggants associated with a unit of measure, and the like to as to distinguish the:

Origin of technology used to create the allotment, or

The type of compound having recycle content from which the allocation is obtained, or The supplier or Site identity, or A combination thereof.

The recycle content value applied to the glycol ester from the recycle inventory does not have to be obtained from allotments having their origin in pyrolyzing recycled waste. The recycle content values deducted from the recycle inventory and/or applied to the glycol ester can be derived from any technology used to generate allocations from recycled waste, such as through methanolysis or gasification of recycled waste. In one embodiment or in combination with any of the mentioned embodiments, however, the recycle content value applied to the glycol ester or withdrawn/deducted from the recycle inventory have their origins or are derived from allotments obtained from pyrolyzing recycled waste.

The following are examples of applying (designating, assigning, or declaring a recycle content) a recycle content value or allotment to glycol ester or to an olefin or aldehyde composition:

1. Applying at least a portion of a recycle content value to a glycol ester composition where the recycle content value is derived directly or indirectly with a recycle content olefin or aldehyde, where such recycle content olefin or aldehyde is obtained directly or indirectly from cracking r-pyoil or obtained from r-pygas, and the olefin or aldehyde composition used to make the glycol ester did not contain any recycle content or it did contain recycle content; or
2. Applying at least a portion of a recycle content value to a glycol ester composition where the recycle content value is derived directly or indirectly from cracking r-pyoil or obtained from r-pygas; or
3. Applying at least a portion of a recycle content value to a glycol ester composition where the recycle content value is derived directly or indirectly with an r-olefin or r-aldehyde, whether or not such olefin or aldehyde volume is used to make the glycol ester; or
4. Applying at least a portion of a recycle content value to a glycol ester composition where the recycle content value is derived directly or indirectly with an r-olefin or r-aldehyde, and the r-olefin or r-aldehyde is used as a feedstock to make the r-glycol ester to which the recycle content value is applied, and:
   a. all of the recycle content in the r-olefin or r-aldehyde is applied to determine the amount of recycle content in the glycol ester, or
   b. only a portion of the recycle content in the r-olefin or r-aldehyde is applied to determine the amount of recycle content applied to the glycol ester, the remainder stored in recycle inventory for use to future glycol ester, or for application to other existing glycol ester made from r-olefin or r-aldehyde not containing any recycle content, or to increase the recycle content on an existing r-glycol ester, or a combination thereof, or
   c. none of the recycle content in the r-olefin or r-aldehyde is applied to the glycol ester and instead is stored in a recycle inventory, and a recycle content from any source or origin is deducted from the recycle inventory and applied to glycol ester; or
5. Applying at least a portion of a recycle content value to an olefin or aldehyde composition used to make a glycol ester to thereby obtain an r-glycol ester, where the recycle content value was obtained with the transfer or purchase of the same olefin or aldehyde composition used to make the glycol ester and the recycle content value is associated with the recycle content in an olefin or aldehyde composition; or
6. Applying at least a portion of a recycle content value to an olefin or aldehyde composition used to make a glycol ester to thereby obtain an r-glycol ester, where the recycle content value was obtained with the transfer or purchase of the same olefin or aldehyde composition used to make the glycol ester and the recycle content value is not associated with the recycle content in an olefin or aldehyde composition but rather on the recycle content of a compound used to make the olefin or aldehyde composition; or
7. Applying at least a portion of a recycle content value to an olefin or aldehyde composition used to make a glycol ester to thereby obtain an r-glycol ester, where the recycle content value was not obtained with the transfer or purchase of the olefin or aldehyde composition and the recycle content value is associated with the recycle content in the olefin or aldehyde composition; or
8. Applying at least a portion of a recycle content value to an olefin or aldehyde composition used to make a glycol ester to thereby obtain an r-glycol ester, where the recycle content value was not obtained with the transfer or purchase of the olefin or aldehyde composition and the recycle content value is not associated with the recycle content in the olefin or aldehyde composition but rather with the recycle content of any compounds used to make the olefin or aldehyde composition; or
9. Obtaining a recycle content value derived directly or indirectly from pyrolyzing recycled waste, such as from cracking of r-pyoil, or obtained from an r-pygas, or associated with an r-composition, or associated with an r-olefin or r-aldehyde, and:

a. no portion of the recycle content value is applied to an olefin or aldehyde composition to make glycol ester and at least a portion is applied to glycol ester to make an r-glycol ester; or b. less than the entire portion is applied to an olefin or aldehyde composition used to make glycol ester and the remainder is stored in recycle inventory or is applied to future made glycol ester or is applied to existing glycol ester in recycle inventory.

As used throughout, the step of deducting an allocation from a recycle inventory does not require its application to a glycol ester product. The deduction also does not mean that the quantity of the deduction disappears or is removed from the inventory logs. A deduction can be an adjustment of an entry, a withdrawal, an addition of an entry as a debit, or any other algorithm that adjusts inputs and outputs based on an amount of recycle content associated with a product and one or a cumulative amount of allocations on deposit in the recycle inventory. For example, a deduction can be a simple step of a reducing/debit entry from one column and an addition/credit to another column within the same program or books, or an algorithm that automates the deductions and entries/additions and/or applications or designations to a product slate. The step of applying a recycle content value to a glycol ester product also does not require the recycle content value or allocation to be applied physically to a glycol ester product or to any document issued in association with the glycol ester product sold. For example, a glycol ester manufacturer may ship glycol ester product to a customer and satisfy the "application" of the recycle content value to the glycol ester product by electronically transferring a recycle content credit or certification document to the customer, or by applying a recycle content value to a package or container containing the glycol ester or r-olefin or r-aldehyde.

Some glycol ester manufacturers may be integrated into making downstream products using glycol ester as a raw material. The integrated glycol ester manufacturers, and other non-integrated glycol ester manufacturers, can also offer to sell or sell glycol ester on the market as containing or obtained with an amount of recycle content. The recycle content designation can also be found on or in association with the downstream product made with the glycol ester.

In one embodiment or in combination with any of the mentioned embodiments, the amount of recycle content in the r-olefin or r-aldehyde or in the r-glycol ester will be based on the allocation or credit obtained by the manufacturer of the glycol ester composition or the amount available in the glycol ester manufacturer's recycle inventory. A portion or all of the recycle content value in an allocation or credit obtained by or in the possession of a manufacturer of glycol ester can be designated and assigned to an r-olefin or r-aldehyde or r-glycol ester on a mass balance basis. The assigned value of the recycle content to the r-olefin or r-aldehyde or r-glycol ester should not exceed the total amount of all allocations and/or credits available to the manufacturer of the glycol ester or other entity authorized to assign a recycle content value to the glycol ester.

There is now also provided a method of introducing or establishing a recycle content in a glycol ester without necessarily using an r-olefin or r-aldehyde feedstock. In this method, a. an olefin supplier either:
   i. cracks a cracker feedstock comprising recycle pyoil to make an olefin or aldehyde composition at least a portion of which is obtained by cracking said recycle pyoil (r-pyoil), or
   ii. makes a pygas at least a portion of which is obtained by pyrolyzing a recycled waste stream (r-pygas), or
   iii. both; and
b. an aldehyde manufacturer:
   i. obtaining an allotment derived directly or indirectly with said r-pyoil or said r-pygas from the supplier or a third-party transferring said allotment,
   ii. making an aldehyde from an olefin, and
   iii. associating at least a portion of the allotment with at least a portion of the aldehyde, whether or not the olefin used to make the glycol ester contains r-olefin; and
c. a glycol ester manufacturer:
   i. obtaining an allotment derived directly or indirectly with said r-pyoil or said r-pygas from the supplier or a third-party transferring said allotment,
   ii. making a glycol ester from an aldehyde, and
   iii. associating at least a portion of the allotment with at least a portion of the glycol ester, whether or not the aldehyde used to make the glycol ester contains r-aldehyde.

In this method, the glycol ester manufacturer need not purchase r-olefin or r-aldehyde from any entity or from the supplier of olefin or aldehyde, and does not require the glycol ester manufacturer to purchase olefin or aldehyde, r-olefin or r-aldehyde, or olefin or aldehyde from a particular source or supplier, and does not require the glycol ester manufacturer to use or purchase an olefin or aldehyde composition having r-olefin or r-aldehyde in order to successfully establish a recycle content in the glycol ester composition. The olefin or aldehyde manufacturer may use any source of olefin or aldehyde and apply at least a portion of the allocation or credit to at least a portion of the olefin or aldehyde feedstock or to at least a portion of the glycol ester product. When the allocation or credit is applied to the feedstock olefin or aldehyde, this would be an example of an r-olefin or r-aldehyde feedstock indirectly derived from the cracking of r-pyoil or obtained from r-pygas. The association by the glycol ester manufacturer may come in any form, whether by on in its recycle inventory, internal accounting methods, or declarations or claims made to a third party or the public.

In another embodiment, an exchanged recycle content value is deducted from a first r-glycol ester and added to the recycle inventory to obtain a second r-glycol ester having a second recycle content value lower than the first r-glycol ester contains, to thereby decrease the recycle content in first r-glycol ester. This embodiment, the above description concerning adding a recycle content value from a recycle inventory to a first r-glycol ester applies in reverse to deducting a recycle content from first r-glycol ester and adding it to a recycle inventory.

The allotment can be obtained from a variety of sources in the manufacturing chain starting from pyrolyzing recycled waste up to making and selling an r-olefin or r-aldehyde. The recycle content value applied to glycol ester or the allocation deposited into the recycle inventory need not be associated with r-olefin or r-aldehyde. In one embodiment or in combination with any of the mentioned embodiments, the process for making r-glycol ester can be flexible and allow for obtaining an allocation anywhere along the manufacturing chain to make glycol ester starting from pyrolyzing recycled waste. For example, one can make r-glycol ester by:

a. pyrolyzing a pyrolysis feed comprising a recycled waste material to thereby form a pyrolysis effluent that contains r-pyoil and/or r-pygas. An allotment associated with the r-pyoil or r-pygas is automatically created by creation of pyoil or pygas from a recycled waste stream. The allotment may travel with the pyoil or pygas, or be dissociated from the pyoil or pygas such as by way of depositing the allotment into a recycle inventory; and
b. optionally cracking a cracker feed that contains at least a portion of the r-pyoil made in step a) to thereby produce a cracker effluent containing r-olefin, including r-propylene; or optionally cracking a cracker feed without r-pyoil to make olefin, including propylene, and applying a recycle content value to the olefin so made by deducting a recycle content value from a recycle inventory (in the case that can be owned, operated, or for the benefit of an olefin producer or its Family of Entities) and applying the recycle content value to the olefin to make r-olefin;
c. reacting any olefin volume in a synthetic process to make an aldehyde composition; optionally using the olefin made in step b) and optionally using an r-olefin made in step b) and optionally applying a recycle content value associated the manufacture of the aldehyde made to make r-aldehyde;
d. reacting any aldehyde volume in a synthetic process to make a glycol ester composition; optionally using the aldehyde made in step c) and optionally using an r r-aldehyde made in step c) and optionally applying a recycle content value associated the manufacture of the glycol ester made to make r-glycol ester; and
e. applying a recycle content value to at least a portion of said glycol ester composition based on:
   i. feeding r-olefin or r-aldehyde as a feedstock or
   ii. depositing at least a portion of an allotment obtained from any one or more of steps a), b), or c) into a recycle inventory and deducting from said inventory a recycle content value and applying at least a portion of either or both of said values to glycol ester to thereby obtain r-glycol ester.

In one embodiment or in combination with any of the mentioned embodiments, there is also provided a comprehensive process for making recycle content glycol esters by:

a. making an r-olefin by either cracking the r-pyoil or separating olefin or aldehyde from the r-pygas; and
b. converting at least a portion of any or said olefin to an aldehyde; and
c. converting at least a portion of any or said aldehyde to a glycol ester; and
d. applying a recycle content value to said glycol ester to make an r-glycol ester; and
e. optionally, also making an r-pyoil or r-pygas or both by pyrolyzing a recycle feedstock In this embodiment, all steps a)-d) can be practiced by and within a Family of Entities, or optionally on the same Site.

In another method, the direct method, a recycle content can be introduced or established in glycol ester by:

obtaining recycle olefin composition at least a portion of which is indirectly derived from cracking r-pyoil or indirectly obtained from r-pygas ("r-olefin"), making an aldehyde composition from a feedstock comprising r-olefin, making a glycol ester composition from a feedstock comprising r-aldehyde, applying a recycle content value to at least a portion of any glycol ester composition made by the same entity that made the glycol ester composition in step c), and the recycle content value is based at least partly on the amount of recycle content contained in the r-olefin or r-aldehyde.

In another more detailed direct method, a recycle content can be introduced or established in glycol ester by:

a. making a recycle olefin composition (e.g., propylene) at least a portion of which is directly derived from the pyrolysis of recycle waste or from cracking r-pyoil or obtained from r-pygas ("dr-olefin");
b. making aldehyde with a feedstock containing dr-olefin ("dr-aldehyde");
c. designating at least a portion of the olefin or aldehyde as containing a recycle content corresponding to at least a portion of the amount of dr-olefin or dr-aldehyde contained in the feedstock to obtain a dr-olefin or dr-aldehyde,
d. making a glycol ester with a feedstock containing dr-olefin or dr-aldehyde,
e. designating at least a portion of the glycol ester as containing a recycle content corresponding to at least a portion of the amount of dr-olefin or dr-aldehyde contained in the feedstock to obtain a dr-glycol ester,
f. and optionally offering to sell or selling the dr-glycol ester as containing or obtained with recycle content corresponding with such designation.

In these direct methods, the r-olefin or r-aldehyde content used to make the glycol ester would be traceable to the olefin or aldehyde made by a supplier by cracking r-pyoil or obtained from r-pygas. Not all of the amount of r-olefin or r-aldehyde used to make the olefin or aldehyde need be designated or associated with the olefin or aldehyde. For example, if 1000 kg of r-olefin or r-aldehyde is used to make r-glycol ester, the olefin or aldehyde manufacturer can designate less than 1000 kg of recycle content toward a particular batch of feedstock used to make the olefin or aldehyde and may instead spread out the 1000 kg recycle content amount over various productions runs to make olefin or aldehyde. The olefin or aldehyde manufacturer may elect to offer for sale its dr-glycol ester and in doing so may also elect to represent the r-glycol ester that is sold as containing, or obtained with sources that contain, a recycle content.

There is also provided a use for an olefin or aldehyde derived directly or indirectly from cracking r-pyoil or obtained from r-pygas, the use including converting r-olefin or r-aldehyde in any synthetic process to make glycol esters.

There is also provided a use for an r-olefin or r-aldehyde allotment or an r-olefin or r-aldehyde allotment that includes converting an olefin or aldehyde in a synthetic process to make glycol esters and applying at least a portion of an r-olefin or r-aldehyde allotment or the r-olefin or r-aldehyde allotment to the glycol ester. An r-olefin or r-aldehyde allotment or an r-olefin or r-aldehyde allotment is an allotment that is created by pyrolyzing recycled waste. Desirably, the allotments originate from the cracking of r-pyoil, or cracking of r-pyoil in a gas furnace, or from r-pygas.

There is also provided a use for a glycol ester formed by hydroformylating olefin to form an aldehyde, and then reacting the aldehyde in the presence of a catalyst to form the glycol ester, and applying at least a portion of a recycle content allotment to at least a portion of the glycol ester to make an r-glycol ester. At least a portion of the recycle inventory from which the recycle content allotment is applied to the glycol ester are allotments originating from pyrolyzing recycled waste. Desirably, the allotments originate from the cracking of r-pyoil, or cracking of r-pyoil in a gas furnace, or from r-pygas. Also, the allotment applied to the glycol ester can be a recycle content allotment originating from pyrolyzing recycled waste.

In one embodiment or in combination with any of the mentioned embodiments, there is also provided a use of a recycle inventory by converting any olefin or aldehyde composition in a synthetic process to make a glycol ester composition ("glycol ester"); deducting a recycle content value from the recycle inventory and applying at least a portion of the deducted recycle content value to the glycol ester, and at least a portion of the inventory contains a recycle content allotment. The recycle content allotment can be present in the inventory at the time of deducting a recycle content value from the recycle inventory, or a recycle content allotment deposit is made into the recycle inventory before deducting a recycle content value (but need not be present or accounted for when a deduction is made), or it can be present within a year from the deduction, or within the same calendar year as the deduction, or within the same month as the deduction, or within the same week as the deduction. In one embodiment or in combination with any of the mentioned embodiments, the recycle content deduction is withdrawn against a recycle content allotment.

In one embodiment or in combination with any of the mentioned embodiments, there is provided a glycol ester composition that is obtained by any of the methods described above.

The same operator, owner, of Family of Entities may practice each of these steps, or one or more steps may be practiced among different operators, owners, or Family of Entities.

The olefin or aldehyde can be stored in a storage vessel and transferred to a glycol ester manufacturing facility by way of truck, pipe, or ship, or as further described below, the olefin or aldehyde production facility can be integrated with the glycol ester facility. The olefin or aldehyde may be shipped or transferred to the operator or facility that makes the glycol ester.

In one embodiment or in combination with any of the mentioned embodiments, one may integrate two or more facilities and make r-glycol ester. The facilities to make r-glycol ester, the r-olefin or r-aldehyde, and the r-pyoil and/or r-pygas, can be stand-alone facilities or facilities integrated to each other. For example, one may establish a system of producing and consuming a recycle olefin or aldehyde composition at least a portion of which is obtained from directly or indirectly from cracking r-pyoil or obtaining r-pygas; or a method of making r-glycol ester, as follows:

a. providing an olefin or aldehyde manufacturing facility that produces at least in part an olefin or aldehyde composition;
b. providing a glycol ester manufacturing facility that makes a glycol ester composition and comprising a reactor configured to accept olefin or aldehyde; and
c. feeding at least a portion of said olefin or aldehyde from the olefin or aldehyde manufacturing facility to the glycol ester manufacturing facility through a supply system providing fluid communication between said facilities;

wherein any one or both of the olefin or aldehyde manufacturing facility or glycol ester manufacturing facility generates or participates in a process to generate allotments and cracks r-pyoil, or makes or supplies an r-olefin or r-aldehyde (r-olefin or r-aldehyde) or recycle content glycol ester (r-glycol ester), respectively, and optionally, wherein the olefin or aldehyde manufacturing facility supplies r-olefin or r-aldehyde to the glycol ester manufacturing facility through the supply system and:

(i) said allotments are applied to the reactants or to the gycol ester, or
(ii) are deposited into an inventory of allotments, and optionally an allotment is withdrawn from the inventory and applied to the reactants or to the glycol ester.

The feeding in step c) can be a supply system providing fluid communication between these two facilities and capable of supplying an olefin or aldehyde composition from the olefin or aldehyde manufacturing facility to the glycol ester manufacturing facility, such as a piping system that has a continuous or discontinuous flow.

The glycol ester manufacturing facility can make r-glycol ester, and can make the r-glycol ester directly or indirectly from the pyrolysis of recycled waste or the cracking of r-pyoil or from r-pygas. For example, in a direct method, the glycol ester manufacturing facility can make r-glycol ester by accepting r-olefin or r-aldehyde from the olefin or aldehyde manufacturing facility and feeding the r-olefin or r-aldehyde as a feed stream to a reactor to make glycol ester. Alternatively, the glycol ester manufacturing facility can make r-glycol ester by accepting any olefin or aldehyde composition from the olefin or aldehyde manufacturing facility and applying a recycle content to glycol ester made with the olefin or aldehyde composition by deducting recycle content value from its recycle inventory and applying them to the glycol ester, optionally in amounts using the methods described above. The allotments obtained and stored in recycle inventory can be obtained by any of the methods described above, and need not necessarily be allotments associated with r-olefin or r-aldehyde.

In one embodiment or in combination with any of the mentioned embodiments, there is also provided a system for producing r-glycol ester as follows:

a. provide an olefin or aldehyde manufacturing facility configured to produce an output composition comprising a recycle content olefin or aldehyde ("r-olefin or r-aldehyde");
b. provide a glycol ester manufacturing facility having a reactor configured to accept an olefin or aldehyde composition and making an output composition comprising an r-glycol ester; and
c. a supply system providing fluid communication between at least two of these facilities and capable of supplying the output composition of one manufacturing facility to another one or more of said manufacturing facilities.

The glycol ester manufacturing facility can make r-glycol ester, and can make the r-glycol ester directly or indirectly from the pyrolysis of recycled waste. In this system, the olefin or aldehyde manufacturing facility can have its output in fluid communication with the olefin or aldehyde manufacturing facility which in turn can have its output in fluid communication with the glycol ester manufacturing facility. Alternatively, the manufacturing facilities of a) and b) alone can be in fluid communication. In the latter case, the glycol ester manufacturing facility can make r-glycol ester directly by having the r-olefin or r-aldehyde or r-olefin or r-aldehyde produced in the olefin or aldehyde manufacturing facility converted all the way to glycol ester, or indirectly by accepting any olefin or aldehyde composition from the olefin or aldehyde manufacturing facility and applying a recycle content to glycol ester by deducting allotments from its recycle inventory and applying them to the glycol ester, optionally in amounts using the methods described above. The allotments obtained and stored in recycle inventory can be obtained by any of the methods described above, and need not necessarily be allotments associated with r-olefin or r-aldehyde. For example, the allotments can be obtained from any facility or source, so long as they originate from the pyrolysis of recycled waste, or the cracking r-pyoil or obtained from r-pygas.

The fluid communication can be gaseous, or liquid if compressed. The fluid communication need not be continuous and can be interrupted by storage tanks, valves, or other purification or treatment facilities, so long as the fluid can be transported from one facility to the subsequent facility through, for example, an interconnecting pipe network and without the use of truck, train, ship, or airplane. For example, one or more storage vessels may be placed in the supply system so that the r-olefin or r-aldehyde facility feeds r-olefin or r-aldehyde to a storage facility and r-olefin or r-aldehyde can be withdrawn from the storage facility as needed by the glycol ester manufacturing facility, with valving and pumps and compressors utilized an in line with the piping network as needed. Further, the facilities may share the same site, or in other words, one site may contain two or more of the facilities. Additionally, the facilities may also share storage tank sites, or storage tanks for ancillary chemicals, or may also share utilities, steam or other heat sources, etc., yet also be considered as discrete facilities since their unit operations are separate. A facility will typically be bounded by a battery limit.

In one embodiment or in combination with any of the mentioned embodiments, the integrated process includes at least two facilities co-located within 5, or within 3, or within 2, or within 1 mile of each other (measured as a straight line). In one embodiment or in combination with any of the mentioned embodiments, at least two facilities are owned by the same Family of Entities.

In one embodiment or in combination with any of the mentioned embodiments, there is also provided an integrated r-olefin or r-aldehyde and r-glycol ester generating and consumption system. This system includes:

a. provide an olefin or aldehyde manufacturing facility configured to produce an output composition comprising a recycle content olefin or aldehyde ("r-olefin or r-aldehyde");
b. provide glycol esters manufacturing facility having a reactor configured to accept an olefin or aldehyde composition and making an output composition comprising an r-glycol ester; and
c. a piping system interconnecting at least two of said facilities, optionally with intermediate processing equipment or storage facilities, capable of taking off the output composition from one facility and accept said output at any one or more of the other facilities.

The system does not necessarily require a fluid communication between the two facilities, although fluid communication is desirable. In this system, olefin or aldehyde or olefin or aldehyde made at the olefin or aldehyde manufacturing facility can be delivered to the olefin or aldehyde facility through the interconnecting piping network that can be interrupted by other processing equipment, such as treatment, purification, pumps, compression, or equipment adapted to combine streams, or storage facilities, all containing optional metering, valving, or interlock equipment. The equipment can be a fixed to the ground or fixed to structures that are fixed to the ground. The interconnecting piping does not need to connect to the olefin or aldehyde reactor or the cracker, but rather to a delivery and receiving point at the respective facilities. The same concept applies between the olefin or aldehyde facility and the glycol ester facility. The interconnecting pipework need not connect all three facilities to each other, but rather the interconnecting pipework can be between facilities a)-b), or b)-c), or between a)-b)-c).

There is also provided a circular manufacturing process comprising:

a. providing an r-pyoil, and
b. a cracker facility cracking the r-pyoil to produce an olefin-containing effluent, and
c. applying (e.g. associating) a recycle content allotment, obtained from said r-pyoil or its cracking, to a glycol ester; and
d. the manufacturer in steps a, b or c receiving back at least a portion of any of glycol esters, or compositions containing glycol esters, or any articles, compounds, or polymers made from glycol esters.

In the above described process, an entirely circular or closed loop process is provided in which glycol ester can be recycled multiple times.

Examples of articles that are included in PIA are fibers, yarns, tow, continuous filaments, staple fibers, rovings, fabrics, textiles, flake, film (e.g. polyolefin films), sheet, compounded sheet, plastic containers, and consumer articles.

In one embodiment or in combination with any mentioned embodiments, the compositions, polymers or articles made from or with glycol esters that are receiving back are of the same family or classification of compositions, polymers or articles used to make r-pyoil.

There can now also be provided a package or a combination of an r-glycol ester and a recycle content identifier associated with r-glycol ester, where the identifier is or contains a representation that the glycol ester contains, or is sourced from or associated with a recycle content. The package can be any suitable package for containing a polymer and/or article, such as a plastic or metal drum, railroad car, isotainer, totes, polytote, bale, IBC totes, bottles, compressed bales, jerricans, and polybags, spools, roving, winding, or cardboard packaging.

The identifier can be a certificate document, a product specification stating the recycle content, a label, a logo or certification mark from a certification agency representing that the article or package contains contents or the glycol ester contains, or is made from sources or associated with recycle content, or it can be electronic statements by the glycol ester manufacturer that accompany a purchase order or the product, or posted on a website as a statement, representation, or a logo representing that the glycol ester contains or is made from sources that are associated with or contain recycle content, or it can be an advertisement transmitted electronically, by or in a website, by email, or by television, or through a tradeshow, in each case that is associated with glycol ester. The identifier need not state or represent that the recycle content is derived directly or indirectly from cracking r-pyoil or obtained from r-pygas. Rather, it is sufficient that the glycol ester is directly or indirectly obtained at least in part from the cracking of r-pyoil, and the identifier can merely convey or communicate that the glycol ester has or is sourced from a recycle content, regardless of the source. Desirably, the glycol ester has a recycle content allotment that, at least in part, is associated with r-pyoil or cracking r-pyoil, optionally is a gas fed thermal steam cracking furnace.

In one embodiment or in combination with any of the mentioned embodiments, there is provided a system or package comprising:

a. glycol ester ("glycol ester"), and b. an identifier (e.g. a credit, label or certification) associated with said glycol ester, said identifier being a representation that said glycol ester has recycle content or is made from a source having recycle content.

The system can be a physical combination, such as a package having at least some glycol ester as its contents and the package has a label, such as a logo, that the contents such as the glycol ester has or is sourced from a recycle content. Alternatively, the label or certification can be issued to a third party or customer as part of a standard operating procedure of an entity whenever it transfers or sells glycol ester having or sourced from recycle content. The identifier does not have to be physically on the glycol ester or on a package, and does not have to be on any physical document that accompanies or is associated with the glycol ester. For example, the identifier can be an electronic credit or certification or representation transferred electronically by the glycol ester manufacturer to a customer in connection with the sale or transfer of the glycol ester product, and by sole virtue of being a credit, it is a representation that the glycol ester has recycle content. The identifier, such as a label (such as a logo) or certification need not state or represent that the recycle content is derived directly or indirectly from cracking r-pyoil or obtained from r-pygas.

Rather, it is sufficient that the glycol ester is directly or indirectly obtained at least in part either (i) from pyrolyzing recycled waste or (ii) from a recycle inventory into which at least a portion of the deposits or credits in the recycle inventory have their origin in pyrolyzing recycled waste. The identifier itself need only convey or communicate that the glycol ester has or is sourced from a recycle content, regardless of the source. In one embodiment or in combination with any of the mentioned embodiments, articles made from the glycol ester may have the identifier, such as a stamp or logo embedded or adhered to the article. In one embodiment or in combination with any of the mentioned embodiments, the identifier is an electronic recycle content credit from any source. In one embodiment or in combination with any of the mentioned embodiments, the identifier is an electronic recycle content credit derived directly or indirectly from pyrolyzing recycled waste.

In one embodiment or in combination with any of the mentioned embodiments, the r-glycol ester, or articles made thereby, can be offered for sale or sold as glycol ester containing or obtained with, or an article containing or obtained with, recycle content. The sale or offer for sale can be accompanied with a certification or representation of the recycle content claim made in association with the glycol ester or article made with the glycol ester.

The obtaining of an allocation and designating (whether internally such as through a bookkeeping or a recycle inventory tracking software program or externally by way of declaration, certification, advertising, representing, etc.) can be by the glycol ester manufacturer or within the glycol ester manufacturer Family of Entities. The designation of at least a portion of the glycol ester as corresponding to at least a portion of the allotment (e.g. allocation or credit) can occur through a variety of means and according to the system employed by the glycol ester manufacturer, which can vary from manufacturer to manufacturer. For example, the designation can occur internally merely through a log entry in the books or files of the glycol ester manufacturer or other inventory software program, or through an advertisement or statement on a specification, on a package, on the product, by way of a logo associated with the product, by way of a certification declaration sheet associated with a product sold, or through formulas that compute the amount deducted from recycle inventory relative to the amount of recycle content applied to a product.

Optionally, the glycol ester can be sold. In one embodiment or in combination with any of the mentioned embodiments, there is provided a method of offering to sell or selling glycol esters by:

a glycol ester manufacturer, or any among their Family of Entities (collectively the Manufacturer) obtains or generates a recycle content allotment, and the allotment can be obtained by any of the means described herein and can be deposited into a recycle content inventory, the recycle content allotment optionally having its origin in recycle waster, r-pyoil, or cracking r-pyoil, converting an olefin or aldehyde composition in a synthetic process to make glycol ester composition ("glycol ester"), applying a recycle content value to at least a portion of the glycol ester to thereby obtain a recycle glycol ester ("r-glycol ester"). The applying step can be designating, assigning or associating, a recycle content to at least a portion of the glycol ester from a recycle content inventory to make r-GE, where the inventory contains at least one entry that is an allotment associated with r-pyoil or its cracking. The amount applied can be the amount of allotment deducted from inventory, or the amount of recycle content declared or determined by the glycol ester manufacturer in its accounts. The amount of recycle content does not necessarily have to be applied to the glycol ester in a physical fashion. The designation can be an internal designation to or by the Manufacturer or a service provider in contractual relationship to the Manufacturer, and offering to sell or selling the r-glycol ester as having a recycle content or obtained or derived from recycled waste.

A glycol ester manufacturer or its Family of Entities can obtain a recycle content allocation, and the allocation can be obtained by any of the means described herein and can be deposited into recycle inventory, the recycle content allocation derived directly or indirectly from the pyrolysis of recycled waste. The olefin or aldehyde converted in a synthetic process to make a glycol ester composition can be any olefin or aldehyde composition obtained from any source, including a non-r-olefin or r-aldehyde composition, or it can be an r-olefin or r-aldehyde composition. The r-glycol ester sold or offered for sale can be designated (e.g. labelled or certified or otherwise associated) as having a recycle content value. In one embodiment or in combination with any of the mentioned embodiments, at least a portion of the recycle content value associated with the r-glycol ester can be drawn from a recycle inventory. In another embodiment, at least a portion of the recycle content value in the glycol ester is obtained by converting r-olefin or r-aldehyde. The recycle content value deducted from the recycle inventory can be a non-pyrolysis recycle content value or can be a pyrolysis recycle content allocation; i.e. a recycle content value that has its origin in pyrolysis of recycled waste.

The recycle inventory can optionally contain at least one entry that is an allocation derived directly or indirectly from pyrolysis of recycled waste. The designation can be the amount of allocation deducted from recycle inventory, or the amount of recycle content declared or determined by the glycol ester manufacturer in its accounts. The amount of recycle content does not necessarily have to be applied to the glycol ester product in a physical fashion. The designation can be an internal designation to or by the glycol ester manufacturer or its Family of Entities or a service provider in contractual relationship to the glycol ester manufacturer or its Family of Entities. The amount of recycle content represented as contained in the glycol ester sold or offered for sale has a relationship or linkage to the designation. The amount of recycle content can be a 1:1 relationship in the amount of recycle content declared on a glycol ester offered for sale or sold and the amount of recycle content assigned or designated to the glycol ester by the glycol ester manufacturer.

The steps described need not be sequential, and can be independent from each other. For example, the steps a) and b) can be simultaneous, such as would be the case if employs an r-olefin or r-aldehyde composition to make the glycol ester since the r-olefin or r-aldehyde is both an olefin or aldehyde composition and has a recycle content allocation associated with it; or where the process of making glycol ester is continuous and the application of the glycol ester application of the recycle content value occurs during the manufacture of glycol ester.

Process for Making Glycol Esters

Glycol esters are commonly used as solvents and/or as intermediates in forming a range of other chemicals, including, for example plasticizers, coatings, paints, and polymer resins. In certain embodiments, isobutyrate esters of 2,2,4-trimethyl-1,3-pentanediol may be formed via reaction of isobutyraldehyde in the presence of a catalyst to form mono- and di-esters of 2,2,4-trimethyl-1,3-pentanediol, as well as 2,2,4-trimethyl-1,3-pentanediol itself. The isobutyraldehyde may be formed via hydroformylation of propylene with syngas (hydrogen and carbon monoxide), and at least a portion of the propylene may comprise recycle content propylene (r-propylene) as discussed in detail herein. The results are recycle content monoesters, diesters, and alcohols, which can be used to form a variety of end products.

Figure 26:
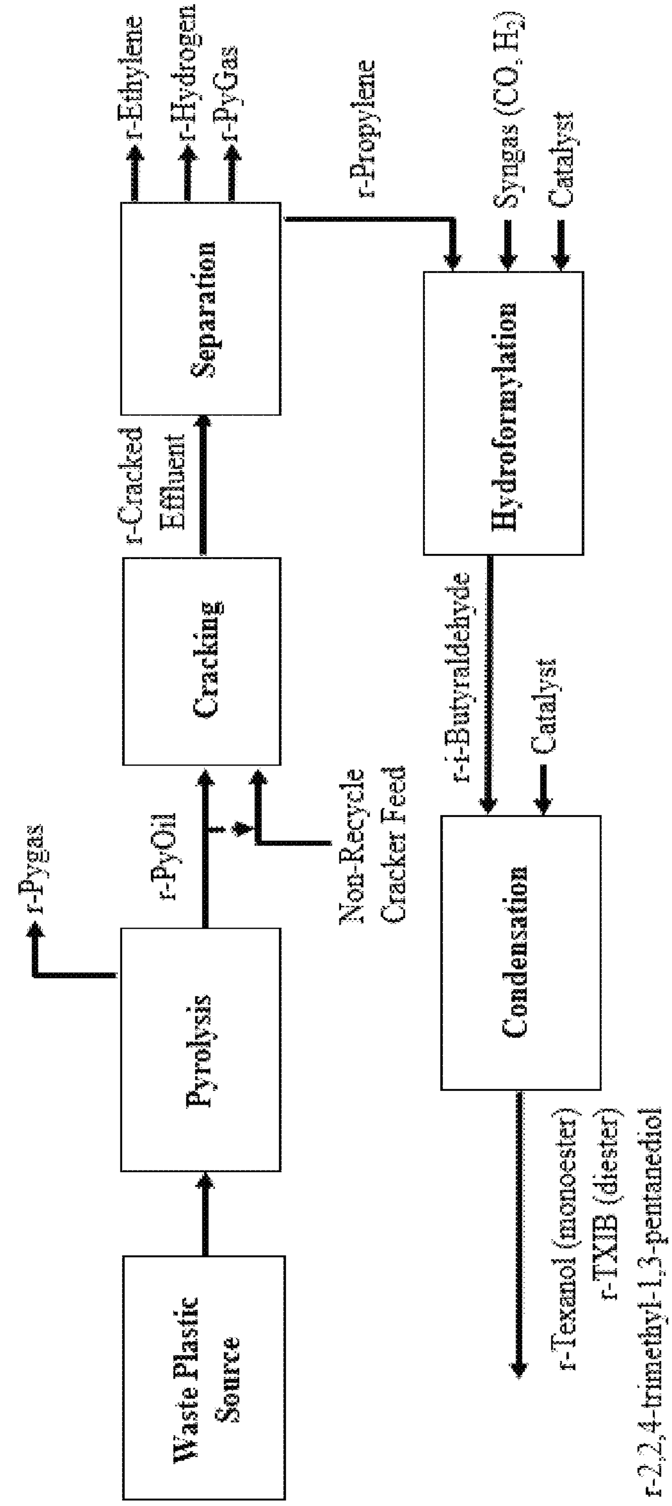
FIG. 26 is a process flow diagram to make r-EG from raw materials obtained by cracking of r-pyoil.

Turning now to FIG. 26, a system suitable for forming a recycle content glycol esters is provided. In particular, the system may be used to form a recycle content glycol monoester, such as 2,2,4-trimethyl-1,3-pentanediol monoisobutyrate (r-texanol), and/or a recycle content glycol diester, such as 2,2,4-trimethyl-1,3-pentanediol diisobutyrate (r-TXIB), and, optionally, a recycle content glycol such as 2,2,4-trimethyl-1,3-pentanediol (r-TMPD) from recycle content propylene (r-propylene).

As depicted in FIG. 26, the system suitable for forming a recycle content 2,2,4-trimethyl-1,3-pentanediol monoisobutyrate (r-texanol) and/or a recycle content 2,2,4-trimethyl-1,3-pentanediol diisobutyrate (r-TXIB) and/or a recycle content 2,2,4-trimethyl-1,3-pentanediol (r-TMPD) from recycle content propylene (r-propylene) may include the following components: (1) a pyrolysis unit/facility configured to i) pyrolyze a pyrolysis feed comprising a recycled waste material and ii) produce a pyrolysis effluent comprising a recycle content pyrolysis oil composition (r-pyoil) and optionally recycle content pyrolysis gas (r-pygas); (2) a cracking unit/facility configured to i) crack a cracker feed stream comprising at least a portion of the r-pyoil and ii) produce a cracker effluent; (3) a separation unit/facility downstream of and in fluid communication with the cracking unit/facility for separating at least a portion of the cracker effluent into one or more product streams including, for example, a stream comprising a recycle content propylene composition (r-propylene); (4) a hydroformylation unit/facility configured to i) react at least a portion of the r-propylene with syngas comprising carbon monoxide (CO) and hydrogen ($H_2$) and ii) produce a hydroformylation effluent comprising recycle content aldehyde (r-aldehyde); and (5) a condensation unit/facility for reacting aliphatic aldehydes comprising r-aldehyde to form glycols and/or mono- and/or di-esters thereof, any of which can comprise a recycle content composition (r-glycol, r-glycol monoester, r-glycol diester).

The pyrolysis units and cracking units shown in the system of FIG. 26 may include those, or components of those, that were previously described herein. In certain embodiments, the pyrolysis unit/facility, the cracking unit/facility, the hydroformylation unit/facility, and/or the condensation unit/facility may be in fluid communication. In some cases, the pyrolysis unit and cracking unit may be separately located and/or operated, while, in other cases, the pyrolysis and cracking units may be co-located as described herein. Similarly, the pyrolysis and/or cracking units may be separately located and/or operated, or co-located, with the hydroformylation and/or condensation unit/facility.

As shown in FIG. 26, a stream comprising r-olefin may be routed from the separation zone/unit of the cracking unit/facility to a hydroformylation unit. Hydroformylation is a process used to produce aldehydes by reacting a starting alkene with syngas (e.g., carbon monoxide and hydrogen) in the presence of a catalyst. The resulting aldehydes can be short, medium or long chain aldehydes and can, for example, include between 3 and 30 carbon atoms per molecule, depending on the specific starting alkenes (olefins). Typically, the starting alkenes include one less carbon atom per molecule than the final aldehyde and can, for example, include between 2 and 29 carbon atoms per molecule. In an embodiment or in combination with any of the embodiments mentioned herein, at least a portion of the starting alkene used in a hydroformylation reaction may be a recycle content alkene (r-alkene). As used herein, the terms “alkene” and “olefin” are interchangeable. Thus, examples of r-alkenes suitable for use in the hydroformylation reaction include r-ethylene, r-butylene, and r-propylene.

In an embodiment or in combination with any of the embodiments mentioned herein, at least 50, 55, 60, 65, 70, 75, 80, 85, 90, or 95 percent of the total weight of the hydroformylation feed stream can comprise olefin, including r-olefin such as r-propylene. In some cases, the r-olefin can comprise, consist essentially of, or consist of r-propylene, or the total amount of r-olefin may include at least about 20, 25, 30, 35, 40, 45, 50, 55, 60, 65, 70, 75, 80, 85, 90, or 95 weight percent of r-propylene, based on the total weight or r-olefin in the feed stream. The total amount of r-olefin in the feed stream to the hydroformylation unit can be at least 20, 25, 30, 35, 40, 45, 50, 55, 60, 65, 70, 75, 80, 85, 90, or 95 weight percent, based on the total weight of the hydroformylation feed stream. Additionally or alternatively, in certain embodiments, the feed stream going into the hydroformylation reactor may comprise not more than 99, 95, 90, 85, 80, 75, 70, 65, 60, 55, 50, 45, 40, 35, 30, 25, 20, 15, 10, 5, or 1 weight percent of the r-propylene.

In certain embodiments, at least 5, 10, 15, 20, 25, 30, 35, 40, 45, 50, 55, 60, 65, 70, 75, 80, 85, 90, 95, or 99 percent of the total amount of propylene fed into the hydroformylation zone comprises r-propylene, with the balance (if any) being non-recycle content propylene. In certain embodiments, the feed stream going into the hydroformylation reactor may comprise an propylene to r-propylene weight ratio of at least 0.1:1, 0.5:1, 1:1, 2:1, 3:1, or 4:1. Additionally or alternatively, in certain embodiments, the feed going into the hydroformylation reactor may comprise an propylene to r-propylene weight ratio of not more than 100:1, 50:1, 25:1, 10:1, 5:1, 4:1, 3:1, 2:1, 1:1, 0.5:1, or 0.1:1.

The propylene (including r-propylene) may be reacted with syngas in the presence of a catalyst in a hydroformylation reactor within the hydroformylation zone. In an embodiment or in combination with any of the embodiments mentioned herein, the syngas stream introduced into the hydroformylation reactor can comprise at least 5, 10, 15, 20, 25, 30, 35, 40, 45, 50, 55, 60, 65, or 70 and/or not more than 90, 85, 80, 75, 70, 65, 60, 55, 50, or 45 weight percent of hydrogen and/or carbon monoxide. The molar ratio of carbon monoxide to hydrogen can be at least 0.5:1, 0.75:1, 1:1, 1.25:1 or 1.5:1 and/or not more than 5:1, 3.5:1, 2.5:1, 2:1, 1.75:1, 1.5:1 or 1:1. The syngas stream may include at least 1, 2, 5, 10, or 15 and/or not more than 45, 40, 35, 30, 25, 20, 15, or 10 weight percent of one or more other components, such as, for example, carbon dioxide, based on the total weight of the stream.

Although it is not essential, an inert solvent can be employed as a hydroformylation reaction medium diluent. A variety of solvents can be used, including ketones such as acetone, methyl ethyl ketone, methyl isobutyl ketone, acetophenone, and cyclohexanone; aromatics such as benzene, toluene and xylenes; halogenated aromatics including orthodichlorobenzene; ethers such as tetrahydrofuran, dimethoxyethane and dioxane; halogenated paraffins including methylene chloride; paraffinic hydrocarbons such as heptane; or combinations thereof.

As shown in FIG. 26, the hydroformylation reaction also takes place in the presence of a catalyst. The catalyst used in the hydroformylation reaction can be a transition metal catalyst such as, for example, a complexed rhodium or cobalt catalyst. The specific catalyst depends, in part, on the specific type of hydroformylation being conducted. Ligands used to complex the metal may include, for example, phosphorous-based ligands such as phosphine or phosphane ligands. Specific examples include, but are not limited to, triphenylphosphines, triphenylphosphanes, and combinations thereof. Other examples of suitable ligands can include, for example, carbonyl-based ligands, which are predominantly used with cobalt. The catalyst may be homogeneous and, optionally, water soluble. Most hydroformylation units/facilities include one or more catalyst separation units for recovery and recycle of at least a portion of the catalyst to the hydroformylation reactor.

In certain embodiments, the hydroformylation process may occur at a temperature in the range of 40 to 200° C., 50 to 150° C., or 60 to 120° C., or even 80 to 105° C.

In certain embodiments, the hydroformylation process may occur at a pressure in the range of 0.01 to 35 MPa, 0.1 to 12 MPa, or 1 to 7 MPa.

Additionally, the hydroformylation unit/facility may further include one or more separators (not shown) for purifying the effluent stream withdrawn from the hydroformylation reactor. The separators may be configured to separate catalyst from the reactor effluent or to separate the aldehydes to form streams of purified aldehydes. For example, in certain embodiments, the effluent stream from the hydroformylation reactor may comprise at least 20, 25, 30, 35, 40, 45, 50, 55, 60, 65, 70, 75, 80, 85, 90, or 95 and/or not more than 99, 95, 90, 85, 80, 75, 70, 65, or 60 weight percent of C4 aldehydes such as, for example, normal and isobutyl aldehydes.

In some cases, the amount of isobutyl aldehyde (i-butyraldehyde) can be at least 20, 25, 30, 35, 40, 45, 50, 55, 60, 65, 70, 75, or 80 percent and/or not more than 99, 95, 90, 85, 80, 75, 70, 65, or 60 percent of the total amount of C4 aldehydes present in the reactor effluent stream with the balance being, for example, normal butyraldehyde. The separators, when present in the hydroformylation facility, may be used to separate the C4 aldehyde isomers from one another so that, for example, the product stream withdrawn from the hydroformylation unit/facility can be at least 50, 55, 60, 65, 70, 75, 80, 85, 90, 95, 97, or 99 weight percent of isobutyraldehyde, based on the total weight of the C4 aldehydes in the stream. Of that, at least a portion, or all, can comprise recycle content isobutyraldehyde (r-isobutyraldehyde). Similar separations may be performed to provide similar streams of normal butyraldehyde, including r-normal butyraldehyde.

Various hydroformylation processes and systems are described in U.S. Pat. Nos. 2,464,916; 4,148,830; 5,264,600; 4,593,127; 7,935,850; 7,420,092; 6,492,564; 4,625,068; 4,169,861; 3,448,157; European Patent No. 0804398; and U.S. Pat. No. 7,049,473, the entire disclosures are incorporated herein by reference to the extent not inconsistent with the present disclosure.

The resulting r-aldehyde may comprise at least one pyoil-derived impurity derived from the r-propylene or other recycle content intermediates used to form the r-plasticizer. In certain embodiments, the r-aldehyde may comprise at least 1, 2, 3, 4, 5, 6, 7, 8, 9, or 10 ppm and/or not more than 1,000, 900, 800, 700, 600, 500, 400, 300, 200, or 100 ppm of at least one pyoil-derived impurity derived from the r-propylene.

As shown in FIG. 26, the effluent from the hydroformylation unit, which can include, in certain embodiments, at least about 50, 55, 60, 65, 70, 75, 80, 85, 90, or 95 weight percent of isobutyraldehyde, based on the total amount of aldehyde in the stream, can be passed into a condensation facility/unit. In an embodiment or in combination with any of the embodiments mentioned herein, at least 50, 55, 60, 65, 70, 75, 80, 85, 90, or 95 percent of the total weight of the feed to the condensation unit/facility can include an aldehyde, including r-aldehyde such as r-butyraldehyde or, in particular, r-isobutyraldehyde. In some cases, the r-butyraldehyde can comprise, consist essentially of, or consist of r-isobutyraldehyde, or the total amount of r-butyraldehyde (or r-isobutyraldehyde) may include at least about 20, 25, 30, 35, 40, 45, 50, 55, 60, 65, 70, 75, 80, 85, 90, or 95 weight percent of r-butyraldehyde (or r-isobutyraldehyde), based on the total weight or r-aldehyde in the feed stream to the aldol condensation unit/facility. The total amount of r-aldehyde (or r-butyraldehyde or r-isobutyraldehyde) in the feed stream to the aldol condensation unit can be at least 20, 25, 30, 35, 40, 45, 50, 55, 60, 65, 70, 75, 80, 85, 90, or 95 weight percent, based on the total weight of the aldol condensation feed stream. Additionally or alternatively, in certain embodiments, the feed stream going into the aldol condensation reactor may comprise not more than 99, 95, 90, 85, 80, 75, 70, 65, 60, 55, 50, 45, 40, 35, 30, 25, 20, 15, 10, 5, or 1 weight percent of r-aldehyde, r-butyraldehyde, or r-isobutyraldehyde.

In certain embodiments, at least 5, 10, 15, 20, 25, 30, 35, 40, 45, 50, 55, 60, 65, 70, 75, 80, 85, 90, 95, or 99 percent of the total amount of aldehyde (or butyraldehyde) fed into the condensation zone comprises r-butyraldehyde (or r-isobutyraldehyde), with the balance (if any) being non-recycle content butyraldehyde (or isobutyraldehyde). In certain embodiments, the feed stream going into the aldol condensation reactor may comprise a butyraldehyde to r-butyraldehyde (or isobutyraldehyde to r-isobutyraldehyde) weight ratio of at least 0.1:1, 0.5:1, 1:1, 2:1, 3:1, or 4:1. Additionally or alternatively, in certain embodiments, the feed going into the aldol condensation reactor may comprise an a butyraldehyde to r-butyraldehyde (or isobutyraldehyde to r-isobutyraldehyde) weight ratio of not more than 100:1, 50:1, 25:1, 10:1, 5:1, 4:1, 3:1, 2:1, 1:1, 0.5:1, or 0.1:1.

In an embodiment or in combination with any of the embodiments mentioned herein, the effluent from the hydroformylation reaction may include a mixture of n-butyraldehyde and i-butyraldehyde, which it may be desirable to separate. For example, the effluent stream may include at least 5, 10, 15, 20, 25, 30, 35, 40, 45, 50, or 55 weight percent and/or not more than 90, 85, 80, 75, 70, 65, 60, 55, 50, or 45 weight percent of n-butyraldehyde or of i-butyraldehyde. Thus, the effluent from the hydroformylation reactor may be passed through one or more separation columns (such as, for example, multi-stage distillation columns) to separate the i-butyraldehyde from the n-butyraldehyde. In some cases, the purified streams of n-butyraldehyde and i-butyraldehyde can include at least 50, 55, 60, 65, 70, 75, 80, 85, 90, 95, 97, or 99 percent by weight of i-butyraldehyde or n-butyraldehyde, respectively.

In the condensation reactor or unit/facility, the isobutyraldehyde can react in the presence of a catalyst to form an isobutyrate ester of 2,2,4-trimethyl-1,3-pentanediol. More particularly, the isobutyraldehyde may self-polymerize, initially forming a C8 aldol condensation product, which can react with monomeric isobutyraldehyde to form 2,2,4-trimethyl-1,3-pentanediol monoisobutyrate (texanol). Coproducts formed during the reaction include 2,2,4-trimethyl-1,3-pentanediol and 2,2,4-trimethyl-1,3-pentadiol diisobutyrate (TXIB). The specific product mixture depends on the reaction conditions, types and amount of starting materials present, and catalyst, but in certain cases, each of the above may be present in an amount of at least 1, 2, 5, 10, 15, 20, 25, 30, 35, 40, 45, 50, 55, 60, 65, 70, 75, 80, 85, 90, or 95 and/or not more than 100, 99, 95, 90, 85, 80, 75, 70, 65, 60, 55, 50, 45, 40, 35, 30, 25, 20, 15, 10, 1, 3, 2, or 1 weight percent, based on the total weight of the reaction mixture.

The aldehyde fed into the aldol condensation reactor may be condensed in the presence of a catalyst. The catalyst may be any type of catalyst suitable for such reactions and can comprise, for example, a basic catalyst. Suitable catalysts can include, but are not limited to, alkali metal oxides or hydroxides, alkaline earth metal hydroxides and combinations thereof. Examples of specific catalyst types can include sodium hydroxide, calcium hydroxide, sodium methoxide, sodium ethoxide, and combinations and solutions thereof. The catalyst may be homogenous or heterogeneous and can be present in the reaction medium in an amount of at least 0.1, 0.5, 0.75, 1, 1.5, 2, 2.5, 3, 3.5, 4, 4.5, 5, or 6 weight percent and/or not more than 15, 12, 10, 8, 6, 5, 4, 3.5, 3, 2.5, 2, 1.5, 1, or 0.5 weight percent, based on the total weight of the reaction mixture.

The condensation reaction may be carried out at a temperature of at least 35, 40, 45, 50, 55, or 60° C. and/or not more than 125, 120, 115, 110, 105, 100, 95, 90, 85, 80, 75, 70 or 65° C., for a period of at least 15, 30 minutes, 1 hour, or 1.5 hours and/or not more than 5, 4, 3, or 2.5 hours. Alternatively, the reaction time can be at least 1, 2, 3, 4, 5, 6, or 7 minutes and/or not more than 20, 18, 16, 12, 10, 8, 6, or 5 minutes. The pressure of the reaction may be near, slightly above or slightly below atmospheric.

Various condensation processes and systems used to form isobutyrates are described in U.S. Pat. No. 4,225,726; PCT Application Publication No. WO9741088; Chinese Patent Application No. 101948386; U.S. Pat. Nos. 3,091,632; 3,291,821; 3,718,689; and 5,180,847, the entire disclosures of which are incorporated herein by reference to the extent not inconsistent with the present disclosure.

In certain embodiments, the resulting effluent stream withdrawn from the condensation unit/facility may comprise predominantly 2,2,4-trimethyl-1,3-pentandiol monoisobutyrate. This product stream may, for example, comprise at least 50, 55, 60, 65, 70, 75, 80, 85, 90, 95, or 99 percent and/or not more than 100, 99, 95, 90, 85, 80, 75, or 70 weight percent of 2,2,4-trimethyl-1,3-pentanediol monoisobutyrate (texanol), based on the total weight of the stream. Of the monoisobutyrate, at least 50, 55, 60, 65, 70, 75, 80, 85, 90, 95, or 99, or all, or not more than 100, 99, 95, 90, 85, 80, 75, 70, 65, 60, or 55 weight percent can be recycle content 2,2,4-trimethyl-1,3-pentanediol monoisobutyrate (r-2,2,4-trimethyl-1,3-pentanediol monoisobutyrate), based on the total amount of monoisobutyrate.

Alternatively, or in addition, the stream may comprise at least 5, 10, 15, 20, 25, 30, 35, 40, or 45 and/or not more than 50, 45, 40, 35, 30, 25, 20, 15, or 10 weight percent of other components, including, for example, 2,2,4-trimethyl-1,3-pentanediol diisobutyrate (TXIB), 2,2,4-trimethyl-1,3-pentanediol, and combinations thereof.

In certain embodiments, the resulting effluent stream withdrawn from the condensation unit/facility may comprise predominantly 2,2,4-trimethyl-1,3-pentandiol diisobutyrate. This product stream may, for example, comprise at least 50, 55, 60, 65, 70, 75, 80, 85, 90, 95, or 99 percent and/or not more than 100, 99, 95, 90, 85, 80, 75, or 70 weight percent of 2,2,4-trimethyl-1,3-pentanediol diisobutyrate (TXIB), based on the total weight of the stream. Of the monoisobutyrate, at least 50, 55, 60, 65, 70, 75, 80, 85, 90, 95, or 99, or all, or not more than 100, 99, 95, 90, 85, 80, 75, 70, 65, 60, or 55 weight percent can be recycle content 2,2,4-trimethyl-1,3-pentanediol diisobutyrate (r-2,2,4-trimethyl-1,3-pentanediol diisobutyrate), based on the total amount of diisobutyrate.

Alternatively, or in addition, the stream may comprise at least 5, 10, 15, 20, 25, 30, 35, 40, or 45 and/or not more than 50, 45, 40, 35, 30, 25, 20, 15, or 10 weight percent of other components, including, for example, 2,2,4-trimethyl-1,3-pentanediol monoisobutyrate (texanol), 2,2,4-trimethyl-1,3-pentanediol, and combinations thereof.

In certain embodiments, the resulting effluent stream withdrawn from the condensation unit/facility may comprise predominantly 2,2,4-trimethyl-1,3-pentandiol. This product stream may, for example, comprise at least 50, 55, 60, 65, 70, 75, 80, 85, 90, 95, or 99 percent and/or not more than 100, 99, 95, 90, 85, 80, 75, or 70 weight percent of 2,2,4-trimethyl-1,3-pentanediol, based on the total weight of the stream. Of the monoisobutyrate, at least 50, 55, 60, 65, 70, 75, 80, 85, 90, 95, or 99, or all, or not more than 100, 99, 95, 90, 85, 80, 75, 70, 65, 60, or 55 weight percent can be recycle content 2,2,4-trimethyl-1,3-pentanediol (r-2,2,4-trimethyl-1,3-pentanediol), based on the total amount of 2,2,4-trimethyl-1,3-pentanediol.

Alternatively, or in addition, the stream may comprise at least 5, 10, 15, 20, 25, 30, 35, 40, or 45 and/or not more than 50, 45, 40, 35, 30, 25, 20, 15, or 10 weight percent of other components, including, for example, 2,2,4-trimethyl-1,3-pentanediol monoisobutyrate (texanol), 2,2,4-trimethyl-1,3-pentanediol diisobutyrate (TXIB), and combinations thereof.

The resulting product or effluent stream comprising r-2,2,4-trimethyl-1,3-pentanediol, its recycle content monoisobutyrate, its recycle content diisobutyrate, or combinations thereof may comprise at least one pyoil-derived impurity derived from the r-propylene or other recycle content intermediates used to form the final diol or isobutyrate. In certain embodiments, the r-2,2,4-trimethyl-1,3-pentanediol, the r-2,2,4-trimethyl-1,3-pentanediol monoisobutyrate, the r-2,2,4-trimethyl-1,3-pentanediol diisobutyrate may comprise at least 1, 2, 3, 4, 5, 6, 7, 8, 9, or 10 ppm and/or not more than 1,000, 900, 800, 700, 600, 500, 400, 300, 200, or 100 ppm of at least one pyoil-derived impurity derived from the r-propylene.

EXAMPLES r-Pyoil Examples 1-4

Table 1 shows the composition of r-pyoil samples by gas chromatography. The r-pyoil samples produced the material from waste high- and low-density polyethylene, polypropylene, and polystyrene. Sample 4 was a lab-distilled sample in which hydrocarbons greater than C21 were removed. The boiling point curves of these materials are shown in FIGS. 13-16.

TABLE 1

Gas Chromatography Analysis of r-Pyoil Examples

| Components | r-Pyoil Feed Examples 1 | 2 | 3 | 4 |
|---|---|---|---|---|
| Propene | 0.00 | 0.00 | 0.00 | 0.00 |
| Propane | 0.00 | 0.19 | 0.20 | 0.00 |
| 1,3-Butadiene | 0.00 | 0.93 | 0.99 | 0.31 |
| Pentene | 0.16 | 0.37 | 0.39 | 0.32 |
| Pentane | 1.81 | 3.21 | 3.34 | 3.05 |
| 1,3-cyclopentadiene | 0.00 | 0.00 | 0.00 | 0.00 |
| 2-methyl-Pentene | 1.53 | 2.11 | 2.16 | 2.25 |
| 2-methyl-Pentane | 2.04 | 2.44 | 2.48 | 3.03 |
| Hexane | 1.37 | 1.80 | 1.83 | 2.10 |
| 2-methyl-1,3-cyclopentadiene | 0.00 | 0.00 | 0.00 | 0.00 |
| l-methyl-1,3-cyclopentadiene | 0.00 | 0.00 | 0.00 | 0.00 |
| 2,4 dimethylpentene | 0.32 | 0.18 | 0.18 | 0.14 |
| Benzene | 0.00 | 0.16 | 0.16 | 0.00 |
| 5-methyl-1,3-cyclopentadiene | 0.00 | 0.17 | 0.17 | 0.20 |
| Heptene | 1.08 | 1.15 | 1.15 | 1.55 |
| Heptane | 2.51 | 0.17 | 2.89 | 3.61 |
| Toluene | 0.58 | 1.05 | 1.09 | 0.84 |
| 4-methylheptane | 1.50 | 1.67 | 1.68 | 1.99 |
| Octene | 1.37 | 1.35 | 1.37 | 1.88 |
| Octane | 2.56 | 2.72 | 2.78 | 3.40 |
| 2,4-dimethylheptene | 1.25 | 1.54 | 1.55 | 1.60 |
| 2,4-dimethylheptane | 5.08 | 4.01 | 4.05 | 6.40 |
| Ethylbenzene | 1.85 | 3.10 | 3.12 | 2.52 |
| m,p-xylene | 0.73 | 0.69 | 0.24 | 0.90 |
| Styrene | 0.40 | 0.13 | 1.13 | 0.53 |
| o-xylene | 0.12 | 0.36 | 0.00 | 0.00 |
| Nonane | 2.66 | 2.81 | 2.84 | 3.47 |
| Nonene | 1.12 | 0.00 | 0.00 | 1.65 |
| MW140 | 2.00 | 1.76 | 1.75 | 2.50 |
| Cumene | 0.56 | 0.96 | 0.97 | 0.73 |
| Decene/methylstyrene | 1.29 | 1.17 | 1.18 | 1.60 |
| Decane | 3.14 | 3.23 | 3.25 | 3.90 |
| Unknown 1 | 0.68 | 0.71 | 0.72 | 0.80 |
| Indene | 0.18 | 0.20 | 0.21 | 0.22 |
| Indane | 0.23 | 0.34 | 0.26 | 0.26 |
| C11 Alkene | 1.50 | 1.32 | 1.33 | 1.77 |
| C11 Alkane | 3.30 | 3.30 | 3.33 | 3.88 |
| C12 Alkene | 1.49 | 1.30 | 0.00 | 0.09 |
| Naphthalene | 0.10 | 0.12 | 3.24 | 3.73 |
| C12 Alkane | 3.34 | 3.21 | 1.31 | 1.66 |
| C13 Alkane | 3.20 | 2.90 | 2.97 | 3.40 |
| C13 Alkene | 1.46 | 1.20 | 1.17 | 1.53 |
| 2-methylnaphthalene | 0.86 | 0.63 | 0.64 | 0.85 |
| C14 Alkene | 1.07 | 0.84 | 0.84 | 1.04 |
| C14 Alkane | 3.34 | 3.04 | 3.05 | 3.24 |

TABLE 1-continued

Gas Chromatography Analysis of r-Pyoil Examples

| Components | r-Pyoil Feed Examples 1 | 2 | 3 | 4 |
|---|---|---|---|---|
| Acenaphthene | 0.31 | 0.28 | 0.28 | 0.28 |
| C15 Alkene | 1.16 | 0.87 | 0.87 | 0.96 |
| C15 Alkane | 3.41 | 3.00 | 3.02 | 2.84 |
| C16 Alkene | 0.85 | 0.58 | 0.58 | 0.56 |
| C16 Alkane | 3.25 | 2.67 | 2.68 | 2.12 |
| C17 Alkene | 0.70 | 0.46 | 0.46 | 0.35 |
| C17 Alkane | 3.04 | 2.43 | 2.44 | 1.50 |
| C18 Alkene | 0.51 | 0.33 | 0.33 | 0.19 |
| C18 Alkane | 2.71 | 2.11 | 2.13 | 0.99 |
| C19 Alkane | 2.39 | 1.82 | 0.38 | 0.15 |
| C19 Alkene | 0.60 | 0.38 | 1.83 | 0.61 |
| C20 Alkene | 0.42 | 0.18 | 0.26 | 0.00 |
| C20 Alkane | 2.05 | 1.55 | 1.55 | 0.37 |
| C21 Alkene | 0.31 | 0.00 | 0.00 | 0.00 |
| C21 Alkane | 1.72 | 1.45 | 1.30 | 0.23 |
| C22 Alkene | 0.00 | 0.00 | 0.00 | 0.00 |
| C22 Alkane | 1.43 | 1.11 | 1.12 | 0.00 |
| C23 Alkene | 0.00 | 0.00 | 0.00 | 0.00 |
| C23 Alkane | 1.09 | 0.87 | 0.88 | 0.00 |
| C24 Alkene | 0.00 | 0.00 | 0.00 | 0.00 |
| C24 Alkane | 0.82 | 0.72 | 0.72 | 0.00 |
| C25 Alkene | 0.00 | 0.00 | 0.00 | 0.00 |
| C25 Alkane | 0.61 | 0.58 | 0.56 | 0.00 |
| C26 Alkene | 0.00 | 0.00 | 0.00 | 0.00 |
| C26 Alkane | 0.44 | 0.47 | 0.44 | 0.00 |
| C27 Alkane | 0.31 | 0.37 | 0.32 | 0.00 |
| C28 Alkane | 0.22 | 0.29 | 0.23 | 0.00 |
| C29 Alkane | 0.16 | 0.22 | 0.15 | 0.00 |
| C30 Alkane | 0.00 | 0.16 | 0.00 | 0.00 |
| C31 Alkane | 0.00 | 0.00 | 0.00 | 0.00 |
| C32 Alkane | 0.00 | 0.00 | 0.00 | 0.00 |
| Unidentified | 13.73 | 18.59 | 15.44 | 15.91 |
| Percent C8+ | 74.86 | 67.50 | 67.50 | 66.69 |
| Percent Cl5+ | 28.17 | 22.63 | 22.25 | 10.87 |
| Percent Aromatics | 5.91 | 8.02 | 11.35 | 10.86 |
| Percent Paraffins | 59.72 | 54.85 | 54.19 | 51.59 |
| Percent C4 to C7 | 11.41 | 13.72 | 16.86 | 17.40 |

r-Pyoil Examples 5-10

Six r-pyoil compositions were prepared by distillation of r-pyoil samples. They were prepared by processing the material according the procedures described below.

Example 5. r-Pyoil with at Least 90% Boiling by 350° C., 50% Boiling Between 95° C. and 200° C., and at Least 10% Boiling by 60° C.

Figure 17:
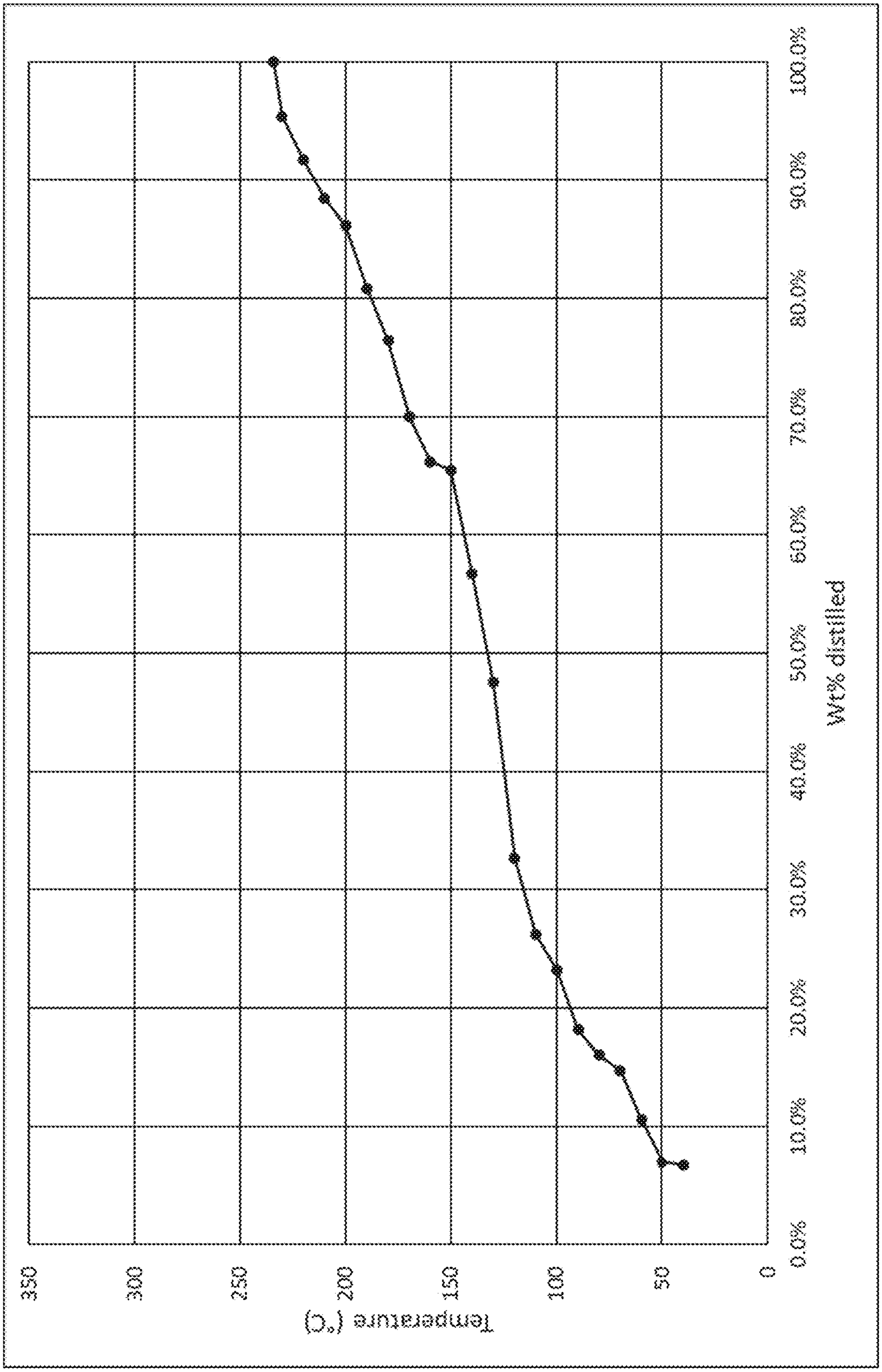
FIG. 17 is a graph of the boiling point curve of r-pyoil distilled in lab with at least 90% boiling by 350° C., 50% boiling between 95° C. and 200° C., and at least 10% boiling by 60° C.

A 250 g sample of r-pyoil from Example 3 was distilled through a 30-tray glass Oldershaw column fitted with glycol chilled condensers, thermowells containing thermometers, and a magnet operated reflux controller regulated by electronic timer. Batch distillation was conducted at atmospheric pressure with a reflux rate of 1:1. Liquid fractions were collected every 20 mL, and the overhead temperature and mass recorded to construct the boiling curve presented in FIG. 17. The distillation was repeated until approximately 635 g of material was collected.

Example 6. r-Pyoil with at Least 90% Boiling by 150° C., 50% Boiling Between 80° C. and 145° C., and at Least 10% Boiling by 60° C.

Figure 18:
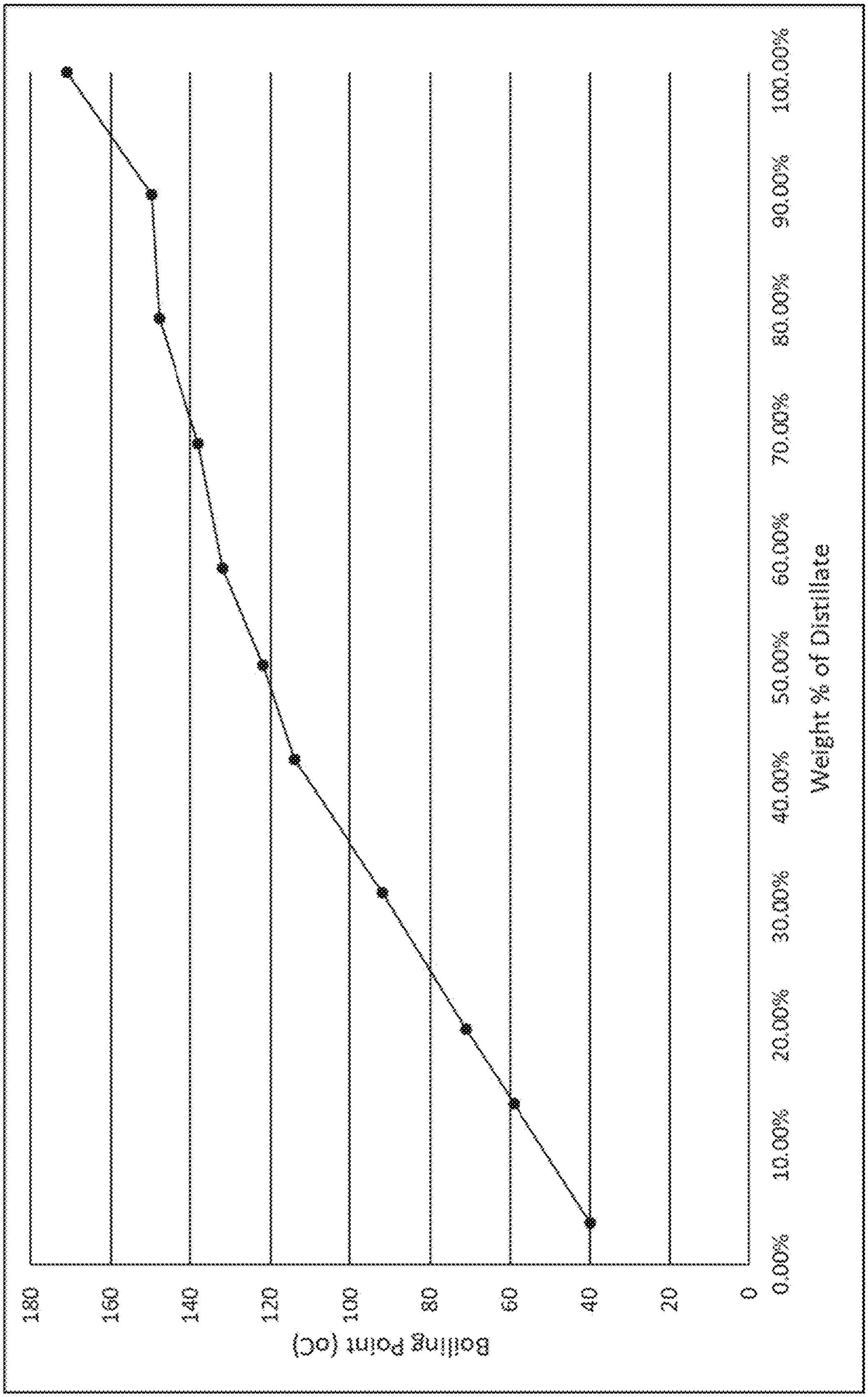
FIG. 18 is a graph of the boiling point curve of r-pyoil distilled in lab with at least 90% boiling by 150° C., 50% boiling between 80° C. and 145° C., and at least 10% boiling by 60° C.

A 150 g sample of r-pyoil from Example 3 was distilled through a 30-tray glass Oldershaw column fitted with glycol chilled condensers, thermowells containing thermometers, and a magnet operated reflux controller regulated by electronic timer. Batch distillation was conducted at atmospheric pressure with a reflux rate of 1:1. Liquid fractions were collected every 20 mL, and the overhead temperature and mass recorded to construct the boiling curve presented in FIG. 18. The distillation was repeated until approximately 200 g of material was collected.

Example 7. r-Pyoil with at Least 90% Boiling by 350° C., at Least 10% by 150° C., and 50% Boiling Between 220° C. and 280° C.

Figure 19:
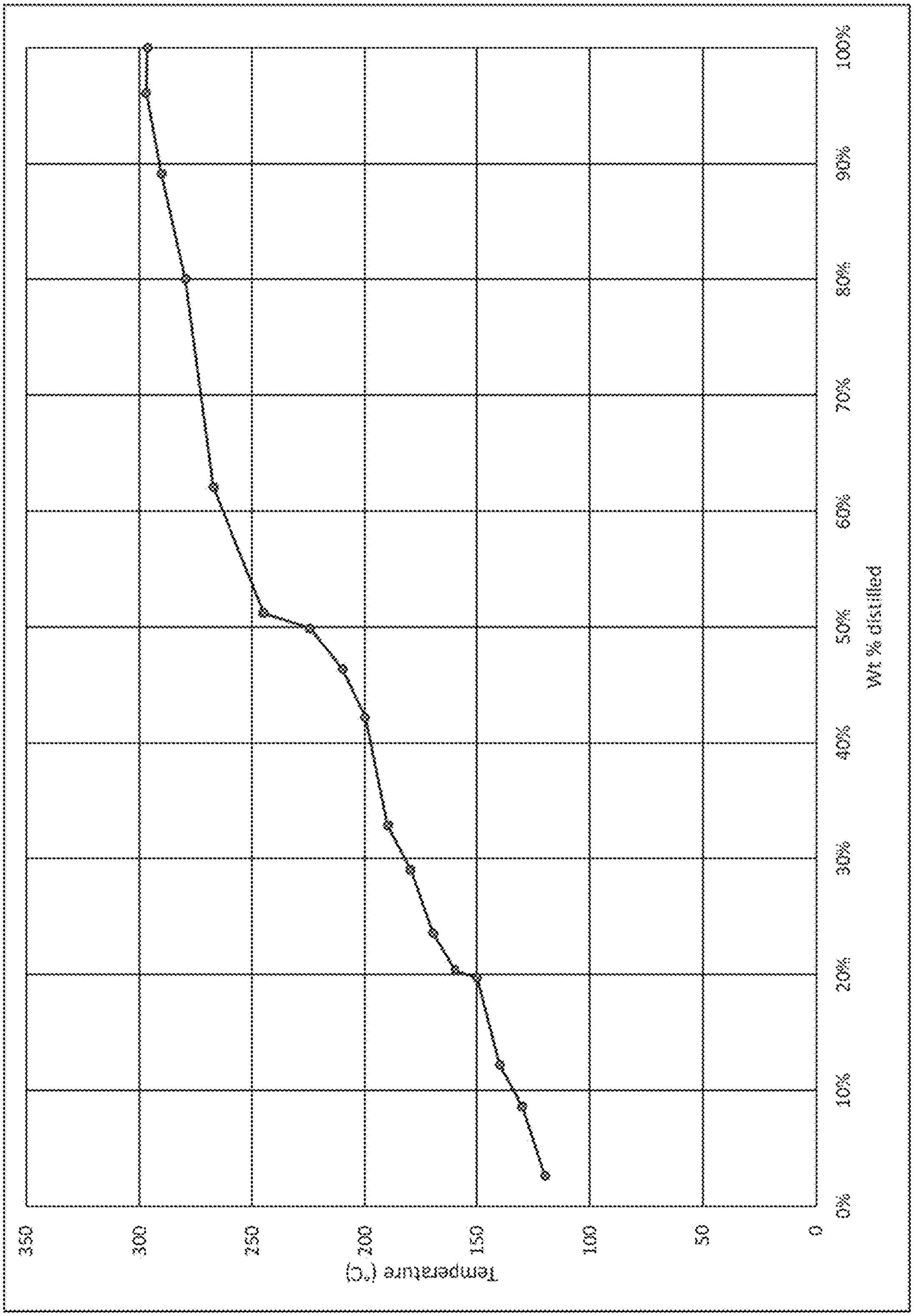
FIG. 19 is a graph of the boiling point curve of r-pyoil distilled in lab with at least 90% boiling by 350° C., at least 10% by 150° C., and 50% boiling between 220° C. and 280° C.

A procedure similar to Example 8 was followed with fractions collected from 120° C. to 210° C. at atmospheric pressure and the remaining fractions (up to 300° C., corrected to atmospheric pressure) under 75 torr vacuum to give a composition of 200 g with a boiling point curve described by FIG. 19.

Example 8. r-Pyoil with 90% Boiling Between 250-300° C.

Figure 20:
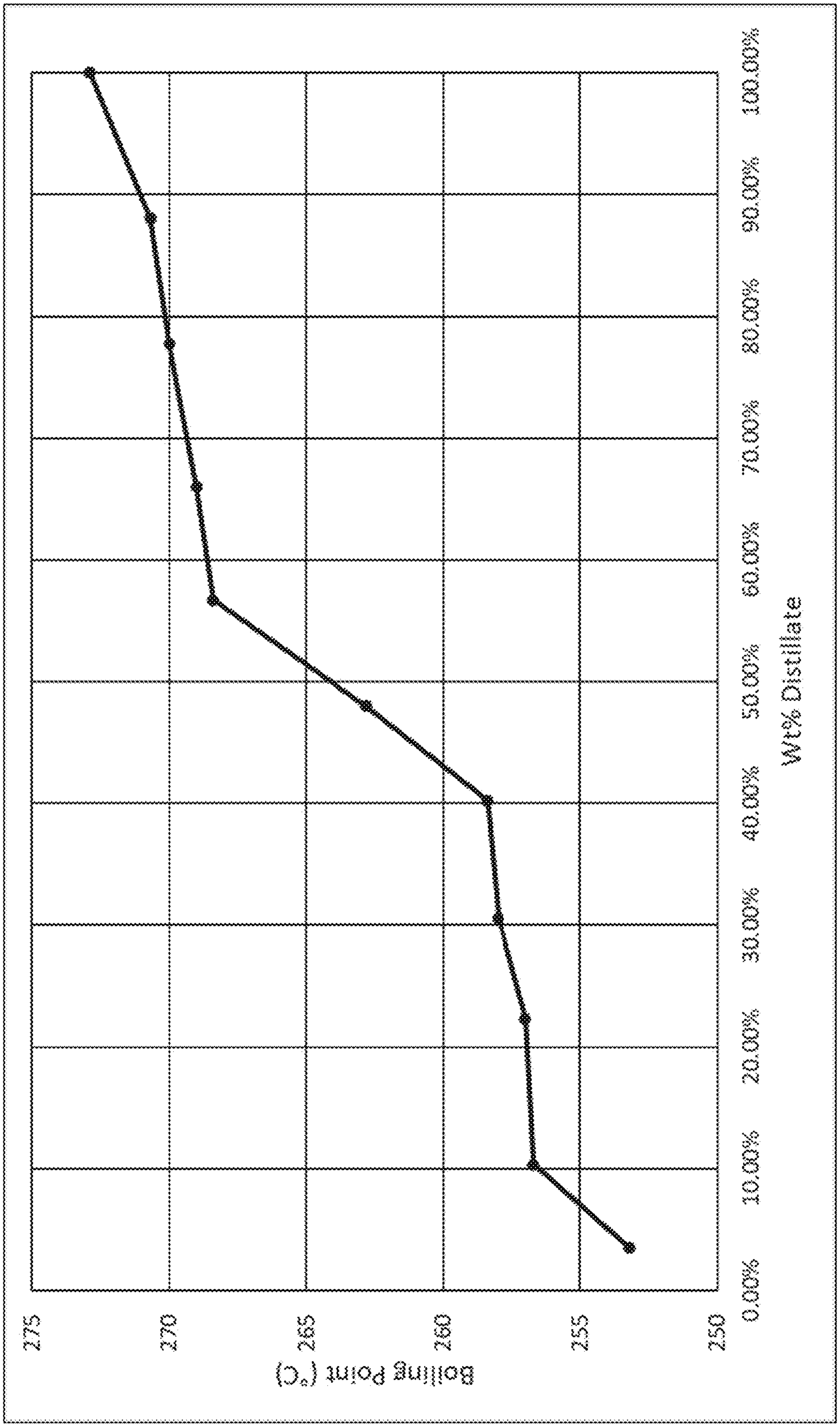
FIG. 20 is a graph of the boiling point curve of r-pyoil distilled in lab with 90% boiling between 250-300° C.

Approximately 200 g of residuals from Example 6 were distilled through a 20-tray glass Oldershaw column fitted with glycol chilled condensers, thermowells containing thermometers, and a magnet operated reflux controller regulated by electronic timer. One neck of the base pot was fitted with a rubber septum, and a low flow $N_2$ purge was bubbled into the base mixture by means of an 18" long, 20-gauge steel thermometer. Batch distillation was conducted at 70 torr vacuum with a reflux rate of 1:2. Temperature measurement, pressure measurement, and timer control were provided by a Camille Laboratory Data Collection System. Liquid fractions were collected every 20 mL, and the overhead temperature and mass recorded. Overhead temperatures were corrected to atmospheric boiling point by means of the Clausius-Clapeyron Equation to construct the boiling curve presented in FIG. 20 below. Approximately 150 g of overhead material was collected.

Example 9. r-Pyoil with 50% Boiling Between 60-80° C.

Figure 21:
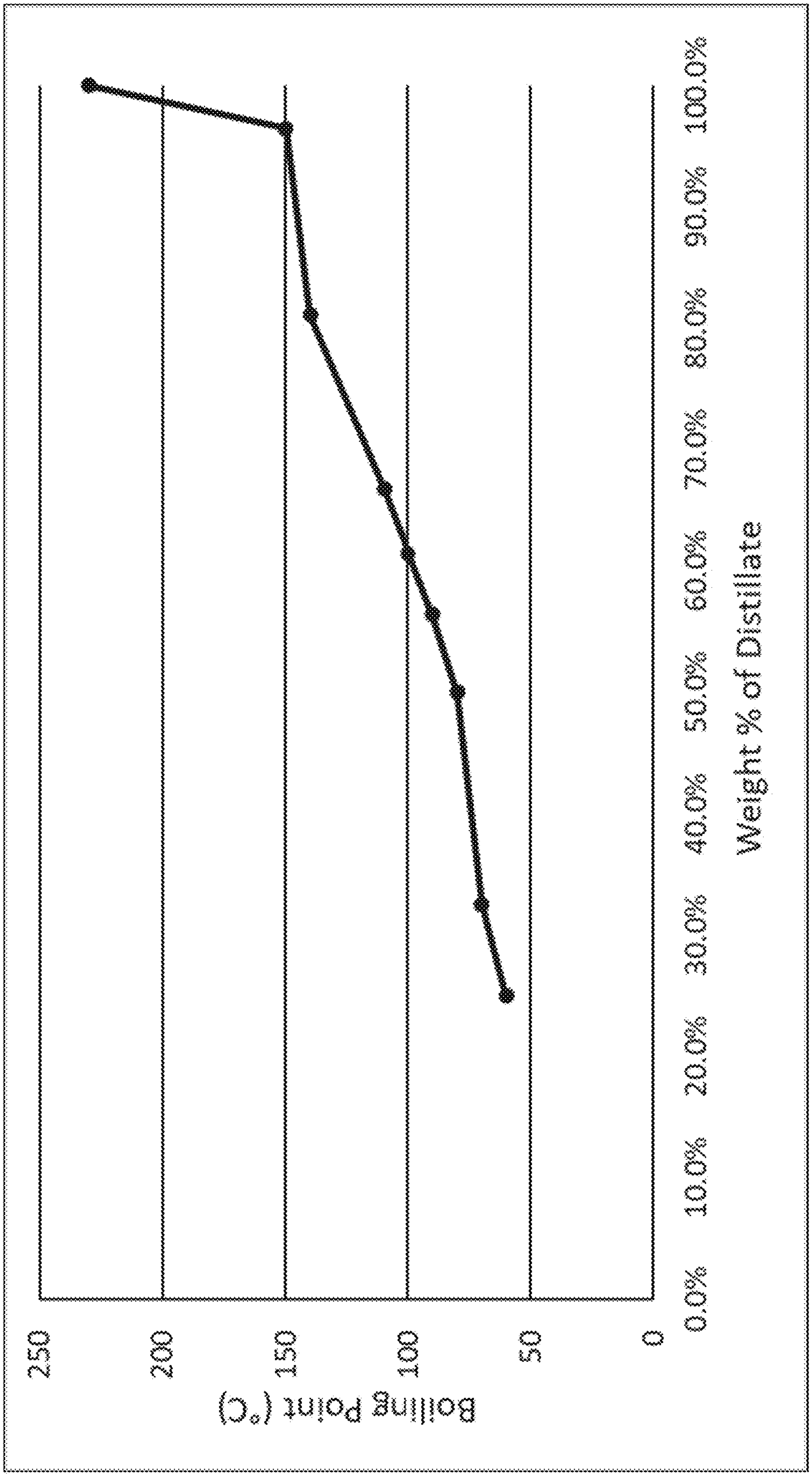
FIG. 21 is a graph of the boiling point curve of r-pyoil distilled in lab with 50% boiling between 60-80° C.

A procedure similar to Example 5 was followed with fractions collected boiling between 60° C. and 230° C. to give a composition of 200 g with a boiling point curve described by FIG. 21.

Example 10. r-Pyoil with High Aromatic Content

Figure 22:
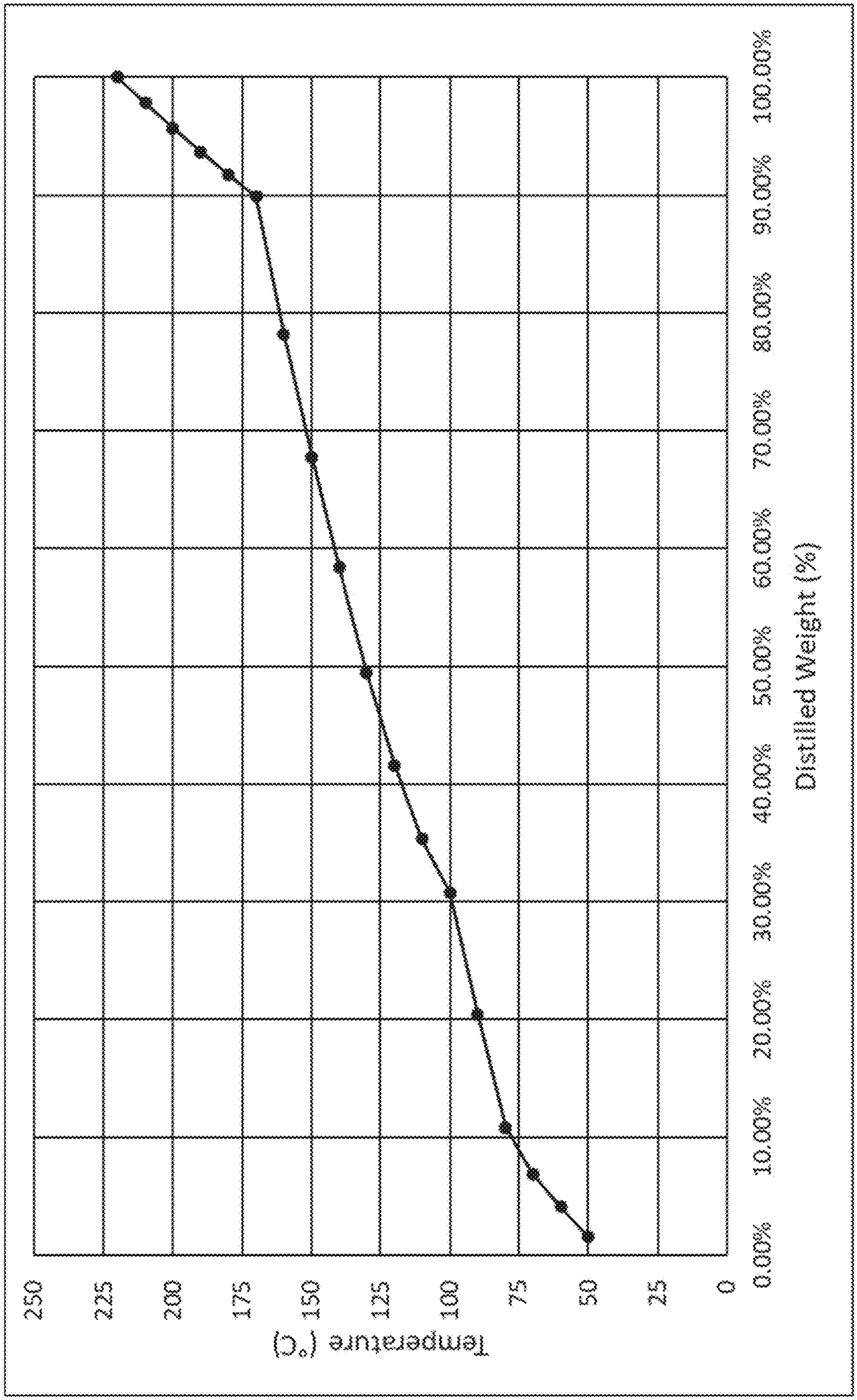
FIG. 22 is a graph of the boiling point curve of r-pyoil distilled in lab with 34.7% aromatic content.

A 250 g sample of r-pyoil with high aromatic content was distilled through a 30-tray glass Oldershaw column fitted with glycol chilled condensers, thermowells containing thermometers, and a magnet operated reflux controller regulated by electronic timer. Batch distillation was conducted at atmospheric pressure with a reflux rate of 1:1. Liquid fractions were collected every 10-20 mL, and the overhead temperature and mass recorded to construct the boiling curve presented in FIG. 22. The distillation ceased after approximately 200 g of material were collected. The material contains 34 weight percent aromatic content by gas chromatography analysis.

Table 2 shows the composition of Examples 5-10 by gas chromatography analysis.

TABLE 2

Gas Chromatography Analysis of r-Pyoil Examples 5-10.

| | r-Pyoil Examples | | | | | |
|---|---|---|---|---|---|---|
| Components | 5 | 6 | 7 | 8 | 9 | 10 |
| Propene | 0.00 | 0.00 | 0.00 | 0.00 | 0.00 | 0.00 |
| Propane | 0.00 | 0.10 | 0.00 | 0.00 | 0.00 | 0.00 |
| 1,3-r-Butadiene | 0.27 | 1.69 | 0.00 | 0.00 | 0.00 | 0.18 |
| Pentene | 0.44 | 1.43 | 0.00 | 0.00 | 0.00 | 0.48 |
| Pentane | 3.95 | 4.00 | 0.00 | 0.00 | 0.37 | 4.59 |
| Unknown 1 | 0.09 | 0.28 | 0.00 | 0.00 | 0.00 | 0.07 |
| 1,3-cyclopentadiene | 0.00 | 0.13 | 0.00 | 0.00 | 0.00 | 0.00 |
| 2-methyl-Pentene | 2.75 | 3.00 | 0.00 | 0.00 | 5.79 | 4.98 |
| 2-methyl-Pentane | 2.63 | 6.71 | 0.00 | 0.00 | 9.92 | 5.56 |
| Hexane | 0.75 | 4.77 | 0.00 | 0.00 | 11.13 | 3.71 |
| 2-methyl-1,3-cyclopentadiene | 0.00 | 0.20 | 0.00 | 0.00 | 0.96 | 0.30 |
| 1-methyl-1,3-cyclopentadiene | 0.00 | 0.00 | 0.00 | 0.00 | 0.00 | 0.00 |
| 2,4 dimethylpentene | 0.00 | 0.35 | 0.00 | 0.00 | 2.06 | 0.26 |
| Benzene | 0.00 | 0.24 | 0.00 | 0.00 | 1.11 | 0.26 |
| 5-methyl-1,3-cyclopentadiene | 0.00 | 0.09 | 0.00 | 0.00 | 0.15 | 0.15 |
| Heptene | 0.52 | 5.50 | 0.00 | 0.00 | 6.22 | 2.97 |
| Heptane | 0.13 | 7.35 | 0.17 | 0.00 | 10.16 | 6.85 |
| Toluene | 1.18 | 2.79 | 0.69 | 0.00 | 2.39 | 6.98 |
| 4-methylheptane | 2.54 | 2.46 | 3.29 | 0.00 | 1.16 | 3.92 |
| Octene | 3.09 | 4.72 | 2.50 | 0.00 | 0.48 | 2.62 |
| Octane | 5.77 | 6.27 | 3.49 | 0.00 | 0.65 | 4.50 |
| 2,4-dimethylheptene | 3.92 | 2.30 | 0.61 | 0.00 | 0.96 | 2.58 |
| 2,4-dimethylheptane | 9.47 | 5.80 | 1.30 | 0.00 | 3.74 | 0.00 |
| Ethylbenzene | 0.00 | 0.00 | 1.32 | 0.00 | 2.43 | 7.81 |
| m,p-xylene | 7.48 | 4.36 | 0.23 | 0.00 | 1.09 | 15.18 |
| Styrene | 0.90 | 1.80 | 0.40 | 0.00 | 2.32 | 1.47 |
| o-xylene | 0.28 | 0.00 | 0.12 | 0.00 | 0.00 | 0.00 |
| Nonane | 3.74 | 5.94 | 0.41 | 0.00 | 6.15 | 2.55 |
| Nonene | 1.45 | 3.87 | 0.84 | 0.00 | 2.53 | 1.14 |
| MW140 | 2.36 | 1.94 | 1.63 | 0.00 | 3.69 | 2.35 |
| Cumene | 1.30 | 1.23 | 0.54 | 0.00 | 2.13 | 2.43 |
| Decene/methylstyrene | 1.54 | 1.60 | 1.55 | 0.00 | 0.30 | 0.48 |
| Decane | 4.31 | 1.68 | 4.34 | 0.00 | 0.48 | 1.08 |
| Unknown 2 | 0.96 | 0.15 | 0.97 | 0.00 | 0.00 | 0.24 |
| Indene | 0.25 | 0.00 | 0.21 | 0.00 | 0.00 | 0.00 |
| Indane | 0.33 | 0.00 | 0.33 | 0.00 | 0.00 | 0.08 |
| C11 Alkene | 1.83 | 0.22 | 1.83 | 0.00 | 0.00 | 0.19 |
| C11 Alkane | 4.54 | 0.18 | 4.75 | 0.00 | 0.00 | 0.39 |
| C12 Alkene | 1.68 | 0.08 | 2.34 | 0.00 | 0.18 | 0.08 |
| Naphthalene | 0.09 | 0.00 | 0.11 | 0.00 | 0.00 | 0.00 |
| C12 Alkane | 4.28 | 0.09 | 6.14 | 0.00 | 0.84 | 0.16 |
| C13 Alkane | 4.11 | 0.00 | 6.80 | 3.32 | 0.68 | 0.08 |
| C13 Alkene | 1.67 | 0.00 | 2.85 | 0.38 | 0.37 | 0.00 |
| 2-methylnaphthalene | 0.70 | 0.00 | 0.00 | 0.93 | 0.14 | 0.00 |
| C14 Alkene | 0.08 | 0.00 | 1.81 | 3.52 | 0.00 | 0.00 |
| C14 Alkane | 0.14 | 0.09 | 6.20 | 14.12 | 0.00 | 0.00 |
| Acenaphthylene | 0.00 | 0.00 | 0.75 | 0.00 | 0.00 | 0.00 |
| C15 Alkene | 0.00 | 0.00 | 2.70 | 3.55 | 0.00 | 0.00 |
| C15 Alkane | 0.00 | 0.09 | 9.40 | 14.16 | 0.00 | 0.07 |
| C16 Alkene | 0.00 | 0.00 | 1.61 | 2.20 | 0.00 | 0.00 |
| C16 Alkane | 0.00 | 0.10 | 5.44 | 12.40 | 0.00 | 0.00 |
| C17 Alkene | 0.00 | 0.00 | 0.10 | 3.35 | 0.00 | 0.00 |
| C17 Alkane | 0.00 | 0.10 | 0.26 | 16.81 | 0.00 | 0.00 |
| C18 Alkene | 0.00 | 0.00 | 0.00 | 0.67 | 0.00 | 0.00 |
| C18 Alkane | 0.00 | 0.10 | 0.00 | 3.31 | 0.00 | 0.00 |
| C19 Alkane | 0.00 | 0.00 | 0.00 | 0.13 | 0.00 | 0.00 |
| C19 Alkene | 0.00 | 0.00 | 0.00 | 0.00 | 0.00 | 0.00 |
| C20 Alkene | 0.00 | 0.00 | 0.00 | 0.00 | 0.00 | 0.00 |
| C20 Alkane | 0.00 | 0.00 | 0.00 | 0.00 | 0.00 | 0.00 |
| C21 Alkene | 0.00 | 0.00 | 0.00 | 0.00 | 0.00 | 0.00 |

TABLE 2-continued

Gas Chromatography Analysis of r-Pyoil Examples 5-10.

| | r-Pyoil Examples | | | | | |
|---|---|---|---|---|---|---|
| Components | 5 | 6 | 7 | 8 | 9 | 10 |
| Unidentified | 18.51 | 16.18 | 21.95 | 21.13 | 19.45 | 13.24 |
| Percent C4-C7 | 12.71 | 38.55 | 0.85 | 0.00 | 50.25 | 37.35 |
| Percent C8+ | 68.78 | 45.17 | 77.20 | 78.87 | 30.30 | 49.41 |
| Percent C15+ | 0.00 | 0.38 | 19.52 | 56.60 | 0.00 | 0.07 |
| Percent Aromatics | 14.04 | 12.02 | 6.27 | 0.93 | 11.90 | 34.70 |
| Percent Paraffins | 52.35 | 59.75 | 55.64 | 64.26 | 56.08 | 44.89 |

Examples 11-58 Involving Steam Cracking r-Pyoil in a Lab Unit

Figure 11:
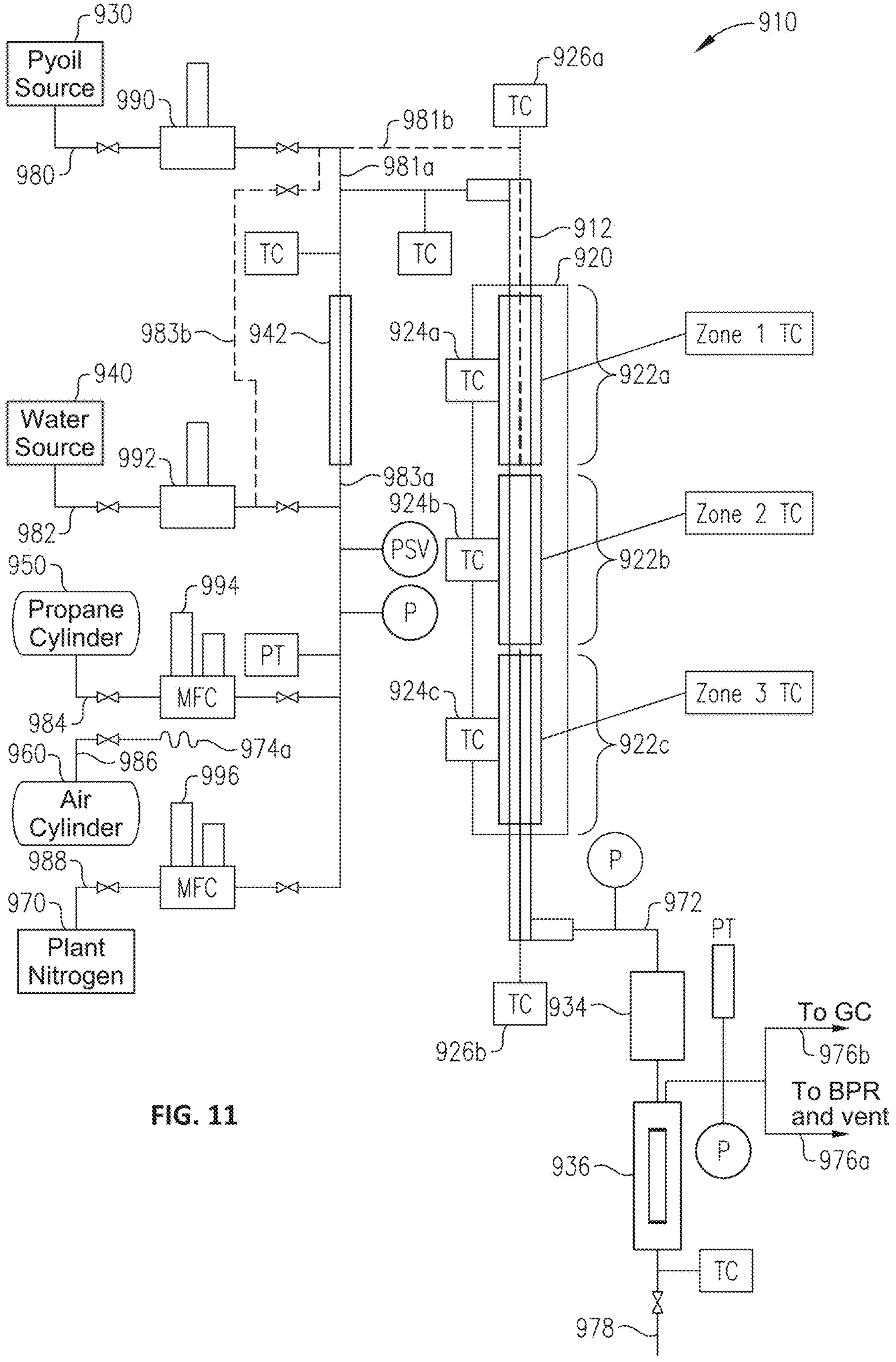
FIG. 11 illustrates the laboratory scale cracking unit design.

The invention is further illustrated by the following steam cracking examples. Examples were performed in a laboratory unit to simulate the results obtained in a commercial steam cracker. A drawing of the lab steam cracker is shown in FIG. 11. Lab Steam Cracker 910 consisted of a section of ⅜ inch Incoloy™ tubing 912 that was heated in a 24-inch Applied Test Systems three zone furnace 920. Each zone (Zone 1 922*a*, Zone 2 922*b*, and Zone 3 922*c*) in the furnace was heated by a 7-inch section of electrical coils. Thermocouples 924*a*, 924*b*, and 924*c* were fastened to the external walls at the mid-point of each zone for temperature control of the reactor. Internal reactor thermocouples 926*a* and 926*b* were also placed at the exit of Zone 1 and the exit of Zone 2, respectively. The r-pyoil source 930 was fed through line 980 to Isco syringe pump 990 and fed to the reactor through line 981*a*. The water source 940 was fed through line 982 to ICSO syringe pump 992 and fed to preheater 942 through line 983*a* for conversion to steam prior to entering the reactor in line 981*a* with pyoil. A propane cylinder 950 was attached by line 984 to mass flow controller 994. The plant nitrogen source 970 was attached by line 988 to mass flow controller 996. The propane or nitrogen stream was fed through line 983*a* to preheater 942 to facilitate even steam generation prior to entering the reactor in line 981*a*. Quartz glass wool was placed in the 1-inch space between the three zones of the furnace to reduce temperature gradients between them. In an optional configuration, the top internal thermocouple 922*a* was removed for a few examples to feed r-pyoil either at the mid-point of Zone 1 or at the transition between Zone 1 and Zone 2 through a section of ⅛ inch diameter tubing. The dashed lines in FIG. 11 show the optional configurations. A heavier dashed line extends the feed point to the transition between Zone 1 and Zone 2. Steam was also optionally added at these positions in the reactor by feeding water from Isco syringe pump 992 through the dashed line 983*b*. r-Pyoil, and optionally steam, were then fed through dashed line 981*b* to the reactor. Thus, the reactor can be operated be feeding various combinations of components and at various locations. Typical operating conditions were heating the first zone to 600° C., the second zone to about 700° C., and the third zone to 375° C. while maintaining 3 psig at the reactor exit. Typical flow rates of hydrocarbon feed and steam resulted in a 0.5 sec residence time in one 7-inch section of the furnace. The first 7-inch section of the furnace 922*a* was operated as the convection zone and the second 7-inch section 922*b* as the radiant zone of a steam cracker. The gaseous effluent of the reactor exited the reactor through line 972. The stream was cooled with shell and tube condenser 934 and any condensed liquids were collected in glycol cooled sight glass 936. The liquid material was removed periodically through line 978 for weighing and gas chromatography analysis. The gas stream was fed through line 976*a* for venting through a back-pressure regulator that maintained about 3 psig on the unit. The flow rate was measured with a Sensidyne Gilian Gilibrator-2 Calibrator. Periodically a portion of the gas stream was sent in line 976*b* to a gas chromatography sampling system for analysis. The unit could be was operated in a decoking mode by physically disconnecting propane line 984 and attaching air cylinder 960 with line 986 and flexible tubing line 974*a* to mass flow controlled 994.

Analysis of reaction feed components and products was done by gas chromatography. All percentages are by weight unless specified otherwise. Liquid samples were analyzed on an Agilent 7890A using a Restek RTX-1 column (30 meters×320-micron ID, 0.5-micron film thickness) over a temperature range of 35° C. to 300° C. and a flame ionization detector. Gas samples were analyzed on an Agilent 8890 gas chromatograph. This GC was configured to analyze refinery gas up to $C_6$ with $H_2S$ content. The system used four valves, three detectors, 2 packed columns, 3 micro-packed columns, and 2 capillary columns. The columns used were the following: 2 ft×1/16 in, 1 mm i.d. HayeSep A 80/100 mesh UltiMetal Plus 41 mm; 1.7 m×1/16 in, 1 mm i.d. HayeSep A 80/100 mesh UltiMetal Plus 41 mm; 2 m×1/16 in, 1 mm i.d. MolSieve 13×80/100 mesh UltiMetal Plus 41 mm; 3 ft×⅛ in, 2.1 mm i.d. HayeSep Q 80/100 mesh in UltiMetal Plus; 8 ft×⅛ in, 2.1 mm i.d. Molecular Sieve 5A 60/80 mesh in UltiMetal Plus; 2 m×0.32 mm, Sum thickness DB-1 (123-1015, cut); 25 m×0.32 mm, 8 um thickness HP-AL/S (19091P-S12). The FID channel was configured to analyze the hydrocarbons with the capillary columns from $C_1$ to C5, while $C_6/C_{6+}$ components are backflushed and measured as one peak at the beginning of the analysis. The first channel (reference gas He) was configured to analyze fixed gases (such as CO2, CO, O2, N2, and H2S). This channel was run isothermally, with all micro-packed columns installed inside a valve oven. The second TCD channel (third detector, reference gas N2) analyzed hydrogen through regular packed columns. The analyses from both chromatographs were combined based on the mass of each stream (gas and liquid where present) to provide an overall assay for the reactor.

A typical run was made as follows:

Nitrogen (130 sccm) was purged through the reactor system, and the reactor was heated (zone1, zone 2, zone 3 setpoints 300° C., 450° C., 300° C., respectively). Preheaters and cooler for post-reactor liquid collection were powered on. After 15 minutes and the preheater was above 100° C., 0.1 mL/min water was added to the preheater to generate steam. The reactor temperature setpoints were raised to 450° C., 600° C., and 350° C. for zones 1, 2, and 3, respectively. After another 10 minutes, the reactor temperature setpoints were raised to 600° C., 700° C., and 375° C. for zones 1, 2, and 3, respectively. The $N_2$ was decreased to zero as the propane flow was increased to 130 sccm. After 100 min at these conditions either r-pyoil or r-pyoil in naphtha was introduced, and the propane flow was reduced. The propane flow was 104 sccm, and the r-pyoil feed rate was 0.051 g/hr for a run with 80% propane and 20% r-pyoil. This material was steam cracked for 4.5 hr (with gas and liquid sampling). Then, 130 sccm propane flow was reestablished. After 1 hr, the reactor was cooled and purged with nitrogen.

Steam Cracking with r-Pyoil Example 1.

Table 3 contains examples of runs made in the lab steam cracker with propane, r-pyoil from Example 1, and various weight ratios of the two. Steam was fed to the reactor in a 0.4 steam to hydrocarbon ratio in all runs. Nitrogen (5% by weight relative to the hydrocarbon) was fed with steam in the run with only r-pyoil to aid in even steam generation. Comparative Example 1 is an example involving cracking only propane.

TABLE 3

Steam Cracking Examples using r-pyoil from Example 1.

| Examples | Comparative Example 1 | 11 | 12 | 13 | 14 | 15 |
|---|---|---|---|---|---|---|
| Zone 2 Control Temp | 700 | 700 | 700 | 700 | 700 | 700 |
| Propane (wt %) | 100 | 85 | 80 | 67 | 50 | 0 |
| r-Pyoil (wt %) | 0 | 15 | 20 | 33 | 50 | 100* |
| Feed Wt, g/hr | 15.36 | 15.43 | 15.35 | 15.4 | 15.33 | 15.35 |
| Steam/Hydrocarbon Ratio | 0.4 | 0.4 | 0.4 | 0.4 | 0.4 | 0.4 |
| Total Accountability, % | 103.7 | 94.9 | 94.5 | 89.8 | 87.7 | 86 |
| Total Products | Weight Percent | | | | | |
| C6+ | 1.15 | 2.61 | 2.62 | 4.38 | 7.78 | 26.14 |
| methane | 18.04 | 18.40 | 17.68 | 17.51 | 17.52 | 12.30 |
| ethane | 2.19 | 2.59 | 2.46 | 2.55 | 2.88 | 2.44 |
| ethylene | 30.69 | 32.25 | 31.80 | 32.36 | 32.97 | 23.09 |
| propane | 24.04 | 19.11 | 20.25 | 16.87 | 11.66 | 0.33 |
| propylene | 17.82 | 17.40 | 17.63 | 16.80 | 15.36 | 7.34 |
| i-butane | 0.00 | 0.04 | 0.04 | 0.03 | 0.03 | 0.01 |
| n-butane | 0.03 | 0.02 | 0.02 | 0.02 | 0.02 | 0.02 |
| propydiene | 0.07 | 0.14 | 0.13 | 0.15 | 0.17 | 0.14 |
| acetylene | 0.24 | 0.40 | 0.40 | 0.45 | 0.48 | 0.41 |
| t-2-butene | 0.00 | 0.19 | 0.00 | 0.00 | 0.00 | 0.11 |
| 1-butene | 0.16 | 0.85 | 0.19 | 0.19 | 0.20 | 0.23 |
| i-butylene | 0.92 | 0.34 | 0.87 | 0.81 | 0.66 | 0.81 |
| c-2-butene | 0.12 | 0.15 | 0.40 | 0.56 | 0.73 | 0.11 |
| i-pentane | 0.13 | 0.00 | 0.00 | 0.00 | 0.00 | 0.00 |
| n-pentane | 0.00 | 0.01 | 0.01 | 0.02 | 0.02 | 0.02 |
| 1,3-butadiene | 1.73 | 2.26 | 2.31 | 2.63 | 3.02 | 2.88 |
| methyl acetylene | 0.20 | 0.26 | 0.26 | 0.30 | 0.32 | 0.28 |
| t-2-pentene | 0.11 | 0.08 | 0.12 | 0.12 | 0.12 | 0.05 |
| 2-methyl-2-butene | 0.02 | 0.01 | 0.03 | 0.03 | 0.02 | 0.02 |
| 1-pentene | 0.05 | 0.09 | 0.01 | 0.02 | 0.02 | 0.03 |
| c-2-pentene | 0.06 | 0.01 | 0.03 | 0.03 | 0.03 | 0.01 |
| pentadiene 1 | 0.00 | 0.01 | 0.02 | 0.02 | 0.02 | 0.08 |
| pentadiene 2 | 0.01 | 0.04 | 0.04 | 0.05 | 0.06 | 0.16 |
| pentadiene 3 | 0.12 | 0.21 | 0.23 | 0.27 | 0.30 | 0.26 |
| 1,3-Cyclopentadiene | 0.48 | 0.85 | 0.81 | 1.01 | 1.25 | 1.58 |
| pentadiene 4 | 0.00 | 0.08 | 0.08 | 0.09 | 0.10 | 0.07 |
| pentadiene 5 | 0.06 | 0.17 | 0.17 | 0.20 | 0.23 | 0.31 |
| CO2 | 0.00 | 0.00 | 0.00 | 0.00 | 0.00 | 0.00 |
| CO | 0.12 | 0.11 | 0.05 | 0.00 | 0.12 | 0.74 |
| hydrogen | 1.40 | 1.31 | 1.27 | 1.21 | 1.13 | 0.67 |
| Unidentified | 0.00 | 0.00 | 0.10 | 1.33 | 2.79 | 19.37 |
| Olefin/Aromatics Ratio | 45.42 | 21.07 | 20.91 | 12.62 | 7.11 | 1.42 |
| Total Aromatics | 1.15 | 2.61 | 2.62 | 4.38 | 7.78 | 26.14 |
| Propylene + Ethylene | 48.51 | 49.66 | 49.43 | 49.16 | 48.34 | 30.43 |
| Ethylene/Propylene Ratio | 1.72 | 1.85 | 1.80 | 1.93 | 2.15 | 3.14 |

*5% N2 was also added to facilitate steam generation. Analysis has been normalized to exclude it.

As the amount of r-pyoil used is increased relative to propane, there was an increase in the formation of dienes. For example, both r-butadiene and cyclopentadiene increased as more r-pyoil is added to the feed. Additionally, aromatics (C6+) increased considerably with increased r-pyoil in the feed.

Accountability decreased with increasing amounts of r-pyoil in these examples. It was determined that some r-pyoil in the feed was being held up in the preheater section. Due to the short run times, accountability was negatively affected. A slight increase in the slope of the reactor inlet line corrected the issue (see Example 24). Nonetheless, even with an accountability of 86% in Example 15, the trend was clear. The overall yield of r-ethylene and r-propylene decreased from about 50% to less than about 35% as the amount of r-pyoil in the feed increased. Indeed, feeding r-pyoil alone produced about 40% of aromatics (C6+) and unidentified higher boilers (see Example 15 and Example 24).

r-Ethylene Yield—r-Ethylene yield showed an increase from 30.7% to >32% as 15% r-pyoil was co-cracked with propane. The yield of r-ethylene then remained about 32% until >50% r-pyoil was used. With 100% r-pyoil, the yield of r-ethylene decreased to 21.5% due to the large amount of aromatics and unidentified high boilers (>40%). Since r-pyoil cracks faster than propane, a feed with an increased amount of r-pyoil will crack faster to more r-propylene. The r-propylene can then react to form r-ethylene, diene and aromatics. When the concentration of r-pyoil was increased the amount of r-propylene cracked products was also increased. Thus, the increased amount of dienes can react with other dienes and olefins (like r-ethylene) leading to even more aromatics formation. So, at 100% r-pyoil in the feed, the amount of r-ethylene and r-propylene recovered was lower due to the high concentration of aromatics that formed. In fact, the olefin/aromatic dropped from 45.4 to 1.4 as r-pyoil was increased to 100% in the feed. Thus, the yield of r-ethylene increased as more r-pyoil was added to the feed mixture, at least to about 50% r-pyoil. Feeding pyoil in propane provides a way to increase the ethylene/propylene ratio on a steam cracker.

r-Propylene Yield—r-Propylene yield decreased with more r-pyoil in the feed. It dropped from 17.8% with propane only to 17.4% with 15% r-pyoil and then to 6.8% as 100% r-pyoil was cracked. r-Propylene formation did not decrease in these cases. r-Pyoil cracks at lower temperature than propane. As r-propylene is formed earlier in the reactor it has more time to converted to other materials—like dienes and aromatics and r-ethylene. Thus, feeding r-pyoil with propane to a cracker provides a way to increase the yield of ethylene, dienes and aromatics.

The r-ethylene/r-propylene ratio increased as more r-pyoil was added to the feed because an increase concentration of r-pyoil made r-propylene faster, and the r-propylene reacted to other cracked products—like dienes, aromatics and r-ethylene.

The ethylene to propylene ratio increased from 1.72 to 3.14 going from 100% propane to 100% r-pyoil cracking. The ratio was lower for 15% r-pyoil (0.54) than 20% r-pyoil (0.55) due to experimental error with the small change in r-pyoil feed and the error from having just one run at each condition.

The olefin/aromatic ratio decreased from 45 with no r-pyoil in the feed to 1.4 with no propane in the feed. The decrease occurred mainly because r-pyoil cracked more readily than propane and thus more r-propylene was produced faster. This gave the r-propylene more time to react further—to make more r-ethylene, dienes, and aromatics. Thus, aromatics increased, and r-propylene decreased with the olefin/aromatic ratio decreasing as a result.

r-Butadiene increased as the concentration of r-pyoil in the feed increased, thus providing a way to increase r-butadiene yield. r-Butadiene increased from 1.73% with propane cracking, to about 2.3% with 15-20% r-pyoil in the feed, to 2.63% with 33% r-pyoil, and to 3.02% with 50% r-pyoil. The amount was 2.88% at 100% r-pyoil. Example 24 showed 3.37% r-butadiene observed in another run with 100% r-pyoil. This amount may be a more accurate value based on the accountability problems that occurred in Example 15. The increase in r-butadiene was the result of more severity in cracking as products like r-propylene continued to crack to other materials.

Cyclopentadiene increased with increasing r-pyoil except for the decrease in going from 15%-20% r-pyoil (from 0.85 to 0.81). Again, some experimental error was likely. Thus, cyclopentadiene increased from 0.48% cracking propane only, to about 0.85% at 15-20% r-pyoil in the reactor feed, to 1.01% with 33% r-pyoil, to 1.25 with 50% r-pyoil, and 1.58% with 100% r-pyoil. The increase in cyclopentadiene was also the result of more severity in cracking as products like r-propylene continued to crack to other materials. Thus, cracking r-pyoil with propane provided a way to increase cyclopentadiene production.

Operating with r-pyoil in the feed to the steam cracker resulted in less propane in the reactor effluent. In commercial operation, this would result in a decreased mass flow in the recycle loop. The lower flow would decrease cryogenic energy costs and potentially increase capacity on the plant if it is capacity constrained. Additionally, lower propane in the recycle loop would debottleneck the r-propylene fractionator if it is already capacity limited.

Steam Cracking with r-Pyoil Examples 1-4.

Table 4 contains examples of runs made with the r-pyoil samples found in Table 1 with a propane/r-pyoil weight ratio of 80/20 and 0.4 steam to hydrocarbon ratio.

TABLE 4

Examples using r-PyOil Examples 1-4 under similar conditions.

| Examples | 16 | 17 | 18 | 19 |
|---|---|---|---|---|
| r-Pyoil from Table 1 | 1 | 2 | 3 | 4 |
| Zone 2 Control Temp | 700 | 700 | 700 | 700 |
| Propane (wt %) | 80 | 80 | 80 | 80 |
| r-Pyoil (wt %) | 20 | 20 | 20 | 20 |
| N2 (wt %) | 0 | 0 | 0 | 0 |
| Feed Wt, g/hr | 15.35 | 15.35 | 15.35 | 15.35 |
| Steam/Hydrocarbon Ratio | 0.4 | 0.4 | 0.4 | 0.4 |
| Total Accountability, % | 94.5 | 96.4 | 95.6 | 95.3 |
| Total Products | | Weight Percent | | |
| C6+ | 2.62 | 2.86 | 3.11 | 2.85 |
| methane | 17.68 | 17.36 | 17.97 | 17.20 |
| ethane | 2.46 | 2.55 | 2.67 | 2.47 |
| ethylene | 31.80 | 30.83 | 31.58 | 30.64 |
| propane | 20.25 | 21.54 | 19.34 | 21.34 |
| propylene | 17.63 | 17.32 | 17.18 | 17.37 |
| i-butane | 0.04 | 0.04 | 0.04 | 0.04 |
| n-butane | 0.02 | 0.01 | 0.02 | 0.03 |
| propadiene | 0.13 | 0.06 | 0.09 | 0.12 |
| acetylene | 0.40 | 0.11 | 0.26 | 0.37 |
| t-2-butene | 0.00 | 0.00 | 0.00 | 0.00 |
| 1-butene | 0.19 | 0.19 | 0.20 | 0.19 |
| i-butylene | 0.87 | 0.91 | 0.91 | 0.98 |
| c-2-butene | 0.40 | 0.44 | 0.45 | 0.52 |
| i-pentane | 0.00 | 0.14 | 0.16 | 0.16 |
| n-pentane | 0.01 | 0.03 | 0.03 | 0.03 |
| 1,3-butadiene | 2.31 | 2.28 | 2.33 | 2.27 |
| methyl acetylene | 0.26 | 0.23 | 0.23 | 0.24 |
| t-2-pentene | 0.12 | 0.13 | 0.14 | 0.13 |
| 2-methyl-2-butene | 0.03 | 0.04 | 0.04 | 0.03 |
| 1-pentene | 0.01 | 0.02 | 0.02 | 0.02 |
| c-2-pentene | 0.03 | 0.06 | 0.05 | 0.04 |
| pentadiene 1 | 0.02 | 0.00 | 0.00 | 0.00 |
| pentadiene 2 | 0.04 | 0.02 | 0.02 | 0.01 |
| pentadiene 3 | 0.23 | 0.17 | 0.00 | 0.25 |
| 1,3-Cyclopentadiene | 0.81 | 0.72 | 0.76 | 0.71 |
| pentadiene 4 | 0.08 | 0.00 | 0.00 | 0.00 |
| pentadiene 5 | 0.17 | 0.08 | 0.09 | 0.08 |
| CO2 | 0.00 | 0.00 | 0.00 | 0.00 |
| CO | 0.05 | 0.00 | 0.00 | 0.00 |
| hydrogen | 1.27 | 1.22 | 1.26 | 1.21 |
| Unidentified | 0.10 | 0.65 | 1.04 | 0.69 |
| Olefin/Aromatics Ratio | 20.91 | 18.66 | 17.30 | 18.75 |
| Total Aromatics | 2.62 | 2.86 | 3.11 | 2.85 |
| Propylene + Ethylene | 49.43 | 48.14 | 48.77 | 48.01 |
| Ethylene/Propylene Ratio | 1.80 | 1.78 | 1.84 | 1.76 |

Steam cracking of the different r-pyoil Examples 1-4 at the same conditions gave similar results. Even the lab distilled sample of r-pyoil (Example 19) cracked like the other samples. The highest r-ethylene and r-propylene yield was for Example 16, but the range was 48.01-49.43. The r-ethylene/r-propylene ratio varied from 1.76 to 1.84. The amount of aromatics (C6+) only varied from 2.62 to 3.11. Example 16 also produced the smallest yield of aromatics. The r-pyoil used for this example (r-Pyoil Example 1, Table 1) contained the largest amount of paraffins and the lowest amount of aromatics. Both are desirable for cracking to r-ethylene and r-propylene.

Steam Cracking with r-Pyoil Example 2.

Table 5 contains runs made in the lab steam cracker with propane (Comparative Example 2), r-pyoil Example 2, and four runs with a propane/pyrolysis oil weight ratio of 80/20. Comparative Example 2 and Example 20 were run with a 0.2 steam to hydrocarbon ratio. Steam was fed to the reactor in a 0.4 steam to hydrocarbon ratio in all other examples.

Nitrogen (5% by weight relative to the r-pyoil) was fed with steam in the run with only r-pyoil (Example 24).

TABLE 5

| Examples using r-Pyoil Example 2. | | | | | | |
|---|---|---|---|---|---|---|
| Examples | Comparative Example 2 | 20 | 21 | 22 | 23 | 24 |
| Zone 2 Control Temp | 700 °C | 700 °C | 700 °C | 700 °C | 700 °C | 700 °C |
| Propane (wt %) | 100 | 80 | 80 | 80 | 80 | 0 |
| r-Pyoil (wt %) | 0 | 20 | 20 | 20 | 20 | 100* |
| Feed Wt, g/hr | 15.36 | 15.35 | 15.35 | 15.35 | 15.35 | 15.35 |
| Steam/Hydrocarbon Ratio | 0.2 | 0.2 | 0.4 | 0.4 | 0.4 | 0.4 |
| Total Accountability, % | 100.3 | 93.8 | 99.1 | 93.4 | 96.4 | 97.9 |
| Total Products | Weight Percent | | | | | |
| C6+ | 1.36 | 2.97 | 2.53 | 2.98 | 2.86 | 22.54 |
| methane | 18.59 | 19.59 | 17.34 | 16.64 | 17.36 | 11.41 |
| ethane | 2.56 | 3.09 | 2.26 | 2.35 | 2.55 | 3.00 |
| ethylene | 30.70 | 32.51 | 31.19 | 29.89 | 30.83 | 24.88 |
| propane | 23.00 | 17.28 | 21.63 | 23.84 | 21.54 | 0.38 |
| propylene | 18.06 | 16.78 | 17.72 | 17.24 | 17.32 | 10.94 |
| i-butane | 0.04 | 0.03 | 0.03 | 0.05 | 0.04 | 0.02 |
| n-butane | 0.01 | 0.03 | 0.03 | 0.03 | 0.01 | 0.09 |
| propadiene | 0.05 | 0.10 | 0.12 | 0.12 | 0.06 | 0.12 |
| acetylene | 0.12 | 0.35 | 0.40 | 0.36 | 0.11 | 0.31 |
| t-2-butene | 0.00 | 0.00 | 0.00 | 0.00 | 0.00 | 0.00 |
| 1-butene | 0.17 | 0.20 | 0.18 | 0.18 | 0.19 | 0.25 |
| i-butylene | 0.87 | 0.80 | 0.91 | 0.94 | 0.91 | 1.22 |
| c-2-butene | 0.14 | 0.40 | 0.40 | 0.44 | 0.44 | 1.47 |
| i-pentane | 0.14 | 0.13 | 0.00 | 0.00 | 0.14 | 0.13 |
| n-pentane | 0.00 | 0.01 | 0.02 | 0.03 | 0.03 | 0.01 |
| 1,3-butadiene | 1.74 | 2.35 | 2.20 | 2.18 | 2.28 | 3.37 |
| methyl acetylene | 0.18 | 0.22 | 0.26 | 0.24 | 0.23 | 0.23 |
| t-2-pentene | 0.13 | 0.14 | 0.12 | 0.12 | 0.13 | 0.14 |
| 2-methyl-2-butene | 0.03 | 0.04 | 0.03 | 0.04 | 0.04 | 0.10 |
| 1-pentene | 0.01 | 0.03 | 0.01 | 0.01 | 0.02 | 0.05 |
| c-2-pentene | 0.04 | 0.04 | 0.03 | 0.04 | 0.06 | 0.18 |
| pentadiene 1 | 0.00 | 0.01 | 0.01 | 0.02 | 0.00 | 0.14 |
| pentadiene 2 | 0.01 | 0.02 | 0.03 | 0.02 | 0.02 | 0.19 |
| pentadiene 3 | 0.00 | 0.24 | 0.19 | 0.24 | 0.17 | 0.50 |
| 1,3-Cyclopentadiene | 0.52 | 0.83 | 0.65 | 0.71 | 0.72 | 1.44 |
| pentadiene 4 | 0.00 | 0.00 | 0.00 | 0.00 | 0.00 | 0.01 |
| pentadiene 5 | 0.06 | 0.09 | 0.08 | 0.08 | 0.08 | 0.15 |
| CO2 | 0.00 | 0.00 | 0.00 | 0.00 | 0.00 | 0.00 |
| CO | 0.07 | 0.00 | 0.00 | 0.00 | 0.00 | 0.19 |
| hydrogen | 1.36 | 1.28 | 1.28 | 1.21 | 1.22 | 0.63 |
| Unidentified | 0.00 | 0.00 | 0.34 | 0.00 | 0.65 | 15.89 |
| Olefin/Aromatics Ratio | 38.54 | 18.39 | 21.26 | 17.55 | 18.66 | 2.00 |
| Total Aromatics | 1.36 | 2.97 | 2.53 | 2.98 | 2.86 | 22.54 |
| Propylene +-Ethylene | 48.76 | 49.29 | 48.91 | 47.13 | 48.14 | 35.82 |
| Ethylene/Propylene Ratio | 1.70 | 1.94 | 1.76 | 1.73 | 1.78 | 2.27 |

*5% N2 was also added to facilitate steam generation. Analysis has been normalized to exclude it.

Comparing Example 20 to Examples 21-23 shows that the increased feed flow rate (from 192 sccm in Example 20 to 255 sccm with more steam in Examples 21-23) resulted in less conversion of propane and r-pyoil due to the 25% shorter residence time in the reactor (r-ethylene and r-propylene: 49.3% for Example 20 vs 47.1, 48.1, 48.9% for Examples 21-23). r-Ethylene was higher in Example 21 with the increased residence time since propane and r-pyoil cracked to higher conversion of r-ethylene and r-propylene and some of the r-propylene can then be converted to additional r-ethylene. And conversely, r-propylene was higher in the higher flow examples with a higher steam to hydrocarbon ratio (Example 21-23) since it has less time to continue reacting. Thus, Examples 21-23 produced a smaller amount of other components: r-ethylene, C6+(aromatics), r-butadiene, cyclopentadiene, etc., than found in Example 20.

Examples 21-23 were run at the same conditions and showed that there was some variability in operation of the lab unit, but it was sufficiently small that trends can be seen when different conditions are used.

Example 24, like example 15, showed that the r-propylene and r-ethylene yield decreased when 100% r-pyoil was cracked compared to feed with 20% r-pyoil. The amount decreased from about 48% (in Examples 21-23) to 36%. Total aromatics was greater than 20% of the product as in Example 15.

Steam Cracking with r-Pyoil Example 3.

Table 6 contains runs made in the lab steam cracker with propane and r-pyoil Example 3 at different steam to hydrocarbon ratios.

TABLE 6

| Examples using r-Pyoil Example 3. | | |
|---|---|---|
| Examples | 25 | 26 |
| Zone 2 Control Temp | 700 °C | 700 °C |
| Propane (wt %) | 80 | 80 |

TABLE 6-continued

| Examples using r-Pyoil Example 3. | | |
|---|---|---|
| Examples | 25 | 26 |
| r-Pyoil (wt %) | 20 | 20 |
| N2 (wt %) | 0 | 0 |
| Feed Wt, g/hr | 15.33 | 15.33 |
| Steam/Hydrocarbon Ratio | 0.4 | 0.2 |
| Total Accountability, % | 95.6 | 92.1 |
| Total Products | Weight Percent | |
| C6+ | 3.11 | 3.42 |
| methane | 17.97 | 18.57 |
| ethane | 2.67 | 3.01 |
| ethylene | 31.58 | 31.97 |
| propane | 19.34 | 17.43 |
| propylene | 17.18 | 17.17 |
| i-butane | 0.04 | 0.04 |
| n-butane | 0.02 | 0.03 |
| propadiene | 0.09 | 0.10 |
| acetylene | 0.26 | 0.35 |
| t-2-butene | 0.00 | 0.00 |
| 1-butene | 0.20 | 0.20 |
| i-butylene | 0.91 | 0.88 |
| c-2-butene | 0.45 | 0.45 |
| i-pentane | 0.16 | 0.17 |
| n-pentane | 0.03 | 0.02 |
| 1,3-butadiene | 2.33 | 2.35 |
| methyl acetylene | 0.23 | 0.22 |
| t-2-pentene | 0.14 | 0.15 |
| 2-methyl-2-butene | 0.04 | 0.04 |
| l-pentene | 0.02 | 0.02 |
| c-2-pentene | 0.05 | 0.04 |
| pentadiene 1 | 0.00 | 0.00 |
| pentadiene 2 | 0.02 | 0.02 |
| pentadiene 3 | 0.00 | 0.25 |
| 1,3-Cyclopentadiene | 0.76 | 0.84 |
| pentadiene 4 | 0.00 | 0.00 |
| pentadiene 5 | 0.09 | 0.10 |
| CO2 | 0.00 | 0.00 |
| CO | 0.00 | 0.00 |
| hydrogen | 1.26 | 1.24 |
| Unidentified | 1.04 | 0.92 |
| Olefin/Aromatics Ratio | 17.30 | 15.98 |
| Total Aromatics | 3.11 | 3.42 |
| Propylene + Ethylene | 48.77 | 49.14 |
| Ethylene/Propylene Ratio | 1.84 | 1.86 |

The same trends observed from cracking with r-pyoil Examples 1-2 were demonstrated for cracking with propane and r-pyoil Example 3. Example 25 compared to Example 26 showed that a decrease in the feed flow rate (to 192 sccm in Example 26 with less steam from 255 sccm in Example 25) resulted in greater conversion of the propane and r-pyoil due to the 25% greater residence time in the reactor (r-ethylene and r-propylene: 48.77% for Example 22 vs 49.14% for the lower flow in Example 26). r-Ethylene was higher in Example 26 with the increased residence time since propane and r-pyoil cracked to higher conversion of r-ethylene and r-propylene and some of the r-propylene was then converted to additional r-ethylene. Thus, Example 25, with the shorter residence time produced a smaller amount of other components: r-ethylene, C6+(aromatics), r-butadiene, cyclopentadiene, etc., than found in Example 26.

Steam Cracking with r-Pyoil Example 4.

Table 7 contains runs made in the lab steam cracker with propane and pyrolysis oil sample 4 at two different steam to hydrocarbon ratios.

TABLE 7

| Examples using Pyrolysis Oil Example 4. | | |
|---|---|---|
| Examples | 27 | 28 |
| Zone 2 Control Temp | 700 °C | 700 °C |
| Propane (wt %) | 80 | 80 |
| r-Pyoil (wt %) | 20 | 20 |
| N2 (wt %) | 0 | 0 |
| Feed Wt, g/hr | 15.35 | 15.35 |
| Steam/Hydrocarbon Ratio | 0.4 | 0.6 |
| Total Accountability, % | 95.3 | 95.4 |
| Total Products | Weight Percent | |
| C6+ | 2.85 | 2.48 |
| methane | 17.20 | 15.37 |
| ethane | 2.47 | 2.09 |
| ethylene | 30.64 | 28.80 |
| propane | 21.34 | 25.58 |
| propylene | 17.37 | 17.79 |
| i-butane | 0.04 | 0.05 |
| n-butane | 0.03 | 0.03 |
| propadiene | 0.12 | 0.12 |
| acetylene | 0.37 | 0.35 |
| t-2-butene | 0.00 | 0.00 |
| 1-butene | 0.19 | 0.19 |
| i-butylene | 0.98 | 1.03 |
| c-2-butene | 0.52 | 0.53 |
| i-pentane | 0.16 | 0.15 |
| n-pentane | 0.03 | 0.05 |
| 1,3-butadiene | 2.27 | 2.15 |
| methyl acetylene | 0.24 | 0.25 |
| t-2-pentene | 0.13 | 0.12 |
| 2-methyl-2-butene | 0.03 | 0.04 |
| l-pentene | 0.02 | 0.02 |
| c-2-pentene | 0.04 | 0.05 |
| pentadiene 1 | 0.00 | 0.00 |
| pentadiene 2 | 0.01 | 0.02 |
| pentadiene 3 | 0.25 | 0.27 |
| 1,3-Cyclopentadiene | 0.71 | 0.65 |
| pentadiene 4 | 0.00 | 0.00 |
| pentadiene 5 | 0.08 | 0.08 |
| CO2 | 0.00 | 0.00 |
| CO | 0.00 | 0.00 |
| hydrogen | 1.21 | 1.15 |
| Unidentified | 0.69 | 0.63 |
| Olefin/Aromatics Ratio | 18.75 | 20.94 |
| Total Aromatics | 2.85 | 2.48 |
| Propylene + Ethylene | 48.01 | 46.59 |
| Ethylene/Propylene Ratio | 1.76 | 1.62 |

The results in Table 7 showed the same trends as discussed with Example 20 vs Examples 21-23 in Table 5 and Example 25 vs Example 26 in Table 6. At a smaller steam to hydrocarbon ratio, higher amounts of r-ethylene and r-propylene and higher amounts of aromatics were obtained at the increased residence time. The r-ethylene/r-propylene ratio was also greater.

Thus, comparing Example 20 with Examples 21-23 in Table 5, Example 25 with Example 26, and Example 27 with Example 28 showed the same effect. Decreasing the steam to hydrocarbon ratio decreased the total flow in the reactor. This increased the residence time. As a result, there was an increase in the amount of r-ethylene and r-propylene produced. The r-ethylene to r-propylene ratio was larger which indicated that some r-propylene reacted to other products like r-ethylene. There was also an increase in aromatics (C6+) and dienes.

Examples of Cracking r-Pyoils from Table 2 with Propane

Table 8 contains the results of runs made in the lab steam cracker with propane (Comparative example 3) and the six r-pyoil samples listed in Table 2. Steam was fed to the reactor in a 0.4 steam to hydrocarbon ratio in all runs.

Examples 30, 33, and 34 were the results of runs with r-pyoil having greater than 35% C4-C7. The r-pyoil used in Example 40 contained 34.7% aromatics. Comparative Example 3 was a run with propane only. Examples 29, 31, and 32 were the results of runs with r-pyoil containing less than 35% C4-C7.

TABLE 8

Examples of steam cracking with propane and r-pyoils.

| Examples | Comparative Example 3 | 29 | 30 | 31 | 32 | 33 | 34 |
|---|---|---|---|---|---|---|---|
| r-Pyoil Feed from Table 2 | | 5 | 6 | 7 | 8 | 9 | 10 |
| Zone 2 Control Temp, °C | 700 | 700 | 700 | 700 | 700 | 700 | 700 |
| Propane (wt %) | 100 | 80 | 80 | 80 | 80 | 80 | 80 |
| r-Pyoil (wt %) | 0 | 20 | 20 | 20 | 20 | 20 | 20 |
| Feed Wt, g/hr | 15.36 | 15.32 | 15.33 | 15.33 | 15.35 | 15.35 | 15.35 |
| Steam/Hydrocarbon Ratio | 0.4 | 0.4 | 0.4 | 0.4 | 0.4 | 0.4 | 0.4 |
| Total Accountability, % | 103 | 100 | 100.3 | 96.7 | 96.3 | 95.7 | 97.3 |
| Total Products | Weight Percent | | | | | | |
| C6+ | 1.13 | 2.86 | 2.64 | 3.03 | 2.34 | 3.16 | 3.00 |
| methane | 17.69 | 17.17 | 15.97 | 17.04 | 16.42 | 18.00 | 16.41 |
| ethane | 2.27 | 2.28 | 2.12 | 2.26 | 2.59 | 2.63 | 2.19 |
| ethylene | 29.85 | 31.03 | 29.23 | 30.81 | 30.73 | 30.80 | 28.99 |
| propane | 24.90 | 21.86 | 25.13 | 21.70 | 23.79 | 20.99 | 24.57 |
| propylene | 18.11 | 17.36 | 17.78 | 17.23 | 18.08 | 17.90 | 17.32 |
| i-butane | 0.05 | 0.04 | 0.05 | 0.04 | 0.05 | 0.04 | 0.05 |
| n-butane | 0.02 | 0.02 | 0.04 | 0.02 | 0.00 | 0.00 | 0.02 |
| propadiene | 0.08 | 0.14 | 0.12 | 0.14 | 0.04 | 0.04 | 0.10 |
| acetylene | 0.31 | 0.42 | 0.36 | 0.42 | 0.04 | 0.06 | 0.31 |
| t-2-butene | 0.00 | 0.00 | 0.00 | 0.00 | 0.00 | 0.00 | 0.00 |
| 1-butene | 0.16 | 0.18 | 0.19 | 0.18 | 0.19 | 0.20 | 0.18 |
| i-butylene | 0.91 | 0.93 | 1.00 | 0.92 | 0.93 | 0.90 | 0.95 |
| c-2-butene | 0.13 | 0.51 | 0.50 | 0.50 | 0.34 | 0.68 | 0.61 |
| i-pentane | 0.14 | 0.00 | 0.15 | 0.00 | 0.16 | 0.16 | 0.15 |
| n-pentane | 0.00 | 0.04 | 0.05 | 0.04 | 0.00 | 0.00 | 0.06 |
| 1,3-butadiene | 1.64 | 2.28 | 2.15 | 2.26 | 2.48 | 2.23 | 2.04 |
| methyl acetylene | 0.19 | 0.28 | 0.24 | 0.28 | n/a | 0.24 | 0.24 |
| t-2-pentene | 0.12 | 0.12 | 0.12 | 0.12 | 0.13 | 0.13 | 0.11 |
| 2-methyl-2-butene | 0.03 | 0.03 | 0.03 | 0.03 | 0.04 | 0.03 | 0.03 |
| 1-pentene | 0.11 | 0.02 | 0.02 | 0.02 | 0.01 | 0.02 | 0.02 |
| c-2-pentene | 0.01 | 0.03 | 0.04 | 0.03 | 0.11 | 0.10 | 0.05 |
| pentadiene 1 | 0.00 | 0.02 | 0.00 | 0.02 | 0.00 | 0.00 | 0.00 |
| pentadiene 2 | 0.01 | 0.03 | 0.03 | 0.04 | 0.01 | 0.05 | 0.02 |
| pentadiene 3 | 0.14 | 0.25 | 0.00 | 0.25 | 0.00 | 0.00 | 0.00 |
| 1,3-Cyclopentadiene | 0.44 | 0.77 | 0.69 | 0.77 | 0.22 | 0.30 | 0.63 |
| pentadiene 4 | 0.00 | 0.00 | 0.00 | 0.00 | 0.00 | 0.00 | 0.00 |
| pentadiene 5 | 0.06 | 0.08 | 0.08 | 0.08 | 0.09 | 0.08 | 0.07 |
| CO2 | 0.00 | 0.00 | 0.00 | 0.00 | 0.00 | 0.00 | 0.00 |
| CO | 0.11 | 0.00 | 0.07 | 0.00 | 0.00 | 0.00 | 0.11 |
| hydrogen | 1.36 | 1.26 | 1.21 | 1.25 | 1.18 | 1.25 | 1.22 |
| unidentified | 0.00 | 0.00 | 0.00 | 0.52 | 0.00 | 0.00 | 0.56 |
| Olefin/Aromatics Ratio | 45.81 | 18.79 | 19.66 | 17.64 | 22.84 | 16.91 | 17.06 |
| Total Aromatics | 1.13 | 2.86 | 2.64 | 3.03 | 2.34 | 3.16 | 3.00 |
| Propylene + Ethylene | 47.96 | 48.39 | 47.01 | 48.04 | 48.82 | 48.70 | 46.31 |
| Ethylene/Propylene Ratio | 1.65 | 1.79 | 1.64 | 1.79 | 1.70 | 1.72 | 1.67 |

The examples in Table 8 involved using an 80/20 mix of propane with the various distilled r-pyoils. The results were like those in previous examples involving cracking r-pyoil with propane. All the examples produced an increase in aromatics and dienes relative to cracking propane only. As a result, the olefins to aromatic ratio was lower for cracking the combined feeds. The amount of r-propylene and r-ethylene produced was 47.01-48.82% for all examples except for the 46.31% obtained with the r-pyoil with 34.7% aromatic content (using r-pyoil Example 10 in Example 34). Except for that difference, the r-pyoils performed similarly, and any of them can be fed with C-2 to C-4 in a steam cracker. r-Pyoils having high aromatic content like r-pyoil Example 10 may not be the preferred feed for a steam cracker, and a r-pyoil having less than about 20% aromatic content should be considered a more preferred feed for co-cracking with ethane or propane.

Steam Cracking r-Pyoil with Ethane

Table 9 shows the results of cracking ethane and propane alone, and cracking with r-pyoil Example 2. The examples from cracking either ethane or ethane and r-pyoil were operated at three Zone 2 control temperatures: 700° C., 705° C., and 710° C.)

TABLE 9

Examples of Cracking Ethane and r-pyoil at different temperatures.

| Examples | Comparative Example 5 | 41 | Comparative Example 6 | 42 | Comparative Example 7 | 43 | Comparative Example 3 | Comparative Example 8 |
|---|---|---|---|---|---|---|---|---|
| Zone 2 Control Temp | 700 °C | 700 °C | 705 °C | 705 °C | 710 °C | 710 °C | 700 °C | 700 °C |
| Propane or Ethane in Feed | Ethane | Ethane | Ethane | Ethane | Ethane | Ethane | Propane | Propane |
| Propane or Ethane (wt %) | 100 | 80 | 100 | 80 | 100 | 80 | 100 | 80 |
| r-Pyoil (wt %) | 0 | 20 | 0 | 20 | 0 | 20 | 0 | 20 |
| Feed Wt, g/hr | 10.48 | 10.47 | 10.48 | 10.47 | 10.48 | 10.47 | 15.36 | 15.35 |
| Steam/Hydrocarbon Ratio | 0.4 | 0.4 | 0.4 | 0.4 | 0.4 | 0.4 | 0.4 | 0.4 |
| Total Accountability, % | 107.4 | 94.9 | 110.45 | 97.0 | 104.4 | 96.8 | 103.0 | 96.4 |
| Total Products | Weight Percent | | | | | | | |
| C6+ | 0.22 | 1.42 | 0.43 | 2.18 | 0.64 | 2.79 | 1.13 | 2.86 |
| methane | 1.90 | 6.41 | 2.67 | 8.04 | 3.69 | 8.80 | 17.69 | 17.36 |
| ethane | 46.36 | 39.94 | 38.75 | 33.77 | 32.15 | 26.82 | 2.27 | 2.55 |
| ethylene | 44.89 | 44.89 | 51.27 | 48.53 | 55.63 | 53.41 | 29.85 | 30.83 |
| propane | 0.08 | 0.18 | 0.09 | 0.18 | 0.10 | 0.16 | 24.90 | 21.54 |
| propylene | 0.66 | 2.18 | 0.84 | 1.99 | 1.03 | 1.86 | 18.11 | 17.32 |
| i-butane | 0.00 | 0.00 | 0.00 | 0.00 | 0.00 | 0.00 | 0.05 | 0.04 |
| n-butane | 0.00 | 0.00 | 0.00 | 0.00 | 0.00 | 0.00 | 0.02 | 0.01 |
| propadiene | 0.41 | 0.26 | 0.37 | 0.22 | 0.31 | 0.19 | 0.08 | 0.06 |
| acetylene | 0.00 | 0.01 | 0.00 | 0.01 | 0.00 | 0.01 | 0.31 | 0.11 |
| t-2-butene | 0.00 | 0.00 | 0.00 | 0.00 | 0.00 | 0.00 | 0.00 | 0.00 |
| 1-butene | 0.04 | 0.07 | 0.05 | 0.07 | 0.06 | 0.07 | 0.16 | 0.19 |
| i-butylene | 0.00 | 0.15 | 0.00 | 0.15 | 0.00 | 0.14 | 0.91 | 0.91 |
| c-2-butene | 0.12 | 0.19 | 0.13 | 0.11 | 0.13 | 0.08 | 0.13 | 0.44 |
| i-pentane | 0.59 | 0.05 | 0.04 | 0.06 | 0.05 | 0.06 | 0.14 | 0.14 |
| n-pentane | 0.01 | 0.01 | 0.00 | 0.00 | 0.00 | 0.00 | 0.00 | 0.03 |
| 1,3-butadiene | 0.96 | 1.45 | 1.34 | 1.69 | 1.72 | 2.06 | 1.64 | 2.28 |
| methyl acetylene | n/a | n/a | n/a | n/a | n/a | n/a | 0.19 | 0.23 |
| t-2-pentene | 0.03 | 0.04 | 0.02 | 0.04 | 0.03 | 0.05 | 0.12 | 0.13 |
| 2-methyl-2-butene | 0.02 | 0.00 | 0.03 | 0.00 | 0.03 | 0.00 | 0.03 | 0.04 |
| 1-pentene | 0.00 | 0.00 | 0.00 | 0.00 | 0.00 | 0.00 | 0.11 | 0.02 |
| c-2-pentene | 0.03 | 0.04 | 0.03 | 0.04 | 0.03 | 0.03 | 0.01 | 0.06 |
| pentadiene 1 | 0.00 | 0.00 | 0.00 | 0.00 | 0.00 | 0.00 | 0.00 | 0.00 |
| pentadiene 2 | 0.00 | 0.00 | 0.00 | 0.00 | 0.00 | 0.00 | 0.01 | 0.02 |
| pentadiene 3 | 0.00 | 0.00 | 0.00 | 0.00 | 0.00 | 0.00 | 0.14 | 0.17 |
| 1,3-Cyclopentadiene | 0.03 | 0.06 | 0.02 | 0.05 | 0.02 | 0.05 | 0.44 | 0.72 |
| pentadiene 4 | 0.00 | 0.00 | 0.00 | 0.00 | 0.00 | 0.00 | 0.00 | 0.00 |
| pentadiene 5 | 0.00 | 0.03 | 0.00 | 0.03 | 0.00 | 0.03 | 0.06 | 0.08 |
| CO2 | 0.00 | 0.00 | 0.00 | 0.00 | 0.00 | 0.00 | 0.00 | 0.00 |
| CO | 0.00 | 0.00 | 0.00 | 0.00 | 0.00 | 0.00 | 0.11 | 0.00 |
| hydrogen | 3.46 | 2.66 | 3.94 | 2.90 | 4.36 | 3.43 | 1.36 | 1.22 |
| unidentified | 0.00 | 0.00 | 0.00 | 0.00 | 0.00 | 0.00 | 0.00 | 0.65 |
| Olefin/Aromatics | 216.63 | 34.87 | 126.61 | 24.25 | 91.78 | 20.80 | 45.81 | 18.66 |
| Total Aromatics | 0.22 | 1.42 | 0.43 | 2.18 | 0.64 | 2.79 | 1.13 | 2.86 |
| Propylene + Ethylene | 45.56 | 47.07 | 52.11 | 50.52 | 56.65 | 55.28 | 47.96 | 48.14 |
| Ethylene/Propylene Ratio | 67.53 | 20.59 | 60.95 | 24.44 | 54.13 | 28.66 | 1.65 | 1.78 |

A limited number of runs with ethane were made. As can be seen in the Comparative Examples 5-7 and Comparative Example 3, conversion of ethane to products occurred more slowly than with propane. Comparative Example 5 with ethane and Comparative Example 3 with propane were run at the same molar flow rates and temperatures. However, conversion of ethane was only 52% (100%— 46% ethane in product) vs 75% for propane. However, the r-ethylene/r-propylene ratio was much higher (67.53 vs 1.65) as ethane cracking produced mainly r-ethylene. The olefin to aromatics ratio for ethane cracking was also much higher for ethane cracking. The Comparative Examples 5-7 and Examples 41-43 compare cracking ethane to an 80/20 mixture of ethane and r-pyoil at 700° C., 705° C. and 710° C. Production of total r-ethylene plus r-propylene increased with both ethane feed and the combined feed when the temperature was increased (an increase from about 46% to about 55% for both). Although the r-ethylene to r-propylene ratio decreased for ethane cracking with increasing temperature (from 67.53 at 700° C. to 60.95 at 705° C. to 54.13 at 710° C.), the ratio increased for the mixed feed (from 20.59 to 24.44 to 28.66). r-Propylene was produced from the r-pyoil and some continued to crack generating more cracked products such as r-ethylene, dienes and aromatics. The amount of aromatics in propane cracking with r-pyoil at 700° C. (2.86% in Comparative Example 8) was about the same as cracking ethane and r-pyoil at 710° C. (2.79% in Example 43).

Co-cracking ethane and r-pyoil required higher temperature to obtain more conversion to products compared to co-cracking with propane and r-pyoil. Ethane cracking produced mainly r-ethylene. Since a high temperature was required to crack ethane, cracking a mixture of ethane and r-pyoil produced more aromatics and dienes as some r-propylene reacted further. Operation in this mode would be appropriate if aromatics and dienes were desired with minimal production of r-propylene.

Example 59—Plant Test

Figure 12:
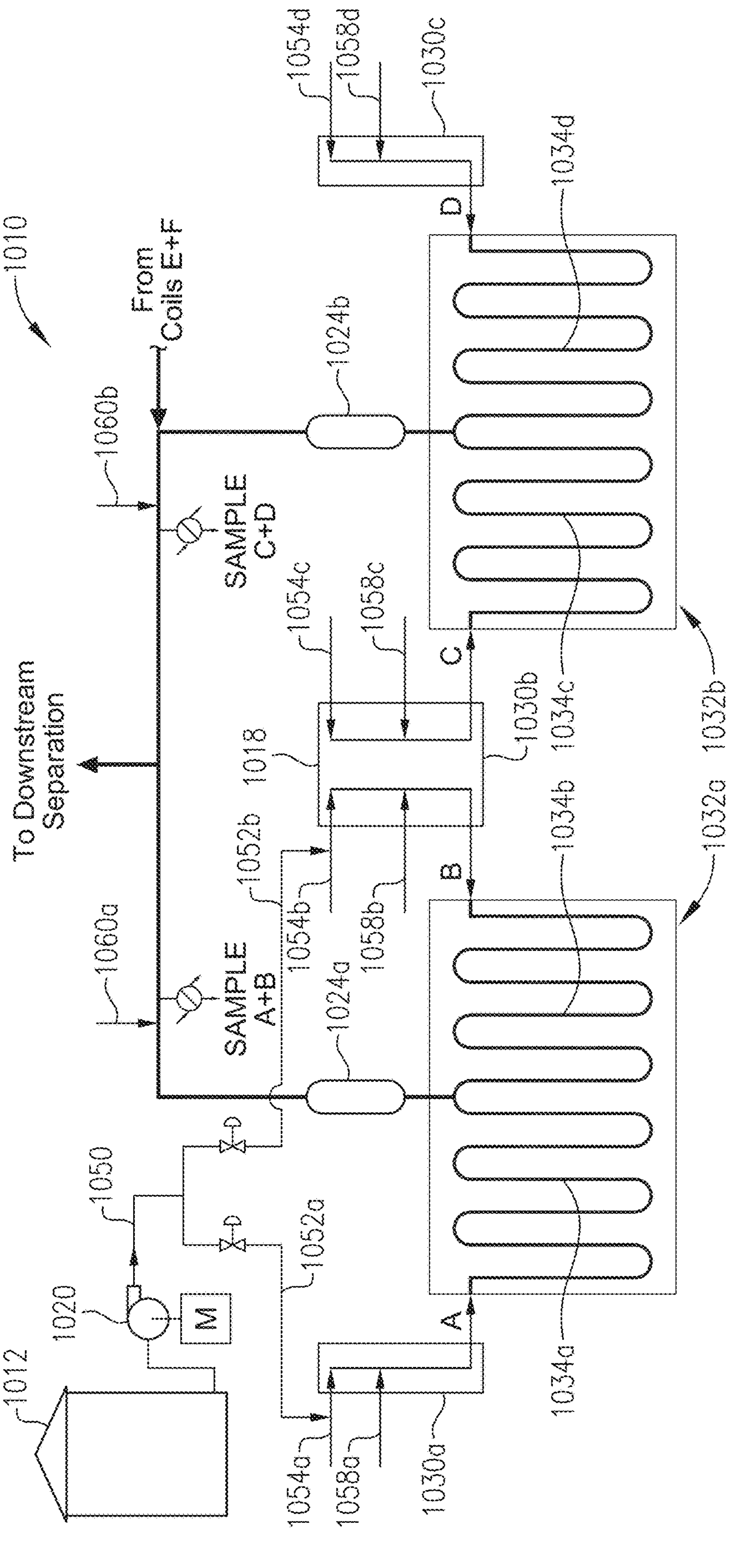
FIG. 12 illustrates design features of a plant-based trial feeding r-pyoil to a gas fed cracker furnace.
Figure 13:
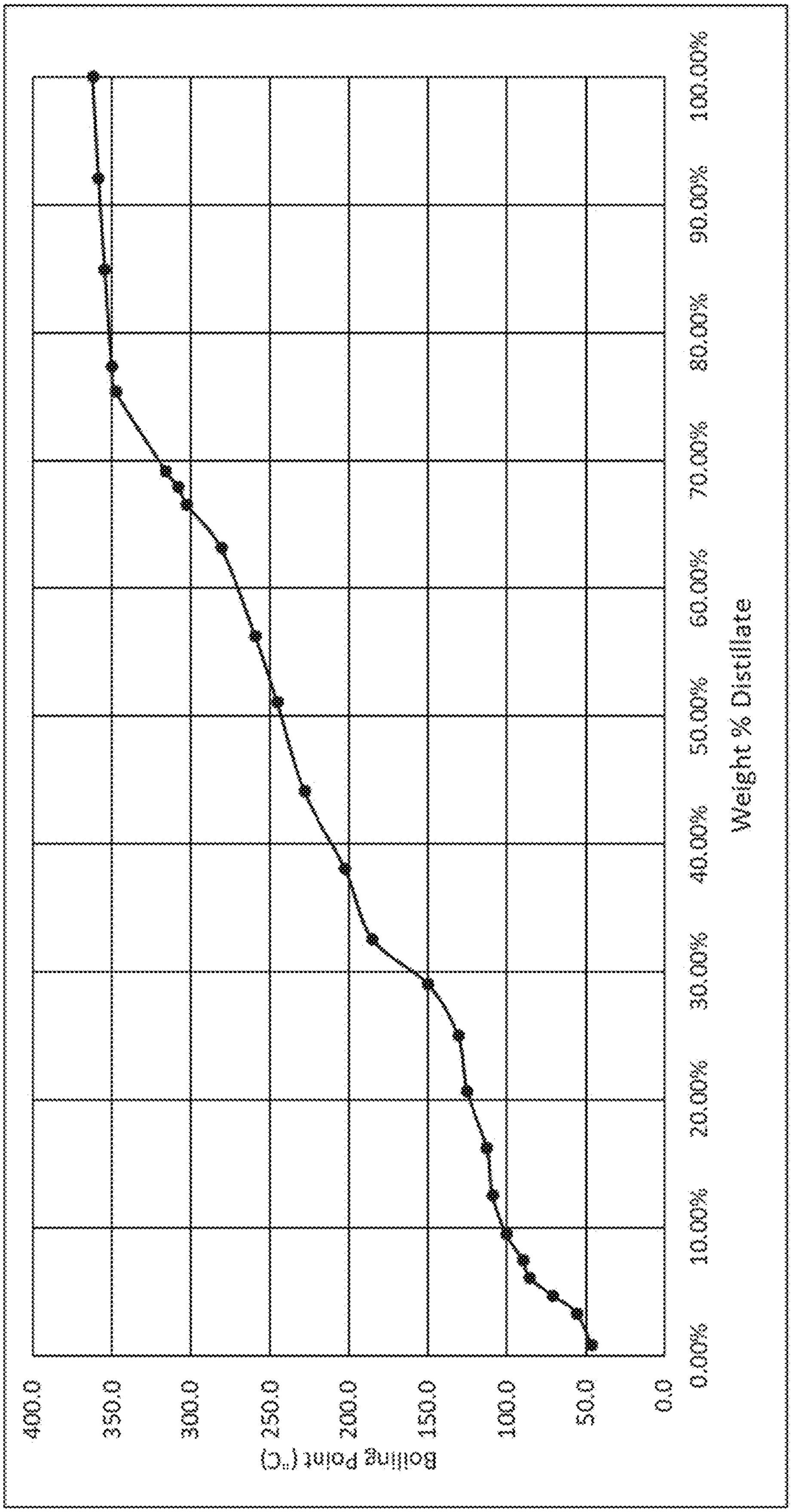
FIG. 13 is a graph of the boiling point curve of a r-pyoil having 74.86% C8+, 28.17% C15+, 5.91% aromatics, 59.72% paraffins, and 13.73% unidentified components by gas chromatography analysis.
Figure 14:
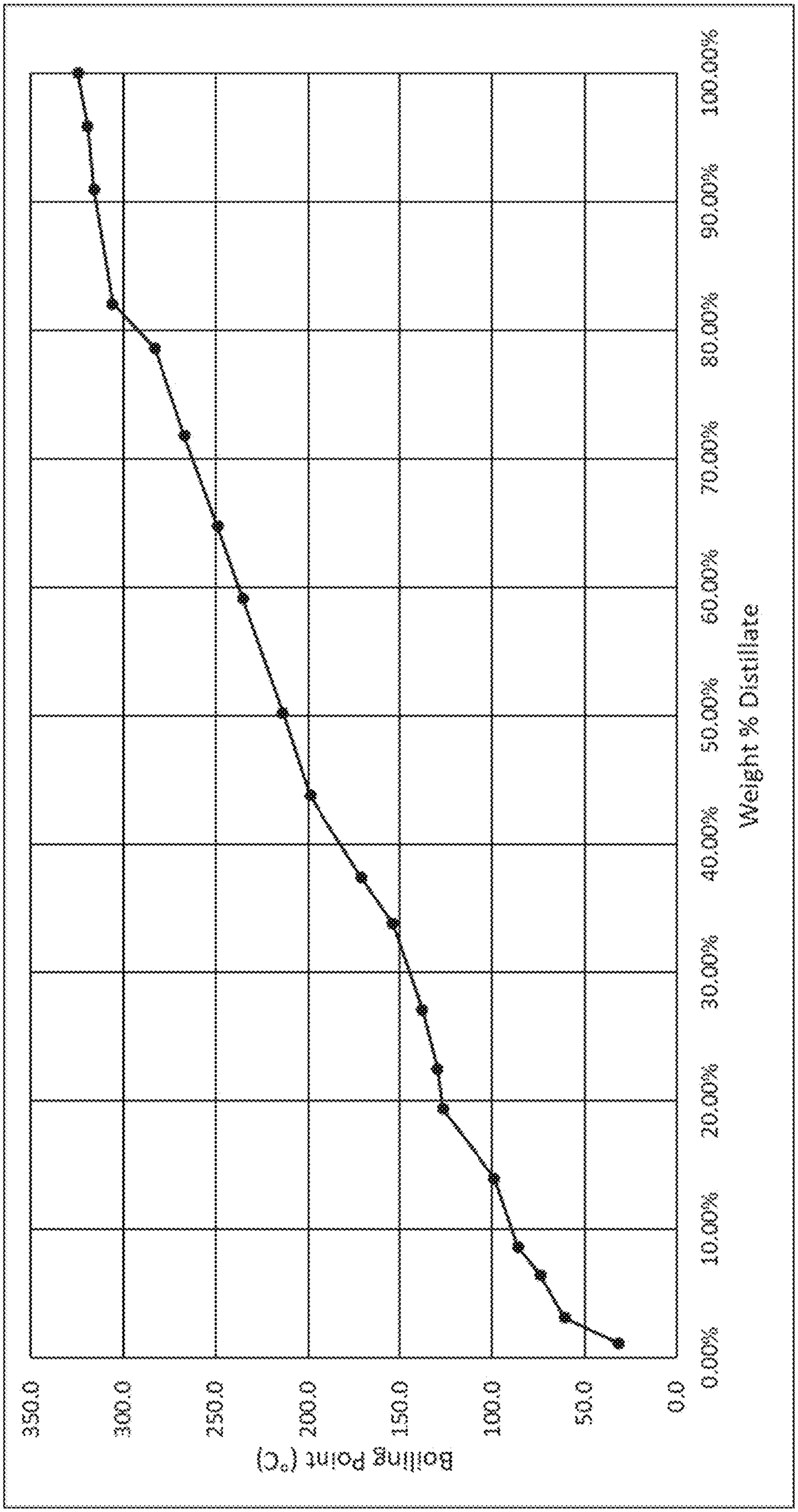
FIG. 14 is a graph of the boiling point curve of a r-pyoil obtained by gas chromatography analysis.
Figure 15:
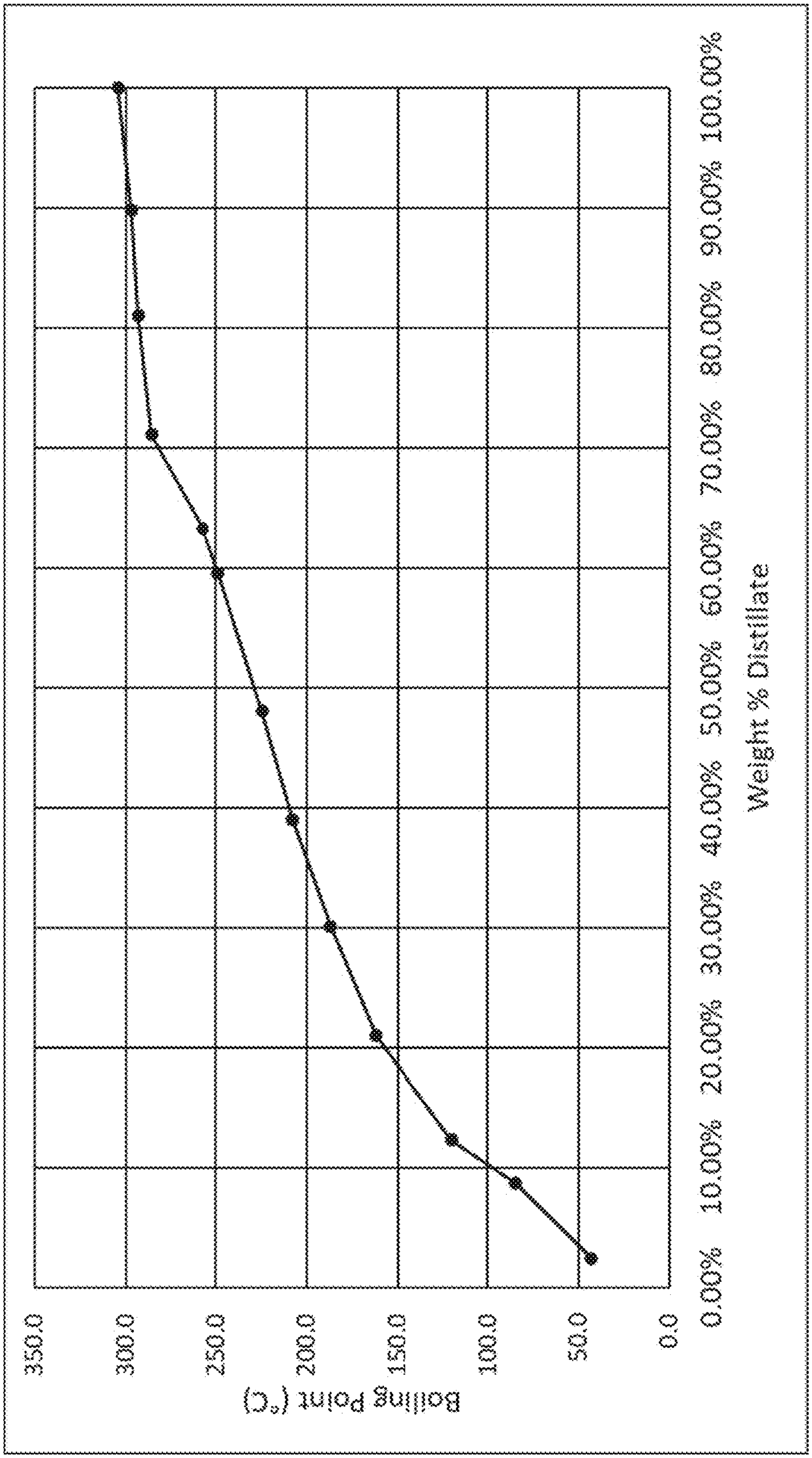
FIG. 15 is a graph of the boiling point curve of a r-pyoil obtained by gas chromatography analysis.
Figure 16:
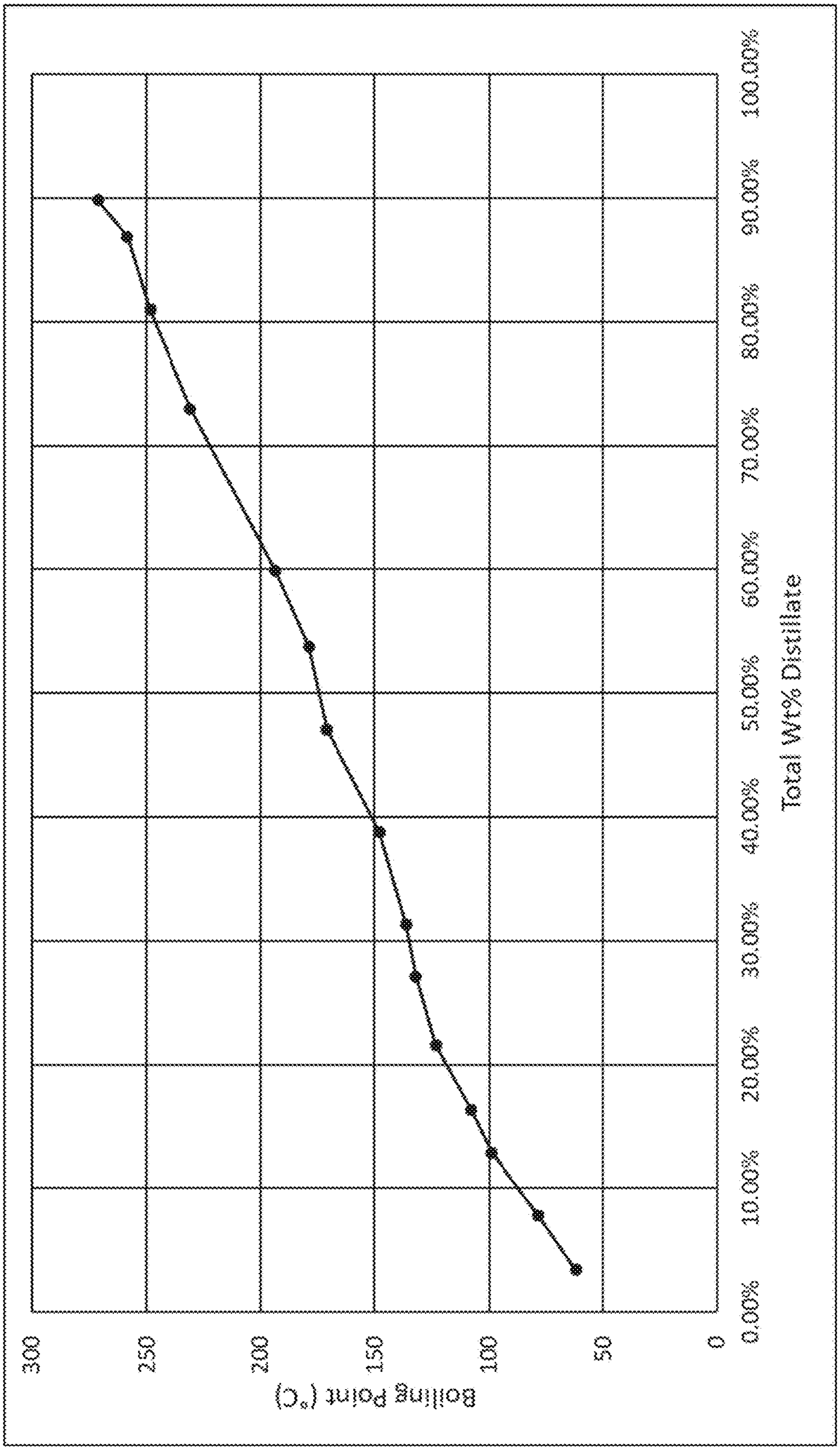
FIG. 16 is a graph of the boiling point curve of a r-pyoil distilled in a lab and obtained by chromatography analysis.

About 13,000 gallons from tank 1012 of r-pyoil were used in the plant test as show in FIG. 12. The furnace coil outlet temperature was controlled either by the testing coil (Coil-A 1034*a* or Coil-B 1034*b*) outlet temperature or by the propane coil (Coil C 1034*c*, coil D 1034*d* through F) outlet temperature, depending on the objective of the test. In FIG. 12 the steam cracking system with r-pyoil 1010; 1012 is the r-pyoil tank; 1020 is the r-pyoil tank pump; 1024*a* and 1226*b* are TLE (transfer line exchanger); 1030*a, b*,c is the furnace convection section; 1034*a, b, c, d* are the coils in furnace firebox (the radiant section); 1050 is the r-pyoil transfer line; 1052*a, b* are the r-pyoil feed that is added into the system; 1054*a, b, c, d* are the regular hydrocarbon feed; 1058*a, b, c, d*—are dilution steam; 1060*a* and 1060*b* are cracked effluent. The furnace effluent is quenched, cooled to ambient temperature and separated out condensed liquid, the gas portion is sampled and analyzed by gas chromatograph.

For the testing coils, propane flow 1054*a* and 1054*b* were controlled and measured independently. Steam flow 1058*a* and 1058*b* were either controlled by Steam/HC ratio controller or in an AUTO mode at a constant flow, depending on the objective of the test. In the non-testing coils, the propane flow was controlled in AUTO mode and steam flow was controlled in a ratio controller at Steam/Propane=0.3.

r-pyoil was obtained from tank 1012 through r-pyoil flow meters and flow control valves into propane vapor lines, from where r-pyoil flowed along with propane into the convection section of the furnace and further down into the radiant section also called the firebox. FIG. 12 shows the process flow.

Figure 23:
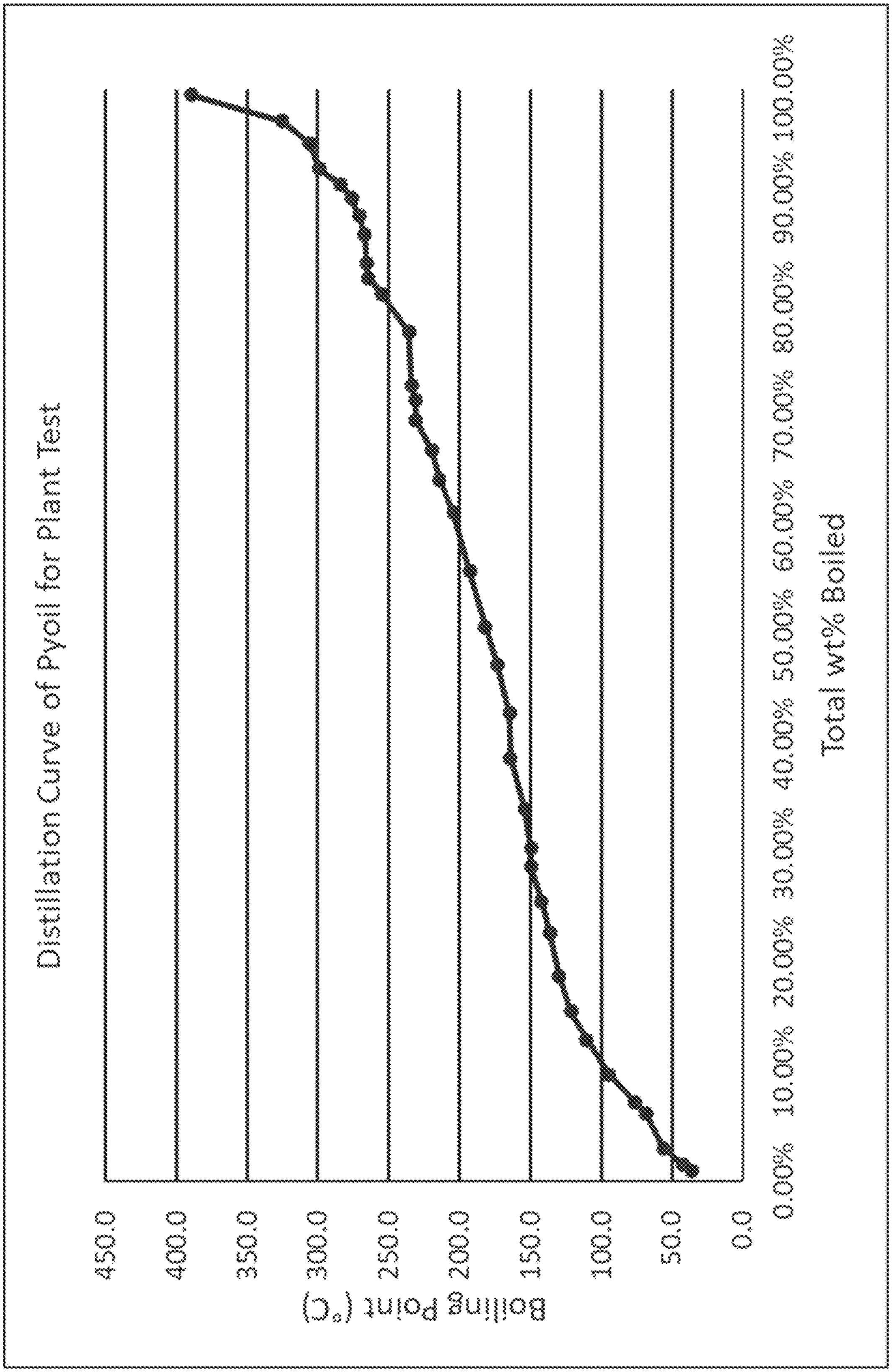
FIG. 23 is a graph of the boiling point curve of r-pyoil used in the plant trial experiments.
Figure 24:
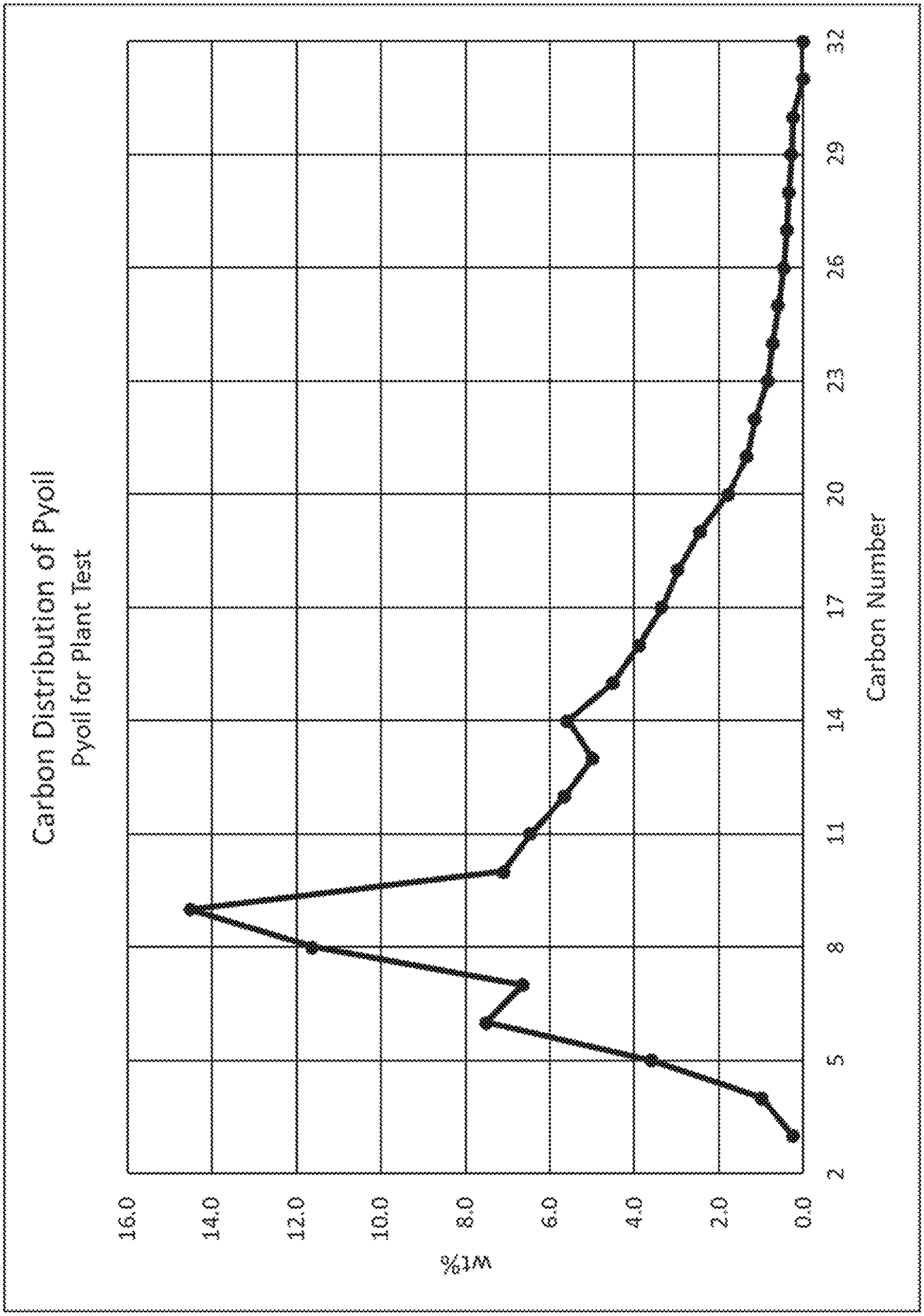
FIG. 24 is a graph of the carbon distribution of the r-pyoil used in the plant experiments.
Figure 25:
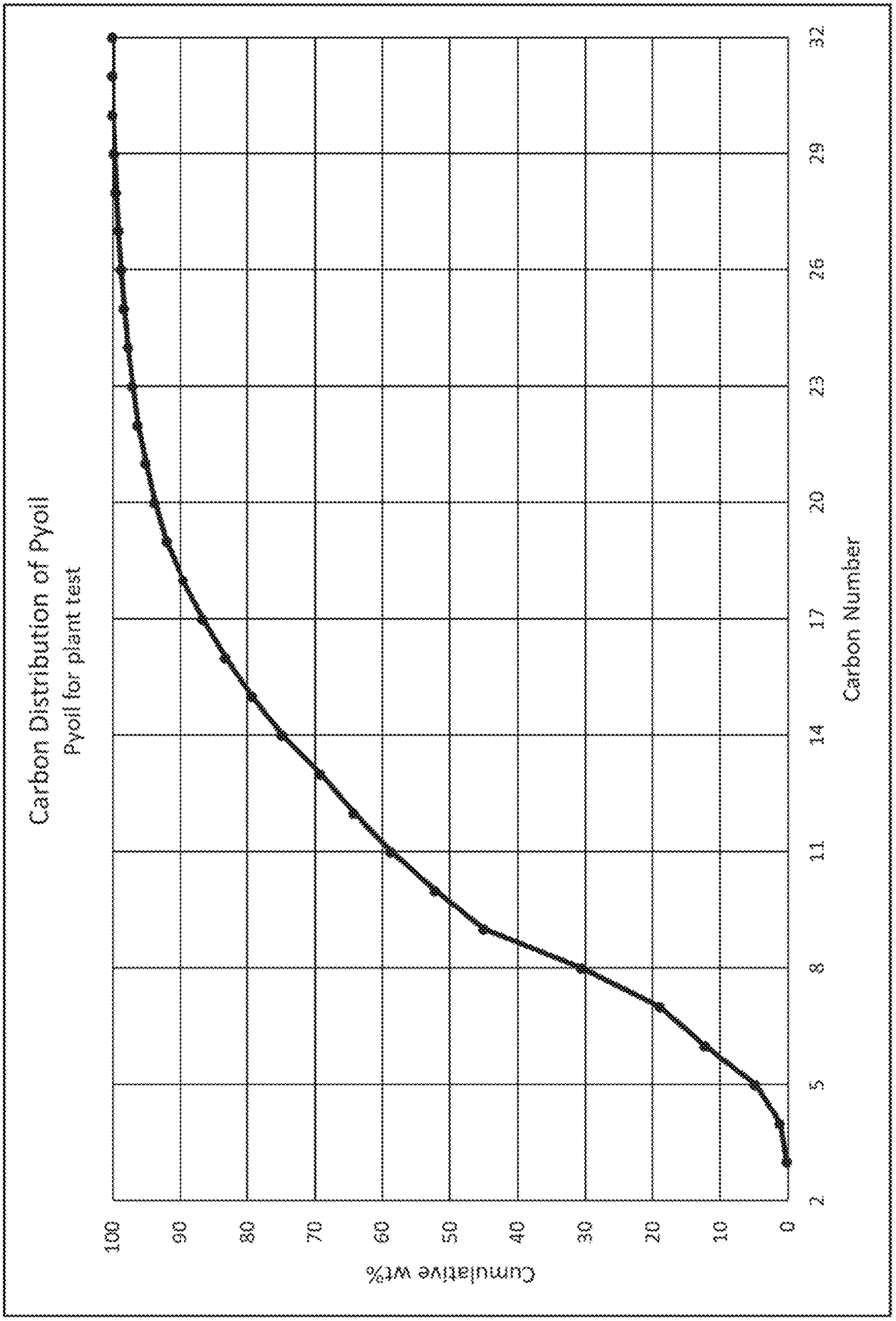
FIG. 25 is a graph of the carbon distribution by cumulative weight percent of the r-pyoil used in the plant experiments.

The r-pyoil properties are shown in and Table 10 and FIG. 23. The r-pyoil contained a small amount of aromatics, less than 8 wt. %, but a lot of alkanes (more than 50%), thus making this material as a preferred feedstock for steam cracking to light olefins. However, the r-pyoil had a wide distillation range, from initial boiling point of about 40° C. to an end point of about 400° C., as shown in Table 10 and FIGS. 24 and 25, covering a wide range of carbon numbers ($C_4$ to $C_{30}$ as shown in Table 10). Another good characteristic of this r-pyoil is its low sulfur content of less than 100 ppm, but the r-pyoil had high nitrogen (327 ppm) and chlorine (201 ppm) content. The composition of the r-pyoil by gas chromatography analysis is shown in Table 11.

TABLE 10

Properties of r-pyoil for plant test.

| | |
|---|---|
| **Physical Properties** | |
| Density, 22.1 °C, g/ml | 0.768 |
| Viscosity, 22.1 C, cP | 1.26 |
| Initial Boiling Point, °C | 45 |
| Flash Point, °C | Below −1.1 |
| Pour Point, °C | −5.5 |
| **Impurities** | |
| Nitrogen, ppmw | 327 |
| Sulfur, ppmw | 74 |
| Chlorine, ppmw | 201 |
| **Hydrocarbons, wt %** | |
| Total Identified alkanes | 58.8 |
| Total Identified Aromatics | 7.2 |
| Total Identified Olefins | 16.7 |
| Total Identified Dienes | 1.1 |
| Total Identified Hydrocarbons | 83.5 |

TABLE 11 r-Pyoil composition.

| Component | wt % | Component | wt % | Component | wt % | Component | wt % |
|---|---|---|---|---|---|---|---|
| Propane | 0.17 | 2,4-dimethylheptene | 1.52 | C12-Alkane | 3.21 | C9-Alkane | 1.81 |
| 1,3-Butadiene | 0.97 | 2,4-dimethylheptane | 3.98 | C13-Alkene | 1.19 | C20-Alkene | 0.25 |
| Pentene | 0.40 | Ethylbenzene | 3.07 | C13-Alkane | 2.91 | C20-Alkane | 1.53 |
| Pentane | 3.13 | m,p-xylene | 0.66 | 2-methylnapthalene | 0.52 | C21-Alkene | 0.00 |
| 2-methyl-Pentene | 2.14 | Styrene | 1.11 | C14-Alkene | 0.83 | C21-Alkane | 1.28 |
| 2-methyl-Pentane | 2.46 | Mol. Weight = 140 | 1.73 | C14-Alkane | 3.02 | C22-Alkane | 1.10 |
| Hexane | 1.83 | Nonane | 2.81 | acenapthalene | 0.19 | C23-Alkane | 0.87 |
| 2,4-dimethylpentene | 0.20 | Cumene | 0.36 | C15-alkene | 0.86 | C24-Alkane | 0.72 |
| Benzene | 0.17 | Decene/methylstyrene | 1.16 | C15-alkane | 3.00 | C25-Alkane | 0.57 |
| 5-methyl-1,3-cydopentadiene | 0.17 | Deane | 3.16 | C16-Alkene | 0.58 | C26-Alkane | 0.47 |
| Heptene | 1.15 | Indene | 0.20 | C16-Alkane | 2.86 | C27-Alkane | 0.36 |
| Heptane | 2.87 | Indane | 0.26 | C17-Alkene | 0.46 | c28-Alkane | 0.28 |
| Toluene | 1.07 | C11-Alkene | 1.31 | C17-Alkne | 2.42 | c29-Alkane | 0.22 |
| 4-methytheptane | 1.65 | C11Alkane | 3.29 | C18-Alkene | 0.32 | C30-Alkane | 0.17 |
| Octene | 1.51 | Napthanlene | 0.00 | C18-Alkane | 2.10 | Total Identified | 83.5% |
| Octane | 2.77 | C12-Alkene | 1.29 | C19-Alkene | 0.37 | | |

Before the plant test started, eight (8) furnace conditions (more specifically speaking, eight conditions on the testing coils) were chosen. These included r-pyoil content, coil outlet temperature, total hydrocarbon feeding rate, and the ratio of steam to total hydrocarbon. The test plan, objective and furnace control strategy are shown in Table 12. "Float Mode" means the testing coil outlet temperature is not controlling the furnace fuel supply. The furnace fuel supply is controlled by the non-testing coil outlet temperature, or the coils that do not contain r-pyoil.

TABLE 12

Plan for the plant test of r-pyoil co-cracking with propane.

| Condition | COT, °F | Pyoil w % | Py/C3H8 | TOTAL, KLB/HR | Pyoil/coil, GPM | Pyoil/coil, lb/hr | Stm/HC ratio | Propane/coil, klb/hr |
|---|---|---|---|---|---|---|---|---|
| Base-line | 1500 | 0 | 0.000 | 6.0 | 0.00 | 0 | 0.3 | 6.00 |
| 1A | Float Mode | 5 | 0.053 | 6.0 | 0.79 | 300 | 0.3 | 5.70 |
| 1B | Float Mode | 10 | 0.111 | 6.0 | 1.58 | 600 | 0.3 | 5.40 |
| 1C & 2A | Float Mode | 15 | 0.176 | 6.0 | 2.36 | 900 | 0.3 | 5.10 |
| 2B | Lower by at least 10F than the base-line | 15 | 0.176 | 6.0 | 2.36 | 900 | 0.3 | 5.10 |
| 3A & 2C | 1500 | 15 | 0.176 | 6.0 | 2.36 | 900 | 0.3 | 5.10 |
| 3B | 1500 | 15 | 0.176 | 6.9 | 2.72 | 1035 | 0.3 | 5.87 |
| 4A | 1500 | 15 | 0.176 | 6.0 | 2.36 | 900 | 0.4 | 5.10 |
| 4B | 1500 | 15 | 0.176 | 6.0 | 2.36 | 900 | 0.5 | 5.10 |
| 5A | Float Mode | 4.8 | 0.050 | 6.3 | 0.79 | 300 | 0.3 | 6.00 |
| 5B | At 2B COT | 4.8 | 0.050 | 6.3 | 0.79 | 302 | 0.3 | 6.00 |

Effect of Addition of r-Pyoil

The results of r-Pyoil addition can be observed differently depending on how propane flow, steam/HC ratio and furnace are controlled. Temperatures at crossover and coil outlet changed differently depending on how propane flow and steam flow are maintained and how the furnace (the fuel supply to the firebox) was controlled. There were six coils in the testing furnace. There were several ways to control the furnace temperature via the fuel supply to the firebox. One of them was to control the furnace temperature by an individual coil outlet temperature, which was used in the test. Both a testing coil and a non-testing coil were used to control the furnace temperature for different test conditions.

Example 59.1—at Fixed Propane Flow, Steam/HC Ratio and Furnace Fuel Supply (Condition 5A)

In order to check the r-pyoil **1052*a* addition effect, propane flow and steam/HC ratio were held constant, and furnace temperature was set to control by a non-testing coil (Coil-C) outlet temperature. Then r-pyoil 1052*a***, in liquid form, without preheating, was added into the propane line at about 5% by weight.

Temperature changes: After the r-pyoil **1052*a* addition, the crossover temperature dropped about 10° F. for A and B coil, COT dropped by about 7° F. as shown in Table 13. There are two reasons that the crossover and COT temperature dropped. One, there was more total flow in the testing coils due to r-pyoil 1052*a* addition, and two, r-pyoil 1052*a*** evaporation from liquid to vapor in the coils at the convection section needed more heat thus dropping the temperature down. With a lower coil inlet temperature at the radiant section, the COT also dropped. The TLE exit temperature went up due to a higher total mass flow through the TLE on the process side.

Cracked gas composition change: As can be seen from the results in Table 13, methane and r-ethylene decreased by about 1.7 and 2.1 percentage points, respectively, while r-propylene and propane increased by 0.5 and 3.0 percentage points, respectively. The propylene concentration increased as did the propylene:ethylene ratio relative to the baseline of no pyoil addition. This was the case even though the propane concentration also increased. Others did not change much. The change in r-ethylene and methane was due to the lower propane conversion at the higher flow rate, which was shown by a much higher propane content in the cracked gas.

TABLE 13

Changes When Hydrocarbon Mass Flow Increases By Adding r-pyoil To Propane At 5% At Constant Propane Flow, Steam/HC Ratio And Firebox Condition.

| | Base-line | Base-line | 5A Add in Pyoil |
|---|---|---|---|
| A&B Propane flow, klb/hr | 11.87 | 11.86 | 11.85 |
| A&B Pyoil Flow, lb/hr | 0 | 0 | 593 |
| A&B Steam flow, lb/hr | 3562 | 3556 | 3737 |
| A&B total HC flow, klb/hr | 11.87 | 11.86 | 12.44 |
| Pyoil/(poil + propane), % | 0.0 | 0.0 | 4.8 |
| Steam/HC, ratio | 0.30 | 0.30 | 0.30 |
| A&B Crossover T, F | 1092 | 1091 | 1081 |
| A&B COT, F | 1499 | 1499 | 1492 |
| A&B TLE Exit T, F | 691 | 691 | 698 |
| A&B TLE inlet, PSIG | 10.0 | 10.0 | 10.0 |
| A&B TLE ExitT, PSIG | 9.0 | 9.0 | 9.0 |
| Cracked Gas Product | wt % | wt % | wt % |
| Hydrogen | 1.26 | 1.39 | 1.29 |
| Methane | 18.83 | 18.89 | 17.15 |
| Ethane | 4.57 | 4.54 | 4.38 |
| Ethylene | 31.25 | 31.11 | 28.94 |
| Acetylene | 0.04 | 0.04 | 0.04 |
| Propane | 20.13 | 21.25 | 24.15 |
| Propylene | 17.60 | 17.88 | 18.36 |
| MAPD | 0.26 | 0.25 | 0.25 |
| Butanes | 0.11 | 0.12 | 0.15 |
| Butadiene | 1.73 | 1.67 | 1.65 |
| Butenes + CPD | 1.41 | 1.41 | 1.62 |
| Other C5s | 0.42 | 0.37 | 0.40 |
| C6s+ | 1.34 | 0.93 | 1.55 |
| CO2 | 0.046 | 0.022 | 0.007 |
| CO | 1.001 | 0.134 | 0.061 |
| Aver. M.W. | 24.5 | 24.2 | 25.1 |

Example 59.2 at Fixed Total HC Flow, Steam/HC Ratio and Furnace Fuel Supply (Conditions 1A, 1B, & 1C)

In order to check how the temperatures and crack gas composition changed when the total mass of hydrocarbons to the coil was held constant while the percent of r-pyoil 1052*a* in the coil varied, steam flow to the testing coil was held constant in AUTO mode, and the furnace was set to control by a non-testing coil (Coil-C) outlet temp to allow the testing coils to be in Float Mode. The r-pyoil 1052*a*, in liquid form, without preheating, was added into propane line at about 5, 10 and 15% by weight, respectively. When r-pyoil 1052*a* flow was increased, propane flow was decreased accordingly to maintain the same total mass flow of hydrocarbon to the coil. Steam/HC ratio was maintained at 0.30 by a constant steam flow.

Temperature Change: As the r-pyoil 1052*a* content increased to 15%, crossover temperature dropped modestly by about 5° F., COT increased greatly by about 15° F., and TLE exit temperature just slightly increased by about 3° F., as shown in Table 14A.

Cracked gas composition change: As r-pyoil 1052*a* content in the feed increased to 15%, methane, ethane, r-ethylene, r-butadiene and benzene in cracked gas all went up by about 0.5, 0.2, 2.0, 0.5, and 0.6 percentage points, respectively. r-Ethylene/r-propylene ratio went up. Propane dropped significantly by about 3.0 percentage points, but r-propylene did not change much, as shown in Table 14A. These results showed the propane conversion increased. The increased propane conversion was due to the higher COT. When the total hydrocarbon feed to coil, steam/HC ratio and furnace fuel supply are held constant, the COT should go down when crossover temperature drops. However, what was seen in this test was opposite. The crossover temperature declined but COT went up, as shown in Table 14A. This indicates that r-pyoil 1052*a* cracking does not need as much heat as propane cracking on the same mass basis.

TABLE 14A

Variation of R-pyoil content and its effect on cracked gas and temperatures (Steam/HC ratio and furnace firebox were held constant).

| | Base-line | Base-line | 1A, 5% Pyoil | 1A, 5% Pyoil | 1B, 10% Pyoil | 1B, 10% Pyoil | 1C, 15% Pyoil | 1C, 15% pyoil |
|---|---|---|---|---|---|---|---|---|
| A & B Propane flow, klb/hr | 11.87 | 11.86 | 11.25 | 11.25 | 10.66 | 10.68 | 10.06 | 10.07 |
| A & B Pyoil Flow, lb/hr | 0 | 0 | 537 | 536 | 1074 | 1074 | 1776 | 1778 |
| A & B Steam flow, lb/hr | 3562 | 3556 | 3544 | 3543 | 3523 | 3523 | 3562 | 3560 |
| A & B total HC flow, klb/hr | 11.87 | 11.86 | 11.79 | 11.78 | 11.74 | 11.75 | 11.84 | 11.85 |
| Pyoil/(poil + propane), % | 0.0 | 0.0 | 4.6 | 4.6 | 9.2 | 9.1 | 15.0 | 15.0 |
| Steam/HC, ratio | 0.30 | 0.30 | 0.30 | 0.30 | 0.30 | 0.30 | 0.30 | 0.30 |
| A & B Crossover T, F | 1092 | 1091 | 1092 | 1092 | 1090 | 1090 | 1088 | 1087 |
| A & B COT, F | 1499 | 1499 | 1503 | 1503 | 1509 | 1509 | 1514 | 1514 |
| A & B TLE Exit T, F | 691 | 691 | 692 | 692 | 692 | 692 | 693 | 693 |
| A & B TLE Inlet, PSIG | 10.0 | 10.0 | 10.5 | 10.5 | 10.0 | 10.0 | 10.0 | 10.0 |
| A & B TLE ExitT, PSIG | 9.0 | 9.0 | 9.0 | 9.0 | 9.0 | 9.0 | 9.0 | 9.0 |
| Cracked Gas Product | wt % | wt % | wt % | wt % | wt % | wt % | wt % | wt % |
| Hydrogen | 1.26 | 1.39 | 1.40 | 1.32 | 1.33 | 1.28 | 1.31 | 1.18 |
| Methane | 18.83 | 18.89 | 18.96 | 18.74 | 19.31 | 19.08 | 19.61 | 19.16 |
| Ethane | 4.57 | 4.54 | 4.59 | 4.69 | 4.70 | 4.81 | 4.67 | 4.85 |
| Ethylene | 31.25 | 31.11 | 31.52 | 31.62 | 32.50 | 32.63 | 33.06 | 33.15 |
| Acetylene | 0.04 | 0.04 | 0.04 | 0.04 | 0.05 | 0.05 | 0.05 | 0.05 |
| Propane | 20.13 | 21.25 | 20.00 | 19.95 | 18.58 | 18.65 | 16.97 | 17.54 |
| Propylene | 17.60 | 17.88 | 17.85 | 17.86 | 17.79 | 17.85 | 17.58 | 17.81 |
| MAPD | 0.26 | 0.25 | 0.27 | 0.27 | 0.29 | 0.29 | 0.30 | 0.30 |
| Butanes | 0.11 | 0.12 | 0.11 | 0.11 | 0.10 | 0.10 | 0.10 | 0.10 |
| Butadiene | 1.73 | 1.67 | 1.86 | 1.86 | 2.04 | 2.03 | 2.23 | 2.17 |
| Butenes + CPD | 1.41 | 1.41 | 1.52 | 1.52 | 1.59 | 1.57 | 1.67 | 1.65 |
| Other C5s | 0.42 | 0.37 | 0.38 | 0.38 | 0.38 | 0.37 | 0.40 | 0.39 |
| C6s+ | 1.34 | 0.93 | 1.37 | 1.50 | 1.24 | 1.21 | 1.95 | 1.56 |
| CO2 | 0.046 | 0.022 | 0.012 | 0.016 | 0.011 | 0.011 | 0,007 | 0.008 |
| CO | 1.001 | 0.134 | 0.107 | 0.107 | 0.085 | 0.088 | 0.086 | 0.084 |
| Aver. M.W. | 24.5 | 24.2 | 24.2 | 24.4 | 24.2 | 24.4 | 24.2 | 24.6 |

Example 59.3 at Constant COT and Steam/HC Ratio (Conditions 2B, & 5B)

In the previous test and comparison, effect of r-pyoil 1052*a* addition on cracked gas composition was influenced not only by r-pyoil 1052*a* content but also by the change of COT because when r-pyoil 1052*a* was added, COT changed accordingly (it was set to Float Mode). In this comparison test, COT was held constant. The test conditions and cracked gas composition are listed in Table 14B. By comparing the data in Table 14B, the same trend in cracked gas composition was found as in the case Example 59.2. When r-pyoil 1052*a* content in the hydrocarbon feed was increased, methane, ethane, r-ethylene, r-butadiene in cracked gas went up, but propane dropped significantly while r-propylene did not change much.

TABLE 14B

Changing r-Pyoil 1052a content in HC feed at constant coil outlet temperature.

| | 5B, Pyoil 5% @lowT | 2B, 15% Pyoil | 2B, 15% Pyoil |
|---|---|---|---|
| A&B Propane flow, klb/hr | 11.85 | 10.07 | 10.07 |
| A&B Pyoil Flow, lb/hr | 601 | 1778 | 1777 |

TABLE 14B-continued

| Changing r-Pyoil 1052a content in HC feed at constant coil outlet temperature. | | | |
|---|---|---|---|
| A&B Steam flow, lb/hr | 3738 | 3560 | 3559 |
| A&B total HC flow, klb/hr | 12.45 | 11.85 | 11.85 |
| Pyoil/(pail + propane), % | 4.8 | 15.0 | 15.0 |
| Steam/HC, ratio | 0.30 | 0.30 | 0.30 |
| A&B Crossover T, F | 1062 | 1055 | 1059 |
| A&B COT, F | 1478 | 1479 | 1479 |
| A&B TLE Exit T, F | 697 | 688 | 688 |
| A&B TLE Inlet, PSIG | 10.0 | 10.0 | 10.0 |
| A&B TLE Exit T, PSIG | 9.0 | 9.0 | 9.0 |
| Cracked Gas Product | wt % | wt % | wt % |
| Hydrogen | 1.20 | 1.12 | 1.13 |
| Methane | 16.07 | 16.60 | 16.23 |
| Ethane | 4.28 | 4.81 | 4.65 |
| Ethylene | 27.37 | 29.33 | 28.51 |
| Acetylene | 0.03 | 0.04 | 0.04 |
| Propane | 27.33 | 24.01 | 25.51 |
| Propylene | 18.57 | 18.45 | 18.59 |
| MAPD | 0.23 | 0.27 | 0.25 |
| Butanes | 0.17 | 0.14 | 0.16 |
| Butadiene | 1.50 | 1.94 | 1.76 |
| Butenes + CPD | 1.63 | 1.65 | 1.73 |

TABLE 14B-continued

| Changing r-Pyoil 1052a content in HC feed at constant coil outlet temperature. | | | |
|---|---|---|---|
| Aver. M.W. | 25.8 | 25.7 | 25.9 |
| C2H4/C3H6, wt/wt | 1.47 | 1.59 | 1.53 |

Example 59.4 Effect of COT on Effluent Composition with R-Pyoil 1052*a* in Feed (Conditions 1C, 2B, 2C, 5A & 5B)

r-Pyoil 1052*a* in the hydrocarbon feed was held constant at 15% for 2B, and 2C. r-pyoil for 5A and 5B were reduced to 4.8%. The total hydrocarbon mass flow and steam to HC ratio were both held constant.

On cracked gas composition. When COT increased from 1479° F. to 1514° F. (by 35° F.), r-ethylene and r-butadiene in the cracked gas went up by about 4.0 and 0.4 percentage points, respectively, and r-propylene went down by about 0.8 percentage points, as shown in Table 15.

When r-pyoil 1052*a* content in the hydrocarbon feed was reduced to 4.8%, the COT effect on the cracked gas composition followed the same trend as that with 15% r-Pyoil 1052*a*.

TABLE 15

Effect of COT on cracked gas composition.
(Steam/HC ratio, R-pyoil 1052a content in the feed and total hydrocarbon mass flow were all held constant)

| | 1C, 15% Pyoil | 1C, 15% pyoil | 2B, 15% Pyoil | 2B, 15% Pyoil | 2C, 15% Pyoil | 2C, 15% Pyoil | 5A, Add in Pyoil 5% to $C_3H_8$ | 5B, Pyoil 5% @ lowT |
|---|---|---|---|---|---|---|---|---|
| A & B Propane flow, klb/hr | 10.06 | 10.07 | 10.07 | 10.07 | 10.07 | 10.06 | 11.85 | 11.85 |
| A & B Pyoil Flow, lb/hr | 1776 | 1778 | 1778 | 1777 | 1777 | 1776 | 593 | 601 |
| A & B Steam flow, lb/hr | 3562 | 3560 | 3560 | 3559 | 3560 | 3559 | 3737 | 3738 |
| A & B total HC flow, klb/hr | 11.84 | 11.85 | 11.85 | 11.85 | 11.84 | 11.84 | 12.44 | 12.45 |
| Pyoil/(poil + propane), % | 15.0 | 15.0 | 15.0 | 15.0 | 15.0 | 15.0 | 4.8 | 4.8 |
| Steam/HC, ratio | 0.30 | 0.30 | 0.30 | 0.30 | 0.30 | 0.30 | 0.30 | 0.30 |
| A & B Crossover T, F | 1088 | 1087 | 1055 | 1059 | 1075 | 1076 | 1081 | 1062 |
| A & B COT, F | 1514 | 1514 | 1479 | 1479 | 1497 | 1497 | 1492 | 1478 |
| A & B TLE ExitT, F | 693 | 693 | 688 | 688 | 690 | 691 | 698 | 697 |
| A & B TLE Inlet, PSIG | 10.0 | 10.0 | 10.0 | 10.0 | 10.0 | 10.0 | 10.0 | 10.0 |
| A & B TLE ExitT, PSIG | 9.0 | 9.0 | 9.0 | 9.0 | 9.0 | 9.0 | 9.0 | 9.0 |
| Cracked Gas Product | wt % | wt % | wt % | wt % | wt % | wt % | wt % | wt % |
| Hydrogen | 1.31 | 1.18 | 1.12 | 1.13 | 1.26 | 1.25 | 1.29 | 1.20 |
| Methane | 19.61 | 19.16 | 16.60 | 16.23 | 18.06 | 17.87 | 17.15 | 16.07 |
| Ethane | 4.67 | 4.85 | 4.81 | 4.65 | 4.72 | 4.75 | 4.38 | 4.28 |
| Ethylene | 33.06 | 33.15 | 29.33 | 28.51 | 31.03 | 30.73 | 28.94 | 27.37 |
| Acetylene | 0.05 | 0.05 | 0.04 | 0.04 | 0.04 | 0.04 | 0.04 | 0.03 |
| Propane | 16.97 | 17.54 | 24.01 | 25.51 | 21.17 | 21.10 | 24.15 | 27.33 |
| Propylene | 17.58 | 17.81 | 18.45 | 18.59 | 18.29 | 18.30 | 18.36 | 18.57 |
| MAPD | 0.30 | 0.30 | 0.27 | 0.25 | 0.27 | 0.28 | 0.25 | 0.23 |
| Butanes | 0.10 | 0.10 | 0.14 | 0.16 | 0.13 | 0.13 | 0.15 | 0.17 |
| Butadiene | 2.23 | 2.17 | 1.94 | 1.76 | 1.87 | 1.99 | 1.65 | 1.50 |
| Butenes + CPD | 1.67 | 1.65 | 1.65 | 1.73 | 1.71 | 1.77 | 1.62 | 1.63 |
| Other C5s | 0.40 | 0.39 | 0.35 | 0.35 | 0.37 | 0.40 | 0.40 | 0.40 |
| C6s+ | 1.95 | 1.56 | 1.21 | 1.03 | 1.00 | 1.30 | 1.55 | 1.17 |
| CO2 | 0.007 | 0.008 | 0.010 | 0.007 | 0.009 | 0.009 | 0.007 | 0.007 |
| CO | 0.086 | 0.084 | 0.065 | 0.054 | 0.070 | 0.072 | 0.061 | 0.047 |
| Aver. M.W. | 24.2 | 24.6 | 25.7 | 25.9 | 24.8 | 24.9 | 25.1 | 25.8 |

TABLE 14B-continued

| Changing r-Pyoil 1052a content in HC feed at constant coil outlet temperature. | | | |
|---|---|---|---|
| Other C5s | 0.40 | 0.35 | 0.35 |
| C6s+ | 1.17 | 1.21 | 1.03 |
| CO2 | 0.007 | 0.010 | 0.007 |
| CO | 0.047 | 0.065 | 0.054 |

Example 59.5 Effect of Steam/HC Ratio (Conditions 4A & 4B)

Steam/HC ratio effect is listed in Table 16A. In this test, r-pyoil 1052*a* content in the feed was held constant at 15%. COT in the testing coils was held constant in SET mode, while the COTs at non-testing coils were allowed to float. Total hydrocarbon mass flow to each coil was held constant.

On temperature. When steam/HC ratio was increased from 0.3 to 0.5, the crossover temperature dropped by about 17° F. since the total flow in the coils in the convection section increased due to more dilution steam, even though the COT of the testing coil was held constant. Due to the same reason, TLE exit temperature went up by about 13 F.

On cracked gas composition. In the cracked gas, methane and r-ethylene were reduced by 1.6 and 1.4 percentage points, respectively, and propane was increased by 3.7 percentage points. The increased propane in the cracked gas indicated propane conversion dropped. This was due to, firstly, a shorter residence time, since in the 4B condition, the total moles (including steam) going into the coils was about 1.3 times of that in 2° C. condition (assuming the average molecular weight of r-pyoil 1052*a* was 160), and secondly, to the lower crossover temperature which was the inlet temperature for the radiant coil, making the average cracking temperature lower.

TABLE 16B

Renormalized cracked gas composition. (R-pyoil in the HC feed at 15%, total hydrocarbon mass flow and COT were held constant).

| | 2C, 15% Pyoil | 4A, Stm ratio 0.4 | 4B, Stm ratio 0.5 |
|---|---|---|---|
| A&B Propane flow, klb/hr | 10.07 | 10.08 | 10.08 |
| Pyoil/(poil + propane), % | 15.0 | 15.0 | 15.0 |
| Steam/HC, ratio | 0.30 | 0.40 | 0.50 |
| A&B Crossover T, F | 1075 | 1063 | 1058 |
| A&B COT, F | 1497 | 1498 | 1498 |
| Renorm. w/o Propane | wt % | wt % | wt % |
| Hydrogen | 1.60 | 1.14 | 1.49 |
| Methane | 22.91 | 21.28 | 21.54 |
| Ethane | 5.99 | 5.94 | 5.83 |
| Ethylene | 39.36 | 39.06 | 39.29 |

TABLE 16A

Effect of steam/HC ratio. (r-Pyoil in the HC feed at 15%, total hydrocarbon mass flow and COT were held constant).

| | 2C, 15% Pyoil 2C, | 15% Pyoil | 4A, Stm ratio 0.4 | 4B, Stm ratio 0.5 |
|---|---|---|---|---|
| A&B Propane flow, klb/hr | 10.07 | 10.06 | 10.08 | 10.08 |
| A&B Pyoil Flow, lb/hr | 1777 | 1776 | 1778 | 1778 |
| A&B Steam flow, lb/hr | 3560 | 3559 | 4748 | 5933 |
| A&B total HC flow, klb/hr | 11.84 | 11.84 | 11.85 | 11.85 |
| Pyoil/(poil + propane), % | 15.0 | 15.0 | 15.0 | 15.0 |
| Steam/HC, ratio | 0.30 | 0.30 | 0.40 | 0.50 |
| A&B Crossover T, F | 1075 | 1076 | 1063 | 1058 |
| A&B COT, F | 1497 | 1497 | 1498 | 1498 |
| A&B TLE ExitT, F | 690 | 691 | 698 | 703 |
| A&B Feed Pres, PSIG | 69.5 | 69.5 | 67.0 | 67.0 |
| A&BTLE Inlet, PSIG | 10.0 | 10.0 | 10.0 | 11.0 |
| A&BTLE ExitT, PSIG | 9.0 | 9.0 | 9.0 | 9.0 |
| Cracked Gas Product | wt % | wt % | wt % | wt % |
| Hydrogen | 1.26 | 1.25 | 0.87 | 1.12 |
| Methane | 18.06 | 17.87 | 16.30 | 16.18 |
| Ethane | 4.72 | 4.75 | 4.55 | 4.38 |
| Ethylene | 31.03 | 30.73 | 29.92 | 29.52 |
| Acetylene | 0.04 | 0.04 | 0.05 | 0.05 |
| Propane | 21.17 | 21.10 | 23.40 | 24.88 |
| Propylene | 18.29 | 18.30 | 18.67 | 18.49 |
| MAPD | 0.27 | 0.28 | 0.29 | 0.28 |
| Butanes | 0.13 | 0.13 | 0.15 | 0.16 |
| Butadiene | 1.87 | 1.99 | 2.01 | 1.85 |
| Butenes + CPD | 1.71 | 1.77 | 1.89 | 1.81 |
| Other C5s | 0.37 | 0.40 | 0.43 | 0.37 |
| C6s+ | 1.00 | 1.30 | 1.38 | 0.84 |
| CO2 | 0.009 | 0.009 | 0.026 | 0.008 |
| CO | 0.070 | 0.072 | 0.070 | 0.061 |

On cracked gas composition. In the cracked gas, methane and r-ethylene were reduced by 1.6 and 1.4 percentage points, respectively, and propane was increased Renormalized cracked gas composition. In order to see what the lighter product composition could be if ethane and propane in the cracked gas would be recycled, the cracked gas composition in Table 16A was renormalized by taking off propane or ethane+propane. The resulting composition is listed in the lower part of Table 16B. It can be seen, olefin (r-ethylene+r-propylene) content went up with steam/HC ratio.

TABLE 16B-continued

Renormalized cracked gas composition. (R-pyoil in the HC feed at 15%, total hydrocarbon mass flow and COT were held constant).

| | | | |
|---|---|---|---|
| Acetylene | 0.05 | 0.06 | 0.06 |
| Propylene | 23.21 | 24.37 | 24.62 |
| MAPD | 0.34 | 0.38 | 0.38 |
| Butanes | 0.17 | 0.20 | 0.21 |
| Butadiene | 2.37 | 2.63 | 2.46 |
| Butenes + CPD | 2.16 | 2.47 | 2.41 |
| Other C5s | 0.46 | 0.56 | 0.50 |
| C6s+ | 1.27 | 1.80 | 1.12 |
| CO2 | 0.011 | 0.033 | 0.010 |
| CO | 0.089 | 0.091 | 0.081 |

TABLE 16B-continued

| Renormalized cracked gas composition. (R-pyoil in the HC feed at 15%, total hydrocarbon mass flow and COT were held constant). | | | |
|---|---|---|---|
| C2H4 + C3H6 | 62.57 | 63.43 | 63.91 |
| Renorm. w/o C2H6 + C3H8 | wt % | wt % | wt % |
| Hydrogen | 1.70 | 1.21 | 1.58 |
| Methane | 24.37 | 22.62 | 22.87 |
| Ethylene | 41.87 | 41.52 | 41.73 |
| Acetylene | 0.06 | 0.06 | 0.06 |
| Propylene | 24.69 | 25.91 | 26.15 |
| MAPD | 0.36 | 0.40 | 0.40 |
| Butanes | 0.18 | 0.21 | 0.22 |
| Butadiene | 2.52 | 2.79 | 2.61 |
| Butenes+CPD | 2.30 | 2.62 | 2.55 |
| Other C5s | 0.49 | 0.60 | 0.53 |
| C6s+ | 1.35 | 1.91 | 1.19 |
| coz | 0.012 | 0.035 | 0.011 |
| co | 0.094 | 0.097 | 0.086 |
| C2H4 + C3H6 | 66.55 | 67.43 | 67.87 |

Effect of total hydrocarbon feed flow (Conditions 2C & 3B). An increase in total hydrocarbon flow to the coil means a higher throughput but a shorter residence time, which reduces conversion. With r-pyoil 1052*a* at 15% in the HC feed, a 10% increase of the total HC feed brought about a slight increase in the propylene:ethylene ratio along with an increase in the concentration of propane without a change in ethane, when COT was held constant. Other changes were seen on methane and r-ethylene. Each dropped about 0.5~0.8 percentage points. The results are listed in Table 17.

TABLE 17

Comparison of more feed to coil (Steam/HC ratio = 0.3, COT is held constant at 1497F).

| | 2C, 15% Pyoil | 2C, 15% Pyoil | 3B, 10% more FD | 3B, 10% more FD |
|---|---|---|---|---|
| A&B Propane flow, klb/hr | 10.07 | 10.06 | 11.09 | 11.09 |
| A&B Pyoil Flow, lb/hr | 1777 | 1776 | 1956 | 1957 |
| A&B Steam flow, lb/hr | 3560 | 3559 | 3916 | 3916 |
| A&B total HC flow, klb/hr | 11.84 | 11.84 | 13.04 | 13.05 |
| Pyoil/(poil + propane), % | 15.0 | 15.0 | 15.0 | 15.0 |
| Steam/HC, ratio | 0.30 | 0.30 | 0.30 | 0.30 |
| A&B Crossover T, F | 1075 | 1076 | 1066 | 1065 |
| A&B COT, F | 1497 | 1497 | 1497 | 1497 |
| A&B TLE Exit T, F | 690 | 691 | 698 | 699 |
| A&BTLE Inlet, PSIG | 10.0 | 10.0 | 10.3 | 10.3 |
| A&B TLE ExitT, PSIG | 9.0 | 9.0 | 9.0 | 9.0 |
| Cracked Gas Product | wt % | wt % | wt % | wt % |
| Hydrogen | 1.26 | 1.25 | 1.19 | 1.24 |
| Methane | 18.06 | 17.87 | 17.23 | 17.31 |
| Ethane | 4.72 | 4.75 | 4.76 | 4.79 |
| Ethylene | 31.03 | 30.73 | 30.02 | 29.95 |
| Acetylene | 0.04 | 0.04 | 0.04 | 0.04 |
| Propane | 21.17 | 21.10 | 22.51 | 22.31 |
| Propylene | 18.29 | 18.30 | 18.44 | 18.28 |
| MAPD | 0.27 | 0.28 | 0.28 | 0.28 |
| Butanes | 0.13 | 0.13 | 0.15 | 0.14 |
| Butadiene | 1.87 | 1.99 | 1.93 | 1.95 |
| Butenes + CPD | 1.71 | 1.77 | 1.82 | 1.82 |
| Other C5s | 0.37 | 0.40 | 0.41 | 0.42 |
| C6s+ | 1.00 | 1.30 | 1.15 | 1.39 |
| CO2 | 0.009 | 0.009 | 0.009 | 0.008 |
| CO | 0.070 | 0.072 | 0.065 | 0.066 |

r-pyoil 1052*a* is successfully co-cracked with propane in the same coil on a commercial scale furnace.

What is claimed is:

1. A method of making a recycle content glycol ester composition ("r-GE"), said method comprising:

(a) pyrolyzing a pyrolysis feed comprising a recycled waste material to thereby form a pyrolysis effluent comprising recycle pyoil ("r-pyoil") and/or a recycle pygas ("r-pygas"), wherein the recycled waste material comprises a pretreated plastic feed;

(b) thermally steam cracking a cracker feed comprising at least a portion of the r-pyoil, in combination with a non-recycle hydrocarbon to thereby produce a cracker effluent comprising r-olefins, wherein the cracker feed stream comprises at least 1 wt % of the r-pyoil based on the weight of the cracker feed stream and at least 50 wt % of the non-recycle cracker feed stream based on the weight of the cracker feed stream, the non-recycle cracker feed stream comprising a C5-C22 hydrocarbon stream; and wherein the r-pyoil feed to the cracking furnace has not been hydrotreated;

(c) reacting the cracker effluent comprising r-olefins in a synthetic process to make an aldehyde composition;

(d) reacting at least a portion of the aldehyde composition in a synthetic process to make a glycol ester composition;

(e) applying a recycle content value to at least a portion of the glycol ester composition based on feeding a pyrolysis recycle content olefin composition ("pr-olefin") or a pyrolysis recycle content aldehyde composition ("pr-aldehyde") as a feedstock; or based on depositing at least a portion of an allotment obtained from any one or more of steps (a) or (b) into a recycle inventory and deducting from the inventory a recycle content value and applying at least a portion of the recycle content value to the glycol ester to thereby obtain the r-glycol ester; and receiving a solid waste plastic-containing feed from a waste plastic source and pretreating the solid waste plastic-containing feed to give the pretreated plastic feed.

2. The method of claim 1, wherein the glycol ester composition is derived directly or indirectly from cracking r-pyoil at least a portion of which is obtained from the pyrolysis of waste plastic, or obtained from r-pygas.

3. The method of claim 2, wherein the glycol ester composition is derived directly or indirectly from cracking r-pyoil in a thermal steam cracker.

4. The method of claim 2, wherein the glycol ester composition is prepared by hydroformylating an r-olefin composition to provide an aldehyde and condensing the aldehyde to provide the glycol ester composition.

5. The method of claim 1, wherein the waste plastic source holds and/or stores the solid waste plastic-containing feed, and wherein the recycle content glycol ester composition comprises 2,2,4-trimethyl-1,3-pentanediol monoisobutyrate or 2,2,4-trimethyl-1,3-pentanediol diisobutyrate, or both.

6. The method of claim 5, wherein the waste plastic source comprises a hopper, a storage bin, a railcar, or an over-the-road trailer, or any combination thereof, that holds and/or stores the solid waste plastic-containing feed.

7. The method of claim 5, wherein the solid waste plastic-containing feed is in form of solid particles.

8. The method of claim 5, wherein the pretreating comprises washing, mechanical agitation, flotation, or size reduction, or any combination thereof.

9. The method of claim 5, comprising providing the pretreated plastic feed to the pyrolyzing via a plastic feed system comprising a screw feeder, a hopper, a pneumatic conveyance system, or a mechanic metal train or chain, or any combinations thereof.

10. The method of claim 1, comprising cracking the cracker feed without r-pyoil to make olefins and applying the recycle content value to the olefins so made by deducting the recycle content value from the recycle inventory and applying it to the olefins to make the r-olefins, thereby providing the cracker effluent comprising r-olefins.

11. The method of claim 1, comprising applying the recycle content value to at least a portion of the glycol ester composition based on depositing at least a portion of the allotment obtained from any one or more of steps (a) or (b) into the recycle inventory and deducting from the recycle inventory the recycle content value and applying at least a portion of the recycle content value to the glycol ester to thereby obtain the r-glycol ester.

* * * * *